United States Patent [19]
Wigler et al.

[11] Patent Number: 5,527,896
[45] Date of Patent: Jun. 18, 1996

[54] CLONING BY COMPLEMENTATION AND RELATED PROCESSES

[75] Inventors: Michael H. Wigler, Lloyd Harbor, N.Y.; John J. Colicelli, Los Angeles, Calif.

[73] Assignee: Cold Spring Harbor Laboratory, Cold Spring Harbor, N.Y.

[21] Appl. No.: 688,352

[22] Filed: Apr. 19, 1991

Related U.S. Application Data

[63] Continuation-in-part of Ser. No. 511,715, Apr. 20, 1990, abandoned.

[51] Int. Cl.$^6$ ............................... C07H 21/04; C12Q 1/68
[52] U.S. Cl. ............................................. 536/23.5; 435/6
[58] Field of Search ............................... 435/6; 536/23.5

[56] References Cited

PUBLICATIONS

Colicelli, J., et al., *Proc. Natl. Acad. Sci. (USA)*, 86:3599–3603 (1989).
DeFeo–Jones, D., et al., *Science*, 228:179–184 (1985).
Field, J., et al., *Molecular and Cellular Biology*, 8:2159–2165 (1988).
Henikoff, S., et al., *Nature* 289:33–37 (1981).
Kataoka, T., et al., *Cell*, 43:493–505 (1985).
Kataoka, T., et al., *Cell*, 40:19–26 (1985).
Nikawa, J–I., et al., *Molecular and Cellular Biology*, 7:3629–3636 (1987).
Powers, S., et al., *Molecular and Cellular Biology*, 9:390–395 (1989).
Sass, P., et al., *Proc. Natl. Acad. Sci. (USA)*, 83:9303–9307 (1986).
Swinnen, J. V., et al., *Proc. Natl. Acad. Sci. (USA)* 86:5325–5329 (1989).
Wigler, M., et al., *Cold Spring Harbor Symposia*, LIII:649–655 (1988).
Kataoka et al, Cell, V. 40, Jan. 1985, 19–26.
Colicelli, et al, PNAS, V. 86, May 1989, 3599–3603.

*Primary Examiner*—Mindy Fleisher
*Attorney, Agent, or Firm*—Marshall, O'Toole, Gerstein, Murray & Borun

[57] ABSTRACT

Disclosed are methods for detecting mammalian genes encoding proteins which can function in microorganisms, particularly yeast, to modify, complement, or suppress a genetic defect associated with an identifiable phenotypic alteration or characteristic in the microorganism. Disclosed also are mammalian DNA sequences cloned by the above method, as well as polypeptide products of the expression of the DNA sequences in procaryotic or eucaryotic host cells and antibody substances which are specifically immunoreactive with said expression products. More specifically, the present invention relates to methods for cloning mammalian genes which encode products which modify, complement or suppress a genetic defect in a biochemical pathway in which cAMP participates or in a biochemical pathway which is controlled, directly or indirectly, by a RAS-related protein, to products (RNA, proteins) encoded by the mammalian genes cloned in this manner, and to antibodies which can bind the encoded proteins.

6 Claims, 26 Drawing Sheets

Fig. 1(A)

```
JC44x   10  GCCGGCGGCCTAGGCCGCATCCCGGAGCTGCAACTGGTGGCCTTCCCGGTGGCGGTG
TM3-     1  gcggGCGGCCTAGGCCGCATCCCGGAGCTGCAACTGGTGCCCTTCCCGGTGGCGGTG JC44x   68  GCGGCTGAGGACGAGGCGTTCCTGCCCGAGCCCCTGGCCCCGCGCGCCCCGCGCCGC
TM3-    62  GCGGCTGAGGACGAGGCGTTCCTGCCCGAGCCCCTGGCCCCGCGCGCCCCGCGCCGC JC44x  129  GTTCGCGCCCTCCTCGCCGTCTCTTCGCCAGCCCCGTCCCCAACTTTCCGCAGACGCCT
TM3-   123  GTTCGCGCCCTCCTCGCCGTCTCTTCGCCAGCCCCGTCCCCAACTTTCCGCAGACGCCT JC44x  190  TCGGCTTCTCCGCAGCTGCCAGGATTTGGGCCGCAGGGTTGGGCTGGGCTTCGAG
TM3-   184  TCGGCTTCTCCGCAGCTGCCAGGATTTGGGCCGCAGGGCTTGGGGCTGGGCTTCGAG JC44x  251  GCAGAGAATGGGGCCGACACCATCCTGGCCGCAGCCCCTGGACTCGCAGGCGAGCCCAG
TM3-   245  GCAGAGAATGGGGCCGACACCATCCTGGCCGCAGCCCCTGGACTCGCAGGCGAGCCCAG JC44x  312  GACTCGTGCTGCACGGCCGGGGGCGCCACCAGCGCCGGGAGTCCTTCCTGTACCGTC
TM3-   306  GACTCGTGCTGCACGGCCGGGGGCG CCACCAGCGCCGGGAGTCCTTCCTGTACCGTC
```

FIG. 1(B)

```
JC44x  373  AGACAGGACTATGACATGTCACCCAAGACCATGTGTCCCGGAACTCATCGGTCACCAGCGAG
TM3-   366  AGACAGGACTATGACATGTCACCCAAGACCATGTGTCCCGGAACTCATCGGTCACCAGCGAG

JC44x  434  GC                                                      GCACGCTGAA
TM3-   427  GCACAGTTGCTTCTCTGCGGACCCCTGCCTCTGTCCTCAATCACAGGCACGCTGAA

JC44x  446  GACCTCATCGTAACACCATTTGCTGTCAGGTGCTGGCCAGCCTCCGGAGCGTCCGGTAGCAACT
TM3-   488  GACCTCATCGTAACACCATTTGCTGTCAGGTGCTGGCCAGCCTCCGGAGCGTCCGGTAGCAACT

JC44x  507  TCTCACTCCTGACCAATGTGCCCCGTTCCCAGTAACAAGCGGTCCCCGTGGGGCCCCA
TM3-   549  TCTCACTCCTGACCAATGTGCCCCGTTCCCAGTAACAAGCGGTCCC   GCTGGGGCCCCA

JC44x  568  CCCCTGTCTGCAAGGGCCACGCTGTC
TM3-   608  CCCCTGTCTGCAAGGGCCACGCTGTCAGACCTTCTCAGTCACTACCCTGGCCCCTTCCT

JC44x  593  AGAAGAAACGTGTCAGCAGTTGGCCCGGGAGACTCTGGAGGAGCTGGACTGGTGTCTGGA
TM3-   669  TAGAAGAAACGTGTCAGCAGTTGGCCCGGGAGACTCTGGAGGAGCTGGACTGGTGTCTGGA
```

Fig. 1(C)

```
JC44x  653  GCAGCTGGAGAGACCATGCAGAGACCTATCGCTCTGTCAGCGAGATGGCCTCGCACAAGTTCAAA
            ||||||||||||||||||||||||||||||||||||||||||||||||||||||||||||||||
TM3-   730  GCAGCTGGAGAGACCATGCAGAGACCTATCGCTCTGTCAGCGAGATGGCCTCGCACAAGTTCAAA

JC44x  714  AGGATGTTGAACCGTGAGCTCACACACCTGTCAGAAATGAGCAGGTCCGGAAACCAGGTCT
            ||||||||||||||||||||||||||||||||||||||||||||||||||||||||||||
TM3-   791  AGGATGTTGAACCGTGAGCTCACACACCTGTCAGAAATGAGCAGGTCCGGAAACCAGGTCT

JC44x  775  CAGAGTACACATTTCCACAACATTCCTGGACAAACAGAATGAAGTGGAGATCCCATCACCCAC
            ||||||||||||||||||||||||||||||||||||||||||||||||||||||||||||||
TM3-   852  CAGAGTACACATTTCCACAACATTCCTGGACAAACAGAATGAAGTGGAGATCCCATCACCCAC

JC44x  836  GATGAAGGAACGAGAAAAACAGCAAGCGCGACCAAGACCCTCCCAGCCGCCCCGCCC
            ||||||||||||||||||||||||||||||||||||||||||||||||||||||||
TM3-   913  GATGAAGGAACGAGAAAAACAGCAAGCGCGACCAAGACCCTCCCAGCCGCCCCGCCC

JC44x  897  CCTGTACCACACTTACAGCCCATGTCCCAAATCACAGGGTTGAAAAAGTTGATGCATAGTA
            ||||||||||||||||||||||||||||||||||||||||||||||||||||||||||||
TM3-   974  CCTGTACCACACTTACAGCCCATGTCCCAAATCACAGGGTTGAAAAAGTTGATGCATAGTA

GB14     8                   AACATTCCCCGATTTGGGGTGAAGACCGATCAAGAAGAGCTCCT
                              ||||||||||||||||||||||||||||||||||||||||||||
JC44x  958  ACAGCCTGAACAACTCTAACATTCCCCGATTTGGGGTGAAGACCGATCAAGAAGAGCTCCT
            ||||||||||||||||||||||||||||||||||||||||||||||||||||||||||||
TM3-  1035  ACAGCCTGAACAACTCTAACATTCCCCGATTTGGGGTGAAGACCGATCAAGAAGAGCTCCT
```

FIG. 1(D)

```
GB14    52  GGCCCAAGAACTGGAGAACCTGAACAAGTGGGGCCTGAACATCTTTTGCGTGTCGGATTAC
JC44x 1019  GGCCCAAGAACTGGAGAACCTGAACAAGTGGGGCCTGAACATCTTTTGCGTGTCGGATTAC
TM3-  1096  GGCCCAAGAACTGGAGAACCTGAACAAGTGGGGCCTGAACATCTTTTGCGTGTCGGATTAC

GB14   113  GCTGGAGGCCGCTCACTCACCTGCATCATGTACATGATATTCCAGGAGCGGGACCTGCTGA
JC44x 1080  GCTGGAGGCCGCTCACTCACCTGCATCATGTACATGATATTCCAGGAGCGGGACCTGCTGA
TM3-  1157  GCTGGAGGCCGCTCACTCACCTGCATCATGTACATGATATTCCAGGAGCGGGACCTGCTGA

GB14   174  AGAAATTCCGCATCCCTGTGGACACGATGGTGACATACATGCTGACGCTGGAGGATCACTA
JC44x 1141  AGAAATTCCGCATCCCTGTGGACACGATGGTGACATACATGCTGACGCTGGAGGATCACTA
TM3-  1218  AGAAATTCCGCATCCCTGTGGACACGATGGTGACATACATGCTGACGCTGGAGGATCACTA

GB14   235  CCACGCTGACGTGGCCTACCATAACAGCCTGCACGCAGCTGACGTGCAGTCCACCCAC
JC44x 1202  CCACGCTGACGTGGCCTACCATAACAGCCTGCACGCAGCTGACGTGCAGTCCACCCAC
TM3-  1279  CCACGCTGACGTGGCCTACCATAACAGCCTGCACGCAGCTGACGTGCAGTCCACCCAC
```

FIG. 1(E)

```
GB14   296  GTACTGCTGGCCACGCCT                GCACTAGATGCAGTGTTCACGGACCTGGAGATTC
JC44x 1263  gtActgctggccAcgcct tggccaaccttaaggaatgcAgtgttcAcggAccttggAgAttc
TM3-  1340  gtActgctggccAcgcct                gcActAgAtgcAgtgttcAcggAccttggAgAttc GB14   348  TCGCCGCCCTCTTCGCGGGCCCTGCCATCCACGATGTGGATCACCCTGGGGTCTCCAACCAGTT
JC44x 1324  tcgccgccctcttcgcgggcctgccAtccAcgAtgtggAtcAccctggggtctccAaccAgtt
TM3-  1392  tcgccgccctcttcgcgggcctgccAtccAcgAtgtggAtcAccctggggtctccAAccAgtt GB14   409  CCTCATCAACACCAATTCGGAGCTGGGCTTCAAGCTGCAGGAGGACAATGAGTCGGTGCTCGAGAAT
JC44x 1385  cctcAtcAacAccAattcggAgctgggcttcAAgctgcAggaggAcaAtgAgtcggtgctcgAgaAt
TM3-  1453  cctcAtcAAcAccAattcggAgctgggcttcAAgctgcAggAggAcAAtgAgtcggtgctcgAgAAt GB14   470  CACCACCTGGCCGTGGGCTTCAAGCTGCAGGAGGACAACTGCGACATCTTCCAGAACC
JC44x 1446  cAccAcctggccgtgggcttcAAgctgcAggaggAcaActgcgAcatcttccAgaAcc
TM3-  1514  cAccAcctggccgtgggcttcAAgctgcAggAggAcAActgcgAcAtcttccAgAAcc
```

Fig. 1(F)

```
GB14    531  TCAGCAAGGCGCCAGCGGGCAGAGC TACGCAAGATGGTCATCG
             ||||||||||||||||||||||||| |||||||||||||||||
Jc44x  1507  TCAGCAAGGCGCCAGCGGGCAGAGCCTACGCAAGATGGTCATCGACATGGTGCTGGCCACGGA
             ||||||||||||||||||||||||  ||||||||||||||||||||||||||||||||||||
TM3-   1575  TCAGCAAGGCGCCAGC GCAGAGCCTACGCAAGATGGTCATCGACATGGTGCTGGCCACGGA

Jc44x  1568  CATGTCCAAGCACACATGACCCTCCTGGCTGACCTGAAGACCATGGTGGAGACCAAGAAAGTG
             ||||||||||||||||||||||||||||||||||||||||||||||||||||||||||||||
TM3-   1635  CATGTCCAAGCACACATGACCCTCCTGGCTGACCTGAAGACCATGGTGGAGACCAAGAAAGTG

Jc44x  1629  ACCAGCTCAGGGGTCCTCCTGCTAGATAACTACTCCGACCGCATCCAGGTCCTCCGGAACA
             ||||||||||||||||||||||||||||||||||||||||||||||||||||||||||||
TM3-   1696  ACCAGCTCAGGGGTCCTCCTGCTAGATAACTACTCCGACCGCATCCAGGTCCTCCGGAACA

GB18ARR   1                                                            ACA
                                                                       |||
Jc44x  1690  TGGTGCACTGTGCCGACCTCAGCAACCCCACCAAGCCGCTGGAGCTGTACCGCCAGTGGAC
             ||||||||||||||||||||||||||||||||||||||||||||||||||||||||||||
TM3-   1757  TGGTGCACTGTGCCGACCTCAGCAACCCCACCAAGCCGCTGGAGCTGTACCGCCAGTGGAC
             ||||||||||||||||||||||||||||||||||||||||||||||||||||||||||||
GB18ARR   4  TGGTGCACTGTGCCGACCTCAGCAACCCCACCAAGCCGCTGGAGCTGTACCGCCAGTGGAC
```

FIG. 1(G)

```
JC44x   1751  AGACCGGCATCATGGCCGAGTTCTTCCAGCAGGGTGACCGAGCGCGAGAGCGTGGCATGGAA
TM3-    1818  AGACCGGCATCATGGCCGAGTTCTTCCAGCAGGGTGACCGAGCGCGAGAGCGTGGCATGGAA
GB18ARR   65  AGACCGGCATCATGGCCGAGTTCTTCCAGCAGGGTGACCGAGCGCGAGAGCGTGGCATGGAA

JC44x   1812  ATCAGCCCCATGTGTGACAAGCACACTGCCTCCGTGGAGAAGTCTCAGGTGGGTTTTATTG
TM3-    1879  ATCAGCCCCATGTGTGACAAGCACACTGCCTCCGTGGAGAAGTCTCAGGTGGGTTTTATTG
GB18ARR  126  ATCAGCCCCATGTGTGACAAGCACACTGCCTCCGTGGAGAAGTCTCAGGTGGGTTTTATTG

JC44x   1873  ACTACATTGTGCACCCATTGTGTGGGCGGAGACCTTGTCCACCCAGATGCCCAGGA
TM3-    1940  ACTACATTGTGCACCCATTGTGTGGGCGGAGACCTTGTCCACCCAGATGCCCAGGA
GB18ARR  187  ACTACATTGTGCACCCATTGTGTGGGCGGAGACCTTGTCCACCCAGATGCCCAGGA

JC44x   1934  GATCTTGGACACTTTGGAGGACAACCGGGACTGGTACTACAGGCCCATCCGGCAGAGCCCA
TM3-    2001  GATCTTGGACACTTTGGAGGACAACCGGGACTGGTACTACAGGCCCATCCGGCAGAGCCCA
GB18ARR  248  GATCTTGGACACTTTGGAGGACAACCGGGACTGGTACTACAGGCCCATCCGGCAGAGCCCA
```

Fig. 1(H)

```
Jc44x  1995  TCTCCGCCACCCCGAGGAGGAGTCAAGGGGGCCAGGCCACCCCTGCCTGACAAGTTCC
TM3-   2062  TCTCCGCCACCCCGAGGAGGAGTCAAGGGGGCCAGGCCACCCCTGCCTGACAAGTTCC
GB18ARR 309  TCTCCGCCACCCCGAGGAGGAGTCAAGGGGGCCAGGCCACCCCTGCCTGACAAGTTCC

Jc44x  2056  AGTTTGAGCTGACGCTGGAGGAGGAAGAGGAAGAAATATCAATGGCCCAGATACCGTG
TM3-   2123  AGTTTGAGCTGACGCTGGAGGAGGAAGAGGAAGAAATATCAATGGCCCAGATACCGTG
GB18ARR 370  AGTTTGACGTGACGCTGGAGGAGGAAGAGGAAGAAATATCAATGGCCCAGATACCGTG

Jc44x  2117  CACAGCCCAAGAGAGGCATTGACTGAGCAGGGATTGTCAGGAGTCGAGGAAGCTCTGGATGCA
TM3-   2184  CACAGCCCAAGAGAGGCATTGACTGAGCAGGGATTGTCAGGAGTCGAGGAAGCTCTGGATGCA
GB18ARR 431  CACAGCCCAAGAGAGGCATTGACTGcGCAGGGATTGTCAGGAGTCGAGGAAGCTCTGGATGCA

Jc44x  2178  ACCATAGCCTGGGAGGCATCCCCGGCCCAGGAGTCGTTGGAAGTTATGGCACAGGAAGCAT
TM3-   2245  ACCATAGCCTGGGAGGCATCCCCGGCCCAGGAGTCGTTGGAAGTTATGGCACAGGAAGCAT
GB18ARR 492  ACCATAGCCTGGGAGGCATCCCCGGCCCAGGAGTCGTTGGAAGTTATGGCACAGGAAGCAT
```

FIG. 1(I)

```
JC44x   2239  CCCTGGAGGCCGAGCTGGAGGCAGTGTATTTGACACAGCAGGCACAGTCCACAGGCAGTGC
TM3-    2306  CCCTGGAGGCCGAGCTGGAGGCAGTGTATTTGACACAGCAGGCACAGTCCACAGGCAGTGC
GB18ARR  553  CCCTGGAGGCCGAGCTGGAGGCAGnGTATTTGACACAGCAGGCACAGTCCACAGGCAGTGC

JC44x   2300  ACCTGTGGCTCCGGATGAGTTCTCGTCCCGGGAGGAATTCGTGGTTGCTGTAAGCCACAGC
TM3-    2367  ACCTGTGGCTCCGGATGAGTTCTCGTCCCGGGAGGAATTCGTGGTTGCTGTAAGCCACAGC
GB18ARR  614  ACCTGTGGCTCCGGATGAGTTCTCGTCCCGGGAGGAATTCGTGGTTGCTGTAAGCCACAGC

JC44x   2361  AGCCCCCTCTGCCCTGGCTCTTCAAAGCCCCCCTTCTCCCTGCTTGGAGGACCCTGTCTGTTT
TM3-    2428  AGCCCCCTCTGCCCTGGCTCTTCAAAGCCCCCCTTCTCCCTGCTTGGAGGACCCTGTCTGTTT
GB18ARR  675  AGCCCCCTCTGCCCTGGCTCTTCAAAGCCCCCCTTCTCCCTGCTTGGAGGACCCTGTCTGTTT

JC44x   2422  CAGAGCATGCCC   GGCCTCCCGGGCCTCCCCACGGCGGCCGAGGTGGAGGCCCAACG
TM3-    2489  CAGAGCATGCCCcgGCCTCCCGGGCCTCCCCACGGCGGCCGAGGTGGAGGCCCAACG
GB18ARR  736  CAGAGCATGCCCCCGGGGGCCTCCCGG CCTCCCCTCCACGGGGGCCCTAGGTGG    AACG
```

FIG. 1(J)

```
Jc44x  2481  AGAGCACCAGGGCTGCCAAGAGGGCTTGCAGTGCCTGCGCAGGGACATTTGGGGAGGACACA
TM3-   2550  AGAGCACCAGGGCTGCCAAGAGGGCTTGCAGTGCCTGCGCAGGGACATTTGGGGAGGACACA
GB18ARR 790  AGAGCACCAGGGCTGCCAAGAGGGCTTGCAGTGCCTGCGCAGGGACATTTGGGGAGGACACA

Jc44x  2542  TCCGCACTCCCAGCTCCTGGTGGCGGGGGTCAGGTGGAGACCCTACCTGATCCCCAGACC
TM3-   2611  TCCGCACTCCCAGCTCCTGGTGGCGGGGGTCAGGTGGAGACCCTACCTGATCCCCAGACC
GB18ARR 851  TCCGCACTCCCAGCTCCTGGTGGCGGGGGTCAGGTGGAGACCCTACCTGATCCCCAGACC

Jc44x  2603  TCTGTCCCTGTTCCCCTCCACTCCTCCCCTGCTCCCCGACCACCTCCTCCT
TM3-   2672  TCTGTCCCTGTTCCCCTCCACTCCTCCCCTGCTCCCCGACCACCTCCTCCT
GB18ARR 912  TCTGTCCCTGTTCCCCTCCACTCCTCCCCTGCTCCCCGACCACCTCCTCCT

Jc44x  2664  CTGCCTCAAAGACTCTTGTCCTCTTGTCC
TM3-   2733  CTGCCTCAAAGACTCTTGTCCTCTTGTCCCTCCTGAGATTTTTTTTTTTTTTTTTT
GB18ARR 973  CTGCCTCAAAGACTCTTGTCCTCTTGTCCCTCCTGAGA
```

FIG. 2(A)

```
PDE2RR     1                                                  GAATTCCTTCTGACGTGGCATATCACAACA
                                                              ||||||||||||||||||||||||||||||
TM72    1300  TTTATAACCTACACATGATGACTTTAGAAGACCATTACCATTCTGACGTGGCATATCACAACA

PDE2RR    31  GCCTGCACTGCTGCTGATGTAGCCCAGTCGACCCATGTNCTCC TTCTACNCCAGCATTAG
              |||||||| ||||||||  ||||||||||||||||   || ||||||| ||||||||||
TM72    1361  GCCTGCAC GCTGCTGATGATGTAGCCCAGTCGACCCATGTTCTCCTTCTACACCAGCATTAG

PDE2RR    91  ACGCTGTCTTCACAGATTTGGAAATCCTGGCTGCCATTTTTGCAGTGCCATCCATGACGT
              |||||||||||||||||  |||||| |||||| ||||||||||||||| ||||||||||
TM72    1422  ACGCTGTCTTCACAGATTGGAGATCCTGGCTGCCATTTTTGCAGTGCCATCCATGACGT

PDE2RR   152  TGATCATCCTGGAGTCTCCAATCAGTTTCTCATCAACACAAATTCAGAACTTGCTTTGATG
              ||||||||||||||||||  |||||||||||||| |||||||||||||||| |||||||
TM72    1483  TGATCATCCTGGAGTCTCCGAGTCAGTTTCTCATCAACACAAATTCAGAACTTGCTTTGATG

PDE2RR   213  TATAATGATGAATCTGTGTTGGAAAATCATCACCTTGCTGTGGGTTTCAAACTGCTGCAAG
              |||||||||||||||| |||  ||||||||||||| ||| |||||||||||||||||||
TM72    1544  TATAATGATGAATCTGTTGTTGGAAAATCATCACCTTGCTGTGGGTTTCAAACTGCTGCAAG

PDE2RR   274  AAGAACACTGTGACATCTTCATGAATCTTCACCAAGAAGCAGCGTCAGACACTCAGGAAGAT
              |||||||||||||| ||||| |||||||| ||||||||||||||||||||||||||||||
TM72    1605  AAGAACACTGTGACATCTTCATGAATCTTCACCAAGAAGCAGCGTCAGACACTCAGGAAGAT
```

FIG. 2(B)

```
PDE2RR   335  GGTTATTGACATGGTGTTAGCAACTGATATGTCTAAACATATGAGCCTGCTGGCAGACCTG
TM72    1666  GGTTATTGACATGGTGTTAGCAACTGATATGTCTAAACATATGAGCCTGCTGGCAGACCTG

PDE2RR   396  AAGACAATGGTAGAGAAACGAAGAAAGTTACAAGTTCAGGCGTTCTTCTCCTAGACAACTATA
TM72    1727  AAGACAATGGTAGAGAAACGAAGAAAGTTACAAGTTCAGGCGTTCTTCTCCTAGACAACTATA

PDE2RR   457  CCGATCGCATTCAGGTCCTTCGCAACATGGTACACTGTGCAGACCTGAGCAACCCCACCAA
TM72    1788  CCGATCGCATTCAGGTCCTTCGCAACATGGTACACTGTGCAGACCTGAGCAACCCCACCAA

PDE2RR   518  GTCCTTGGAATTGTATCGGCAATGGACAGACCGCATCATGGAGGAATTTTCCAGCAGGGA
TM72    1849  GTCCTTGGAATTGTATCGGCAATGGACAGACCGCATCATGGAGGAATTTTCCAGCAGGGA

PDE2RR   579  GACAAAGAGCGGGAGAGGGAATGGAAATTAGCCCAATGTGTGATAAACACACAGCTTCTG
TM72    1910  GACAAAGAGCGGGAGAGGGAATGGAAATTAGCCCAATGTGTGATAAACACACAGCTTCTG

PDE2RR   640  TGGAAAAATCCCAGGTTGGTTTCATCGACTACATTGTCCATCCATTGTGGGAGACATGGGC
TM72    1971  TGGAAAAATCCCAGGTTGGTTTCATCGACTACATTGTCCATCCATTGTGGGAGACATGGGC
```

FIG. 2(C)

```
PDE2RR  701   AGATTTGGTACAGCCTGATGCTCAGGACATTCTCGATACCTTAGAAGATAACAGGAACTGG
TM72   2032   AGATTTGGTACAGCCTGATGCTCAGGACATTCTCGATACCTTAGAAGATAACAGGAACTGG

PDE2RR  762   TATCAGAGCATGATACCTCAAAGTCCCTCACCACTGGACGAGCAGAACAGGGACTGCC
TM72   2093   TATCAGAGCATGATACCTCAAAGTCCCTCACCACTGGACGAGCAGAACAGGGACTGCC

PDE2RR  823   AGGGTCTGATGGAGAAGTTTCAGTTTGAACTGACTCTCGATGAGGAAGATTCTGAAGGACC
TM72   2154   AGGGTCTGATGGAGAAGTTTCAGTTTGAACTGACTCTCGATGAGGAAGATTCTGAAGGACC

PDE2RR  884   TGAGAAGGAGGAGAGGGACACAGCTATTTCAGCAGCAGTGACATAGACATTGCAACAGAAGACAAGTCCC
TM72   2215   TGAGAAGGAGGAGAGGGACACAGCTATTTCAGCAGCAGTGACATAGACATTGCAACAGAAGACAAGTCCC

PDE2RR  945   CCAGAAAAACAGAGATTCCCTGGGAGAGACTGACACTGACATAGACATGACAGAAGACAAGTCCC
TM72   2276   CCAGAAAAACAGAGATTCCCTGGGAGAGACTGACACTGACATAGACATGACAGAAGACAAGTCCC

PDE2RR 1006   CCGTGGATACATAATCCCCCTCTCCCTGTGGAGATGAACATTCTATCCTTGATGAGCATGC
TM72   2337   CCGTGGATACATAATCCCCCTCTCCCTGTGGAGATGAACATTCTATCCTTGATGAGCATGC
```

FIG. 2(D)

```
PDE2RR   1067  CAGCTATGTGTGGTAGGGCCAGCCCACCATGGGGGCCAAGACCTGCACAGGACAAGGCCACC
TM72     2337  CAGCTATGTGTGGTAGGGCCAGCCCACCATGGGGGCCAAGACCTGCACAGGACAAGGCCACC
PDE7       20                      CCCACCATGGGGGCCAAGACCTGCACAGGACAAGGCCACC
PDE10X-INV  7                      CCCACCATGGGGGCCAAGACCTGCACAGGACAA GGCCACC

PDE2RR   1128  TGGCCTTTCAGTTACTTGAGTTTGGAGTCAGAAAGCAAGACCAGGAAGCAAATAGCAGCTC
TM72     2398  TGGCCTTTCAGTTACTTGAGTTTGGAGTCAGAAAGCAAGACCAGGAAGCAAATAGCAGCTC
PDE7       62  TGGCCTTTCAGTTACTTGAGTTTGGAGTCAGAAAGCAAGACCAGGAAGCAAATAGCAGCTC
PDE10X-INV 48  TGGCCTTTCAGTTACTTGAGTTTGGAGTCAGAAAGCAAGACCAGGAAGCAAATAGCAGCTC

PDE2RR   1189  AGGAAATCCCACGGTTGACTTGCCTTGATGGCAAGCTTGGTGGAGAGGGCTGAAGCTGTTG
TM72     2459  AGGAAATCCCACGGTTGACTTGCCTTGATGGCAAGCTTGGTGGAGAGGGCTGAAGCTGTGG
PDE7      123  AGGAAATCCCACGGTTGACTTGCCTTGATGGCAAGCTTGGTGGAGAGGGCTGAAGCTGTTG
PDE10X-INV 109 AGGAAATCCCACGGTTGACTTGCCTTGATGGCAAGCTTGGTGGAGAGGGCTGAAGCTGTTG
```

Fig. 2(E)

```
PDE2RR    1250  CTGGGGGCCGATTCTGATCAAGACACATGGCTTGAAAATGGAAGACACAAAACCGAGAGAT
TM72      2520  CTGGGGGCCGATTCTGATCAAGACACATGGCTTGAAAATGGAAGACACAAAACTGAGAGAT
PDE7       184  CTGGGGGCCGATTCTGATCAAGACACATGGCTTGAAAATGGAAGACACAAAACTGAGAGAT
PDE10X-INV 170  CTGGGGGCCCGNTTCTGATCAAGACACATGGCTTGAAAATGGAAGACACAAAACTGAGAGAT

PDE2RR    1311  CATTCTGCACTAAGTTTCGGGAACTTATCCCCGACAGTGACTGAACTCACTGACTAATAAC
TM72      2581  CATTCTGCACTAAGTTTCGGGAACTTATCCCCGACAGTGACTGAACTCACTGACTAATAAC
PDE7       245  CATTCTGCACTAAGTTTCGGGAACTTATCCCCGACAGTGACTGAACTCACTGACTAATAAC
PDE10X-INV 231  CATTCTGCACTAAGTTTCGGGAACTTATCCCCGACAGTGACTGAACTCACTGACTAATAAC

PDE2RR    1372  TTCATTTATGAATCTTCTCCCTTGTCTGCCAACCTGTGTGCCTTTTTGTAAA
TM72      2642  TTCATTTATGAATCTTCTCACTTGTCTGCCAACCTGTGTGCCTTTTTGTAAA
PDE7       306  TTCATTTATGAATCTTCTCCCTTGTCTGCCAACCTGTGTGCCTTTTTGTAAA
PDE10X-INV 292  TTCATTTATGAATCTTCTCCCTTGTCTGCCAACCTGTGTGCCTTTTTGTAAA
```

Fig. 2(F)

```
PDE2RR   1433  ACATTTTCATGTCTTTAAAATGCCTGTTGAATACCTGGAGTTAGTATCAACTTCTACACA
TM72     2703  ACATTTTCATGTCTTTAAAATGCCTGTTGAATACCTGGAGTTAGTATCAACTTCTACACA
PDE7      367  ACATTTTCATGTCTTTAAAATGCCTGTTGAATACCTGGAGTTTAGTATCAACTTCTACACA
PDE10X-INV 353 ACATNTTCANGTCTTTAAAATGCCTGTTGAATACCTGGAGTT  AGATCAACTTCTACACA

PDE2RR   1494  GATAAGCTTTCAAAGTTGACAAACTTTTTGACTCTTTCTGGAAAAGGGAAAGAAAATAGT
TM72     2764  GATAAGCTTTCAAAGTTGACAAACTTTTTGACTCTTTCTGGAAAAGGGAAAGAAAATAGT
PDE7      428  GATAAGCTTTCAAAGTTGACAAACTTTTTGACTCTTTCTGGAAAAGGGAAAGAAAATAGT
PDE10X-INV 412 GATAAGCTTTCAAAGTTGACAAACTTTTTGACTCTT CTGGAAAAGGGAAAGAAAATAGT

PDE2RR   1555  CTTCCTTCTTTCTTGGGCAATATCCTTCACTTACTACAGTTACTTTTGCAAACAGACAGA
TM72     2825  CTTCCTTCTTTCTTGGGCAATATCCTTCACTTACTACAGTTACTTTTGCAAACAGACAGA
PDE7      488  CTTCCTTCTTTCTTGGGCAATATCCTTCACTTACTACAGTTACTTTTGCAAACAGACAGA
PDE10X-INV 471 CTTCCTTCTTTCTTGGGCAATATCCTTCACTTACTACAGTTACTTTTGCAAACAGACAGA
```

FIG. 2(G)

```
PDE2RR    1616  AAGGATACACTTCTAACCACATTTTAC
TM72      2886  AAGGATACACTTCTAACCACATTTAC TTCCTTCCCTGTTGTCCAGTCCAACTCCACAGT
PDE7       549  AAGGATACACTTCTAACCACATTTAC TTCCTTCCCTGTTGTCCAGTCCAACTCCACAGT
PDE10X-INV 532  AAGGATACACTTCTAACCACATTTAC TTCCTTCCCTGTTGTCCAGTCCAACTCCACAGT

TM72      2947  CACTCTTAAAACTTCTCTCTGTTTGCCTGCCTCCAACAGT      ACTTTAACTTTT
PDE7       610  CACTCTTAAAACTTCTCTCTGTTTGCCTGCCTCCAACAGT      ACTTTAACTTTT
PDE10X-INV 593  CACTCTTAAAACTTCTCTCTGTTTGCCTGCCTCCAACAGTACTTTAACTTTTAACTTTT

TM72       662  GCTGTAAACAGAATAAAATTGAACAAATTAGGGGTAGAAAGGAGCAGTGGTCGTTCAC
PDE7       664  GCTGTAAACAGAATAAAATTGAACAAATTAGGGGTAGAAAGGAGCAGTGGTGTCGTTCAC
PDE10X-INV 654  GCTGTAAACAGAATAAAATTGAACAAATTAGGGGGTAGAAAGGAGCAGTGGTGTCGTTCAC

TM72       723  CGTGAGAGTCTGCATAGAACTCAGCAGTGTGCCCTGCTGTCTTGGACCCTGC
PDE7       725  CGTGAGAGTCTGCATAGAACTCAGCAGTGTGCCCTGTGTCTTGGACCCTGCCCCCAC
PDE10X-IND 715  CGTGAGAGTCTGCATAGAACTCAGCAGTGTGCCCTGTGTCTTGGACCCTGCCCCCAC
```

FIG. 2(H)

```
PDE7       786  AGGAGTTGTACAGTCCCTGGCCCTGTTCCCTACCTCCTCTCTTCACCCGTTAGGCTGTTT
PDE10X-INV 776  AGGAGTTGTACAGTCCCTGGCCCTGTTCCCTACCTCCTCTCTTCACCCGTTAGGCTGTTT

PDE7       847  TCAATGTAATGCTGCCGTCCTTCTTGCACTGCCTTCTGCGCTAACACCTCCATTCCTGT
PDE10X-INV 837  TCAATGTAATGCTGCCGTCCTTCTTGCACTGCCTTCTGCGCTAACACCTCCATTCCTGT

PDE7       908  TTATAACCGTGTATTATTATTAATGTATATAATGTTTGTAAGTTATTAATTA
PDE10X-INV 898  TTATAACCGTGTATTATTATTAATGTATATAATGTTTGTAAGTTATTAATTA

PDE7       969  TATATCTAACATTGCCTGCCAATGGTGGTGTTAAATTTGTGTAGAAAACTCTGCCTAAGAG
PDE10X-INV 959  TATATCTAACATTGCCTGCCAATGGTGGTGTTAAATTTGTGTAGAAAACTCTGCCTAAGAG

PDE7       1030 TTACGACTTTTCTTGTAATGTTTTGTATTGTATTGTGTATTATATAACCCAAACGTCACTTAGTA
PDE10X-INV 1020 TTACGACTTTTCTTGTAATGTTTTGTATTGTATTGTGTATTATATAACCCAAACGTCACTTAGTA

PDE7       1091 GAGACATATGGCCCCTTGGCAGAGAGGACAGGGGTGGGCTTTTGTTCAAAGGGTCTGCCC
PDE10X-INV 1081 GAGACATATGGCCCCTTGGCAGAGAGGACAGGGGTGGGCTTTTGTTCAAAGGGTCTGCCC
```

FIG. 2(I)

```
PDE7       1152  TTCCCTGCCTGAGTTGCTACTTCTGCACAACCCCTTTATGAACCAGTTTTGGAAACAATA
                 |||||||||||||||||||||||||||||||||||||||||||||||||||||||||||
PDE10X-INV 1142  TTCCCTGCCTGAGTTGCTACTTCTGCACAACCCCTTTATGAACCAGTTTTGGAAACAATA

PDE7       1213  TTCTCACATTAGATACTAAATGGTTATACTGAGCTTTTACTTTTGTATAGCTTGATAGGG
                 |||||||||||||||||||||||||||||||||||||||||||||||||||||||||||
PDE10X-INV 1203  TTCTCACATTAGATACTAAATGGTTATACTGAGCTTTTACTTTTGTATAGCTTGATAGGG

PDE7       1274  GCAGGGGGCAATGGGATGTAGTTTTACCCAGGTTCTATCCAAATCTATGTGGGCATGAGT
                 |||||||||||||||||||||||||||||||||||||||||||||||||||||||||||
PDE10X-INV 1264  GCAGGGGGCAATGGGATGTAGTTTTACCCAGGTTCTATCCAAATCTATGTGGGCATGAGT

PDE7       1335  TGGGTTATAACTGGATCCTACTATCATTGTGGCTTTGGTTCAAAAGGAAACACTACATTTG
                 |||||||||||||||||||||||||||||||||||||||||||||||||||||||||||
PDE10X-INV 1325  TGGGTTATAACTGGATCCTACTATCATTGTGGCTTTGGTTCAAAAGGAAACACTACATTTG

PDE7       1396  CTCACAGATGATTCTTCTGAATGCTCCCGAACTACTGACTTTGAAGAGGTAGCCTCCTGCC
                 |||||||||||||||||||||||||||||||||||||||||||||||||||||||||||
PDE10X-INV 1386  CTCACAGATGATTCTTCTGAATGCTCCCGAACTACTGACTTTGAAGAGGTAGCCTCCTGCC

PDE7       1457  TGCCATTAAGCAGGAATGTCATGTTCCAGTTCATTACAAAAGAAAATAAAACAATGTG
                 |||||||||||||||||||||||||||||||||||||||||||||||||||||||||||
PDE10X-INV 1447  TGCCATTAAGCAGGAATGTCATGTTCCAGTTCATTACAAAAGAAAATAAAACAATGTG
```

FIG. 2(J)

```
PDE7       1518  AATTTTTATAATAAAATGTGAACTGATGTAGCAAATTACGCAAATGTGAAGCCTCTTCTGA
                 ||||||||||||||||||||||||||||||||||||||||||||||||||||||||||||
PDE10X-INV 1508  AATTTTTATAATAAAATGTGAACTGATGTAGCAAATTACGCAAATGTGAAGCCTCTTCTGA

PDE7       1579  TAACACTTGTTAGGCCTCTTACTGATGTCAGTTTGTAAAATATGTTTCATGCTTT
                 ||||||||||||||||||||||||||||||||||||||||||||||||||||||
PDE10X-INV 1569  TAACACTTGTTAGGCCCTCTTACTGATGTCAGTTTGTAAAATATGTTTCATGCTTT

PDE7       1640  CAGTTCAGCATTGTGACTCAGTAATTACAGAAAATGGCACAAATGTGCATGACCAATGGGT
                 |||||||||||||||||||||||||||||||||||||
PDE10X-INV 1630  CAGTTCAGCATTGTGACTCAGTAATTACAGAAAA
```

FIG. 3(A)

```
PDE18    1  GAATTCCT     TTGTTCA                                              CATCTTCTAGTT
            ||||||||     ||||||                                               ||||||||||||
GB25     1  GAATTCCTctgactAATTCAagtatcccaaggtttggagttaaaactgaacaagaagATGT PDE18   28  CCTTGGCAAGGA                                         CATCTTCATGTTTTCAGAATAGCAGAG
            ||||||||||||                                         |||||||||||||||||||||||||||
GB25    62  CCTTGcCAAGGAaactagaagatgtgaacaaatggggTCTTCATGTTTTCAGAATAGCAGAG PDE18   67  TTGTCTGGTAACCGGCCCTTGACTGTTATCATGCACACCATTTTTCAGGAACGGGATTTAT
            ||||||||||||||||||||||||||||||||||||||||||||||||||||||||||||
GB25   123  TTGTCTGGTAACCGGCCCTTGACTGTTATCATGCACACCATTTTTCAGGAACGGGATTTAT PDE18  128  TAAAAACATTTAAAATTCCAGTAGATACTTTAATTACATATCTTATGACTCTCGAAGACCA
            ||||||||||||||||||||||||||||||||||||||||||||||||||||||||||||
GB25   184  TAAAAACATTTAAAATTCCAGTAGATACTTTAATTACATATCTTATGACTCTCGAAGACCA PDE18  189  TTACCATGCTGATGTGGCCTATCACAACAATATCCATGCTGCAGATGTTGTCCAGTCTACT
            ||||||||||||||||||||||||||||||||||||||||||||||||||||||||||||
GB25   245  TTACCATGCTGATGTGGCCTATCACAACAATATCCATGCTGCAGATGTTGTCCAGTCTACT PDE18  250  CATGTGCTATTATCTACACCTGCTTTGGAGGCTGTGTTACAGATTTGGAGATTCTTGCAG
            |||||||||||||||||||||||||||||||||||||||||||||||||||||||||||
GB25   306  CATGTGCTATTATCTACACCTGCTTTGGAGGCTGTGTTACAGATTTGGAGATTCTTGCAG
```

FIG. 3(B)

```
PDE18  311  CAATTTTTGCCAGTGCAATACATGATGTAGATCATCCTGGTGTCCAATCAATTTCTGAT
            |||||||||||||||||||||||||||||||||||||||||||||||||||||||||||
GB25   367  CAATTTTTGCCAGTGCAATACATGATGTAGATCATCCTGGTGTCCAATCAATTTCTGAT

PDE18  372  CAATACAAACTCTGAACTTGCCTTGATGTACAATGATTCCTCAGTCTTAGAGAACCATCAT
            |||||||||| |||||||||||||||||||||||||| ||||||||||||||||||||||
GB25   428  CAATACAAACTCTGAACTTGCCTTGATGTACAATGATTCCTCAGTCTTAGAGAACCATCAT

PDE18  433  TTGGCTGTGGGCTTTAAATTGCTTCAGGAAGAAAACTGTGACATTTTCCAGAATTTGACCA
            |||||||||||||||||||||||||||||||||||||||||||||||||||||||||||||
GB25   489  TTGGCTGTGGGCTTTAAATTGCTTCAGGAAGAAAACTGTGACATTTTCCAGAATTTGACCA

PDE18  494  AAAAACAAAGACAATCTTTAAGGAAAAATGGTCATTGACATCGTACTTGCAACAGATATGTC
            |||||||||||||||||||||||||||||||||||||||||||||||||||||||||||||
GB25   550  AAAAACAAAGACAATCTTTAAGGAAAAATGGTCATTGACATCGTACTTGCAACAGATATGTC

PDE18  555  AAAACACATGAATCTACTGGCTGATTTGAAGACTATGGTTGAAACTAAGAAAGTGACAAGC
            |||||||||||||||||||||||||||||||||||||||||||||||||||||||||||||
GB25   611  AAAACACATGAATCTACTGGCTGATTTGAAGACTATGGTTGAAACTAAGAAAGTGACAAGC

PDE18  616  TCTGGAGTTCTTCTTCTTGATAATTATTCCGATAGGATTCAGGTTCTTCAGAATATGGTGC
            |||||||||||||||||||||||||||||||||||||||||||||||||||||||||||||
GB25   672  TCTGGAGTTCTTCTTCTTGATAATTATTCCGATAGGATTCAGGTTCTTCAGAATATGGTGC

PDE19  677  ACTGTGCAGATCTGAGCAACCCAACAAAGCCTCTCCAGCTGTACCGCCAGTGGACGGACCG
            ||||||||||||||||||||||||||||||||||||||||||||||||||||||||||||
GB25   733  ACTGTGCAGATCTGAGCAACCCAACAAAGCCTCTCCAGCTGTACCGCCAGTGGACGGACC
```

FIG. 4(A)

| | | |
|---|---|---|
| TM72 | 212 | SLRsVRNNFTiLTNL |
| RATDPD | 1 | SLRiVRNNFTlLTNL |
| TM72 | 219 | HGtSNKRSPAASQpPVsRVnpQEESYQKLAMETLEELDWCLDQLETIQTYRSVSEMASNKF |
| RATDPD | 8 | HGaPNKRSPAASQaPVtRVSLQEESYQKLAMETLEELDWCLDQLETIQTYRSVSEMASNKF |
| JC44X | 25 | EETCQqLAretETLEELDWCLEQLETmQTYYSVSEMASHKF |
| TM72 | 287 | KRMLNRELTHLSEMSRSGNQVSEYISNTFLDKQNDVEIPSPTQKDREK |
| RATDPD | 72 | KRMLNRELTHLSEMSRSGNQVSEYISNTFLDKQNDVEIPSPTQKDREK |
| JC44X | 59 | KRMLNRELTHLSEMSRSGNQVSEYISTFFLDKQNeVEIPSPTmKeREKQQAPRPRPSQPPP |
| TM72 | 335 | KKKQQLMTQISGVKKLMHSSSLNNTSISRFGVNTENEDHLAKELEDLNKWGLNIFNVAG |
| RATDPD | 124 | KKKQQLMTQISGVKKLMHSSSLNNTSISRFGVNTENEDHLAKELEDLNKWGLNIFNVAG |
| JC44X | 123 | PPVPHLQPMSQITGLKKLMHSnSLNNSNIPRFGVKTDQEELLAQELLENLNKWGLNIFCVSD |

FIG. 4(B)

```
PDE18   25   GNRPLTvIMhtIFQERDLLKTFkIPvDTLITYLMTLEDHYHADVAYHNnIHAADVvQST
TM72    394  YSHNRPLtCIMYAIFQERDLLKTFrISSDTFIITYMMTLEDHYHSDVAYHNSLHAADVAQST
RATDPD  183  YSHNRPLtCIMYAIFQERDLLKTFkISSDTFVTYMMTLEDHYHSDVAYHNSLHAADVAQST
JC44X   184  YaggRsLtCIMYMIFQERDLLKkFrIPvDTmVTYMLTLEDHYHADVAYHNSLHAADVLQST PDE18   85        ALEAVFTDLEILAAIFASAIHDVDHPGVSNQFLINTNSELALMYNDSSVLE
TM72    455       ALDAVFTDLEILAAIFAAAIHDVDHPGVSNQFLINTNSELALMYNDESVLE
RATDPD  244  HVLLSTP ALDAVFTDLEILAAIFAAAIHDVDHPGVSNQFLINTNSELALMYNDESVLE
JC44X   245  HVLLATPwPTLRNAVFTDLEILAALFAAAIHDVDHPGVSNQFLINTNSELALMYNDESVLE PDE21   3       LAVGFKLLQAENCDIFQNLSAKQRLSLRRMVIDMVLATDMSKHMNLLADLKTMVETKK
PDE18   143  NHHLAVGFKLLQEENCDIFQNLTKKQRQSLRKMVIDIvVLATDMSKHMNLLADLKTMVETKK
TM72    513  NHHLAVGFKLLQEEHCDIFMNLTKKQRQTLRKMVIDMVLATDMSKHMSLLADLKTMVETKK
RATDPD  302  NHHLAVGFKLLQEEHCDIFQNLTKKQRQTLRKMVIDMVLATDMSKHMSLLADLKTMVETKK
JC44X   306  NHHLAVGFKLLQEDnCDIFQNLsKrQRQSLRKMVIDMVLATDMSKHMtLLADLKTMVETKK
```

FIG. 4(C)

| | | |
|---|---|---|
| PDE21 | 61 | VTSLGVLLLDNYSDRIQVLQNLVHCADLSNPTKPLPLYRQWTDRIMAEFFQQGDRERESGL |
| PDE18 | 204 | VTSSGVLLLDNYSDRIQVLQNMVHCADLSNPTKPLQLYRQWTDRIMEEFFRQGDRERERGM |
| TM72 | 574 | VTSSGVLLLDNYTDRIQVLRNMVHCADLSNPTKSLELYRQWTDRIMEEFFQQGDKERERGM |
| RATDPD | 363 | VTSSGVLLLDNYTDRIQVLRNMVHCADLSNPTKSLELYRQWTDRIMEEFFQQGDKERERGM |
| MC44X | 367 | VTSSGVLLLDNYsDRIQVLRNMVHCADLSNPTKPLELYRQWTDRIMAEFFQQGDRERERGM |
| | | |
| PDE21 | 122 | DISPMCDKHTASVEKSQVGFIDYIAHPLWETWADLVHPDAQDLLDTLEDNREWYQSKIPRS |
| PDE18 | 265 | EISPMCDKHNASVEKSQVGFIDYIVHPLWETWADLVHPDAQDILDTLEDNREWYQSTIPQS |
| TM72 | 635 | EISPMCDKHTASVEKSQVGFIDYIVHPLWETWADLVQPDAQDILDTLEDNRNWYQSMIPQS |
| RATDPD | 424 | EISPMCDKHTASVEKSQVGFIDYIVHPLWETWADLVQPDAQDILDTLEDNRNWYQSMIPQS |
| JC44X | 428 | EISPMCDKHTASVEKSQVGFIDYIVHPLWETWADLVHPDAQEILDTLEDNRDWYYSAIRQS |

FIG. 4(D)

```
PDE21   183   PS         DLTNPE     RDGPDRFQFELTLEE                          AEEEDEEEEGEETALAKE
PDE18   326   pSpApD     dPEegRQGqTEKFQFELTLEEdgesdTEKdsGSQVEEDtscSdsKTLCTQDSE
TM72    696   pSPPLDEqnR  DCQGLMEKFQFELTLdEEDSEGPEK
RATDPD  485   pSPPLDErSR  DCQGLMEKFQFELTLEEEDSEGPEK                           EGEGhsYFSSTKTLC
JC44X   489   pSPPpEEeSRGPGHPPLPDKFQFELTLEEEEEEISMAQIPCTAQEALTEQGLSGVEEALD     EGEGPNYFSSTKTLC PDE21   225   ALELPDTELLSPEAGPDPGDLPLDNQRT
PDE18   386   stEiPLDEQVEEEAVGEEEESQPEACVIDDRSPDT
TM72    743   VIDPENRDSLGE                        TDIDIATEDKSPVDT
RATDPD  536   VIDPENRDSLEE                        TDIDIATEDKSLIDT
JC44X   551   ATIAWEASPAQESLEVMAQEASLEAELEAVYLTQQ
```

CLONING BY COMPLEMENTATION AND RELATED PROCESSES

FUNDING

Work described herein was supported by the National Cancer Institute of the National Institutes of Health.

CROSS-REFERENCE TO RELATED PATENT APPLICATION

This application is a continuation-in-part of U.S. Ser. No. 07/511,715; filed Apr. 20, 1990, now abandoned.

BACKGROUND

The present invention relates generally to novel cloning methods, to the DNA sequences obtained using these methods, the corresponding expression products of the DNA sequences and antibodies thereto, as well as to novel screening methods for compounds affecting protein activity. More specifically, the present invention provides novel complementation screening methods particularly useful in the isolation of DNAs encoding cyclic nucleotide phosphodiesterase polypeptides (PDEs) and RAS-related proteins. These DNAs, in turn, provide valuable materials useful as hybridization probes for related DNAs and useful in obtaining polypeptide expression products when used to transform suitable host cells.

Of interest to the present invention are the following discussions relating to the cyclic nucleotide phosphodiesterases and RAS related proteins.

The RAS genes were first discovered as the transforming principles of the Harvey and Kirsten murine sarcoma viruses [Ellis et al., *Nature*, 292:506 (1981)]. The cellular homologs of the oncogenes of Harvey and Kirsten murine sarcoma viruses (H-RAS and K-RAS) constitute two members of the RAS gene family [Shimizu et al., *Proc. Natl. Acad. Sci.*, 80:2112 (1983)]. A third member is N-RAS [Shimizu et al., *Proc. Natl. Acad. Sci.*, 80:2112 (1983)]. These genes are known as oncogenes since point mutations in RAS can result in genes capable of transforming non-cancerous cells into cancerous cells [Tabin et al., *Nature*, 300:143 (1982); Reddy et al., *Nature*, 300:149 (1982); Taparowsky et al., *Nature*, 300:762 (1982)]. Many tumor cells contain RAS genes with such mutations [Capon et al., *Nature*, 302:33 (1983); Capon et al., *Nature*, 304:507 (1983); Shimizu et al., *Nature*, 304:497 (1983); Taparowsky et al., *Cell* 34:581 (1983); Taparowsky et al., *Nature*, 300:762 (1982); Barbacid, *Ann. Rev. Biochem.*, 56:779 (1987)].

Despite the importance of the RAS oncogenes to our understanding of cancer, the function of RAS genes in mammals is not known. The RAS proteins are small proteins (21,000 daltons in mammals) which bind GTP and GDP [Papageorge et al., *J. Virol.*, 44:509 (1982)]. The RAS proteins hydrolyze GTP slowly; specific cellular proteins can accelerate this process [McGrath et al., *Nature*, 310:644 (1984); Trahey et al., *Science*, 238:542 (1987)]. RAS proteins bind to the inner surface of the plasma membrane [Willingham et al., *Cell*, 19:1005 (1980)] and undergo a complex covalent modification at their carboxy termini [Hancock et al., *Cell*, 57:1167 (1989)]. The crystal structure of H-RAS is known [De Vos et al., *Science*, 239:888 (1988)].

The yeast *Saccharomyces cerevisiae* contains two genes, RAS1 and RAS2, that have structural and functional homology with mammalian RAS oncogenes [Powers et al., *Cell*, 36:607 (1984); Kataoka et al., *Cell*, 40:19 (1985); Defeo-Jones et al., *Science*, 228:179 (1985); Dhar et al., *Nucl. Acids Res.*, 12:3611 (1984)]. Both RAS1 and RAS2 have been cloned from yeast plasmid libraries and the complete nucleotide sequence of their coding regions has been determined [Powers et al., *Cell*, 36:607 (1984); DeFeo-Jones et al., *Nature*, 306:707 (1983)]. The two genes encode proteins with nearly 90% identity to the first 80 amino acid positions of the mammalian RAS proteins, and nearly 50% identity to the next 80 amino acid positions. Yeast RAS1 and RAS2 proteins are more homologous to each other, with about 90% identity for the first 180 positions. After this, at nearly the same position that the mammalian RAS proteins begin to diverge from each other, the two yeast RAS proteins diverge radically. The yeast RAS proteins, like proteins encoded by the mammalian genes, terminate with the sequence cysAAX, where A is an aliphatic amino acid, and X is the terminal amino acid [Barbacid, *Ann. Rev. Biochem.*, 56:779 (1987)]. Monoclonal antibody directed against mammalian RAS proteins immumoprecipitates RAS proteins in yeast cells [Powers et al., *Cell*, 47:413 (1986)]. Thus, the yeast RAS proteins have the same overall structure and interrelationship as is found in the family of mammalian RAS proteins.

RAS genes have been detected in a wide variety of eukaryotic species, including *Schizosaccharomyces pombe*, *Dictyostelium discoidiem* and *Drosophila melanogaster* [Fukui et al., *EMBO*, 4:687 (1985); Reymond et al., *Cell*, 39:141 (1984); Shilo et al., *Proc. Natl. Acad. Sci. (U.S.A.)*, 78:6789 (1981); Neuman-Silberberg, *Cell*, 37:1027 (1984)]. The widespread distribution of RAS genes in evolution indicates that studies of RAS in simple eukaryotic organisms may elucidate the normal cellular functions of RAS in mammals.

Extensive genetic analyses of the RAS1 and RAS2 of *S. cerevisiae* have been performed. By constructing in vitro RAS genes disrupted by selectable biochemical markers and introducing these by gene replacement into the RAS chromosomal loci, it has been determined that neither RAS1 nor RAS2 is, by itself, an essential gene. However, doubly RAS deficient (ras1$^-$ ras2$^-$) spores of doubly heterozygous diploids are incapable of resuming vegetative growth. At least some RAS function is therefore required for viability of *S. cerevisiae* [Kataoka et al., *Cell*, 37:437 (1984)]. It has also been determined that RAS1 is located on chromosome XV, 7 cM from ADE2 and 63 cM from HIS3; and that RAS2 is located on chromosome XIV, 2 cM from MET4 [Kataoka et al., *Cell*, 37:437 (1984)].

Mammalian RAS expressed in yeast can function to correct the phenotypic defects that otherwise would result from the loss of both RAS1 and RAS2 [Kataoka et al., *Cell*, 40:19 (1985)]. Conversely, yeast RASI is capable of functioning in vertebrate cells [De Feo-Jones et al., *Science*, 228:179 (1985)]. Thus, there has been sufficient conservation of structure between yeast and human RAS proteins to allow each to function in heterologous host cells.

The missense mutant, RAS2$^{val119}$ which encodes valine in place of glycine at the nineteenth amino acid position, has the same sort of mutation that is found in some oncogenic mutants of mammalian RAS genes [Tabin et al., *Nature*, 300:143 (1982); Reddy et al., *Nature*, 300:149 (1982); Taparowsk et al., *Nature*, 300:762 (1982)]. Diploid yeast cells that contain this mutation are incapable of sporulating efficiently, even when they contain wild-type RAS alleles [Kataoka et al., *Cell*, 37:437 (1984)]. When an activated form of the RAS2 gene (e.g., RAS2$^{val119}$) is present in haploid cells, yeast cells fail to synthesize glycogen, are unable to arrest in G1, die rapidly upon nutrient starvation, and are acutely sensitive to heat shock [Toda et al., *Cell*, 40:27 (1985); Sass et al., *Proc. Natl. Acad. Sci.*, 83:9303 (1986)].

*S. cerevisiae* strains containing RAS2$^{val19}$ have growth and biochemical properties strikingly similar to yeast carrying the IAC or bcy1 mutations, which activate the cAMP pathway in yeast [Uno et al., *J. Biol. Chem.*, 257:14110 (1981)]. Yeast strains carrying the IAC mutation have elevated levels of adenylylate cyclase activity. bcy1$^-$ cells lack the regulatory component of the cAMP dependent protein kinase [Uno et al., *J. Biol. Chem.*, 257:14110 (1982); Toda et al., *Mol. Cell. Biol.*, 7:1371 (1987)]. Yeast strains deficient in RAS function exhibit properties similar to adenylyl cyclase-deficient yeast [Toda et al., *Cell*, 40:27 (1985)]. The bcy1$^-$ mutation suppresses lethality in ras1$^-$ ras2$^-$ yeast. These results suggest that in the yeast *S. cerevisiae*, RAS proteins function in the cAMP signalling pathway.

Adenylyl cyclase has been shown to be controlled by RAS proteins [Toda et al., *Cell*, 40:27 (1985)]. RAS proteins, either from yeast or mutans, can stimulate adenylyl cyclase up to fifty fold in in vitro biochemical assays. RAS proteins will stimulate adenylyl cyclase only when bound with GTP [Field et al., *Mol. Cell. Biol.*, 8:2159 (1988)].

The phenotypes resulting from the activation of RAS, including sensitivity to heat shock and starvation, are primarily the result of overexpression or uncontrolled activation of the cAMP effector pathway via adenylyl cyclase [Kataoka et al., *Cell*, 37:437 (1984); Kataoka et al., *Cell*, 43:493 (1985); Toda et al., *Cell*, 40:27 (1985); Field et al., *Mol. Cell. Biol.*, 8:2159 (1988)].

Two *S. cerevisiae* yeast genes, PDE1 and PDE2, which encode the low and high affinity cAMP phosphodiesterases, respectively, have been isolated [Sass et al., *Proc. Natl. Acad. Sci.*, 83:9303 (1986); Nikawa et al., *Mol. Cell. Biol.*, 7:3629 (1987)]. These genes were cloned from yeast genomic libraries by their ability to suppress the heat shock sensitivity in yeast cells harboring an activated RAS2$^{val19}$ gene. Cells lacking the PDE genes (i.e., pde1$^-$ pde2$^-$ yeast) are heat shock sensitive, are deficient in glycogen accumulation, fail to grow on an acetate carbon source, and in general have defects due to activation of the cAMP signaling pathway [Nikawa et al., *Mol. Cell. Biol.*, 7:3629 (1987)].

Genetic analysis clearly indicates that RAS proteins have other functions in *S. cerevisiae* in addition to stimulating adenylyl cyclase [Toda et al., *Japan Sci Soc. Press.*, Tokyo/VNU *Sci. Press.*, pp. 253 (1987); Wigler et al., *Cold Spring Harbor Symposium*, LIII:649 (1988); Michaeli et al., *EMBO*, 8:3039 (1989)]. The precise biochemical nature of these functions is unknown. Experiments with other systems, such as *S. pombe* and *Xenopus laevis* oocytes, indicate that RAS stimulation of adenylyl cyclase is not widespread in evolution [Birchmeier et al., *Cell*, 43:615 (1985)]. It is unlikely that RAS stimulates adenylyl cyclase in mammals (Beckner et al., *Nature*, 317:1 (1985)).

Phosphodiesterases (PDEs) are the enzymes responsible for the degradation of cyclic AMP (cAMP) to AMP and cGMP to GMP. Cyclic AMP is a "second messenger" that mediates the response of cells to a variety of hormones and neurotransmitters including calcitonin, chorionic gonadotropin, corticotropin, epinephrine, follicle-stimulating hormone, glucagon, leutenizing hormone, lipotropin, melanocyte-stimulating hormone, norepinephrine, parathyroid hormone, thyroid-stimulating hormone, and vasopressin.

Cellular concentrations of cyclic adenosine monophosphate (cAMP) are controlled not only the rate of cAMP production by adenylyl cyclase, but also by the rate of cAMP degradation by phosphodiesterases. In humans, a number of important physiological responses are controlled by cAMP levels, including mental function, smooth muscle relaxation, strength of cardiac contractility, release of histamine and other immunoreactive molecules, lymphocyte proliferation, and platelet aggregation [Robison et al., *Cyclic AMP*, Academic Press, New York and London (1971)]. Thus, the range of diseases which can potentially be affected by agents or pharmaceutical compounds which alter cAMP levels include inflammatory processes (e.g., arthritis and asthma), heart failure, smooth muscle cramps, high blood pressure, blood clotting, thrombosis, and mental disorders.

Given the importance of cAMP in the regulation of a variety of metabolic processes, considerable effort has been directed toward developing and evaluating cAMP analogues, as well as inhibitors of phosphodiesterases. One way to modulate cAMP levels in cells is through the modulation of cAMP phosphodiesterase activity. Certain drugs useful in treating heart failure, asthma, depression, and thrombosis, appear to work by inhibiting cAMP phosphodiesterases. The pharmaceutical industry has not been notably successful in finding suitably specific drugs, in part because effective drug screens have not been available. Most tissues contain so many different isoforms of phosphodiesterases that drug screening based on traditional methods involving inhibition of crude tissue extracts is unlikely to yield anything other than a broadly acting inhibitor of phosphodiesterases. Broadly acting inhibitors of cAMP phosphodiesterases, such as theophylline, have many deleterious side effects.

As noted above, PDE inhibitor research has as its goal the development of highly specific PDE inhibitors. This lack of PDE inhibitor specificity is in part attributable to the existence of several distinct molecular forms of PDE present within a single tissue type, indeed, present among the various cell-types comprising a particular tissue type. These various forms can be distinguished according to substrate specificity (cAMP vs. cGMP), intracellular location (soluble vs. membrane bound), response to calmodulin, and can, in certain instances, be selectively inhibited by various therapeutic agents. Developing agents that will selectively act upon PDEs is directed toward reproducing the desirable effects of cyclic nucleotides, e.g., bronchodilation, increased myocardial contractility, anti-inflammation, yet without causing the undesirable effects, e.g., increased heart rate or enhanced lipolysis.

One approach to screening agents for their potential utility as PDE inhibitors, e.g. drug screening, requires "kinetically pure" preparations of PDE enzymes. That is, the use of whole tissue homogenates or extracts is unlikely to identify inhibitors selective for an individual PDE isozyme because most tissues are heterogeneous with respect to cell type and even many cell types contain multiple PDE isozymes.

At least five different families of PDEs have been described based on characteristics such as substrate specificity, kinetic properties, cellular regulatory control, size, and in some instances, modulation by selective inhibitors. [Beavo, *Adv. in. Second Mess. and Prot. Phosph. Res.* 22.:1–38 (1988)]. The five families include:

| | |
|---|---|
| I | Ca$^{2+}$/calmodulin-stimulated |
| II | cGMP-stimulated |
| III | cGMP-inhibited |
| IV | cAMP-specific |

| | |
|---|---|
| V | cGMP-specific |

Within each family there are multiple forms of closely related PDEs. See Beavo, "Multiple Phosphodiesterase Isozymes Background, Nomenclature and Implications", pp. 3–15 In: *Cyclic Nucleotide Phosphodiesterases: Structure, Regulation and Drug Action,* Beavo, J. and Houslay, M. D., Eds.; John Wiley & Sons, New York (1990). See, also, Beavo, *TIPS,* 11:150 (1990).

Of the many distinct PDE enzymes now recognized, for only certain of the cGMP specific PDEs is complete cDNA sequence information available. With the acquisition of complete structural information for all PDEs, it may be possible to identify and localize (cellular and subcellular distribution) each PDE isozyme and thereby design isozyme-selective PDE inhibitors as therapeutic agents for specific diseases allowing avoidance of untoward side-effects. However, the heterogeneity, instability, and relatively low abundance of some of the PDE isozymes have presented major obstacles in purifying and characterizing these enzymes.

Several methods are presently available for cloning mammalian genes. A standard approach to cloning mammalian genes requires obtaining purified protein, determining a partial amino acid sequence of the purified protein, using the partial amino acid sequence to produce degenerate oligonucleotide probes, and screening cDNA libraries with these probes to obtain cDNA encoding the protein. This method is time consuming and, because of the degeneracy of the probes used, may identify sequences other than those encoding the protein(s) of interest. Many mammalian genes have been cloned this way including, for example, the gene encoding the cGMP phosphodiesterase expressed in retina Ovchinnikov et al.; *FEBS,* 223:169 (1987)].

A second approach to cloning genes encoding a protein of interest is to use a known gene as a probe to find homologs. This approach is particularly useful when members of a gene family or families are sufficiently homologous. The *Drosophila melanogaster dunce* phosphodiesterase gene was used, for example to clone rat homologs. Davis et al., *Proc. Natl. Acad. Sci. (U.S.A.),* 86:3604 (1989); and Swinnen et al., *Proc. Natl. Acad. Sci. (U.S.A.),* 86:5325 (1989). Although additional members of one family of phosphodiesterase genes might be cloned once a first member of that family has been cloned, it is never known in advance whether the nucleotide sequences of genes belonging to different phosphodiesterase gene families will exhibit sufficient homology to use probes derived from one family to identify members of another family.

Yet another approach to cloning genes is known as complementation, A number of researchers have reported the isolation of yeast genes by their ability to complement a mutation/defect in the corresponding gene in another yeast. See, for example: McKnight et al., *EMBO J.,* 4:2093 (1985)—*Aspergillus nidulans* gene encoding alcohol dehydrogenase isolated by its ability to complement an adh1 mutation in *S. cerevisiae;* Sass et al., *PNAS (U.S.A.),* 83:9303 (1986)—*S. cerevisiae* PDE2 gene isolated by its ability to complement a $RAS2^{val119}$ allele in *S. cerevisiae* strain TK161-R2V; Nikawa et al., *Mol. Cell. Biol.,* 7:3629 (1987)—*S. cerevisiae* PDE1 gene isolated by transforming *S. cerevisiae* strain TK161-R2V; and Wilson, *Molec. Cell. Biol.,* 8:505 (1988)—*S. cerevisiae* SRA5 gene isolated by virtue of its ability to rescue a $RAS^{+}$ sra5-5 *S. cerevisiae* strain RW60-12C.

Yeast have also been used to isolate non-yeast genes. For example, Henikoff et al., *Nature,* 289:33 (1981), reported the isolation of a *D. melanogaster* gene by complementation of yeast mutants and Lee et al., *Nature,* 327:31 (1987), reported the isolation of human gene by its ability to complement a mutation in the cdc2 gene in *S. pombe*. The expression vector employed included a viral (SV40) promoter.

More recently, complementation screening has been used by the applicants herein to detect and isolate mammalian cDNA clones encoding certain types of phosphodiesterases (PDEs). Colicelli et al., *PNAS (U.S.A.),* 86:3599 (1989) reports the construction of a rat brain cDNA library in a *Saccharomyces cerevisiae* expression vector and the isolation therefrom of genes having the capacity to function in yeast to suppress the phenotypic effects of $RAS2^{val119}$, a mutant form of the RAS2 gene analogous to an oncogenic mutant of the human H-RAS gene. A rat species cDNA so cloned and designated DPD (dunce-like phosphodiesterase) has the capacity to complement the loss of growth control associated with an activated $RAS2^{val119}$ gene harbored in yeast strains TK161-R2V. The gene encodes a high-affinity cAMP specific phosphodiesterase that is highly homologous to the cAMP phosphodiesterase encoded by the dunce locus of *D. melanogaster.*

Relatively few PDE genes have been cloned to date. Of those cloned, most belong to the cAMP-specific family of phosphodiesterases (cAMP-PDEs). See Davis, "Molecular Genetics of the Cyclic Nucleotide Phosphodiesterases", pp. 227–241 in *Cyclic Nucleotide Phosphodiesterases: Structure, Regulation, and Drug Action,* Beavo, J. and Houslay, M. D., Eds.; John Wiley & Sons, New York; 1990. See also, e.g., Faure et al., *PNAS (U.S.A.),* 85:8076 (1988)—*D. discoideum;* Sass et al., supra—*S. cerevisiae,* PDE class IV, designated PDE2; Nikawa et al., supra—*S. cerevisiae,* designated PDE1; Wilson et al., supra—*S. cerevisiae,* designated SRA5; Chen et al., *PNAS (U.S.A.),* 83:9313 (1986)—*D. melanogaster,* designated dnc$^{+}$; Ovchinnikov, et al., supra—bovine retina, designated GMP PDE; Davis et al., supra—rat liver, designated Sat dnc-1; Colicelli, et al., supra—rat brain, designated DPD; Swinnen, et al., *PNAS (U.S.A.),* 86:5325 (1989)—rat testis, rat PDE1, PDE2, PDE3 and PDE4; and Livi, et al., *Mol. Cell. Biol.,* 10:2678 (1990)—human monocyte, designated hPDE1. See also, LeTrong et al., *Biochemistry,* 29:10280 (1990) reporting cloning of a DNA encoding a fragment of a bovine adrenal cGMP stimulated PDE and Thompson et al., *FASEBJ.,* 5(6):A1592 (Abstract No. 7092, 1991) reporting the cloning of a "Type II PDE" from rat pheochromocytoma cells.

Thus, there continues to exist a need in the art for improved cloning procedures effective for isolating genes, both of known and unknown function, for expression products sufficiently kinetically pure so as to be suitable for use in drug improved immunological specificity, and for drug screening methods that do not require kinetically pure protein preparations.

BRIEF SUMMARY OF THE INVENTION

The present invention relates to methods for cloning mammalian genes encoding proteins which can function in microorganisms, particularly yeast, and can modify, complement, or suppress a genetic defect associated with an identifiable phenotypic alteration or characteristic in the microorganism. Provided by the invention are mammalian genes cloned according to the method, as well as products encoded by such genes, and antibodies immunologically reactive with the encoded proteins.

More specifically, the present invention relates to a method of detecting mammalian genes that encode products that modify, complement or suppress a genetic defect in a biochemical pathway in which cAMP participates, or in a biochemical pathway which is controlled, directly or indirectly, by a RAS protein (i.e., "RAS-related Protein); to the genes so cloned; to products (nucleic acids, proteins) encoded by the mammalian genes cloned including novel mammalian genes that encode, for example, cAMP phosphodiesterases, proteins that interact with RAS proteins, and other proteins affecting cell growth and maintenance.

The present method can be used to detect a mammalian gene of interest that functions in a microorganism that is genetically altered or defective in a defined manner (an altered microorganism) to correct the genetic alteration or defect and, as a result, modifies an identifiable phenotypic alteration or characteristic associated with the genetic alteration or defect (produces a phenotype more like that off normal or unaltered microorganism). Altered microorganisms illustrating those useful in practice of methods of the invention include *S. cerevisiae* strains TK161-R2V, 10DAB and SKN37 and *S. pombe* strain SP65.

The present invention thus provides novel methods for detecting, in a genetically altered microorganism (such as a mutant yeast or mammalian host cell), a mammalian gene that is capable of modifying a phenotypic alteration associated with a genetic alteration. The steps of the novel methods include: (a) providing mammalian cDNA in an expression vector capable of expressing the mammalian cDNA in the genetically altered microorganism (preferred vectors including an endogenous host cell promoter DNA sequence operatively associated with the cDNA); (b) introducing the expression vector into the genetically altered microorganism; (c) maintaining the genetically altered microorganisms containing the expression vector under conditions appropriate for growth; and (d) identifying genetically altered microorganisms in which the phenotypic alteration associated with the genetic alteration in the microorganism is modified. Optionally included is the step of isolating the cDNA inserted in microorganisms identified in step (d).

Although use of the present method to clone mammalian genes is described in detail in respect to cAMP phosphodiesterases and proteins that interact with RAS proteins, it can be used to clone and identify other mammalian genes that function in an appropriately-selected altered microorganism to correct, complement or supplement the genetic alteration and, as a result, correct the associated phenotypic alteration. Phenotypic alterations of yeast cells which illustrate the invention include heat shock sensitivity, nitrogen starvation, failure to synthesize normal amounts of glycogen, failure to grow on acetate and failure to sporulate.

In presently preferred forms, the novel DNA sequences comprise cDNA sequences; however, alternate DNA forms such as genomic DNA, and DNA prepared by partial or total chemical synthesis from nucleotides, as well as DNA with deletions or mutations, is also within the contemplation of the invention.

Association of DNA sequences provided by the invention with homologous or heterologous species expression control DNA sequences, such as promoters, operators, regulators and the like, allows for in vivo and in vitro transcription to form messenger RNA which, in turn, is susceptible to translation to provide the invention proteins, and related poly- and oligo-peptides in large quantities. Presently preferred vectors for use in practice of the invention include plasmids pADNS, pADANS, pAAUN and pAAUN-ATG.

Specifically provided by the invention are mammalian DNA sequences encoding cyclic nucleotide phosphodiesterases and fragments thereof as well as RAS protein-related DNA sequences which are present as mammalian DNA inserts in bacterial plasmids which are the subject of deposits made Apr. 15, 1991 with the American Type Culture Collection, 12301 Parklawn Drive, Rockville, Md. 20852 in accordance with U.S. Patent and Trademark Office and Budapest Treaty requirements. Mammalian PDE DNAs made subject of the deposits include:

1. Plasmid pRATDPD in *E. coli* (A.T.C.C. accession No. 68586) containing a rat brain cDNA insert encoding a dunce-like PDE;
2. Plasmid pJC44x in *E. coli* (A.T.C.C. accession No. 68603) containing a human glioblastoma cell cDNA insert encoding a cAMP specific PDE;
3. Plasmid pTM3 in *E. coli* (A.T.C.C. accession No. 68600) containing a human glioblastoma cell cDNA insert encoding a cAMP specific PDE;
4. Plasmid pTM72 in *E. coli* (A.T.C.C. accession No. 68602) containing a human glioblastoma cell cDNA insert encoding a cAMP specific PDE;
5. Plasmid pPDE21 In *E. coli* (A.T.C.C. accession No. 68595) containing a human temporal cortical cell cDNA insert encoding a cAMP specific PDE;
6. Plasmid pGB18ARR in *E. coli* (A.T.C.C. accession No. 68596) containing a human temporal cortical cell cDNA insert encoding a cAMP specific PDE;
7. Plasmid pGB25 In *E. coli* (A.T.C.C. accession No. 68594) containing a human temporal cortical cell cDNA insert encoding a cAMP specific PDE; and,
8. Plasmid pTM22 In *E. coli* (A.T.C.C. accession No. 68601) containing a human glioblastoma cell cDNA insert encoding a PDE of unclassifiable family designation.

Mammalian RAS-related DNAs made the subject of deposit include:

9. Plasmid pJC99 in *E. coli* (A.T.C.C. accession No. 68599) containing a human glioblastoma cell cDNA insert encoding a RAS-related polypeptide;
10. Plasmid pJC265 in *E. coli* (A.T.C.C. accession No. 68598) containing a human glioblastoma cell cDNA insert encoding a BAS-related polypeptide;
11. Plasm pJC310 in *E. coli* (A.T.C.C. accession No. 68597) containing a human glioblastoma cell cDNA insert encoding a RAS-related polypeptide;
12. Plasmid pML5 in *E. coli* (A.T.C.C. accession No. 68593) containing a human glioblastoma cell cDNA insert encoding a RAS-related polypeptide;
13. Plasmid pATG16 in *E. coli* (A.T.C.C. accession No. 68592) containing a human glioblastoma cell cDNA insert encoding a RAS-related polypeptide; and,
14. Plasmid pATG29 in *E. coli* (A.T.C.C. accession No. 68591) containing a human glioblastoma cell cDNA insert encoding a RAS-related polypeptide.

Yeast expression plasmids deposited in connection with the present invention include:

15. Plasmid pAAUN in *E. coli* (A.T.C.C. accession No. 68590);
16. Plasmid pAAUN-ATG in *E. coli* (A.T.C.C. accession No. 68589);
17. Plasmid pADANS in *E. coli* (A.T.C.C. accession No. 68587); and,
18. Plasmid pADNS in *E. coli* (A.T.C.C. accession No. 68588).

Yeast host cells made the subject of deposit in connection with the present invention include:

19. *S. pombe* SP565 (A.T.C.C. accession No. 74047);
20. *S. cerevisiae* SKN37 (A.T.C.C. accession No. 74048);
21. *S. cerevisiae* 10DAB (A.T.C.C. accession No. 74049); and,
22. *S. cerevisiae* TK161-R2V (A.T.C.C. accession No. 74050).

Novel protein products of the invention include polypeptides having the primary structural conformation (i.e., amino acid sequence) of phosphodiesterase proteins as well as those having the primary structural conformation of non-phosphodiesterase proteins, including peptide fragments thereof and synthetic peptides assembled to be duplicative of amino acid sequences thereof. Proteins, protein fragments, and synthetic peptides of the invention are projected to have numerous uses including therapeutic, diagnostic and prognostic uses and will provide the basis for preparation of monoclonal and polyclonal antibodies specifically immunoreactive with these proteins. Preferred protein fragments and synthetic peptides include those duplicating regions of the proteins which are not involved in substrate binding functions and the most preferred are those which share at least one antigenic epitope with the proteins of the invention.

Use of mammalian host cells for expression of DNAs of the invention is expected to provide for such post-translational modifications (e.g., truncation, lipidation, glycosylation, and tyrosine, serine or threonine phosphorylation) as may be needed to confer optimal biological activity on recombinant expression products of the invention.

Also provided by the present invention are antibody substances (including polyclonal and monoclonal antibodies, chimeric antibodies and single chain antibodies) characterized by their ability to bind with high immunospecificity to the proteins and to their fragments and peptides, recognizing unique epitopes which are not common to other proteins, especially phosphodiesterases.

Also provided by the present invention are novel procedures for the detection and/or quantification of normal, abnormal, or mutated forms of the proteins as well as nucleic acids (e.g., DNA and mRNA) associated therewith. Illustratively, antibodies of the invention may be employed in known immunological procedures for quantitative detection of the proteins in fluid and tissue samples, of DNA sequences of the invention that may be suitably labelled and employed for quantitative detection of mRNA encoding these proteins.

Among the multiple aspects of the present invention, therefore, is the provision of (a) novel nucleic acid sequences encoding cyclic nucleic acid phosphodiesterase polypeptides and RAS-related proteins as hereinafter described, and (b) DNA sequences which hybridize thereto under hybridization conditions of the stringency equal to or greater than the conditions described herein and employed in the initial isolation of certain cDNAs of the invention, as well as (c) DNA sequences encoding the same, or allelic variant, or analog polypeptides through use of, at least in part, degenerate codons. Correspondingly provided are viral vectors or circular plasmid DNA vectors incorporating such DNA sequences and procaryotic and eucaryotic host cells transformed or transfected with such DNA sequences and vectors as well as novel methods for the recombinant production of proteins encoded by the DNA sequences through cultured growth of such hosts and isolation of these proteins from the hosts or their culture media.

The present invention further relates to a method of identifying agents that modify or alter (i.e., reduce or stimulate) the activity of the protein products of such mammalian genes expressed in microorganisms, such as yeast. Identification of such agents can be carried out using two types of screening procedures: one based on biochemical assays of mammalian proteins of known enzymatic function and one based on phenotypic assays for proteins of determined or as yet undetermined function. In the former case, if the encoded proteins are phosphodiesterases, for example, pharmacological screens include assays for chemical agents that alter (i.e., reduce or stimulate) phosphodiesterase activity. In the latter case, if the encoded proteins interact with RAS proteins, for example, pharmacological screens include the assay for agents that reduce or stimulate interactions with RAS proteins. These screening methods can be used with either whole cell preparations or cell extracts and do not require enzyme purification.

Other aspects and advantages of the present invention will be apparent upon consideration of the following detailed description thereof which includes numerous illustrative examples of the practice of the invention, reference being made to the drawing wherein:

BRIEF DESCRIPTION OF THE DRAWINGS

FIG. 1 [FIG. 1(A), 1(B), 1(C) and 1(D), 1(E), 1(F), 1(G), 1(H), 1(I), and 1(J)] is a comparative alignment of the nucleotide sequences of the human cDNA inserts of plasmids pJC44X, pTM3, pGB14 and pGB18ARR, wherein smaller letters designate lack of homology and gaps indicate absence of corresponding base positions;

FIG. 2 [FIG. 2(A), 2(B), 2(C) and 2(D), 2(E), 2(F), 2(G), 2(H), 2(I), and 2(J)] is a comparative alignment of the nucleotide sequences of the human cDNA inserts of plasmids pPDE2RR, pTM72, pPDE7 and pPDE 10x-INV, with smaller letters designating lack of homology and gaps indicating the absence of corresponding base positions;

FIGS. 3(A) and 3(B) is a comparative alignment of the nucleotide sequences of the human cDNA inserts of plasmids pPDE18 and pGB25, with smaller letters designating lack of homology and gaps indicating the absence of corresponding base positions; and FIG. 4 [FIG. 4(A) 4(B), 4(C) and 4(D)] is a comparative alignment of deduced amino acid sequences of plasmids pTM72 (TM72), pRATDPD, pJC44X, pPDE18 and pPDE21, wherein smaller letters designate non-homologous residues and gaps indicate lack of any residue at the aligned position.

DETAILED DESCRIPTION

The following examples illustrate practice of the invention. Example 1 relates to cloning and identification of mammalian genes by complementation in yeast. Example 2 relates to cloning and identification of mammalian genes by hybridization with mammalian genes cloned by complementation. Example 3 relates to characterization of cloned genes by complementation capacity. Example 4 relates to further characterization of cloned genes by nucleotide sequence analysis. Example 5 relates to screening and identification of agents which alter phosphodiesterase enzymatic activity.

EXAMPLE 1

Cloning of Mammalian Genes by Complementation in Yeast

In its most general form, the methods of the present invention are as follows.

Make mammalian cDNA library then

Insert cDNA library into appropriate expression vector then

Introduce cDNA-containing expression vector into microorganism (host cells) having genetic alteration associated with identifiable phenotype alteration then Maintain host cells under conditions appropriate for cell growth then Select host cells in which phenotypic alteration is corrected then Recover mammalian gene expressed in selected host cells then Analyze recovered mammalian gene and/or encoded products First, a cDNA library of mammalian mRNAs is produced using known techniques. This library can be made by cloning double stranded cDNA into an expression vector. The cDNA can be prepared from a pre-existing cDNA library, or it can be prepared by the reverse transcription of mRNA purified from a tissue or cell line of choice, using standard procedures. Watson et al., In: *DNA Cloning, a Practical Approach*, IRL Press Oxford (1984)).

The cDNA so obtained is cloned into an expression vector capable of expressing mammalian. cDNA inserts as mRNA which in turn can be translated into protein in a host cell of choice, e.g., altered yeast such as *S. pombe* SP565 (ras1::Leu2/ras1::Leu2) (A.T.C.C. 74047), *S. cerevisiae* SKN37 (cap::H1S3) (A.T.C.C. 74048), *S. cerevisiae* 10DAB (pde1⁻, pde2⁻) (A.T.C.C. 74049); and *S. cerevisiae* TK161-R2V (RAS2$^{val19}$) (A.T.C.C. 74050). Expression vectors which have been used for this purpose are described in the examples which follow and include pAAUN (A.T.C.C. 68590), pAAUNATG (A.T.C.C. 68589), pADNS (A.T.C.C. 68587), and pADANS (A.T.C.C. 68588).

Preferred expression vectors contain a transcriptional promoter specific for the host cell into which the vector is introduced, e.g., promoters specific for expression in *S. cerevisiae*. The transcribed mRNA may utilize the ATG of the cDNA insert as the "start" codon or may express the cDNA product as a fusion protein.

The cDNA library (present as cDNA inserts in a selected expression vector) is introduced into a suitable host cell. This host cell contains genetic alterations which cause the host cell to have an identifiable phenotypic alteration or abnormality associated with the genetic alteration. The host cell may be a eukaryotic microorganism, such as the yeast *S. cerevisiae* or a mammalian cell.

Known methods, such as lithium acetate-induced transformation, are used to introduce the cDNA-containing expression vector. In the examples that follow, transformation of yeast cells was performed with lithium acetate. Yeast cells were grown in either rich medium (YPD) or synthetic medium with appropriate auxotrophic supplements (SC). Mortimer et al., In: *The Yeast*, 1:385 (1969). Ito et al., *J. Bacteriol.*, 153:163 (1983).

The genetic alterations of the selected host cell, may for example, lead to defects in the metabolic pathways controlled by the RAS proteins and the associated readily discernible phenotype may be sensitivity to heat shock or nitrogen starvation, failure to synthesize normal amounts of glycogen, failure to grow on certain carbon sources, failure to sporulate, failure to mate, or other properties associated with defects in the pathways controlled by or controlling RAS proteins. For example, the genetic alteration can be the presence of the RAS2$^{val19}$ gene Yeast containing such an alteration-exhibit heat shock sensitivity, which can be overcome by expression of mammalian genes. In the examples that follow, heat shock experiments were performed by replica plating onto preheated SC plates which were maintained at 55° C. for 10 minutes, allowed to cool, and incubated at 30° C. for 24–48 hrs.

Other host cells with genetic alterations can be chosen, such as disruptions of the PDE1 and PDE2 genes in *S. cerevisiae* or disruptions of, or the presence of an activated allele of ras1 in *S. pombe*. Other genetic alterations in a host cell may be correctable by different subsets of mammalian cDNA genes.

After introduction of the cDNA insert-containing expression vector, host cells are maintained under conditions appropriate for host cell growth. Those host cells which have been corrected for their phenotypic alteration are selected or otherwise identified and the mammalian gene which they express can be recovered e.g., by transformation of *E. coli* with DNA isolated from the host cell. Segregation analysis in the examples that follow was performed by growing yeast transformants in YPD for 2–3 days, plating onto YPD plates, and replica plating onto YPD, SC-leucine (plasmid selection), and YPD heat shock plates. *E. coli* strain HB101 was used for plasmid propagation and isolation, and strain SCS1 (Stratagene) was used for transformation and maintenance of the cDNA library. Mandel et al., *Mol. Biol.*, 53:159 (1970); Hanahan *J. Mol. Biol.*, 166:557 (1983).

If desired, the mammalian gene can be isolated and sequenced; alternatively, the protein encoded by the gene can be identified and expressed in cultured cells for use in further processes.

Parts A, B, and C below describe the isolation of mammalian genes by complementation in yeast and their subsequent biochemical characterization.

A. Isolation and Biochemical Characterization of a Rat Brain cDNA Encoding a Phosphodiesterase A rat brain cDNA library was produced and cloned into the yeast expression vector, pADNS. RNA was purified from Sprague-Dawley rat brains by published procedures. Chirgwin et al., *Biochem.*, 18:5294 (1979); Lizardi, *Methods Enzymol.*, 96:24 (1983); Watson et al., In: *DNA cloning, a practical approach*, IRL, Press Oxford (1984). pADNS consists of a 2.2 kbp BglII to HpaI fragment containing the *S. cerevisiae* LEU2 gene from YEp213 [Sherman et al.,

*Laboratory Manual for Methods in Yeast Genetics*, Sherman, F., Fink, G. R. and Hicks, J. B., eds., Cold Spring Harbor Laboratory, Cold Spring Harbor, N.Y. (1986)], a 1.6 kbp HpaI to HindIII fragment of the *S. cerevisiae* 2μ plasmid containing the origin of replication, and a 2.1 kbp SspI to EcoRI fragment containing the ampicillin resistance gene from the plasmid pUC18. It also contains a 1.5 kbp BamHI to HindIII fragment of the modified *S. cerevisiae* alcohol dehydrogenase (ADH1) promoter [Bennetzen et al., *J. Biol. Chem.*, 257:3018 (1982); Ammerer, *Meth. Enzymol.*, 101:192 (1983)] and a 0.6 kbp HindIII to BamHI fragment containing the ADH1 terminator sequences. The promoter and terminator sequences are separated by a polylinker that contains the restriction endonuclease sites NotI, SacII, and SfiI between the existing HindIII and SacI sites.

Double stranded cDNAs were prepared and ligated to NotI linkers, cleaved with NotI restriction enzyme, and cloned into pADNS at the NotI site situated between the alcohol dehydrogenase promoter and termination sequences of the vector. The use of the rare cutting NotI obviated the need for restriction site methylases commonly used in cDNA cloning. cDNAs were ligated to the NotI linker oligonucleotides:

SEQ ID NO: 1

5'-AAGCGGCCGC, and

SEQ ID NO: 2

5'-GCGGCCGCTT.

Approximately 1.5×10⁵ independent cDNA inserts were contained in the library, with an average insert size of 1.5 kbp. DNA prepared from the cDNA expression library was used to transform the RAS2$^{val119}$ yeast strain TK161-R2V. The 50,000 Leu⁺ transformants obtained were subsequently tested for heat shock sensitivity. Only one transformant displayed heat shock resistance which was conditional upon retention of the expression plasmid. The plasmid, designated pRATDPD, was isolated from this transformant and the 2.17 kb NotI insert was analyzed by restriction site mapping and nucleotide sequencing. SEQ ID NO: 3 and SEQ ID NO: 4 provide the nucleotide sequence of the insert and the corresponding deduced amino acid sequence. Sequencing was performed using the dideoxy chain termination method. Sanger et al., *Proc. Natl. Acad. Sci. (U.S.A.)*, 74:5463 (1977); Biggin, et al., *Proc. Natl. Acad. Sci. (U.S.A.)*, 80:3963 (1983)). Genalign was used to align the DPD and dunce sequences (GENALIGN is a copyrighted software product of IntelliGenetics, Inc.; developed by Dr. Hugo Martinez).

A large open reading frame of 562 codons was found. The first ATG appears at codon 46 and a protein which initiates at this codon would have a predicted molecular weight of approximately 60 kDa. This rat gene is designated RATDPD. A search for similar sequences was performed by computer analysis of sequence data banks, and the *Drosophila melanogaster dunce* gene was found. The two genes would encode proteins with an 80% amino acid identity, without the introduction or gaps, over a 252 amino acid region located in the center of the rat DPD cDNA. The dunce gene has been shown to encode a high affinity cAMP phosphodiesterase. Chen et al., *Proc. Natl. Acad. Sci. (U.S.A.)*, 83:9313 (1986); Davis et al., *J. Cell Biol.*, 90:101 (1981); Walter et al., *Neurosci.*, 4:494 (1984)).

To demonstrate that the sequences upstream and downstream of the large sequence identity region were in fact contiguous with that region in the mRNA, rather than artifacts of the method for cDNA cloning, the structure of the cloned cDNA was compared with the structure of DPD cDNAs contained in an independently prepared, first strand cDNA population obtained by reverse transcribing total rat brain poly (A)⁺ RNA With an oligo dT primer. Oligonucleotide primers complementary to sequences located within the identity region, and to sequences near the 5' or 3' ends of the coding strand, were made. Using either the cloned pRATDPD DNA or the total first strand cDNA material as template, polymerase chain reactions (PCR) were carried out using four different primer sets and the reaction products were analysed by polyacrylamide gel electrophoresis.

Polymerase chain reactions (PCRs) were carried out in thermocycler (Perkin Elmer, Cetus) using a modification of published procedures. Saiki et al., *Science*, 239:487 (1988). Reaction mixtures contained template DNA (1 ng of cloned DNA, or 1 μg of total first strand cDNA), 25 pmoles of oligonucleotide primers, 200 μM deoxyribonucleotide triphosphates, 10 mM Tris HCl (pH 8.4), 50 mM KCl, 3 mM MgCl₂, and 0.01% (w/v) gelatin. The oligonucleotide primers used were:

SEQ ID NO: 5

A, 5'-CACCCTGCTGACAAACCT$^{44}$;

SEQ ID NO: 6

B, 5'-ATGGAGACGCTGGAGGAA$^{153}$;

SEQ ID NO: 7

C, 5'-ATACGCCACATCAGAATG$^{676}$;

SEQ ID NO: 8

D, 5'-TACCAGAGTATGATTCCC$^{1449}$;

SEQ ID NO: 9

E, 5'-GTGTCGATCAGAGACTTG$^{1668}$; and

SEQ ID NO: 10

F, 5'-GCACACAGGTTGGCAGAC$^{2048}$.

The superscript numbers indicate position coordinates in pRATDPD SEQ ID NO: 3. Primers C, E and F are noncoding strand sequences. Thirty cycles (1.5 min at 94° C., 3 min at 55° C., and 7 min at 72° C.) were performed and the reaction products were analyzed by polyacrylamide gel electrophoresis.

In each case, a fragment of the predicted length was obtained using either of the template DNAs. The band assignments were confirmed by cleavage with restriction endonucleases having recognition sites within the amplified DNA product. Again, in each case, the primary PCR product obtained using either source of template yielded cleavage products of the predicted sizes. The results indicate that the sequence arrangement in the cloned cDNA faithfully reflects the structure of the rat mRNA.

To analyse the biochemical properties of the pRATDPD gene product, crude cell extracts were prepared from one liter cultures of 10DAB yeast cells which had been transformed with either pADNS or pRATDPD. Yeast strain 10DAB cells are pde1⁻ and pde2⁻ and do not have a measureable level of endogenous cyclic nucleotide phosphodiesterase activity. Phosphodiesterase activity assays were performed using cAMP as substrate as follows. Yeast cells were grown at 30° C. for 36 hours in one liter cultures of synthetic media (SC-leucine). Cells were harvested and washed with buffer C (20 mM MES (pH 6.2), 0.1 mM MgCl₂, 0.1 mM EGTA, 1 mM β-mercaptoethanol), were resuspended in 30 ml buffer C with 50 μl 1M PMSF, and were disrupted with a French press. The extracts Were centrifuged at 1,600 g for 10 min and the supernatants were spun at 18,000 g for 90 min (4° C.). The supernatant was assayed for phosphodiesterase activity as in Collicelli et al., supra. All the reactions contained Tris-HCl (pH7.5) (100 mM), cell extract (50 μg protein/ml), 5'-nucleotidase (Sigma, 20 ng/ml) and 10 mM Mg²⁺ (unless otherwise stated) and the indicated cyclic nucleotide concentrations.

Assays for the cGMP hydrolysis used 1.5 μM cGMP. Inhibition studies employed 5 μM cAMP in the presence of varying amounts of cGMP up to 500 μM. [$^3$H]cAMP and [$^3$H]cGMP were obtained from NEN (New England Nuclear). Reactions were incubated for 10 min at 30° C. and stopped with 5× stop solution (250 mM EDTA, 25 mM AMP, 100 mM cAMP).

Control extracts (10DAB with pADNS) showed no cAMP phosphodiesterase activity. Results with the controls were unchanged when performed at 0° C. or in the absence of $Mg^{2+}$ and were comparable to results obtained when no extract was added. These results indicate that there is no detectable background phosphodiesterase activity in the non-transformed control strain 10DAB.

In contrast, considerable cAMP phosphodiesterase activity was seen in the 10AB yeast strain transformed with pRATDPD. The rate of cAMP hydrolysis in the resulting transformants was measured as a function of cAMP concentration. The deduced $K_m$ for cAMP is 3.5 μM and the calculated $V_{max}$ is 1.1 nmol/min/mg.

The assay conditions were varied to ascertain the cation preferences of the enzyme and to determine the ability of calcium and calmodulin to stimulate its activity. In these assays, $Mn^{2+}$ can be utilized as well as $Mg^{2+}$, and either cation in 1 mM final concentration was sufficient. Calcium/calmodulin was unable to stimulate the measured phosphodiesterase activity in the extract. A parallel assay using beef heart phosphodiesterase (Boeringer Mannheim) yielded a 6.5 fold stimulation with the addition of calcium/calmodulin. Finally, no cGMP phosphodiesterase activity was detected in these assays. Beef heart phosphodiesterase was again used as a positive control. In addition, cGMP present in amounts 100 fold over substrate concentrations was unable to inhibit cAMP phosphodiesterase activity.

Biochemical characterization of the pRATDPD cDNA product expressed in yeast indicates that it is a high affinity cAMP specific phosphodiesterase, as is dunce. Davis et al., *J. Cell. Biol.*, 90:101 (1981); Walter et al., *J. Neurosci.*, 4 (1984). In addition, the phosphodiesterase activity is not stimulated by the presence of calcium/calmodulin. This property is shared with dunce and is distinct from some other phosphodiesterases. Beavo, *In Advances in second messenger and phosphoprotein research* Greengard et al., eds., Raven Press (1988). The two proteins, pRATDPD and dunce, thus appear to have similar biochemical characteristics. However, it should also be noted that pRATDPD encodes a protein product which shows much less significant homology (35%) to dunce beyond the previously described highly conserved core region. These non-conserved sequences could result in an altered or refined function for this mammalian dunce homolog.

The pRATDPD nucleotide sequence as set forth in SEQ ID NO: 3 encodes a methionine codon at position 46 and the established reading frame remains open through to position 563, resulting in a protein with a predicted molecular weight of 60 kDa. The same reading frame, however, is open beyond the 5' end of the coding strand. At present, it is not known if the methionine codon at position 46 is the initiating condon for the DPD protein. The coding sequence is interrupted by three closely spaced terminator codons. However, the established reading frame then remains open for an additional 116 codons, followed by more terminator codons, a polyadenylylation consensus signal and a polyadenine stretch. This 3' open reading frame could be incorporated into another dunce-like phosphodiesterase through alternate splicing.

B. Cloning of Human Glioblastoma Cell cDNAs by Complementation

A cDNA library was constructed in λZAP using NotI linkers. In this example, the cDNA derived from mRNA was purified from the human glioblastoma cell line U118MG. Inserts from the λ vector were transferred into two yeast expression vectors pADNS and pADANS. Plasmid pADANS differs from pADNS in that the mRNA transcribed will direct the synthesis of a fusion protein including an N terminal portion derived from the alcohol dehydrogenase protein and the remainder from the mammalian cDNA insert.

The two mammalian cDNA expression libraries so constructed were screened, as in the previous example, for cDNAs capable of correcting the heat shock sensitivity of the *S. cerevisiae* host TK161-R2V. Several cDNAs were isolated and analysed by sequencing. Four different cDNAs, contained as inserts in plasmids pJC44x, pJC99, pJC265, and pJC310, were thereby discovered, and their DNA and deduced amino acid sequences are provided in SEQ ID NOs: 11 and 112; 13 and 14; 15 and 16; 17 and 118 respectively.

The insert of pJC44x was shown by computer analysis to be homologous to the rat pRATDPD gene and biochemical analysis of cellular lysates demonstrated that it encodes a cAMP phosphodiesterase. The inserts in pJC99, pJC265, and pJC310, show no significant homology to previously isolated genes.

C. Cloning of Human Glioblastoma Cell Phosphodiesterase cDNAs by Complementation The human gliobastoma cDNA expression library previously described was screened for cDNAs capable of correcting the heat shock sensitivity of the phosphodiesterase deficient yeast strain 10DAB. Several cDNAs were so isolated and analyzed by nucleotide and restriction endonuclease sequencing mapping. The cDNA insert in pTM22 encodes a novel human gene. Its nucleotide sequence and deduced amino acid sequence are shown in SEQ ID NOs: 19 and 20.

From a computer analysis of the nucleotide sequence of the pTM22 insert putatively encodes a protein homologous to various cAMP phosphodiesterases, such as the bovine $Ca^{2+}$/calmodulin dependent cAMP phosphodiesterase and the rat DPD phosphodiesterase described in Example 1A. Biochemical analysis has proven that the isolated DNA encodes a novel cAMP phosphodiesterase.

Sequences related to the pTM22 insert were found to be expressed in the human heart as well, and splicing variants of TM22 were isolated from a human heart cDNA library using pTM22 insert sequences as a nucleic acid hybridization probe.

Plasmid pTM22 was unable to correct the heat shock sensitivity of $RAS2^{val19}$ yeast strains, i.e., of TK161-R2V. It thus appears that the pde1$^-$ pde2$^-$ yeast strain 10DAB is more sensitive to phenotypic reversion by mammalian cAMP phosphodiesterase clones than is the $RAS2^{val19}$ yeast strain.

Several other human glioblastoma cDNAs, isolated as inserts in the plasmids designated pTM3 and pTM72, were similarly characterized. These two different cAMP phosphodiesterase cDNAs were found to be very closely related to, but distinct from, the pRATDPD cDNA insert and the pJC99 cDNA insert. Their nucleotide sequences and deduced amino acid sequences are shown in SEQ ID NOs: 21 and 22 (pTM3) 23 and 24 (pTM72), respectively.

Biochemical analysis of cell lysates has established that the cDNAs of pTM3 and pTM72, pJC44x and pRATDPD encode rolipram sensitive cAMP phosphodiesterases.

D. Kinetic Analysis of pPDE cDNA Expression Products

Samples containing approximately $10^{10}$ transformed *S. cerevisiae* 10DAB cells expressing the human cDNAs inserted in pJC44x, pTM3, a pTM22-like plasmid (designated L22 Met and including a 1.7 kb fragment insert derived from pTM22 and encoding the PDE activity) and pAD72 (a TM72-like clone) were resuspended in 2.5 ml PBS and disrupted by vortexing in the presence of glass beads at 4° C. The supernatant fraction following. Centrifugation for 5 min at 12,000×g was the source for enzyme in these studies.

Phosphodiesterase activity was determined as described, with minor modifications, in Davis et al., *J. Cyc. Nuc. Res.*, 5:65–74 (1979). Incubation mixtures contained 40 mM Tris pH 8.0, 1 mM EGTA, 5 mM $MgCl_2$, 0.1 mg/ml BSA, diluted yeast extract, [$^3$H]cAMP, and varying amounts of unlabeled cyclic nucleotides to a final volume of 0.25 ml. Reactions were terminated by the addition of 0.25 ml stop buffer containing 0.5 carbonate pH 9.3, 0.5M·NaCl and 0.1% SDS. Nucleotide products and unreacted substrates were separated on boronate columns (8×33 mm). The products were eluted from the boronate columns with sorbitol into scintillation vials for tritium analysis. All kinetic data represent measurements of initial rates, determined by incubations for multiple time intervals at suitable dilutions of enzyme. Analysis of kinetic data by the Lineweaver-Burk transformation of the Michaelis-Menten kinetic model demonstrates a linear double reciprocal plot indicative of a simple kinetic model for each enzyme tested. Cyclic nucleotide concentrations varied from $3\times10^{-8}$ to $1\times10^{-4}$ M [cAMP]. The results obtained are shown in Table 1, below.

TABLE 1

Preliminary Kinetic Analysis of Human Cyclic Nucleotide Phosphodiesterases Derived by Yeast Complementation

| Clone Name | $K_m^1$ | $V_{max}^2$ |
| --- | --- | --- |
| pJC44x | 3 µM | 830 |
| pAD72 | 1.3 µM | 670 |
| pTM3 | 4.5 µM | 16 |
| pL22Met | 0.1 µM | 240 |

[1] expressed as µM cAMP
[2] expressed as nmol/min/$10^{12}$ cells

E. Cloning of Human Glioblastoma Cell RAS-related cDNAs by Complementation in Yeast In this example, four human glioblastoma cell cDNAs were isolated which do not encode PDEs. They were obtained by complementation of two genetically altered *S. cerevisiae* and *S. Pombe* yeast strains.

Clone S46 was selected by complementation in *S. cerevisiae* strain RS60.15B. This strain contains a mutant allele of RAS2, $RAS2^{val119ala15}$, which renders cells unable to grow at 36° C. [Powers et al., *Mol. Cell Biol.*, 9:390–395 (1989)], because such cells are defective in RAS function at elevated temperatures. Human cDNAs from a human glioblastoma cell library were selected that could complement this defect. One cDNA found this way was designated S46. Its nucleotide and deduced amino acid sequences are provided in SEQ ID NOs: 25 and 26. The deduced amino acid sequence is homologous to a *Xenopus laevis* gene that encodes a known protein kinase, the S6 protein kinase.

Plasmid pML5 was selected by complementation in another *S. cerevisiae* strain, SKN37. This particular strain contains a disrupted allele of CAP, cap::HIS3. CAP encodes an adenylyl cyclase associated protein of undetermined function. [Field et al., *Cell*, 61:319–327 (1990)]. As a consequence of this gene disruption, SKN37 fails to grow in medium rich in amino acids [Gerst et al., *Mol. Cell Biol.*, 11:1248–1257 (1991)]. Human cDNAs were selected that could complement this defect. One cDNA insert found this way is present in pML5. Its nucleotide and deduced amino acid sequences are provided in SEQ ID NOs: 27 and 28. Its coding capacity is not yet certain.

Plasmids pATG16 and pATG29 were selected by complementation in the *S. pombe* diploid strain SP565. This strain is homozygous for disruptions of ras1 (ras1::LEU2). As a consequence, this strain fails to sporulate [Fukui et al., *Cell*, 44:329–336 (1986)] and human cDNAs were selected that could complement this defect. DNA sequence information for the inserts of pATG16 and pATG29 is set forth in SEQ ID NOs: 29 and 30; and 31 and 32, respectively. These genes have unknown function The vector used for screening in *S. pombe* differs from the vector used for screening in *S. cerevisiae*. This vector, pAAUN-ATG, utilizes an *S. pombe* specific promoter, the adh promoter, and was constructed as follows. The cloning vector pAAUN was derived from plasmid pART1 (McLeod et al., *EMBO J.*, 6:729–736 (1987) by replacing the *S. cerevisiae* LEU2 gene with a 1.8 kbp HindIII ura4 fragment from *S. pombe* and adding NotI linkers at the SmaI site of the polylinker (PL) derived from Viera et al., *Methods in Enzymology*, 153:3–11 (1987). pAAUN contains the *S. pombe* adh promter for gene expression and an ARS region for DNA replidation. Plasmid pAAUN-ATG, was derived from plasmid pART8, obtained from David Beach, at Cold Spring Harbor Laboratory, and from pAAUN. The fragment of BamHI-EcoRV in pAAUN was replaced with the fragment of BamHI and EcoRV in pART8 which had a ATG start codon supplied by NdeI site in the polylinker.

EXAMPLE 2

Cloning and Identification of Mammalian Genes by Hybridization with Mammalian Genes Cloned by Complementation This example relates to the cloning and identification of additional mammalian genes by hybridization to probes having sequences derived from the genes described in Example 1, i.e., those genes cloned via complementation in yeast.

Low and high stringency hybridizations were done under the same conditions for 12 to 16 hours at 65° C. in an aqueous solution consisting of 6 times the normal concentration of sodium citrate (SSC), 5 times the normal concentration of Denhardt's solution, 0.5% sodium dodecyl sulfate (SDS), 0.05 mg/ml of denatured salmon sperm DNA and probe. After hybridization, nitrocellulose filters are incubated for five minutes in 2×SSC, 0.5% SDS, at room temperature, and for twenty minutes in fresh 2×SSC, 0.5% SDS, at 60° C.

For high stringency hybridizations only, a third wash is performed for twenty minutes at 60° C. in 0.1×SSC, 0.1% SDS. The normal concentration of SSC is 0.15M sodium citrate and 0.15M sodium chloride, and the normal concentration of Denhardt's solution is 0.2 g/l Ficoll, 0.2 g/l polyvinyl/pyrrolidone, and 0.2 g/l bovine serum albumin.

Plasmids pPDET, pPDE10X inv, and pPDE2RR were isolated by low stringency hybridization screens of a human temporal lobe cDNA library using the pRATDPD insert as probe. Nucleotide sequence (SEQ ID NOs: 33, 34 and 35, respectively) comparisons indicate that the inserts are representatives of the same genetic locus as the insert in pTM72. SEQ ID NO: 36 sets out the deduced amino acid sequence of the insert of pPDE2RR.

Plasmids pGB14 and pGB18ARR were obtained in the same manner. DNA sequence analysis (SEQ ID NOs: 37 and 39, respectively) revealed that they are representatives of the same genetic locus as the inserts in pTM3 and pJC44x. The deduced amino acid sequences of the inserts are set out in SEQ ID NOs: 38 and 40, respectively.

Plasmid pGB25 was also obtained by low stringency hybridization using the pRATDPD insert as a probe. Judged by its nucleotide and deduced amino acid sequence as set out in SEQ ID NOS: 41 and 42 it represents a novel member of PDE family IV.

The cDNA insert of pGB25 was used as a probe to obtain pPDE18 and pPDE21. The cDNA of pPDE18 (SEQ ID NO: 43) represents the same locus as that of pGB25 (SEQ ID NO: 41) and contains more sequence information than the pGB25 cDNA. The pPDE21 insert represents a fourth member of PDE family IV. Its DNA and deduced amino acid sequences are set out in SEQ ID NOs: 45 and 46.

No biochemical data on expression products of these clones has yet been obtained. Their assignment to class IV is made solely based on sequence relationships.

EXAMPLE 3

Characterization of Cloned Genes by Complementation Capacity

This example relates to the further characterization of the genes cloned in Example 1 by their capacity to complement yeast strains other than the yeast strain originally used to clone the gene.

For example, 10DAB cells (pde1⁻ pde2⁻) were transformed with the DPD expression plasmid, pRATDPD, and assayed for heat shock sensitivity. Expression of the rat DPD gene indeed rendered this host resistant to heat shock. Similarly, pJC44x was able to correct the phenotypic defects of this pde1⁻ pde2⁻ yeast strain.

In contrast, pJC99, pJC265, and pJC310 were unable to do so. This suggests that the cDNAs of the latter inserts do not encode cAMP phosphodiesterases. Rather, these genes encode proteins of undetermined function which appear to be able to correct phenotypic defects in yeast with activated RAS proteins as reflected by their capacity to complement yeast strain TK161-R2V.

The procedures described below operate to establish that cDNAs need not be cloned by complementation (or by hybridization to DNAs cloned by complementation) in order to be functional in a genetically altered host. Put another way, the following procedures demonstrate that chemical agent screening methodologies according to the present invention need not involve initial direct or indirect cloning of pertinent DNAs by means of complementation.

A. Yeast Phenotype Complementation by Expression of a cDNA Encoding Bovine Brain CaM-PDE Plasmid pCAM-40 (in *E. coli*, A.T.C.C. accession No. 68576) includes a bovine brain cDNA insert encoding a 61 kDa $Ca^{2+}$/calmodulin stimulated cyclic nucleotide phosphodiesterase.

A 2.2 kb cDNA fragment, adapted for insertion into yeast expression plasmids pADNS and pADANS was derived from the plasmid pCAM-40 by polymerase chain reaction. Briefly, the following PCR amplification was employed to alter the pCAM-40 DNA insert to align it appropriately with the ADH1 promoter in the vectors.

One oligonucleotide primer (Oligo A) used in the PCR reaction
SEQ ID NO: 47

5'-TACGAAGCTTTGATGGGGTCTACTGCTAC-3'
anneals to the pCaM-40 cDNA clone at base pair positions 100–116 and includes a HinDIII site before the initial methionine codon. A second oligonucleotide primer (Oligo B)
SEQ ID NO: 48

5'-TACGAAGCTTTGATGGTTGGCTTGGCATATC-3'
was designed to anneal at positions 520–538 and also includes a HinDIII site two bases before a methionine codon. The third oligonucleotide
SEQ ID NO: 49

5'-ATTACCCCTCATAAAG-3'
annealed to a position in the plasmid that was 3' of the insert. For one reaction, Oligo A and Oligo C were used as primers with pCAM-40 as the template. The nucleic acid product of this reaction included the entire open reading frame. A second reaction used Oligo B and Oligo C as primers on the template pCAM-40 and yielded a nucleic acid product that lacked the portion of the cDNA sequence encoding the calmodulin binding domain. These amplified products were digested with HinDIII and NotI and ligated to HinDIII/NotI-digested yeast expression vectors pADNS and pADANS. Plasmid clones containing inserts were selected and transformed into *S. cerevisiae* strain 10DAB by lithium acetate transformation.

Transformed yeast were streaked in patches on agar plates containing synthetic medium lacking the amino acid-leucine (SC-leucine agar) and grown for 3 days at 30° C. Replicas of this agar plate were made with three types of agar plates: one replica on SC-leucine agar, one replica on room temperature YPD agar, and three replicas on YPD agar plates that had been warmed to 56° C. The three warmed plates were maintained at 56° C. for 10, 20, or 30 minutes. These replicas were than allowed to cool to room temperature and then all of the plates were placed at 30° C. Yeast transformed with plasmids constructed to express the CaM-PDE were resistant to the thermal pulse. More specifically, both the construct designed too express the complete open reading frame and that designed to express the truncated protein (including the catalytic region but not the calmodulin binding domain), in either pADNS or pADANS, complemented the heat shock sensitivity phenotype of the 10DAB host cells, i.e., rendered them resistant to the 56° C. temperature pulse.

B. Biochemical Assay of Expression Products

The CaM-PDE expression product was evaluated by preparing cell-free extracts from the yeast and measuring the extracts' biochemical phosphodiesterase activity. For this purpose, 200 ml cultures of transformed yeast Were grown in liquid SC-leucine to a density of about 6 million cells per ml. The cells were collected by centrifugation and the cell pellets were frozen. Extracts were prepared by thawing the frozen cells on ice, mixing the cells with 1 ml of PBS and an equal volume of glass beads, vortexing them to disrupt the yeast cells, and centrifuging the disrupted cells at approximately 12,000×g for 5 min to remove insoluble debris. The supernatant was assayed for phosphodiesterase activity.

Extracts of yeast cells, up to 50 µl, were assayed for phosphodiesterase activity in 50 mM Tris (pH 8.0), 1.0 mM EGTA, 0.01 mg/ml BSA (bovine serum albumin), [$^3$H]-cyclic nucleotide (4–10,000 cpm/pmol), and 5 mM $MgCl_2$ in a final volume of 250 µl at 30° C. in 10×75 mm glass test tubes. The incubations were terminated by adding 250 µl of 0.5M sodium carbonate (pH 9.3), 1M NaCl, and 0.1% SDS. The products of the phosphodiesterase reaction were separated from the cyclic nucleotide by chromatography on 8×33 mm columns of BioRad Affi-Gel 601 boronic acid gel. The columns were equilibrated with 0.25M sodium bicarbonate (pH 9.3) and 0.5M NaCl. The reactions were applied to the columns. The assay tubes were rinsed with 0.25M sodium bicarbonate (pH 9.3) and 0.5M NaCl and this rinse was applied to the columns. The boronate columns were washed twice with 3.75 ml of 0.25M sodium bicarbonate (pH 9.3) and 0.5M NaCl followed by 0.5 ml of 50 mM sodium acetate (pH 4.5). The product was eluted with 2.5 ml of 50 mM sodium acetate (pH 4.5) containing 0.1M sorbitol and collected in scintillation vials. The eluate was mixed with 4.5 ml Ecolite Scintillation Cocktail and the radioactivity measured by liquid scintillation spectrometry.

Both the construct designed to express the complete open reading frame and that designed to express a truncated protein, in either pADNS or pADANS, expressed active protein as determined by biochemical phosphodiesterase assay of cell extracts using cAMP substrate.

C. Yeast Phenotype Complementation by Expression of a cDNA Encoding a Bovine Adrenal cGS-PDE The plasmid p3CGS-5 (A.T.C.C. 68579) which contains a 4.2-kb DNA fragment encoding the bovine cGMP stimulated cyclic nucleotide phosphodiesterase (cGS-PDE), was adapted for cloning into pADNS and pADANS by replacing the first 147 bases of the cDNA with a restriction site suitable for use in the insertion into the plasmids. The oligonucleotide BS1, having the sequence
SEQ ID NO: 50

5'-TACGAAGCTTTGATGCGCCGACAGCCTGC-3',
encodes a HinDIII site and anneals to positions 148–165 of the cDNA insert. An oligonucleotide designated BS3
SEQ ID NO: 51

5'-GGTCTCCTGTTGCAGATATTG-3',
anneals to positions 835–855 just 3' of a unique NsiI site The resulting. PCR-generated fragment following digestion with HinDIII and NsiI was then ligated to HinDIII- and NsiI-digested p3CGS-5 thereby replacing the original 5' end of the bovine cDNA. A plasmid derived from this ligation was digested with HinDIII and NotI to release the modified cDNA insert. The insert was cloned into pADNS and pADANS at their HinDIII and NotI sites. These plasmids were then transformed into the yeast strain 10DAB by the lithium acetate method and the transformed cells were grown and subjected to elevated temperatures as in Section A, above. Both transformations resulted in complementation of the heat shock sensitivity phenotype of the 10DAB host cells.

D. Biochemical Assay of Expression Product

The expression of the cGS-PDE was also evaluated by preparing cell-free extracts from the yeast and measuring the extracts' biochemical phosphodiesterase activity. For this purpose, 50 ml cultures of transformed yeast were grown in liquid SC-leucine to a density of about 10 million cells per ml. Sherman et al., *Methods in Yeast Genetics,* Cold Spring Harbor Laboratory, Cold Spring Harbor, N.Y. (1986). The cells were collected by centrifugation, the cell pellets were washed once with water, and the final cell pellets were frozen. To prepare an extract, the frozen cells were thawed on ice, mixed with 1 ml of PBS and an equal volume of glass beads, vortexed to disrupt the yeast cells, and centrifuged to remove debris. The supernatant was then assayed for phosphodiesterase activity as in Section B, above.

Constructs in either pADNS or pADANS expressed active protein as determined by biochemical phosphodiesterase assay of cell extracts using cGMP.

EXAMPLE 4

Further Characterization of Cloned Genes by Nucleotide Sequence Analysis

This example describes the family-relatedness of the various human PDE clones described in the preceeding examples. These clones include both those obtained by complementation and those obtained by hybridization.

| COMPLEMENTATION | HYBRIDIZATION |
| --- | --- |
| pJC44x | pPDE7 |
| pTM22 | pPDE10 × inv |
| pTM3 | pPE2RR |
| pTM72 | pGB14 |
|  | pGB18ARR |
|  | pGB25 |
|  | pPDE21 |
|  | pPDE18 |

The uniqueness of its DNA sequence indicates that the pPDE21 cDNA derives from a locus herein designated PDE Class IV1. Plasmid pTM3, pJC44x, pGB18ARR and pGB14 cDNA all derive from the same genetic locus, herein designated PDE Class IV2. Evidence for this relation is shown in FIGS. 1(A)–1(J) demonstrating virtual sequence identity.

Likewise pTM72, pPDE7, pPDE10Xinv, and pPDE2RR cDNAs all derive from a genetic locus, herein designated PDE Class IV4. Evidence for this relation is shown in FIGS. 2(A)–2(J) demonstrating virtual sequence identity.

The cDNAs of pGB25 and pPDE18 derive from yet another genetic locus, herein designated PDE class IV3. Evidence of this relation is shown in FIGS. 3(A)–(B) which demonstrates virtual sequence identity.

The sequences derived from any given locus are not precisely identical. These sequence deviations can derive from a number of different sources including, sequencing errors, true polymorphisms in human populations, cloning artifacts, and differences in splicing patterns. Differences in splicing patterns perhaps account for the major differences in the pTM3 and pJC44x inserts. The pJC44x insert cDNA also may contain some cloning artifacts. Sequence errors, not only for the clones described above, but also for published PDE sequences may have occurred. Naturally occurring sequence variations, or polymorphisms, may also account for the observed results. This introduces some uncertainty into the deduced amino acid sequence of the product of a given locus. Accordingly, it is to be appreciated that the nucleotide sequences claimed encompass not only the specific sequences claimed but also DNA sequences which are substantially the same as those provided herein for cloned cDNAs of interest.

The PDE family IV classes 1–4 comprise a gene family that is related to the rat DPD. The evidence for this is based on the similarity of the encoded amino acid sequences of representatives of this family.

Ostensibly, there are just four members of PDE family IV. In the description that follows, the term "human dunce PDEs" refers to all members of family IV, i.e., the genes that show nucleotide sequence homology to the *Drosophila dunce* PDE.

Only a subset of the members of a gene family may be expressed in any given tissue. Attempts to quantitate a gene family by studying cDNAs cloned from one, or only a few, tissues may therefore underestimate the total number of members of the family. However, analysis of genomic DNA avoids this problem. Human genomic DNA was used as a substrate in PCR reactions performed in parallel, each containing one of a number of different pairs of oligonucleotides corresponding to various regions of the family IV PDEs. The regions chosen were those strongly conserved in evolution and/or present in all the known members of this human gene family. The oligonucleotides were comprised of mixtures representing the full degeneracy of codons specifying the desired amino acid sequence. The vast majority of the oligonucleotide pairs tested produced several different PCR products, which were heterogenous in length but always equal to or longer than those produced from the corresponding cDNA. However, two pairs produced only products identical in length to the cDNA. The longer, heterogenous populations of products resulted from the priming of oligonucleotide pairs located on two separate exons. The two oligonucleotide pairs that produced identical length products primed off the same exon.

To confirm that the heterogenous fragment populations truly represented priming from separate exons, human family. IV PDE genomic DNA clones were used as substrates in control PCR reactions. In these experiments, each of these clones produced a single PCR product, which was always equal in length to one of the heterogenous products obtained from genomic DNA.

The products from one of the reactions using oligonucleotides pairs that primed from one exon were cloned and sequenced. The oligonucleotides used were
SEQ ID NO: 52

5'TTYAARTCTNYTNCARGRNGA, and
SEQ ID NO: 53

5'ACNATRTCTRATNACCATYTT
wherein: N is any of the four-nucleotides; Y is C or T; and R is G or A. This corresponds to the fully degenerate codons specifying four potential amino acid sequences FKLLQ(E/G)EN
represented by SEQ ID NOs: 54 and 55, and DMVID(M/I)V
represented by SEQ ID NOs: 56 and 57
respectively, the two conserved domains boxed in FIG. 4. Using these primers, four different PCR clones were obtained, each corresponding in nucleotide sequence to one of the members of the known human family IV PDEs. The numbers of clones falling into each category were as follows:

| TYPE | TOTALS |
|---|---|
| TM72 type (Class IV4): | 16 |
| JC44 type (Class IV2): | 29 |
| PDE18 type (Class IV3): | 25 |
| PDE21 type (Class IV1): | 9 |
| Total: | 79 |

Assuming that the human genes each exist as single copies (which is consistent with this analysis of the available genomic clones), the four PCR products should be obtained ideally at equal frequency. The slightly skewed distribution obtained here probably reflects differing efficiencies in the production of these products in a PCR reaction due to mismatches with the PCR oligonucleotides. However, all four previously known genes were represented in the final PCR product, and no new sequences were identified. Therefore, the human PDE family IV most likely consists of a total of four members. Had this method identified a novel member of the family, the PCR clone could have been used as a probe to isolate cDNA clones. It is possible, however, that this family IV family has other members which have diverged at the codons specifying the amino acids sequences boxed in FIGS. 4(A)–(D).

The cDNA insert pTM22 represents a genetic locus that is not a member of family IV. The evidence for this is that while the deduced amino acid sequence of the pTM22 insert has the general features expected of a cAMP phosphodiesterase, this sequence is not particularly closely related to the sequences of members of the family IV or of the family I, the $Ca^{2+}$/calmodulin sensitive PDEs, or of the other known PDE families.

EXAMPLE 5

Screening and Identification of Agents Which Alter Enzymatic Activity

In their most general form, the pharmacological screening methods of the invention permit screening for agents that reduce or stimulate the activity of any mammalian protein whose presence or expression in an altered microbial host cell in which a genetic alteration is associated with an identifiable phenotypic alteration results in correction of the phenotypic alteration. Two general types of screens are possible. Both methods are applicable to either living cells, or cell preparations, or cell extracts.

A. Identification of Agents that Affect Proteins of Known Activity

The first type of pharmacological screen is applicable when the mammalian gene encodes a protein of known and assayable biochemical function. The mammalian gene is first expressed in a microbial host by utilizing an appropriate host expression vector of the type already described. Either whole cells or extracts of host cells can be used. Extracts are prepared, using known techniques, i.e., the cells are disrupted and their cellular constituents released. Crude cellular extract of purified mammalian protein is assayed for the known biochemical function in the presence of agents, the effects of which on the protein are to be assessed. In this manner, agents which inhibit or stimulate the activity of the mammalian protein can be identified.

This type of procedure can be carried out to analyze the effects of selected agents on mammalian cAMP phosphodiesterases. For example, a yeast strain lacking both endogenous PDE1 and PDE2 genes can be used as the host cell, into which cDNA encoding mammalian cAMP phosphodiesterase is introduced in an appropriate expression vector and expressed. Such a host cell is particularly useful because there is no endogenous (background) cAMP phosphodiesterase activity. [Colicelli et al., Proc. Natl. Acad. Sci. (U.S.A.), 86:3599 (1989)]. Hence, activity of the mammalian enzyme can be cleanly assayed even in crude cell extracts. This procedure is illustrated below, in which it is demonstrated that the enzymatic activity of the rat DPD gene product is readily inhibited by the pharmacological agents Rolipram and R020 1724, but not as readily by the pharmacological agent theophylline.

The genes and cells described in the preceeding examples can be used to identify chemical compounds which inhibit the activity of a known enzyme, the rat DPD phosphodiesterase. To test the efficiency of known inhibitory compounds, cell free extracts were made. Yeast cells deficient in endogenous phosphodiesterase (10DAB), and expressing the rat DPD or yeast PDE2 genes from the described expression vector, were used. One liter cultures were harvested, washed in buffer C (20 mM MES(pH 6.2)/0.1 mM $MgCl_2$/0.1 mM EGTA/1 mM 2-mercaptoethanol), resuspended in buffer C containing 1.5 mM phenylmethylsulfonyl fluoride, and disrupted in a French press at 4° C. Cell extracts were clarified at 100 g for 10 minutes and at 18000 g for 90 minutes. PDE activities were assayed as published (Charbonneau et al., Proc. Natl. Acad. Sci. (U.S.A.), 83:9308–9312 (1986); Tempel et al., Proc. Natl. Acad. Sci. (U.S.A.), 80:1482–1486 (1983)) in a reaction mix containing 50 µg of cell protein/ml, 100 mM Tris (pH 7.5), 10 mM $Mg^{++}$, 5 µM cAMP, 5'-nucleotidase and [$^3$H] cAMP. AMP was separated from cAMP using AG1-X8 resin from Bio Rad. About $10^4$ cpm were obtained for 10 min reactions and backgrounds (phosphodiesterase deficient-yeast or no extract) were about 300 cpm. The cytosolic fraction was assayed in the presence or absence of inhibitory compounds. These assays measure the amount of adenosine 5' monophosphate (AMP) produced by phosphodiesterase-catalysed hydrolysis of adenosine 3', 5'-cyclic adenosine monophosphate (cAMP). For each extract the percent inhibition for various concentrations of known inhibitors is given in Table 2. The percent inhibition represents the decrease in phosphodiesterase activity relative to measurements made in the absence of inhibitors. Rolipram, and the related compound R020 1724, were the most effective inhibitors of DPD activity.

TABLE 2

Inhibition of Phosphodiesterases by Chemicals

| Phosphodiesterase | Agent | Concentration (µM) | Inhibition (%) |
|---|---|---|---|
| PDE2 | Theophylline | 250 | 0.0 |
|  | IBMX | 250 | 0.0 |
|  | R020 1724 | 100 | 3.0 |
|  | Rolipram | 100 | 0.0 |
| rat DPD | Theophylline | 250 | 42. |
|  | IBMX | 250 | 87. |
|  | R020 1724 | 0.1 | 35. |
|  |  | 1.0 | 52. |
|  |  | 10.0 | 79. |
|  |  | 100.0 | 92. |
|  | Rolipram | 0.1 | 50. |

TABLE 2-continued

Inhibition of Phosphodiesterases by Chemicals

| Phosphodiesterase | Agent | Concentration (µM) | Inhibition (%) |
|---|---|---|---|
|  |  | 1.0 | 72. |
|  |  | 10.0 | 92. |
|  |  | 100.0 | 95. |

This analysis can, of course, be extended to test new or related chemical compounds for their ability to inhibit PDE activity, or the activity of another phosphodiesterase expressed in this system. Clearly, this form of analysis can also be extended to other genes cloned and expressed in a similar manner for which there is an assayable enzymatic activity.

Phosphodiesterase activity was determined as described in the previous table using 0.04 and 1.0 µM cAMP for pL22 Met and pJC44x, respectively. These concentrations of cAMP were specifically chosen to be below the $K_m$ for their respective enzymes. Thus, the $EC_{50}$ closely approximates the inhibitor constant or $K_i$ of each enzyme. All kinetic data represent initial velocities of enzyme catalysis.

TABLE 3

Inhibitor Sensitivities of Human Cyclic AMP Phosphodiesterases Derived by Yeast Complementation

| | $EC_{50}$[1] | |
|---|---|---|
| Agent | pJC44x | pL22 Met |
| cAMP | 3 | 0.2 |
| cGMP | >300 | >300 |
| Rolipram | 0.4 | >300 |
| RO 20-1724 | 3 | >300 |
| Milrinone | 30 | 30 |
| Theophylline | 300 | >300 |

[1]$EC_{50}$ = Inhibitor concentration at 50% enzyme velocity, concentration expressed in µM The following procedure was applied to the screening of whole transformed host cells. The yeast strain 10DAB was transformed with the expression vector pAD72, which expresses a human family IV phosphodiesterase, i.e., a cAMP specific PDE. This transformed strain was grown in SC-leucine medium for three days at 30° C. These cultures achieved a cell density of about 50 million cells per ml. Aliquots of this culture (300 µl) were taken and mixed with 4.8 µl 10% DMSO or 10% DMSO containing an appropriate concentration of phosphodiesterase inhibitor. The treated cultures were then incubated for two hours at 30° C., after which two 3 µl aliquots were removed and transferred to an SC-leucine agar plate. Then, a 100 µl aliquot was removed from the treated cultures and transferred to a glass 12×75 mm test tube and the test tubes were incubated at 50° C. in a mineral oil-containing hot block for 30 min. The test tubes were removed from the hot block and placed at room temperature. Two 3 µl aliquots were removed and transferred to an SC-leucine plate. The agar plates were then incubated at 30° C. and examined at various times to evaluate growth.

Yeast treated with 10% DMSO alone showed a slight decrease in the number of viable cells following the 50° C. heat treatment. Treatment of cells with Rolipram reduced the number of viable cells, such that at 100 µM Rolipram, less than 10 out of approximately 150,000 cells remained viable.

Milrinone up, to 100 μM, had no observable effect on the culture.

B. Identification of Agents Which Affect Proteins of Unspecified Function

This example illustrates the use of the genes and methods described above for use in identifying chemical compounds which affect the function of the encoded mammalian proteins expressed in yeast, even when the function of that protein has not yet been determined.

10DAB cells, which are phosphodiesterase deficient, are sensitive to heat shock. As already discussed, when these cells acquire the capacity to express the cDNA of pRAT-DPD, they become resistant to heat shock. 10DAB cells expressing the cDNA of pRATDPD were maintained in rich medium (YPD) for three days at stationary phase. These cultures were then treated with Rolipram, a known phosphodiesterase inhibitor, for 40 minutes at a final concentration of 100 μM. Control cultures were not treated with any inhibitor. These cultures were then heat shocked in glass tubes at 50° C. for 30 minutes. One microliter of each culture was plated. Cultures treated with Rolipram were much more sensitive to heat shock, reflecting an inhibition of enzymatic function.

The second type of pharmacological screen is applicable even when the mammalian gene encodes a protein of undetermined function, and, thus, cannot be assayed by a biochemical activity. In this method, agents to be tested are applied or introduced directly to the genetically altered microbial host expressing the mammalian protein. Agents capable of inhibiting the mammalian gene or gene product are identified by their ability to reverse the phenotype originally corrected by expression of the mammalian protein in the altered host.

This procedure has been used for mammalian cDNAs encoding cyclic nucleotide phosphodiesterases and a yeast containing $RAS2^{val19}$ as the host strain. When the rat DPD gene is introduced into the heat shock sensitive host and expressed, the host strain becomes heat shock resistant. When the now resistant cells are incubated in Rolipram, they become heat shock sensitive again, indicating that Rolipram inhibits the activity of the rat DPD gene product. This pharmacological screen does not require that the function of the DPD gene product be known. This same approach can be applied to assess other genes.

In addition, and other phenotype that is dependent on DPD phosphodiesterase activity should be affected by the presence of the inhibitory drug. The effect of a drug or agent can be assessed as described. Finally, in the most generalized case, inhibitory chemicals for proteins of unknown function, expressed from mammalian cDNAs in yeast can be discovered in a similar way. This approach depends only on the phenotype consequent to expression of the protein and not on knowledge of its function.

For example, tyrosine kinases comprise a very large and diverse superfamily of proteins. They are important in regulation of cell growth. Certain tyrosine kinases are expressed ubiquitously in cells. Other tyrosine kinases display tissue specific distribution. Truly specific inhibitors of such tyrosine kinases could thus be expected to have specific and desirable therapeutic effects without unwanted side effects. For example, specific inhibitors of the PDGF receptor-tyrosine kinase could be expected to retard the growth of atherosclerotic plaques or retard scar formation; specific inhibitors of the lck tyrosine kinase, which mediates signals from the CD4 and CD8 T-cell receptors, could be expected to be anti-inflammatory without being cytotoxic.

It is probable that yeast can be used to screen pharmacological agents for inhibition of specific tyrosine kinases. Brugge et al., *Mol. Cell. Biol.*, 7:2180–2187 (1987) demonstrated that expression of the avian v-src gene in the yeast *S. cerevisiae* inhibits growth. This vital gene encodes a tyrosine specific protein kinase that closely resembles the cellular src genes that are expressed ubiquitously in mammalian and avian cells. If this is a general property of active mammalian tyrosine kinases expressed in yeast, then the following design for a pharmacological screen would be expected to be effective.

A specific mammalian tyrosine kinase cDNA gene can thus be inserted in a yeast shuttle vector such that it is under the control of an inducible yeast promoter, such as the GAL10 promoter which is inducible in the presence of galactose and in the absence of glucose. Introduction of this vector into a yeast cell can be anticipated to render that cell unable to grow in induction medium (containing galatose in the absence of glucose), since under such conditions the mammalian tyrosine kinase would be expressed to the detriment of the cell. In the presence of an inhibitor of the tyrosine kinase, such cells would thrive on induction medium. This provides a simple screen for pharmacological agents that inhibit mammalian tyrosine kinases. False positives would include agents that blocked induction of the expression of kinase. Such false positives could be distinguished by the failure of the masalian kinase to be induced, which can be determined by quantitation with specific antibodies.

While the present invention has been described in terms of specific illustrative methods and materials, it is understood that modifications and variations thereof will occur to those skilled in the art upon consideration of the above detailed description. Consequently only such limitations as appear in the appended claims should be placed thereon.

---

What is claimed is:

1. A purified, isolated DNA encoding a RAS-related polypeptide capable of complementing a defective RAS function in yeast, said DNA comprising a DNA selected from the group consisting of the mammalian cDNA inserts present in plasmids pJC99 (A.T.C.C. 68599), pJC265 (A.T.C.C. 68598), pJC310 (A.T.C.C. 68597), pML5 (A.T.C.C. 68593), pATG16 (A.T.C.C. 68592), and pATG29 (A.T.C.C. 68591 ) and wherein said DNA encodes a polypeptide as set out in SEQ ID NO. 14, 16, 18, 28, 30, or 32, respectively.

2. A purified, isolated DNA encoding a RAS-related polypeptide capable of complementing a defective RAS function in yeast, which DNA hybridizes under stringent conditions to a DNA sequence according to claim 1.

3. A purified isolated DNA encoding a polypeptide according to claim 1 or 2 by means of degenerate codons.

4. A purified, isolated DNA encoding a mammalian cyclic nucleotide phosphodiesterase, said DNA comprising a DNA selected from the group consisting of the mammalian cDNA inserts present in plasmids pRATDPD (A.T.C.C. 68586), pJC44x (A.T.C.C. 68603), pTM3 (A.T.C.C. 68600), pTM72 (A.T.C.C. 68602), and pTM22 (A.T.C.C. 68601) and wherein said DNA encodes a mammalian cyclic nucleotide phosphodiesterase as set out in SEQ ID NO. 4, 12, 22, 24, or 20, respectively.

5. A purified and isolated DNA encoding a mammalian cyclic nucleotide phosphodiesterase which DNA hybridizes under stringent conditions to a DNA selected from the group consisting of DNA sequences according to claim 4 and SEQ ID NOS: 33, 34, 35, 37, 39, 41, 43 and 45.

6. A purified and isolated DNA encoding a polypeptide encoded by a DNA according to claim 4 or 5 by means of degenerate codons.

* * * * *

UNITED STATES PATENT AND TRADEMARK OFFICE
CERTIFICATE OF CORRECTION

PATENT NO.  : 5,527,896
DATED       : June 18, 1996
INVENTOR(S) : Wigler et al.

It is certified that error appears in the above-identified patent and that said Letters Patent is hereby corrected as shown below:

Drawings,
Figure 2G, Sheet 15 of 26, line 13, replace "PDE10X-IND" with -- PDE10X-INV --.
Figure 3B, Sheet 22 of 26, line 13, replace "PDE19" with -- PDE18 --.

Column 1,
Line 7, after "National Institutes of Health" and before the period, insert -- under Grant No. CA39829. The United States government may own certain rights in the invention --.
Line 11, after "continuation-in-part of insert -- co-pending --.

Column 2,
Line 18, replace "immumoprecipitates" with -- immunoprecipitates --.
Line 61, replace "Taparowsk" with -- Taparowsky --.

Column 3,
Line 21, replace "mutans" with -- humans --.

Column 6,
Line 17, replace "H-RAS" with -- H-ras --.
Line 38, replace "GMP" with -- cGMP --.
Line 39, replace "Sat" with -- rat --.

Column 7,
Line 7, replace "(i.e., "RAS-related Protein);" with -- (i.e., "RAS-related protein"); --.
Line 18, replace "off" with -- of --.

Column 8,
Line 7, replace "Md." with -- Maryland --.
Line 43, replace "BAS-related" with -- RAS-related --.
Line 45, replace "Plasm" with -- Plasmid --.

Column 10,
Lines 28-29, replace "FIG. 1 [FIG. 1(A), 1(B), 1(C) and 1(D), 1(E), 1(F), 1(G), 1(H), 1(I), and 1(J)]" with -- FIG. 1 [FIG. 1(A), 1(B), 1(C), 1(D), 1(E), 1(F), 1(G), 1(H), l(I), and 1(J)] --.
Lines 35-36, replace "FIG. 2 [FIG. 2(A), 2(B), 2(C) and 2(D), 2(E), 2(F), 2(G), 2(H), 2(I), and 2(J)]" with -- FIG. 2 [2(A), 2(B), 2(C), 2(D), 2(E), 2(F), 2(G), 2(H), 2(I), and 2(J)] --.
Line 47, replace "FIG. 4 [FIG. 4(A), 4(B), 4(C) and 4(D)]" with -- FIG. 4 [4(A), 4(B), 4(C), and 4(D)] --.

UNITED STATES PATENT AND TRADEMARK OFFICE
CERTIFICATE OF CORRECTION

PATENT NO.   : 5,527,896
DATED        : June 18, 1996
INVENTOR(S)  : Wigler et al.

It is certified that error appears in the above-identified patent and that said Letters Patent is hereby corrected as shown below:

Column 12,
Line 20, replace "gene Yeast" with -- gene. Yeast --.
Line 21, replace "alteration-exhibit" with -- alteration exhibit --.

Column 14,
Line 2, replace "With" with -- with --.
Line 60, replace "Were" with -- were --.

Column 16,
line 65, replace "pJC99" with -- pJC44x --.

Column 17,
Line 14, replace "following. Centrifugation" with -- following centrifugation --.
Line 24, replace "0.5 carbonate" with -- 0.5 M carbonate --.

Column 18,
Line 24, replace "function The" with -- function. The --.
Line 36, replace "replidation" with -- replication --.

Column 19,
Line 4, replace "pPDET" with -- pPDE7 --.

Column 20,
Line 8, replace "the-vectors" with -- the vectors --.
Line 50, replace "too" with -- to --.
Line 63, replace "Were" with -- were --.

Column 21,
Line 50, replace "site The" with -- site. The --.
Line 51, replace "resulting. PCR-generated" with --resulting PCR-generated --.

Column 23,
Line 41, replace "family. IV" with -- family IV --.

Column 26,
Line 39, replace "$^1$ EC$_{50}$" with -- 1 EC$_{50}$ --.

UNITED STATES PATENT AND TRADEMARK OFFICE
CERTIFICATE OF CORRECTION

PATENT NO.    : 5,527,896
DATED         : June 18, 1996
INVENTOR(S)   : Wigler et al.

It is certified that error appears in the above-identified patent and that said Letters Patent is hereby corrected as shown below:

Column 28,
Line 35, replace "galatose" with -- galactose --.
Line 44, replace "masalian" with -- mammalian --.

Signed and Sealed this

Sixth Day of August, 2002

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single ( D ) TOPOLOGY: linear ( x i ) SEQUENCE DESCRIPTION: SEQ ID NO:1:

AAGCGGCCGC                                                                                      10

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCGGCCGCTT                                                                                      10

( 2 ) INFORMATION FOR SEQ ID NO:3:

( i ) SEQUENCE CHARACTERISTICS:
        ( A ) LENGTH: 2158 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1688

( x i ) SEQUENCE DESCRIPTION: SEQ ID NO:3:

```
AGC TTG CGA ATC GTA AGA AAC AAT TTC ACC CTG CTG ACA AAC CTT CAC      48
Ser Leu Arg Ile Val Arg Asn Asn Phe Thr Leu Leu Thr Asn Leu His
 1               5                  10                  15

GGA GCA CCG AAC AAG AGG TCG CCA GCG GCT AGT CAG GCT CCA GTC ACC      96
Gly Ala Pro Asn Lys Arg Ser Pro Ala Ala Ser Gln Ala Pro Val Thr
            20                  25                  30

AGA GTC AGC CTG CAA GAA GAA TCA TAT CAG AAA CTA GCA ATG GAG ACG     144
Arg Val Ser Leu Gln Glu Glu Ser Tyr Gln Lys Leu Ala Met Glu Thr
        35                  40                  45

CTG GAG GAA CTA GAC TGG TGC CTA GAC CAG CTA GAG ACC ATC CAG ACC     192
Leu Glu Glu Leu Asp Trp Cys Leu Asp Gln Leu Glu Thr Ile Gln Thr
    50                  55                  60

TAC CGC TCT GTC AGC GAG ATG GCT TCA AAC AAG TTC AAA AGG ATG CTG     240
Tyr Arg Ser Val Ser Glu Met Ala Ser Asn Lys Phe Lys Arg Met Leu
65                  70                  75                  80

AAC CGG GAG CTG ACA CAC CTC TCA GAG ATG AGC AGA TCA GGG AAC CAA     288
Asn Arg Glu Leu Thr His Leu Ser Glu Met Ser Arg Ser Gly Asn Gln
                85                  90                  95

GTG TCT GAA TAC ATT TCG AAC ACG TTC TTA GAC AAG CAG AAC GAT GTG     336
Val Ser Glu Tyr Ile Ser Asn Thr Phe Leu Asp Lys Gln Asn Asp Val
           100                 105                 110

GAA ATC CCA TCT CCC ACC CAG AAG GAC AGG GAG AAG AAG AAG AAG CAG     384
Glu Ile Pro Ser Pro Thr Gln Lys Asp Arg Glu Lys Lys Lys Lys Gln
       115                 120                 125

CAG CTC ATG ACC CAG ATA AGT GGA GTG AAG AAA CTG ATG CAC AGC TCA     432
Gln Leu Met Thr Gln Ile Ser Gly Val Lys Lys Leu Met His Ser Ser
   130                 135                 140

AGC CTG AAC AAC ACA AGC ATC TCA CGC TTT GGA GTC AAC ACG GAA AAT     480
Ser Leu Asn Asn Thr Ser Ile Ser Arg Phe Gly Val Asn Thr Glu Asn
145                 150                 155                 160

GAG GAT CAT CTA GCC AAG GAG CTG GAA GAC CTG AAC AAA TGG GGC CTT     528
Glu Asp His Leu Ala Lys Glu Leu Glu Asp Leu Asn Lys Trp Gly Leu
                165                 170                 175
```

| | | | | | | | | | | | | | | | | |
|---|---|---|---|---|---|---|---|---|---|---|---|---|---|---|---|---|
| AAC | ATC | TTC | AAC | GTG | GCT | GGG | TAC | TCC | CAT | AAT | CGG | CCC | CTC | ACA | TGC | 576 |
| Asn | Ile | Phe | Asn | Val | Ala | Gly | Tyr | Ser | His | Asn | Arg | Pro | Leu | Thr | Cys | |
| | | | 180 | | | | | 185 | | | | | 190 | | | |
| ATC | ATG | TAC | GCC | ATT | TTC | CAG | GAA | AGA | GAC | CTT | CTA | AAG | ACG | TTT | AAA | 624 |
| Ile | Met | Tyr | Ala | Ile | Phe | Gln | Glu | Arg | Asp | Leu | Leu | Lys | Thr | Phe | Lys | |
| | | 195 | | | | | 200 | | | | | 205 | | | | |
| ATC | TCC | TCC | GAC | ACC | TTC | GTA | ACC | TAC | ATG | ATG | ACT | TTA | GAA | GAC | CAT | 672 |
| Ile | Ser | Ser | Asp | Thr | Phe | Val | Thr | Tyr | Met | Met | Thr | Leu | Glu | Asp | His | |
| | | 210 | | | | | 215 | | | | | 220 | | | | |
| TAC | CAT | TCT | GAT | GTG | GCG | TAT | CAC | AAC | AGC | CTG | CAC | GCT | GCT | GAC | GTG | 720 |
| Tyr | His | Ser | Asp | Val | Ala | Tyr | His | Asn | Ser | Leu | His | Ala | Ala | Asp | Val | |
| 225 | | | | | 230 | | | | | 235 | | | | | 240 | |
| GCC | CAG | TCA | ACG | CAC | GTT | CTC | CTC | TCT | ACG | CCA | GCA | CTG | GAT | GCT | GTC | 768 |
| Ala | Gln | Ser | Thr | His | Val | Leu | Leu | Ser | Thr | Pro | Ala | Leu | Asp | Ala | Val | |
| | | | | 245 | | | | | 250 | | | | | 255 | | |
| TTC | ACA | GAC | CTG | GAA | ATC | CTG | GCT | GCC | ATT | TTT | GCA | GCT | GCC | ATC | CAT | 816 |
| Phe | Thr | Asp | Leu | Glu | Ile | Leu | Ala | Ala | Ile | Phe | Ala | Ala | Ala | Ile | His | |
| | | | | 260 | | | | | 265 | | | | | 270 | | |
| GAT | GTT | GAT | CAT | CCT | GGA | GTC | TCC | AAT | CAG | TTT | CTC | ATC | AAT | ACA | AAT | 864 |
| Asp | Val | Asp | His | Pro | Gly | Val | Ser | Asn | Gln | Phe | Leu | Ile | Asn | Thr | Asn | |
| | | 275 | | | | | 280 | | | | | 285 | | | | |
| TCC | GAA | CTT | GCT | TTG | ATG | TAT | AAT | GAC | GAA | TCT | GTG | CTG | GAA | AAC | CAT | 912 |
| Ser | Glu | Leu | Ala | Leu | Met | Tyr | Asn | Asp | Glu | Ser | Val | Leu | Glu | Asn | His | |
| | 290 | | | | | 295 | | | | | 300 | | | | | |
| CAC | CTC | GCT | GTG | GGA | TTC | AAG | CTC | CTT | CAA | GAG | GAA | CAT | TGC | GAC | ATC | 960 |
| His | Leu | Ala | Val | Gly | Phe | Lys | Leu | Leu | Gln | Glu | Glu | His | Cys | Asp | Ile | |
| 305 | | | | | 310 | | | | | 315 | | | | | 320 | |
| TTT | CAG | AAT | CTT | ACC | AAG | AAG | CAA | CGC | CAG | ACA | CTC | AGG | AAA | ATG | GTG | 1008 |
| Phe | Gln | Asn | Leu | Thr | Lys | Lys | Gln | Arg | Gln | Thr | Leu | Arg | Lys | Met | Val | |
| | | | | 325 | | | | | 330 | | | | | 335 | | |
| ATT | GAC | ATG | GTG | TTA | GCA | ACT | GAT | ATG | TCC | AAG | CAC | ATG | AGC | CTC | CTG | 1056 |
| Ile | Asp | Met | Val | Leu | Ala | Thr | Asp | Met | Ser | Lys | His | Met | Ser | Leu | Leu | |
| | | | 340 | | | | | 345 | | | | | 350 | | | |
| GCT | GAC | CTT | AAA | ACG | ATG | GTA | GAA | ACC | AAA | AAG | GTG | ACG | AGC | TCC | GGT | 1104 |
| Ala | Asp | Leu | Lys | Thr | Met | Val | Glu | Thr | Lys | Lys | Val | Thr | Ser | Ser | Gly | |
| | | 355 | | | | | 360 | | | | | 365 | | | | |
| GTT | CTC | CTC | CTG | GAC | AAC | TAT | ACT | GAC | CGG | ATA | CAG | GTT | CTT | CGC | AAC | 1152 |
| Val | Leu | Leu | Leu | Asp | Asn | Tyr | Thr | Asp | Arg | Ile | Gln | Val | Leu | Arg | Asn | |
| | 370 | | | | | 375 | | | | | 380 | | | | | |
| ATG | GTA | CAT | TGT | GCA | GAC | CTG | AGC | AAC | CCT | ACC | AAG | TCC | TTG | GAG | TTG | 1200 |
| Met | Val | His | Cys | Ala | Asp | Leu | Ser | Asn | Pro | Thr | Lys | Ser | Leu | Glu | Leu | |
| 385 | | | | | 390 | | | | | 395 | | | | | 400 | |
| TAT | CGG | CAA | TGG | ACT | GAT | CGC | ATC | ATG | GAG | GAG | TTT | TTC | CAA | CAG | GGA | 1248 |
| Tyr | Arg | Gln | Trp | Thr | Asp | Arg | Ile | Met | Glu | Glu | Phe | Phe | Gln | Gln | Gly | |
| | | | | 405 | | | | | 410 | | | | | 415 | | |
| GAC | AAA | GAA | CGG | GAG | AGG | GGA | ATG | GAG | ATT | AGC | CCA | ATG | TGT | GAT | AAA | 1296 |
| Asp | Lys | Glu | Arg | Glu | Arg | Gly | Met | Glu | Ile | Ser | Pro | Met | Cys | Asp | Lys | |
| | | | 420 | | | | | 425 | | | | | 430 | | | |
| CAC | ACA | GCT | TCT | GTG | GAA | AAG | TCC | CAG | GTT | GGT | TTC | ATT | GAC | TAC | ATT | 1344 |
| His | Thr | Ala | Ser | Val | Glu | Lys | Ser | Gln | Val | Gly | Phe | Ile | Asp | Tyr | Ile | |
| | | 435 | | | | | 440 | | | | | 445 | | | | |
| GTC | CAT | CCA | TTG | TGG | GAG | ACC | TGG | GCA | GAC | CTG | GTT | CAG | CCT | GAT | GCT | 1392 |
| Val | His | Pro | Leu | Trp | Glu | Thr | Trp | Ala | Asp | Leu | Val | Gln | Pro | Asp | Ala | |
| 450 | | | | | 455 | | | | | 460 | | | | | | |
| CAA | GAC | ATT | TTG | GAC | ACA | CTA | GAA | GAT | AAC | AGG | AAC | TGG | TAC | CAG | AGT | 1440 |
| Gln | Asp | Ile | Leu | Asp | Thr | Leu | Glu | Asp | Asn | Arg | Asn | Trp | Tyr | Gln | Ser | |
| 465 | | | | | 470 | | | | | 475 | | | | | 480 | |
| ATG | ATT | CCC | CAG | AGC | CCC | TCT | CCA | CCA | CTG | GAC | GAG | AGG | AGC | AGG | GAC | 1488 |
| Met | Ile | Pro | Gln | Ser | Pro | Ser | Pro | Pro | Leu | Asp | Glu | Arg | Ser | Arg | Asp | |
| | | | | 485 | | | | | 490 | | | | | 495 | | |

| | | | | | | | | | | | | | | | |
|---|---|---|---|---|---|---|---|---|---|---|---|---|---|---|---|
| TGC | CAA | GGC | CTT | ATG | GAG | AAG | TTT | CAG | TTC | GAA | CTG | ACC | CTT | GAA | GAA | 1536 |
| Cys | Gln | Gly | Leu | Met | Glu | Lys | Phe | Gln | Phe | Glu | Leu | Thr | Leu | Glu | Glu | |
| | | | 500 | | | | | 505 | | | | | 510 | | | |
| GAG | GAT | TCT | GAA | GGA | CCG | GAA | AAG | GAG | GGA | GAA | GGC | CCC | AAC | TAT | TTC | 1584 |
| Glu | Asp | Ser | Glu | Gly | Pro | Glu | Lys | Glu | Gly | Glu | Gly | Pro | Asn | Tyr | Phe | |
| | | 515 | | | | | 520 | | | | | 525 | | | | |
| AGC | AGC | ACA | AAG | ACA | CTT | TGT | GTG | ATC | GAT | CCA | GAG | AAC | AGG | GAT | TCT | 1632 |
| Ser | Ser | Thr | Lys | Thr | Leu | Cys | Val | Ile | Asp | Pro | Glu | Asn | Arg | Asp | Ser | |
| | | 530 | | | | 535 | | | | | 540 | | | | | |
| CTG | GAA | GAG | ACT | GAC | ATA | GAC | ATT | GCC | ACA | GAA | GAC | AAG | TCT | CTG | ATC | 1680 |
| Leu | Glu | Glu | Thr | Asp | Ile | Asp | Ile | Ala | Thr | Glu | Asp | Lys | Ser | Leu | Ile | |
| 545 | | | | | 550 | | | | | 555 | | | | | 560 | |

```
GAC ACA TA ATCTCCCTCT GTGTGGAGGT GAACATTCTA TCCTTGACGA GCATGCCAGC    1738
Asp Thr
TGAGTGGTAG GGCCCACCTA CCAGAGCCAA GGCCTGCACA AAACAAAGGC CACCTGGCTT    1798

TGCAGTTACT TGAGTTTGGA GCCAGAATGC AAGGCCGTGA AGCAAATAGC AGTTCCGTGC    1858

TGCCTTGCCT TGCCGGCGAG CTTGGCGAGA CCCGCAGCTG TAGTAGAAGC CAGTTCCCAG    1918

CACAGCTAAA TGGCTTGAAA ACAGAGGACA GAAAGCTGAG AGATTGCTCT GCAATAGGTG    1978

TTGAGGGGCT GTCCCGACAG GTGACTGAAC TCACTAACAA CTTCATCTAT AAATCTCACC    2038

CATCCTGTTG TCTGCCAACC TGTGTGCCTT TTTTGTAAAA TGTTTTCGTG TCTTTGAAAT    2098

GCCTGTTGAA TATCTAGAGT TTAGTACCTC CTTCTACAAA CTTTTTTGAG TCTTTCTGGG    2158
```

( 2 ) INFORMATION FOR SEQ ID NO:4:

( i ) SEQUENCE CHARACTERISTICS:
            ( A ) LENGTH: 562 amino acids
            ( B ) TYPE: amino acid
            ( D ) TOPOLOGY: linear ( i i ) MOLECULE TYPE: protein ( x i ) SEQUENCE DESCRIPTION: SEQ ID NO:4:

```
Ser Leu Arg Ile Val Arg Asn Asn Phe Thr Leu Leu Thr Asn Leu His
 1               5                  10                  15

Gly Ala Pro Asn Lys Arg Ser Pro Ala Ala Ser Gln Ala Pro Val Thr
                20                  25                  30

Arg Val Ser Leu Gln Glu Glu Ser Tyr Gln Lys Leu Ala Met Glu Thr
             35                  40                  45

Leu Glu Glu Leu Asp Trp Cys Leu Asp Gln Leu Glu Thr Ile Gln Thr
 50                  55                  60

Tyr Arg Ser Val Ser Glu Met Ala Ser Asn Lys Phe Lys Arg Met Leu
 65                  70                  75                  80

Asn Arg Glu Leu Thr His Leu Ser Glu Met Ser Arg Ser Gly Asn Gln
                 85                  90                  95

Val Ser Glu Tyr Ile Ser Asn Thr Phe Leu Asp Lys Gln Asn Asp Val
            100                 105                 110

Glu Ile Pro Ser Pro Thr Gln Lys Asp Arg Glu Lys Lys Lys Lys Gln
         115                 120                 125

Gln Leu Met Thr Gln Ile Ser Gly Val Lys Lys Leu Met His Ser Ser
130                 135                 140

Ser Leu Asn Asn Thr Ser Ile Ser Arg Phe Gly Val Asn Thr Glu Asn
145                 150                 155                 160

Glu Asp His Leu Ala Lys Glu Leu Glu Asp Leu Asn Lys Trp Gly Leu
                165                 170                 175

Asn Ile Phe Asn Val Ala Gly Tyr Ser His Asn Arg Pro Leu Thr Cys
            180                 185                 190
```

```
Ile Met Tyr Ala Ile Phe Gln Glu Arg Asp Leu Leu Lys Thr Phe Lys
        195                 200                 205
Ile Ser Ser Asp Thr Phe Val Thr Tyr Met Met Thr Leu Glu Asp His
        210                 215                 220
Tyr His Ser Asp Val Ala Tyr His Asn Ser Leu His Ala Ala Asp Val
225                 230                 235                 240
Ala Gln Ser Thr His Val Leu Leu Ser Thr Pro Ala Leu Asp Ala Val
                245                 250                 255
Phe Thr Asp Leu Glu Ile Leu Ala Ala Ile Phe Ala Ala Ala Ile His
                260                 265                 270
Asp Val Asp His Pro Gly Val Ser Asn Gln Phe Leu Ile Asn Thr Asn
            275                 280                 285
Ser Glu Leu Ala Leu Met Tyr Asn Asp Glu Ser Val Leu Glu Asn His
    290                 295                 300
His Leu Ala Val Gly Phe Lys Leu Leu Gln Glu His Cys Asp Ile
305                 310                 315                 320
Phe Gln Asn Leu Thr Lys Lys Gln Arg Gln Thr Leu Arg Lys Met Val
                325                 330                 335
Ile Asp Met Val Leu Ala Thr Asp Met Ser Lys His Met Ser Leu Leu
            340                 345                 350
Ala Asp Leu Lys Thr Met Val Glu Thr Lys Lys Val Thr Ser Ser Gly
            355                 360                 365
Val Leu Leu Leu Asp Asn Tyr Thr Asp Arg Ile Gln Val Leu Arg Asn
370                 375                 380
Met Val His Cys Ala Asp Leu Ser Asn Pro Thr Lys Ser Leu Glu Leu
385                 390                 395                 400
Tyr Arg Gln Trp Thr Asp Arg Ile Met Glu Glu Phe Phe Gln Gln Gly
                405                 410                 415
Asp Lys Glu Arg Glu Arg Gly Met Glu Ile Ser Pro Met Cys Asp Lys
            420                 425                 430
His Thr Ala Ser Val Glu Lys Ser Gln Val Gly Phe Ile Asp Tyr Ile
        435                 440                 445
Val His Pro Leu Trp Glu Thr Trp Ala Asp Leu Val Gln Pro Asp Ala
    450                 455                 460
Gln Asp Ile Leu Asp Thr Leu Glu Asp Asn Arg Asn Trp Tyr Gln Ser
465                 470                 475                 480
Met Ile Pro Gln Ser Pro Ser Pro Pro Leu Asp Glu Arg Ser Arg Asp
                485                 490                 495
Cys Gln Gly Leu Met Glu Lys Phe Gln Phe Glu Leu Thr Leu Glu Glu
                500                 505                 510
Glu Asp Ser Glu Gly Pro Glu Lys Glu Gly Glu Gly Pro Asn Tyr Phe
            515                 520                 525
Ser Ser Thr Lys Thr Leu Cys Val Ile Asp Pro Glu Asn Arg Asp Ser
    530                 535                 540
Leu Glu Glu Thr Asp Ile Asp Ile Ala Thr Glu Asp Lys Ser Leu Ile
545                 550                 555                 560
Asp Thr
```

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CACCCTGCTG ACAAACCT                    18

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ATGGAGACGC TGGAGGAA                    18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:7:

ATACGCCACA TCAGAATG                    18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TACCAGAGTA TGATTCCC                    18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:9:

GTGTCGATCA GAGACTTG                    18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:10:

GCACACAGGT TGGCAGAC                    18

( 2 ) INFORMATION FOR SEQ ID NO:11:

( i ) SEQUENCE CHARACTERISTICS:
        ( A ) LENGTH: 2702 base pairs (B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 2..2701

(xi) SEQUENCE DESCRIPTION: SEQ ID NO:11:

| | | | | | | | | | | | | | | | | |
|---|---|---|---|---|---|---|---|---|---|---|---|---|---|---|---|---|
| A | AGC | TTG | CGG | CCG | CGC | GGC | CTA | GGC | CGC | ATC | CCG | GAG | CTG | CAA | CTG | 46 |
| | Ser | Leu | Arg | Pro | Arg | Gly | Leu | Gly | Arg | Ile | Pro | Glu | Leu | Gln | Leu | |
| | 1 | | | | 5 | | | | | 10 | | | | | 15 | |
| GTG | GCC | TTC | CCG | GTG | GCG | GTG | GCG | GCT | GAG | GAC | GAG | GCG | TTC | CTG | CCC | 94 |
| Val | Ala | Phe | Pro | Val | Ala | Val | Ala | Ala | Glu | Asp | Glu | Ala | Phe | Leu | Pro | |
| | | | | 20 | | | | | 25 | | | | | 30 | | |
| GAG | CCC | CTG | GCC | CCG | CGC | GCG | CCC | CGC | CGC | CGC | GTT | CGC | CGC | CCT | CCT | 142 |
| Glu | Pro | Leu | Ala | Pro | Arg | Ala | Pro | Arg | Arg | Arg | Val | Arg | Arg | Pro | Pro | |
| | | | 35 | | | | | 40 | | | | | 45 | | | |
| CGC | CCG | TCT | TCT | TCG | CCA | GCC | CGT | CCC | CAA | CTT | TCC | GCA | GAC | GCC | TTC | 190 |
| Arg | Pro | Ser | Ser | Ser | Pro | Ala | Arg | Pro | Gln | Leu | Ser | Ala | Asp | Ala | Phe | |
| | | 50 | | | | | 55 | | | | | 60 | | | | |
| GGC | TTC | TCC | GCA | GCT | GCC | AGG | ATT | TGG | GCC | GCC | AGG | CTT | GGG | CTG | GGG | 238 |
| Gly | Phe | Ser | Ala | Ala | Ala | Arg | Ile | Trp | Ala | Ala | Arg | Leu | Gly | Leu | Gly | |
| | 65 | | | | | 70 | | | | | 75 | | | | | |
| CTG | GCT | TCG | AGG | CAG | AGA | ATG | GGC | CGA | CAC | CAT | CTC | CTG | GCC | GCA | GCC | 286 |
| Leu | Ala | Ser | Arg | Gln | Arg | Met | Gly | Arg | His | His | Leu | Leu | Ala | Ala | Ala | |
| 80 | | | | | 85 | | | | | 90 | | | | | 95 | |
| CCT | GGA | CTG | CAG | GCG | AGC | CCA | GGA | CTC | GTG | CTG | CAC | GCC | GGG | GCG | GCC | 334 |
| Pro | Gly | Leu | Gln | Ala | Ser | Pro | Gly | Leu | Val | Leu | His | Ala | Gly | Ala | Ala | |
| | | | 100 | | | | | 105 | | | | | 110 | | | |
| ACC | AGC | CAG | CGC | CGG | GAG | TCC | TTC | CTG | TAC | CGC | TCA | GAC | AGC | GAC | TAT | 382 |
| Thr | Ser | Gln | Arg | Arg | Glu | Ser | Phe | Leu | Tyr | Arg | Ser | Asp | Ser | Asp | Tyr | |
| | | 115 | | | | | 120 | | | | | 125 | | | | |
| GAC | ATG | TCA | CCC | AAG | ACC | ATG | TCC | CGG | AAC | TCA | TCG | GTC | ACC | AGC | GAG | 430 |
| Asp | Met | Ser | Pro | Lys | Thr | Met | Ser | Arg | Asn | Ser | Ser | Val | Thr | Ser | Glu | |
| | 130 | | | | | 135 | | | | | 140 | | | | | |
| GCG | CAC | GCT | GAA | GAC | CTC | ATC | GTA | ACA | CCA | TTT | GCT | CAG | GTG | CTG | GCC | 478 |
| Ala | His | Ala | Glu | Asp | Leu | Ile | Val | Thr | Pro | Phe | Ala | Gln | Val | Leu | Ala | |
| 145 | | | | | 150 | | | | | 155 | | | | | | |
| AGC | CTC | CGG | AGC | GTC | CGT | AGC | AAC | TTC | TCA | CTC | CTG | ACC | AAT | GTG | CCC | 526 |
| Ser | Leu | Arg | Ser | Val | Arg | Ser | Asn | Phe | Ser | Leu | Leu | Thr | Asn | Val | Pro | |
| 160 | | | | | 165 | | | | | 170 | | | | | 175 | |
| GTT | CCC | AGT | AAC | AAG | CGG | TCC | CCG | CTG | GGC | GGC | CCC | ACC | CCT | GTC | TGC | 574 |
| Val | Pro | Ser | Asn | Lys | Arg | Ser | Pro | Leu | Gly | Gly | Pro | Thr | Pro | Val | Cys | |
| | | | | 180 | | | | | 185 | | | | | 190 | | |
| AAG | GCC | ACG | CTG | TCA | GAA | GAA | ACG | TGT | CAG | CAG | TTG | GCC | CGG | GAG | ACT | 622 |
| Lys | Ala | Thr | Leu | Ser | Glu | Glu | Thr | Cys | Gln | Gln | Leu | Ala | Arg | Glu | Thr | |
| | | | 195 | | | | | 200 | | | | | 205 | | | |
| CTG | GAG | GAG | CTG | GAC | TGG | TGT | CTG | GAG | CAG | CTG | GAG | ACC | ATG | CAG | ACC | 670 |
| Leu | Glu | Glu | Leu | Asp | Trp | Cys | Leu | Glu | Gln | Leu | Glu | Thr | Met | Gln | Thr | |
| | | 210 | | | | | 215 | | | | | 220 | | | | |
| TAT | CGC | TCT | GTC | AGC | GAG | ATG | GCC | TCG | CAC | AAG | TTC | AAA | AGG | ATG | TTG | 718 |
| Tyr | Arg | Ser | Val | Ser | Glu | Met | Ala | Ser | His | Lys | Phe | Lys | Arg | Met | Leu | |
| | 225 | | | | | 230 | | | | | 235 | | | | | |
| AAC | CGT | GAG | CTC | ACA | CAC | CTG | TCA | GAA | ATG | AGC | AGG | TCC | GGA | AAC | CAG | 766 |
| Asn | Arg | Glu | Leu | Thr | His | Leu | Ser | Glu | Met | Ser | Arg | Ser | Gly | Asn | Gln | |
| 240 | | | | | 245 | | | | | 250 | | | | | 255 | |
| GTC | TCA | GAG | TAC | ATT | TCC | ACA | ACA | TTC | CTG | GAC | AAA | CAG | AAT | GAA | GTG | 814 |
| Val | Ser | Glu | Tyr | Ile | Ser | Thr | Thr | Phe | Leu | Asp | Lys | Gln | Asn | Glu | Val | |
| | | | 260 | | | | | 265 | | | | | 270 | | | |

```
GAG ATC CCA TCA CCC ACG ATG AAG GAA CGA GAA AAA CAG CAA GCG CCG      862
Glu Ile Pro Ser Pro Thr Met Lys Glu Arg Glu Lys Gln Gln Ala Pro
            275             280                 285

CGA CCA AGA CCC TCC CAG CCG CCC CCG CCC CCT GTA CCA CAC TTA CAG      910
Arg Pro Arg Pro Ser Gln Pro Pro Pro Pro Pro Val Pro His Leu Gln
            290             295                 300

CCC ATG TCC CAA ATC ACA GGG TTG AAA AAG TTG ATG CAT AGT AAC AGC      958
Pro Met Ser Gln Ile Thr Gly Leu Lys Lys Leu Met His Ser Asn Ser
            305             310                 315

CTG AAC AAC TCT AAC ATT CCC CGA TTT GGG GTG AAG ACC GAT CAA GAA     1006
Leu Asn Asn Ser Asn Ile Pro Arg Phe Gly Val Lys Thr Asp Gln Glu
320             325             330                 335

GAG CTC CTG GCC CAA GAA CTG GAG AAC CTG AAC AAG TGG GGC CTG AAC     1054
Glu Leu Leu Ala Gln Glu Leu Glu Asn Leu Asn Lys Trp Gly Leu Asn
                340             345                 350

ATC TTT TGC GTG TCG GAT TAC GCT GGA GGC CGC TCA CTC ACC TGC ATC     1102
Ile Phe Cys Val Ser Asp Tyr Ala Gly Gly Arg Ser Leu Thr Cys Ile
            355             360                 365

ATG TAC ATG ATA TTC CAG GAG CGG GAC CTG CTG AAG AAA TTC CGC ATC     1150
Met Tyr Met Ile Phe Gln Glu Arg Asp Leu Leu Lys Lys Phe Arg Ile
            370             375                 380

CCT GTG GAC ACG ATG GTG ACA TAC ATG CTG ACG CTG GAG GAT CAC TAC     1198
Pro Val Asp Thr Met Val Thr Tyr Met Leu Thr Leu Glu Asp His Tyr
            385             390                 395

CAC GCT GAC GTG GCC TAC CAT AAC AGC CTG CAC GCA GCT GAC GTG CTG     1246
His Ala Asp Val Ala Tyr His Asn Ser Leu His Ala Ala Asp Val Leu
400             405             410                 415

CAG TCC ACC CAC GTA CTG CTG GCC ACG CCT TGG CCA ACC TTA AGG AAT     1294
Gln Ser Thr His Val Leu Leu Ala Thr Pro Trp Pro Thr Leu Arg Asn
            420             425                 430

GCA GTG TTC ACG GAC CTG GAG ATT CTC GCC GCC CTC TTC GCG GCT GCC     1342
Ala Val Phe Thr Asp Leu Glu Ile Leu Ala Ala Leu Phe Ala Ala Ala
            435             440                 445

ATC CAC GAT GTG GAT CAC CCT GGG GTC TCC AAC CAG TTC CTC ATC AAC     1390
Ile His Asp Val Asp His Pro Gly Val Ser Asn Gln Phe Leu Ile Asn
            450             455                 460

ACC AAT TCG GAG CTG GCG CTC ATG TAC AAC GAT GAG TCG GTG CTC GAG     1438
Thr Asn Ser Glu Leu Ala Leu Met Tyr Asn Asp Glu Ser Val Leu Glu
465             470             475

AAT CAC CAC CTG GCC GTG GGC TTC AAG CTG CTG CAG GAG GAC AAC TGC     1486
Asn His His Leu Ala Val Gly Phe Lys Leu Leu Gln Glu Asp Asn Cys
480             485             490                 495

GAC ATC TTC CAG AAC CTC AGC AAG CGC CAG CGG CAG AGC CTA CGC AAG     1534
Asp Ile Phe Gln Asn Leu Ser Lys Arg Gln Arg Gln Ser Leu Arg Lys
            500             505                 510

ATG GTC ATC GAC ATG GTG CTG GCC ACG GAC ATG TCC AAG CAC ATG ACC     1582
Met Val Ile Asp Met Val Leu Ala Thr Asp Met Ser Lys His Met Thr
            515             520                 525

CTC CTG GCT GAC CTG AAG ACC ATG GTG GAG ACC AAG AAA GTG ACC AGC     1630
Leu Leu Ala Asp Leu Lys Thr Met Val Glu Thr Lys Lys Val Thr Ser
            530             535                 540

TCA GGG GTC CTC CTG CTA GAT AAC TAC TCC GAC CGC ATC CAG GTC CTC     1678
Ser Gly Val Leu Leu Leu Asp Asn Tyr Ser Asp Arg Ile Gln Val Leu
545             550             555

CGG AAC ATG GTG CAC TGT GCC GAC CTC AGC AAC CCC ACC AAG CCG CTG     1726
Arg Asn Met Val His Cys Ala Asp Leu Ser Asn Pro Thr Lys Pro Leu
560             565             570                 575

GAG CTG TAC CGC CAG TGG ACA GAC CGC ATC ATG GCC GAG TTC TTC CAG     1774
Glu Leu Tyr Arg Gln Trp Thr Asp Arg Ile Met Ala Glu Phe Phe Gln
            580             585                 590
```

| | | | | | | | | | | | | | | | | |
|---|---|---|---|---|---|---|---|---|---|---|---|---|---|---|---|---|
| CAG | GGT | GAC | CGA | GAG | CGC | GAG | CGT | GGC | ATG | GAA | ATC | AGC | CCC | ATG | TGT | 1822 |
| Gln | Gly | Asp | Arg | Glu | Arg | Glu | Arg | Gly | Met | Glu | Ile | Ser | Pro | Met | Cys | |
| | | 595 | | | | 600 | | | | | 605 | | | | | |
| GAC | AAG | CAC | ACT | GCC | TCC | GTG | GAG | AAG | TCT | CAG | GTG | GGT | TTT | ATT | GAC | 1870 |
| Asp | Lys | His | Thr | Ala | Ser | Val | Glu | Lys | Ser | Gln | Val | Gly | Phe | Ile | Asp | |
| | 610 | | | | | 615 | | | | | 620 | | | | | |
| TAC | ATT | GTG | CAC | CCA | TTG | TGG | GAG | ACC | TGG | GCG | GAC | CTT | GTC | CAC | CCA | 1918 |
| Tyr | Ile | Val | His | Pro | Leu | Trp | Glu | Thr | Trp | Ala | Asp | Leu | Val | His | Pro | |
| 625 | | | | | 630 | | | | | 635 | | | | | | |
| GAT | GCC | CAG | GAG | ATC | TTG | GAC | ACT | TTG | GAG | GAC | AAC | CGG | GAC | TGG | TAC | 1966 |
| Asp | Ala | Gln | Glu | Ile | Leu | Asp | Thr | Leu | Glu | Asp | Asn | Arg | Asp | Trp | Tyr | |
| 640 | | | | | 645 | | | | | 650 | | | | | 655 | |
| TAC | AGC | GCC | ATC | CGG | CAG | AGC | CCA | TCT | CCG | CCA | CCC | GAG | GAG | GAG | TCA | 2014 |
| Tyr | Ser | Ala | Ile | Arg | Gln | Ser | Pro | Ser | Pro | Pro | Pro | Glu | Glu | Glu | Ser | |
| | | | | 660 | | | | | 665 | | | | | 670 | | |
| AGG | GGG | CCA | GGC | CAC | CCA | CCC | CTG | CCT | GAC | AAG | TTC | CAG | TTT | GAG | CTG | 2062 |
| Arg | Gly | Pro | Gly | His | Pro | Pro | Leu | Pro | Asp | Lys | Phe | Gln | Phe | Glu | Leu | |
| | | | 675 | | | | | 680 | | | | | 685 | | | |
| ACG | CTG | GAG | GAG | GAA | GAG | GAG | GAA | GAA | ATA | TCA | ATG | GCC | CAG | ATA | CCG | 2110 |
| Thr | Leu | Glu | Glu | Glu | Glu | Glu | Glu | Ile | Ser | Met | Ala | Gln | Ile | Pro | | |
| | | 690 | | | | | 695 | | | | | 700 | | | | |
| TGC | ACA | GCC | CAA | GAG | GCA | TTG | ACT | GAG | CAG | GGA | TTG | TCA | GGA | GTC | GAG | 2158 |
| Cys | Thr | Ala | Gln | Glu | Ala | Leu | Thr | Glu | Gln | Gly | Leu | Ser | Gly | Val | Glu | |
| | 705 | | | | | 710 | | | | | 715 | | | | | |
| GAA | GCT | CTG | GAT | GCA | ACC | ATA | GCC | TGG | GAG | GCA | TCC | CCG | GCC | CAG | GAG | 2206 |
| Glu | Ala | Leu | Asp | Ala | Thr | Ile | Ala | Trp | Glu | Ala | Ser | Pro | Ala | Gln | Glu | |
| 720 | | | | | 725 | | | | | 730 | | | | | 735 | |
| TCG | TTG | GAA | GTT | ATG | GCA | CAG | GAA | GCA | TCC | CTG | GAG | GCC | GAG | CTG | GAG | 2254 |
| Ser | Leu | Glu | Val | Met | Ala | Gln | Glu | Ala | Ser | Leu | Glu | Ala | Glu | Leu | Glu | |
| | | | | 740 | | | | | 745 | | | | | 750 | | |
| GCA | GTG | TAT | TTG | ACA | CAG | CAG | GCA | CAG | TCC | ACA | GGC | AGT | GCA | CCT | GTG | 2302 |
| Ala | Val | Tyr | Leu | Thr | Gln | Gln | Ala | Gln | Ser | Thr | Gly | Ser | Ala | Pro | Val | |
| | | | | 755 | | | | | 760 | | | | | 765 | | |
| GCT | CCG | GAT | GAG | TTC | TCG | TCC | CGG | GAG | GAA | TTC | GTG | GTT | GCT | GTA | AGC | 2350 |
| Ala | Pro | Asp | Glu | Phe | Ser | Ser | Arg | Glu | Glu | Phe | Val | Val | Ala | Val | Ser | |
| | | 770 | | | | | 775 | | | | | 780 | | | | |
| CAC | AGC | AGC | CCC | TCT | GCC | CTG | GCT | CTT | CAA | AGC | CCC | CTT | CTC | CCT | GCT | 2398 |
| His | Ser | Ser | Pro | Ser | Ala | Leu | Ala | Leu | Gln | Ser | Pro | Leu | Leu | Pro | Ala | |
| | 785 | | | | | 790 | | | | | 795 | | | | | |
| TGG | AGG | ACC | CTG | TCT | GTT | TCA | GAG | CAT | GCC | CGG | CCT | CCC | GGG | CCT | CCC | 2446 |
| Trp | Arg | Thr | Leu | Ser | Val | Ser | Glu | His | Ala | Arg | Pro | Pro | Gly | Pro | Pro | |
| 800 | | | | | 805 | | | | | 810 | | | | | 815 | |
| CTC | CAC | GGC | GGC | CGA | GGT | GGA | GGC | CCA | ACG | AGA | GCA | CCA | GGC | TGC | CAA | 2494 |
| Leu | His | Gly | Gly | Arg | Gly | Gly | Gly | Pro | Thr | Arg | Ala | Pro | Gly | Cys | Gln | |
| | | | | 820 | | | | | 825 | | | | | 830 | | |
| GAG | GGC | TTG | CAG | TGC | CTG | CGC | AGG | GAC | ATT | TGG | GGA | GGA | CAC | ATC | CGC | 2542 |
| Glu | Gly | Leu | Gln | Cys | Leu | Arg | Arg | Asp | Ile | Trp | Gly | Gly | His | Ile | Arg | |
| | | | 835 | | | | | 840 | | | | | 845 | | | |
| ACT | CCC | AGC | TCC | TGG | TGG | CGG | GGG | GTC | AGG | TGG | AGA | CCC | TAC | CTG | ATC | 2590 |
| Thr | Pro | Ser | Ser | Trp | Trp | Arg | Gly | Val | Arg | Trp | Arg | Pro | Tyr | Leu | Ile | |
| | | 850 | | | | | 855 | | | | | 860 | | | | |
| CCC | AGA | CCT | CTG | TCC | CTG | TTC | CCC | TCC | ACT | CCT | CCC | CTC | ACT | CCC | CTG | 2638 |
| Pro | Arg | Pro | Leu | Ser | Leu | Phe | Pro | Ser | Thr | Pro | Pro | Leu | Thr | Pro | Leu | |
| | 865 | | | | | 870 | | | | | 875 | | | | | |
| CTC | CCC | CGA | CCA | CCT | CCT | CCT | CTG | CCT | CAA | AGA | CTC | TTG | TCC | TCT | TGT | 2686 |
| Leu | Pro | Arg | Pro | Pro | Pro | Pro | Leu | Pro | Gln | Arg | Leu | Leu | Ser | Ser | Cys | |
| 880 | | | | | 885 | | | | | 890 | | | | | 895 | |
| CCG | CGG | CCG | CAA | GCT | T | | | | | | | | | | | 2702 |
| Pro | Arg | Pro | Gln | Ala | | | | | | | | | | | | |
| | | | | 900 | | | | | | | | | | | | |

( 2 ) INFORMATION FOR SEQ ID NO:12:

( i ) SEQUENCE CHARACTERISTICS:
        ( A ) LENGTH: 900 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Ser Leu Arg Pro Arg Gly Leu Gly Arg Ile Pro Glu Leu Gln Leu Val
 1               5                  10                 15

Ala Phe Pro Val Ala Val Ala Ala Glu Asp Glu Ala Phe Leu Pro Glu
                20                  25                 30

Pro Leu Ala Pro Arg Ala Pro Arg Arg Arg Val Arg Arg Pro Pro Arg
            35                  40                 45

Pro Ser Ser Ser Pro Ala Arg Pro Gln Leu Ser Ala Asp Ala Phe Gly
        50                  55                 60

Phe Ser Ala Ala Ala Arg Ile Trp Ala Ala Arg Leu Gly Leu Gly Leu
 65                 70                  75                 80

Ala Ser Arg Gln Arg Met Gly Arg His His Leu Leu Ala Ala Ala Pro
                85                  90                 95

Gly Leu Gln Ala Ser Pro Gly Leu Val Leu His Ala Gly Ala Ala Thr
                100                 105                110

Ser Gln Arg Arg Glu Ser Phe Leu Tyr Arg Ser Asp Ser Asp Tyr Asp
            115                 120                125

Met Ser Pro Lys Thr Met Ser Arg Asn Ser Ser Val Thr Ser Glu Ala
    130                 135                 140

His Ala Glu Asp Leu Ile Val Thr Pro Phe Ala Gln Val Leu Ala Ser
145                 150                 155                160

Leu Arg Ser Val Arg Ser Asn Phe Ser Leu Leu Thr Asn Val Pro Val
                165                 170                175

Pro Ser Asn Lys Arg Ser Pro Leu Gly Gly Pro Thr Pro Val Cys Lys
                180                 185                190

Ala Thr Leu Ser Glu Glu Thr Cys Gln Gln Leu Ala Arg Glu Thr Leu
            195                 200                205

Glu Glu Leu Asp Trp Cys Leu Glu Gln Leu Glu Thr Met Gln Thr Tyr
    210                 215                 220

Arg Ser Val Ser Glu Met Ala Ser His Lys Phe Lys Arg Met Leu Asn
225                 230                 235                240

Arg Glu Leu Thr His Leu Ser Glu Met Ser Arg Ser Gly Asn Gln Val
                245                 250                255

Ser Glu Tyr Ile Ser Thr Thr Phe Leu Asp Lys Gln Asn Glu Val Glu
                260                 265                270

Ile Pro Ser Pro Thr Met Lys Glu Arg Glu Lys Gln Gln Ala Pro Arg
            275                 280                285

Pro Arg Pro Ser Gln Pro Pro Pro Pro Val Pro His Leu Gln Pro
    290                 295                 300

Met Ser Gln Ile Thr Gly Leu Lys Lys Leu Met His Ser Asn Ser Leu
305                 310                 315                320

Asn Asn Ser Asn Ile Pro Arg Phe Gly Val Lys Thr Asp Gln Glu Glu
                325                 330                335

Leu Leu Ala Gln Glu Leu Glu Asn Leu Asn Lys Trp Gly Leu Asn Ile
            340                 345                350

Phe Cys Val Ser Asp Tyr Ala Gly Gly Arg Ser Leu Thr Cys Ile Met
            355                 360                365
```

```
Tyr  Met  Ile  Phe  Gln  Glu  Arg  Asp  Leu  Leu  Lys  Lys  Phe  Arg  Ile  Pro
     370                 375                 380

Val  Asp  Thr  Met  Val  Thr  Tyr  Met  Leu  Thr  Leu  Glu  Asp  His  Tyr  His
385                      390                 395                           400

Ala  Asp  Val  Ala  Tyr  His  Asn  Ser  Leu  His  Ala  Ala  Asp  Val  Leu  Gln
                    405                 410                      415

Ser  Thr  His  Val  Leu  Leu  Ala  Thr  Pro  Trp  Pro  Thr  Leu  Arg  Asn  Ala
               420                 425                           430

Val  Phe  Thr  Asp  Leu  Glu  Ile  Leu  Ala  Ala  Leu  Phe  Ala  Ala  Ala  Ile
               435                 440                 445

His  Asp  Val  Asp  His  Pro  Gly  Val  Ser  Asn  Gln  Phe  Leu  Ile  Asn  Thr
     450                 455                 460

Asn  Ser  Glu  Leu  Ala  Leu  Met  Tyr  Asn  Asp  Glu  Ser  Val  Leu  Glu  Asn
465                      470                 475                           480

His  His  Leu  Ala  Val  Gly  Phe  Lys  Leu  Leu  Gln  Glu  Asp  Asn  Cys  Asp
                    485                 490                      495

Ile  Phe  Gln  Asn  Leu  Ser  Lys  Arg  Gln  Arg  Gln  Ser  Leu  Arg  Lys  Met
               500                 505                           510

Val  Ile  Asp  Met  Val  Leu  Ala  Thr  Asp  Met  Ser  Lys  His  Met  Thr  Leu
               515                 520                      525

Leu  Ala  Asp  Leu  Lys  Thr  Met  Val  Glu  Thr  Lys  Lys  Val  Thr  Ser  Ser
530                      535                 540

Gly  Val  Leu  Leu  Leu  Asp  Asn  Tyr  Ser  Asp  Arg  Ile  Gln  Val  Leu  Arg
545                      550                 555                           560

Asn  Met  Val  His  Cys  Ala  Asp  Leu  Ser  Asn  Pro  Thr  Lys  Pro  Leu  Glu
                    565                 570                      575

Leu  Tyr  Arg  Gln  Trp  Thr  Asp  Arg  Ile  Met  Ala  Glu  Phe  Phe  Gln  Gln
               580                 585                           590

Gly  Asp  Arg  Glu  Arg  Glu  Arg  Gly  Met  Glu  Ile  Ser  Pro  Met  Cys  Asp
               595                 600                      605

Lys  His  Thr  Ala  Ser  Val  Glu  Lys  Ser  Gln  Val  Gly  Phe  Ile  Asp  Tyr
     610                 615                      620

Ile  Val  His  Pro  Leu  Trp  Glu  Thr  Trp  Ala  Asp  Leu  Val  His  Pro  Asp
625                      630                 635                           640

Ala  Gln  Glu  Ile  Leu  Asp  Thr  Leu  Glu  Asp  Asn  Arg  Asp  Trp  Tyr  Tyr
                    645                 650                      655

Ser  Ala  Ile  Arg  Gln  Ser  Pro  Ser  Pro  Pro  Glu  Glu  Glu  Ser  Arg
               660                 665                      670

Gly  Pro  Gly  His  Pro  Pro  Leu  Pro  Asp  Lys  Phe  Gln  Phe  Glu  Leu  Thr
               675                 680                      685

Leu  Glu  Glu  Glu  Glu  Glu  Glu  Ile  Ser  Met  Ala  Gln  Ile  Pro  Cys
     690                 695                 700

Thr  Ala  Gln  Glu  Ala  Leu  Thr  Glu  Gln  Gly  Leu  Ser  Gly  Val  Glu  Glu
705                      710                 715                           720

Ala  Leu  Asp  Ala  Thr  Ile  Ala  Trp  Glu  Ala  Ser  Pro  Ala  Gln  Glu  Ser
                    725                 730                      735

Leu  Glu  Val  Met  Ala  Gln  Glu  Ala  Ser  Leu  Glu  Ala  Glu  Leu  Glu  Ala
               740                 745                      750

Val  Tyr  Leu  Thr  Gln  Gln  Ala  Gln  Ser  Thr  Gly  Ser  Ala  Pro  Val  Ala
               755                 760                      765

Pro  Asp  Glu  Phe  Ser  Ser  Arg  Glu  Glu  Phe  Val  Val  Ala  Val  Ser  His
     770                 775                      780

Ser  Ser  Pro  Ser  Ala  Leu  Ala  Leu  Gln  Ser  Pro  Leu  Leu  Pro  Ala  Trp
```

```
785                        790                           795                              800
Arg Thr Leu Ser Val Ser Glu His Ala Arg Pro Pro Gly Pro Pro Leu
                805                   810                       815

His Gly Gly Arg Gly Gly Gly Pro Thr Arg Ala Pro Gly Cys Gln Glu
                820                   825                       830

Gly Leu Gln Cys Leu Arg Arg Asp Ile Trp Gly Gly His Ile Arg Thr
                835                   840                       845

Pro Ser Ser Trp Trp Arg Gly Val Arg Trp Arg Pro Tyr Leu Ile Pro
    850                       855                   860

Arg Pro Leu Ser Leu Phe Pro Ser Thr Pro Pro Leu Thr Pro Leu Leu
865                     870                   875                   880

Pro Arg Pro Pro Pro Pro Leu Pro Gln Arg Leu Leu Ser Ser Cys Pro
                885                   890                       895

Arg Pro Gln Ala
            900
```

( 2 ) INFORMATION FOR SEQ ID NO:13:

( i ) SEQUENCE CHARACTERISTICS:
       ( A ) LENGTH: 1721 base pairs
       ( B ) TYPE: nucleic acid
       ( C ) STRANDEDNESS: single
       ( D ) TOPOLOGY: linear ( i i ) MOLECULE TYPE: cDNA ( i x ) FEATURE:
       ( A ) NAME/KEY: CDS
       ( B ) LOCATION: 60..1274

( x i ) SEQUENCE DESCRIPTION: SEQ ID NO:13:

```
AAGCTTGCGG  CCGCATTGGG  TACCGCGTGC  CAGCAGGCAG  TGGCCCTAGC  CTTCCGCCT              59

ATG CCC TCC CTC CAA GAG GTG GAC TGC GGC TCC CCC AGC AGC TCC GAG                   107
Met Pro Ser Leu Gln Glu Val Asp Cys Gly Ser Pro Ser Ser Ser Glu
 1               5                   10                  15

GAG GAG GGG GTG CCA GGG TCC CGG GGG AGC CCA GCG ACC TCA CCC CAC                   155
Glu Glu Gly Val Pro Gly Ser Arg Gly Ser Pro Ala Thr Ser Pro His
             20                  25                  30

CTG GGC CGC CGA CGA CCT CTG CTT CGG TCC ATG AGC GCC GCC TTC TGC                   203
Leu Gly Arg Arg Arg Pro Leu Leu Arg Ser Met Ser Ala Ala Phe Cys
         35                  40                  45

TCC CTA CTG GCA CCG GAG CGG CAG GTG GGC CGG GCT GCG GCA GCA CTG                   251
Ser Leu Leu Ala Pro Glu Arg Gln Val Gly Arg Ala Ala Ala Ala Leu
     50                  55                  60

ATG CAG GAC CGA CAC ACA GCC GCG GGC CAG CTG GTG CAG GAC CTA CTG                   299
Met Gln Asp Arg His Thr Ala Ala Gly Gln Leu Val Gln Asp Leu Leu
 65              70                  75                  80

ACC CAG GTG CGG GAT GGG CAG AGG CCC CAG GAG CTC GAG GGC ATC CGT                   347
Thr Gln Val Arg Asp Gly Gln Arg Pro Gln Glu Leu Glu Gly Ile Arg
             85                  90                  95

CAG GCG CTG AGC CGG GCC CGG GCC ATG CTG AGT GCG GAG CTG GGC CCT                   395
Gln Ala Leu Ser Arg Ala Arg Ala Met Leu Ser Ala Glu Leu Gly Pro
         100                 105                 110

GAG AAG CTC GTG TCG CCT AAG AGG CTG GAA CAT GTC CTG GAG AAG TCA                   443
Glu Lys Leu Val Ser Pro Lys Arg Leu Glu His Val Leu Glu Lys Ser
     115                 120                 125

TTG CAT TGC TCT GTG CTC AAG CCT CTC CGG CCC ATC CTG GCA GCC CGC                   491
Leu His Cys Ser Val Leu Lys Pro Leu Arg Pro Ile Leu Ala Ala Arg
 130                 135                 140

CTG CGG CGC CGG CTT GCC GCA GAC GGC TCC CTG GGC CGC CTA GCT GAG                   539
Leu Arg Arg Arg Leu Ala Ala Asp Gly Ser Leu Gly Arg Leu Ala Glu
```

-continued

| | | | | | | | | | | | | | | | | |
|---|---|---|---|---|---|---|---|---|---|---|---|---|---|---|---|---|
| 145 | | | | | 150 | | | | | 155 | | | | | 160 | |
| GGC | CTC | CGC | CTG | GCC | CGG | GCC | CAG | GGC | CCC | GGA | GCC | TTC | GGG | TCC | CAC | 587 |
| Gly | Leu | Arg | Leu | Ala | Arg | Ala | Gln | Gly | Pro | Gly | Ala | Phe | Gly | Ser | His | |
| | | | 165 | | | | | 170 | | | | | 175 | | | |
| CTG | AGC | CTG | CCC | TCC | CCA | GTA | GAG | TTG | GAG | CAA | GTG | CGC | CAG | AAG | CTG | 635 |
| Leu | Ser | Leu | Pro | Ser | Pro | Val | Glu | Leu | Glu | Gln | Val | Arg | Gln | Lys | Leu | |
| | | | 180 | | | | | 185 | | | | | 190 | | | |
| CTG | CAG | CTC | GTC | CGC | ACC | TAC | TCA | CCC | AGC | GCC | CAG | GTC | AAG | CGG | CTC | 683 |
| Leu | Gln | Leu | Val | Arg | Thr | Tyr | Ser | Pro | Ser | Ala | Gln | Val | Lys | Arg | Leu | |
| | | | 195 | | | | | 200 | | | | | 205 | | | |
| CTG | CAG | GCC | TGC | AAG | CTG | CTC | TAC | ATG | GCC | CTG | AGG | ACC | CAG | GAA | GGG | 731 |
| Leu | Gln | Ala | Cys | Lys | Leu | Leu | Tyr | Met | Ala | Leu | Arg | Thr | Gln | Glu | Gly | |
| | | 210 | | | | | 215 | | | | | 220 | | | | |
| GAG | GGC | TCG | GGT | GCC | GAC | GGG | TTC | CTG | CCT | CTG | CTG | AGC | CTC | GTC | TTG | 779 |
| Glu | Gly | Ser | Gly | Ala | Asp | Gly | Phe | Leu | Pro | Leu | Leu | Ser | Leu | Val | Leu | |
| 225 | | | | | 230 | | | | | 235 | | | | | 240 | |
| GCC | CAC | TGT | GAC | CTT | CCT | GAG | CTG | CTG | CTG | GAG | GCC | GAG | TAC | ATG | TCG | 827 |
| Ala | His | Cys | Asp | Leu | Pro | Glu | Leu | Leu | Leu | Glu | Ala | Glu | Tyr | Met | Ser | |
| | | | | 245 | | | | | 250 | | | | | 255 | | |
| GAG | CTG | CTG | GAG | CCC | AGC | CTG | CTT | ACT | GGA | GAG | GGT | GGC | TAC | TAC | CTG | 875 |
| Glu | Leu | Leu | Glu | Pro | Ser | Leu | Leu | Thr | Gly | Glu | Gly | Gly | Tyr | Tyr | Leu | |
| | | | 260 | | | | | 265 | | | | | 270 | | | |
| ACC | AGC | CTC | TCT | GCC | AGC | CTG | GCC | CTG | CTG | AGT | GGC | CTG | GGT | CAG | GCC | 923 |
| Thr | Ser | Leu | Ser | Ala | Ser | Leu | Ala | Leu | Leu | Ser | Gly | Leu | Gly | Gln | Ala | |
| | | | 275 | | | | | 280 | | | | | 285 | | | |
| CAC | ACC | CTC | CCA | CTG | AGC | CCC | GTG | CAG | GAG | CTA | CGG | CGC | TCC | CTC | AGC | 971 |
| His | Thr | Leu | Pro | Leu | Ser | Pro | Val | Gln | Glu | Leu | Arg | Arg | Ser | Leu | Ser | |
| | | 290 | | | | | 295 | | | | | 300 | | | | |
| CTC | TGG | GAG | CAG | CGC | CGC | CTG | CCT | GCC | ACC | CAC | TGC | TTC | CAG | CAC | CTC | 1019 |
| Leu | Trp | Glu | Gln | Arg | Arg | Leu | Pro | Ala | Thr | His | Cys | Phe | Gln | His | Leu | |
| 305 | | | | | 310 | | | | | 315 | | | | | 320 | |
| CTC | CGA | GTA | GCC | TAT | CAG | GAT | CCC | AGC | AGT | GGC | TGC | ACC | TCC | AAG | ACC | 1067 |
| Leu | Arg | Val | Ala | Tyr | Gln | Asp | Pro | Ser | Ser | Gly | Cys | Thr | Ser | Lys | Thr | |
| | | | | 325 | | | | | 330 | | | | | 335 | | |
| CTG | GCC | GTG | CCC | CCA | GAG | GCC | TCG | ATT | GCC | ACC | CTG | AAC | CAG | CTC | TGT | 1115 |
| Leu | Ala | Val | Pro | Pro | Glu | Ala | Ser | Ile | Ala | Thr | Leu | Asn | Gln | Leu | Cys | |
| | | | 340 | | | | | 345 | | | | | 350 | | | |
| GCC | ACC | AAG | TTC | CGA | GTG | ACC | CAG | CCC | AAC | ACT | TTT | GGC | CTC | TTC | CTG | 1163 |
| Ala | Thr | Lys | Phe | Arg | Val | Thr | Gln | Pro | Asn | Thr | Phe | Gly | Leu | Phe | Leu | |
| | | 355 | | | | | 360 | | | | | 365 | | | | |
| TAC | AAG | GAG | CAG | GGC | TAC | CAC | CGC | CTG | CCC | CCT | GGG | CCC | TGG | CCC | ACA | 1211 |
| Tyr | Lys | Glu | Gln | Gly | Tyr | His | Arg | Leu | Pro | Pro | Gly | Pro | Trp | Pro | Thr | |
| | | 370 | | | | | 375 | | | | | 380 | | | | |
| GGC | TGC | CCA | CCA | CTG | GCT | ACC | TCG | TCT | ACC | GCC | GGG | CAG | AGT | GGC | CTG | 1259 |
| Gly | Cys | Pro | Pro | Leu | Ala | Thr | Ser | Ser | Thr | Ala | Gly | Gln | Ser | Gly | Leu | |
| 385 | | | | | 390 | | | | | 395 | | | | | 400 | |
| AGA | CCC | AGG | GGG | CTG | TGACAGAGGA | | | GGAGGGCAGT | | | GGGCAGTCAG | | | AGGCAAGAAG | | 1314 |
| Arg | Pro | Arg | Gly | Leu | | | | | | | | | | | | |
| | | | | 405 | | | | | | | | | | | | |

CAGAGGGGAG GAGCAAGGGT GCCAGGGAGA TGGGGATGCT GGGGTCAAAG CCAGCCCCAG    1374

GGACATTCGG GAACAGTCTG AGACAACTGC TGAAGGGGGC CAGGGTCAAG CCCAGGAAGG    1434

CCCTGCTCAG CCAGGGGAAC CAGAGGCAGA GGGAAGCCGG GCAGCAGAGG AGTAGCTTGA    1494

AGTGGCCAGA AGGGTCATTC GGGGCGGGAG ACCCTGAGCC TGCTGAGAAA TCCTTTTAGC    1554

GCCAGCAAGC CCCACCCAGG GCCCTGTCCT GTGTCTGCCA CCACCTTTGT CTGATACTTG    1614

TTTCCAGGGA AGCTGGGGGA ACTGCCACAT CTGAGGAACT GGAATAAAGA TGAGGGGCCT    1674

TCGGGGGCCA ATGCGGCCGC CGCGGCCTTT TTGGCCAGCT CGAATTC    1721

(2) INFORMATION FOR SEQ ID NO:14:

(i) SEQUENCE CHARACTERISTICS:
    (A) LENGTH: 405 amino acids
    (B) TYPE: amino acid
    (D) TOPOLOGY: linear (ii) MOLECULE TYPE: protein (xi) SEQUENCE DESCRIPTION: SEQ ID NO:14:

```
Met Pro Ser Leu Gln Glu Val Asp Cys Gly Ser Pro Ser Ser Ser Glu
 1               5                  10                  15

Glu Glu Gly Val Pro Gly Ser Arg Gly Ser Pro Ala Thr Ser Pro His
                20                  25                  30

Leu Gly Arg Arg Arg Pro Leu Leu Arg Ser Met Ser Ala Ala Phe Cys
            35                  40                  45

Ser Leu Leu Ala Pro Glu Arg Gln Val Gly Arg Ala Ala Ala Ala Leu
     50                  55                  60

Met Gln Asp Arg His Thr Ala Ala Gly Gln Leu Val Gln Asp Leu Leu
65                  70                  75                  80

Thr Gln Val Arg Asp Gly Gln Arg Pro Gln Glu Leu Glu Gly Ile Arg
                 85                  90                  95

Gln Ala Leu Ser Arg Ala Arg Ala Met Leu Ser Ala Glu Leu Gly Pro
            100                 105                 110

Glu Lys Leu Val Ser Pro Lys Arg Leu Glu His Val Leu Glu Lys Ser
        115                 120                 125

Leu His Cys Ser Val Leu Lys Pro Leu Arg Pro Ile Leu Ala Ala Arg
    130                 135                 140

Leu Arg Arg Arg Leu Ala Ala Asp Gly Ser Leu Gly Arg Leu Ala Glu
145                 150                 155                 160

Gly Leu Arg Leu Ala Arg Ala Gln Gly Pro Gly Ala Phe Gly Ser His
                165                 170                 175

Leu Ser Leu Pro Ser Pro Val Glu Leu Glu Gln Val Arg Gln Lys Leu
            180                 185                 190

Leu Gln Leu Val Arg Thr Tyr Ser Pro Ser Ala Gln Val Lys Arg Leu
        195                 200                 205

Leu Gln Ala Cys Lys Leu Leu Tyr Met Ala Leu Arg Thr Gln Glu Gly
    210                 215                 220

Glu Gly Ser Gly Ala Asp Gly Phe Leu Pro Leu Leu Ser Leu Val Leu
225                 230                 235                 240

Ala His Cys Asp Leu Pro Glu Leu Leu Leu Glu Ala Glu Tyr Met Ser
                245                 250                 255

Glu Leu Leu Glu Pro Ser Leu Leu Thr Gly Glu Gly Gly Tyr Tyr Leu
            260                 265                 270

Thr Ser Leu Ser Ala Ser Leu Ala Leu Leu Ser Gly Leu Gly Gln Ala
        275                 280                 285

His Thr Leu Pro Leu Ser Pro Val Gln Glu Leu Arg Arg Ser Leu Ser
    290                 295                 300

Leu Trp Glu Gln Arg Arg Leu Pro Ala Thr His Cys Phe Gln His Leu
305                 310                 315                 320

Leu Arg Val Ala Tyr Gln Asp Pro Ser Ser Gly Cys Thr Ser Lys Thr
                325                 330                 335

Leu Ala Val Pro Pro Glu Ala Ser Ile Ala Thr Leu Asn Gln Leu Cys
            340                 345                 350

Ala Thr Lys Phe Arg Val Thr Gln Pro Asn Thr Phe Gly Leu Phe Leu
        355                 360                 365
```

```
Tyr Lys Glu Gln Gly Tyr His Arg Leu Pro Pro Gly Pro Trp Pro Thr
    370                 375                 380

Gly Cys Pro Pro Leu Ala Thr Ser Ser Thr Ala Gly Gln Ser Gly Leu
385                 390                 395                 400

Arg Pro Arg Gly Leu
            405
```

( 2 ) INFORMATION FOR SEQ ID NO:15:

( i ) SEQUENCE CHARACTERISTICS:
        ( A ) LENGTH: 1829 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 30..1421

( x i ) SEQUENCE DESCRIPTION: SEQ ID NO:15:

```
GCGGCCGCGG CCGGCAGCGG CTGAGCGAC ATG AGC ATT TCT ACT TCC TCC TCC      53
                                Met Ser Ile Ser Thr Ser Ser Ser
                                 1               5

GAC TCG CTG GAG TTC GAC CGG AGC ATG CCT CTG TTT GGC TAC GAG GCG     101
Asp Ser Leu Glu Phe Asp Arg Ser Met Pro Leu Phe Gly Tyr Glu Ala
         10                  15                  20

GAC ACC AAC AGC AGC CTG GAG GAC TAC GAG GGG GAA AGT GAC CAA GAG     149
Asp Thr Asn Ser Ser Leu Glu Asp Tyr Glu Gly Glu Ser Asp Gln Glu
 25                  30                  35                  40

ACC ATG GCG CCC CCC ATC AAG TCC AAA AAG AAA AGG AGC AGC TCC TTC     197
Thr Met Ala Pro Pro Ile Lys Ser Lys Lys Lys Arg Ser Ser Ser Phe
                 45                  50                  55

GTG CTG CCC AAG CTC GTC AAG TCC CAG CTG CAG AAG GTG AGC GGG GTG     245
Val Leu Pro Lys Leu Val Lys Ser Gln Leu Gln Lys Val Ser Gly Val
         60                  65                  70

TTC AGC TCC TTC ATG ACC CCG GAG AAG CGG ATG GTC CGC AGG ATC GCC     293
Phe Ser Ser Phe Met Thr Pro Glu Lys Arg Met Val Arg Arg Ile Ala
     75                  80                  85

GAG CTT TCC CGG GAC AAA TGC ACC TAC TTC GGG TGC TTA GTG CAG GAC     341
Glu Leu Ser Arg Asp Lys Cys Thr Tyr Phe Gly Cys Leu Val Gln Asp
 90                  95                 100

TAC GTG AGC TTC CTG CAG GAG AAC AAG GAG TGC CAC GTG TCC AGC ACC     389
Tyr Val Ser Phe Leu Gln Glu Asn Lys Glu Cys His Val Ser Ser Thr
105                 110                 115                 120

GAC ATG CTG CAG ACC ATC CGG CAG TTC ATG ACC CAG GTC AAG AAC TAT     437
Asp Met Leu Gln Thr Ile Arg Gln Phe Met Thr Gln Val Lys Asn Tyr
                125                 130                 135

TTG TCT CAG AGC TCG GAG CTG GAC CCC CCC ATC GAG TCG CTG ATC CCT     485
Leu Ser Gln Ser Ser Glu Leu Asp Pro Pro Ile Glu Ser Leu Ile Pro
        140                 145                 150

GAA GAC CAA ATA GAT GTG GTG CTG GAA AAA GCC ATG CAC AAG TGC ATC     533
Glu Asp Gln Ile Asp Val Val Leu Glu Lys Ala Met His Lys Cys Ile
    155                 160                 165

TTG AAG CCC CTC AAG GGG CAC GTG GAG GCC ATG CTG AAG GAC TTT CAC     581
Leu Lys Pro Leu Lys Gly His Val Glu Ala Met Leu Lys Asp Phe His
170                 175                 180

ATG GCC GAT GGC TCA TGG AAG CAA CTC AAG GAG AAC CTG CAG CTT GTG     629
Met Ala Asp Gly Ser Trp Lys Gln Leu Lys Glu Asn Leu Gln Leu Val
185                 190                 195                 200

CGG CAG AGG AAT CCG CAG GAG CTG GGG GTC TTC GCC CCG ACC CCT GAT     677
```

```
        Arg Gln Arg Asn Pro Gln Glu Leu Gly Val Phe Ala Pro Thr Pro Asp
                    205                 210                 215

TTT GTG GAT GTG GAG AAA ATC AAA GTC AAG TTC ATG ACC ATG CAG AAG           725
Phe Val Asp Val Glu Lys Ile Lys Val Lys Phe Met Thr Met Gln Lys
            220                 225                 230

ATG TAT TCG CCG GAA AAG AAG GTC ATG CTG CTG CTG CGG GTC TGC AAG           773
Met Tyr Ser Pro Glu Lys Lys Val Met Leu Leu Leu Arg Val Cys Lys
            235                 240                 245

CTC ATT TAC ACG GTC ATG GAG AAC AAC TCA GGG AGG ATG TAT GGC GCT           821
Leu Ile Tyr Thr Val Met Glu Asn Asn Ser Gly Arg Met Tyr Gly Ala
            250                 255                 260

GAT GAC TTC TTG CCA GTC CTG ACC TAT GTC ATA GCC CAG TGT GAC ATG           869
Asp Asp Phe Leu Pro Val Leu Thr Tyr Val Ile Ala Gln Cys Asp Met
265                 270                 275                 280

CTT GAA TTG GAC ACT GAA ATC GAG TAC ATG ATG GAG CTC CTA GAC CCA           917
Leu Glu Leu Asp Thr Glu Ile Glu Tyr Met Met Glu Leu Leu Asp Pro
                285                 290                 295

TCG CTG TTA CAT GGA GAA GGA GGC TAT TAC TTG ACA AGC GCA TAT GGA           965
Ser Leu Leu His Gly Glu Gly Gly Tyr Tyr Leu Thr Ser Ala Tyr Gly
            300                 305                 310

GCA CTT TCT CTG ATA AAG AAT TTC CAA GAA GAA CAA GCA GCG CGA CTG          1013
Ala Leu Ser Leu Ile Lys Asn Phe Gln Glu Glu Gln Ala Ala Arg Leu
            315                 320                 325

CTC AGC TCA GAA ACC AGA GAC ACC CTG AGG CAG TGG CAC AAA CGG AGA          1061
Leu Ser Ser Glu Thr Arg Asp Thr Leu Arg Gln Trp His Lys Arg Arg
            330                 335                 340

ACC ACC AAC CGG ACC ATC CCC TCT GTG GAC GAC TTC CAG AAT TAC CTC          1109
Thr Thr Asn Arg Thr Ile Pro Ser Val Asp Asp Phe Gln Asn Tyr Leu
345                 350                 355                 360

CGA GTT GCA TTT CAG GAG GTC AAC AGT GGT TGC ACA GGA AAG ACC CTC          1157
Arg Val Ala Phe Gln Glu Val Asn Ser Gly Cys Thr Gly Lys Thr Leu
            365                 370                 375

CTT GTG AGA CCT TAC ATC ACC ACT GAG GAT GTG TGT CAG ATC TGC GCT          1205
Leu Val Arg Pro Tyr Ile Thr Thr Glu Asp Val Cys Gln Ile Cys Ala
            380                 385                 390

GAG AAG TTC AAG GTG GGG GAC CCT GAG GAG TAC AGC CTC TTT CTC TTC          1253
Glu Lys Phe Lys Val Gly Asp Pro Glu Glu Tyr Ser Leu Phe Leu Phe
            395                 400                 405

GTT GAC GAG ACA TGG CAG CAG CTG GCA GAG GAC ACT TAC CCT CAA AAA          1301
Val Asp Glu Thr Trp Gln Gln Leu Ala Glu Asp Thr Tyr Pro Gln Lys
    410                 415                 420

ATC AAG GCG GAG CTG CAC AGC CGA CCA CAG CCC CAC ATC TTC CAC TTT          1349
Ile Lys Ala Glu Leu His Ser Arg Pro Gln Pro His Ile Phe His Phe
425                 430                 435                 440

GTC TAC AAA CGC ATC AAG AAC GAT CCT TAT GGC ATC ATT TTC CAG AAC          1397
Val Tyr Lys Arg Ile Lys Asn Asp Pro Tyr Gly Ile Ile Phe Gln Asn
            445                 450                 455

GGG GAA GAA GAC CTC ACC ACC TCC TAGAAGACAG GCGGGACTTC CCAGTGGTGC         1451
Gly Glu Glu Asp Leu Thr Thr Ser
            460

ATCCAAAGGG GAGCTGGAAG CCTTGCCTTC CCGCTTCTAC ATGCTTGAGC TTGAAAAGCA        1511

GTCACCTCCT CGGGGACCCC TCAGTGTAGT GACTAAGCCA TCCACAGGCC AACTCGGCCA        1571

AGGGCAACTT TAGCCACGCA AGGTAGCTGA GGTTTGTGAA ACAGTAGGAT TCTCTTTTGG        1631

CAATGGAGAA TTGCATCTGA TGGTTCAAGT GTCCTGAGAT TGTTTGCTAC CTACCCCCAG        1691

TCAGGTTCTA GGTTGGCTTA CAGGTATGTA TATGTGCAGA AGAAACACTT AAGATACAAG        1751

TTCTTTTGAA TTCAACAGCA GATGCTTGCG ATGCAGTGCG TCAGGTGATT CTCACTCCTG        1811

TGGATGGCTT CATCCCTG                                                      1829
```

( 2 ) INFORMATION FOR SEQ ID NO:16:

( i ) SEQUENCE CHARACTERISTICS:
        ( A ) LENGTH: 464 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Ser Ile Ser Thr Ser Ser Ser Asp Ser Leu Glu Phe Asp Arg Ser
 1               5                  10                  15

Met Pro Leu Phe Gly Tyr Glu Ala Asp Thr Asn Ser Ser Leu Glu Asp
            20                  25                  30

Tyr Glu Gly Glu Ser Asp Gln Glu Thr Met Ala Pro Pro Ile Lys Ser
        35                  40                  45

Lys Lys Lys Arg Ser Ser Ser Phe Val Leu Pro Lys Leu Val Lys Ser
50                  55                  60

Gln Leu Gln Lys Val Ser Gly Val Phe Ser Ser Phe Met Thr Pro Glu
65                  70                  75                  80

Lys Arg Met Val Arg Arg Ile Ala Glu Leu Ser Arg Asp Lys Cys Thr
                85                  90                  95

Tyr Phe Gly Cys Leu Val Gln Asp Tyr Val Ser Phe Leu Gln Glu Asn
            100                 105                 110

Lys Glu Cys His Val Ser Ser Thr Asp Met Leu Gln Thr Ile Arg Gln
        115                 120                 125

Phe Met Thr Gln Val Lys Asn Tyr Leu Ser Gln Ser Ser Glu Leu Asp
130                 135                 140

Pro Pro Ile Glu Ser Leu Ile Pro Glu Asp Gln Ile Asp Val Val Leu
145                 150                 155                 160

Glu Lys Ala Met His Lys Cys Ile Leu Lys Pro Leu Lys Gly His Val
                165                 170                 175

Glu Ala Met Leu Lys Asp Phe His Met Ala Asp Gly Ser Trp Lys Gln
            180                 185                 190

Leu Lys Glu Asn Leu Gln Leu Val Arg Gln Arg Asn Pro Gln Glu Leu
        195                 200                 205

Gly Val Phe Ala Pro Thr Pro Asp Phe Val Asp Val Glu Lys Ile Lys
210                 215                 220

Val Lys Phe Met Thr Met Gln Lys Met Tyr Ser Pro Glu Lys Lys Val
225                 230                 235                 240

Met Leu Leu Leu Arg Val Cys Lys Leu Ile Tyr Thr Val Met Glu Asn
                245                 250                 255

Asn Ser Gly Arg Met Tyr Gly Ala Asp Asp Phe Leu Pro Val Leu Thr
            260                 265                 270

Tyr Val Ile Ala Gln Cys Asp Met Leu Glu Leu Asp Thr Glu Ile Glu
        275                 280                 285

Tyr Met Met Glu Leu Leu Asp Pro Ser Leu Leu His Gly Glu Gly Gly
290                 295                 300

Tyr Tyr Leu Thr Ser Ala Tyr Gly Ala Leu Ser Leu Ile Lys Asn Phe
305                 310                 315                 320

Gln Glu Glu Gln Ala Ala Arg Leu Leu Ser Ser Glu Thr Arg Asp Thr
                325                 330                 335

Leu Arg Gln Trp His Lys Arg Arg Thr Thr Asn Arg Thr Ile Pro Ser
            340                 345                 350

Val Asp Asp Phe Gln Asn Tyr Leu Arg Val Ala Phe Gln Glu Val Asn
```

```
                      355                         360                         365
Ser  Gly  Cys  Thr  Gly  Lys  Thr  Leu  Leu  Val  Arg  Pro  Tyr  Ile  Thr  Thr
     370                      375                      380

Glu  Asp  Val  Cys  Gln  Ile  Cys  Ala  Glu  Lys  Phe  Lys  Val  Gly  Asp  Pro
385                      390                      395                      400

Glu  Glu  Tyr  Ser  Leu  Phe  Leu  Phe  Val  Asp  Glu  Thr  Trp  Gln  Gln  Leu
               405                      410                      415

Ala  Glu  Asp  Thr  Tyr  Pro  Gln  Lys  Ile  Lys  Ala  Glu  Leu  His  Ser  Arg
               420                      425                      430

Pro  Gln  Pro  His  Ile  Phe  His  Phe  Val  Tyr  Lys  Arg  Ile  Lys  Asn  Asp
          435                      440                      445

Pro  Tyr  Gly  Ile  Ile  Phe  Gln  Asn  Gly  Glu  Glu  Asp  Leu  Thr  Thr  Ser
     450                      455                      460
```

( 2 ) INFORMATION FOR SEQ ID NO:17:

( i ) SEQUENCE CHARACTERISTICS:
        ( A ) LENGTH: 1299 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1299

( x i ) SEQUENCE DESCRIPTION: SEQ ID NO:17:

```
GGC  CGC  ATT  GCC  GAC  CCG  GCC  CGT  AGT  GTG  GAA  GCA  GCT  TCA  GCT  CAA    48
Gly  Arg  Ile  Ala  Asp  Pro  Ala  Arg  Ser  Val  Glu  Ala  Ala  Ser  Ala  Gln
1                   5                        10                       15

AGA  TTA  GAA  CGA  CTC  CGA  AAA  GAG  AGA  CAA  AAC  CAG  ATC  AAA  TGC  AAA    96
Arg  Leu  Glu  Arg  Leu  Arg  Lys  Glu  Arg  Gln  Asn  Gln  Ile  Lys  Cys  Lys
               20                       25                       30

AAT  ATT  CAG  TGG  AAA  GAA  AGA  AAT  TCT  AAG  CAA  TCA  GCC  CAG  GAG  TTA   144
Asn  Ile  Gln  Trp  Lys  Glu  Arg  Asn  Ser  Lys  Gln  Ser  Ala  Gln  Glu  Leu
          35                       40                       45

AAG  TCA  CTG  TTT  GAA  AAA  AAA  TCT  CTC  AAA  GAG  AAG  CCT  CCA  ATT  TCT   192
Lys  Ser  Leu  Phe  Glu  Lys  Lys  Ser  Leu  Lys  Glu  Lys  Pro  Pro  Ile  Ser
     50                       55                       60

GGG  AAG  CAG  TCG  ATA  TTA  TCT  GTA  CGC  CTA  GAA  CAG  TGC  CCT  CTG  CAG   240
Gly  Lys  Gln  Ser  Ile  Leu  Ser  Val  Arg  Leu  Glu  Gln  Cys  Pro  Leu  Gln
65                       70                       75                       80

CTG  AAT  AAC  CCT  TTT  AAC  GAG  TAT  TCC  AAA  TTT  GAT  GGC  AAG  GGT  CAT   288
Leu  Asn  Asn  Pro  Phe  Asn  Glu  Tyr  Ser  Lys  Phe  Asp  Gly  Lys  Gly  His
                    85                       90                       95

GTA  GGT  ACA  ACA  GCA  ACC  AAG  AAG  ATC  GAT  GTC  TAC  CTC  CCT  CTG  CAC   336
Val  Gly  Thr  Thr  Ala  Thr  Lys  Lys  Ile  Asp  Val  Tyr  Leu  Pro  Leu  His
               100                      105                      110

TCG  AGC  CAG  GAC  AGA  CTG  CTG  CCA  ATG  ACC  GTG  GTG  ACA  ATG  GCC  AGC   384
Ser  Ser  Gln  Asp  Arg  Leu  Leu  Pro  Met  Thr  Val  Val  Thr  Met  Ala  Ser
          115                      120                      125

GCC  AGG  GTG  CAG  GAC  CTG  ATC  GGG  CTC  ATC  TGC  TGG  CAG  TAT  ACA  AGC   432
Ala  Arg  Val  Gln  Asp  Leu  Ile  Gly  Leu  Ile  Cys  Trp  Gln  Tyr  Thr  Ser
     130                      135                      140

GAA  GGA  CGG  GAG  CCG  AAG  CTC  AAT  GAC  AAT  GTC  AGT  GCC  TAC  TGC  CTG   480
Glu  Gly  Arg  Glu  Pro  Lys  Leu  Asn  Asp  Asn  Val  Ser  Ala  Tyr  Cys  Leu
145                      150                      155                      160

CAT  ATT  GCT  GAG  GAT  GAT  GGG  GAG  GTG  GAC  ACC  GAT  TTC  CCC  CCG  CTG   528
His  Ile  Ala  Glu  Asp  Asp  Gly  Glu  Val  Asp  Thr  Asp  Phe  Pro  Pro  Leu
                    165                      170                      175
```

| | | | | | | | | | | | | | | | | |
|---|---|---|---|---|---|---|---|---|---|---|---|---|---|---|---|---|
| GAT | TCC | AAT | GAG | CCC | ATT | CAT | AAG | TTT | GGC | TTC | AGT | ACT | TTG | GCC | CTG | 576 |
| Asp | Ser | Asn | Glu | Pro | Ile | His | Lys | Phe | Gly | Phe | Ser | Thr | Leu | Ala | Leu | |
| | | | 180 | | | | 185 | | | | | 190 | | | | |
| GTT | GAA | AAG | TAC | TCA | TCT | CCT | GGT | CTG | ACA | TCC | AAA | GAG | TCA | CTC | TTT | 624 |
| Val | Glu | Lys | Tyr | Ser | Ser | Pro | Gly | Leu | Thr | Ser | Lys | Glu | Ser | Leu | Phe | |
| | | 195 | | | | | 200 | | | | | 205 | | | | |
| GTT | CGA | ATA | AAT | GCT | GCT | CAT | GGA | TTC | TCC | CTT | ATT | CAG | GTG | GAC | AAC | 672 |
| Val | Arg | Ile | Asn | Ala | Ala | His | Gly | Phe | Ser | Leu | Ile | Gln | Val | Asp | Asn | |
| | | 210 | | | | | 215 | | | | | 220 | | | | |
| ACA | AAG | GTT | ACC | ATG | AAG | GAA | ATC | TTA | CTG | AAG | GCA | GTG | AAG | CGA | AGA | 720 |
| Thr | Lys | Val | Thr | Met | Lys | Glu | Ile | Leu | Leu | Lys | Ala | Val | Lys | Arg | Arg | |
| 225 | | | | | 230 | | | | | 235 | | | | | 240 | |
| AAA | GGA | TCC | CAG | AAA | GTT | TCA | GGC | CCT | CAG | TAC | CGC | CTG | GAG | AAG | CAG | 768 |
| Lys | Gly | Ser | Gln | Lys | Val | Ser | Gly | Pro | Gln | Tyr | Arg | Leu | Glu | Lys | Gln | |
| | | | | 245 | | | | | 250 | | | | | 255 | | |
| AGC | GAG | CCC | AAT | GTC | GCC | GTT | GAC | CTG | GAC | AGC | ACT | TTG | GAG | AGC | CAG | 816 |
| Ser | Glu | Pro | Asn | Val | Ala | Val | Asp | Leu | Asp | Ser | Thr | Leu | Glu | Ser | Gln | |
| | | | 260 | | | | | 265 | | | | | 270 | | | |
| AGC | GCA | TGG | GAG | TTC | TGC | CTG | GTC | CGC | GAG | AAC | AGT | TCA | AGG | GCA | GAC | 864 |
| Ser | Ala | Trp | Glu | Phe | Cys | Leu | Val | Arg | Glu | Asn | Ser | Ser | Arg | Ala | Asp | |
| | | 275 | | | | | 280 | | | | | 285 | | | | |
| GGG | GTT | TTT | GAG | GAG | GAT | TCG | CAA | ATT | GAC | ATA | GCC | ACA | GTA | CAG | GAT | 912 |
| Gly | Val | Phe | Glu | Glu | Asp | Ser | Gln | Ile | Asp | Ile | Ala | Thr | Val | Gln | Asp | |
| | | 290 | | | | | 295 | | | | | 300 | | | | |
| ATG | CTT | AGC | AGC | CAC | CAT | TAC | AAG | TCA | TTC | AAA | GTC | AGC | ATG | ATC | CAC | 960 |
| Met | Leu | Ser | Ser | His | His | Tyr | Lys | Ser | Phe | Lys | Val | Ser | Met | Ile | His | |
| 305 | | | | | 310 | | | | | 315 | | | | | 320 | |
| AGA | CTG | CGA | TTC | ACA | ACC | GAC | GTA | CAG | CTA | GGT | ATC | TCT | GGA | GAC | AAA | 1008 |
| Arg | Leu | Arg | Phe | Thr | Thr | Asp | Val | Gln | Leu | Gly | Ile | Ser | Gly | Asp | Lys | |
| | | | | 325 | | | | | 330 | | | | | 335 | | |
| GTA | GAG | ATA | GAC | CCT | GTT | ACG | AAT | CAG | AAA | GCC | AGC | ACT | AAG | TTT | TGG | 1056 |
| Val | Glu | Ile | Asp | Pro | Val | Thr | Asn | Gln | Lys | Ala | Ser | Thr | Lys | Phe | Trp | |
| | | | 340 | | | | | 345 | | | | | 350 | | | |
| ATT | AAG | CAG | AAA | CCC | ATC | TCA | ATC | GAT | TCC | GAC | CTG | CTC | TGT | GCC | TGT | 1104 |
| Ile | Lys | Gln | Lys | Pro | Ile | Ser | Ile | Asp | Ser | Asp | Leu | Leu | Cys | Ala | Cys | |
| | | 355 | | | | | 360 | | | | | 365 | | | | |
| GAC | CTT | GCT | GAA | GAG | AAA | AGC | CCC | AGT | CAC | GCA | ATA | TTT | AAA | CTC | ACG | 1152 |
| Asp | Leu | Ala | Glu | Glu | Lys | Ser | Pro | Ser | His | Ala | Ile | Phe | Lys | Leu | Thr | |
| | 370 | | | | | 375 | | | | | 380 | | | | | |
| TAT | CTA | AGC | AAT | CAC | GAC | TAT | AAA | CAC | CTC | TAC | TTT | GAA | TCG | GAC | GCT | 1200 |
| Tyr | Leu | Ser | Asn | His | Asp | Tyr | Lys | His | Leu | Tyr | Phe | Glu | Ser | Asp | Ala | |
| 385 | | | | | 390 | | | | | 395 | | | | | 400 | |
| GCT | ACC | GTC | AAT | GAA | ATT | GTG | CTC | AAG | GTT | AAC | TAC | ATC | CTG | GAA | TCG | 1248 |
| Ala | Thr | Val | Asn | Glu | Ile | Val | Leu | Lys | Val | Asn | Tyr | Ile | Leu | Glu | Ser | |
| | | | | 405 | | | | | 410 | | | | | 415 | | |
| CGA | GCT | AGC | ACT | GCC | CGG | GCT | GAC | TAC | TTT | GCT | CAA | AAA | AAA | AGC | GGC | 1296 |
| Arg | Ala | Ser | Thr | Ala | Arg | Ala | Asp | Tyr | Phe | Ala | Gln | Lys | Lys | Ser | Gly | |
| | | | 420 | | | | | 425 | | | | | 430 | | | |
| CGC | | | | | | | | | | | | | | | | 1299 |
| Arg | | | | | | | | | | | | | | | | |

( 2 ) INFORMATION FOR SEQ ID NO:18:

( i ) SEQUENCE CHARACTERISTICS:
        ( A ) LENGTH: 433 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| | | | | | | | | | | | | | | | |
|---|---|---|---|---|---|---|---|---|---|---|---|---|---|---|---|
| Gly | Arg | Ile | Ala | Asp | Pro | Ala | Arg | Ser | Val | Glu | Ala | Ala | Ser | Ala | Gln |
| 1 | | | | 5 | | | | | 10 | | | | | 15 | |
| Arg | Leu | Glu | Arg | Leu | Arg | Lys | Glu | Arg | Gln | Asn | Gln | Ile | Lys | Cys | Lys |
| | | | 20 | | | | | 25 | | | | | 30 | | |
| Asn | Ile | Gln | Trp | Lys | Glu | Arg | Asn | Ser | Lys | Gln | Ser | Ala | Gln | Glu | Leu |
| | | 35 | | | | | 40 | | | | | 45 | | | |
| Lys | Ser | Leu | Phe | Glu | Lys | Lys | Ser | Leu | Lys | Glu | Lys | Pro | Pro | Ile | Ser |
| | 50 | | | | | 55 | | | | | 60 | | | | |
| Gly | Lys | Gln | Ser | Ile | Leu | Ser | Val | Arg | Leu | Glu | Gln | Cys | Pro | Leu | Gln |
| 65 | | | | | 70 | | | | | 75 | | | | | 80 |
| Leu | Asn | Asn | Pro | Phe | Asn | Glu | Tyr | Ser | Lys | Phe | Asp | Gly | Lys | Gly | His |
| | | | | 85 | | | | | 90 | | | | | 95 | |
| Val | Gly | Thr | Thr | Ala | Thr | Lys | Lys | Ile | Asp | Val | Tyr | Leu | Pro | Leu | His |
| | | | 100 | | | | | 105 | | | | | 110 | | |
| Ser | Ser | Gln | Asp | Arg | Leu | Leu | Pro | Met | Thr | Val | Val | Thr | Met | Ala | Ser |
| | | | 115 | | | | 120 | | | | | 125 | | | |
| Ala | Arg | Val | Gln | Asp | Leu | Ile | Gly | Leu | Ile | Cys | Trp | Gln | Tyr | Thr | Ser |
| | 130 | | | | | 135 | | | | | 140 | | | | |
| Glu | Gly | Arg | Glu | Pro | Lys | Leu | Asn | Asp | Asn | Val | Ser | Ala | Tyr | Cys | Leu |
| 145 | | | | | 150 | | | | | 155 | | | | | 160 |
| His | Ile | Ala | Glu | Asp | Asp | Gly | Glu | Val | Asp | Thr | Asp | Phe | Pro | Pro | Leu |
| | | | | 165 | | | | | 170 | | | | | 175 | |
| Asp | Ser | Asn | Glu | Pro | Ile | His | Lys | Phe | Gly | Phe | Ser | Thr | Leu | Ala | Leu |
| | | | 180 | | | | | 185 | | | | | 190 | | |
| Val | Glu | Lys | Tyr | Ser | Ser | Pro | Gly | Leu | Thr | Ser | Lys | Glu | Ser | Leu | Phe |
| | | 195 | | | | | 200 | | | | | 205 | | | |
| Val | Arg | Ile | Asn | Ala | Ala | His | Gly | Phe | Ser | Leu | Ile | Gln | Val | Asp | Asn |
| | 210 | | | | | 215 | | | | | 220 | | | | |
| Thr | Lys | Val | Thr | Met | Lys | Glu | Ile | Leu | Leu | Lys | Ala | Val | Lys | Arg | Arg |
| 225 | | | | | 230 | | | | | 235 | | | | | 240 |
| Lys | Gly | Ser | Gln | Lys | Val | Ser | Gly | Pro | Gln | Tyr | Arg | Leu | Glu | Lys | Gln |
| | | | | 245 | | | | | 250 | | | | | 255 | |
| Ser | Glu | Pro | Asn | Val | Ala | Val | Asp | Leu | Asp | Ser | Thr | Leu | Glu | Ser | Gln |
| | | | 260 | | | | | 265 | | | | | 270 | | |
| Ser | Ala | Trp | Glu | Phe | Cys | Leu | Val | Arg | Glu | Asn | Ser | Ser | Arg | Ala | Asp |
| | | 275 | | | | | 280 | | | | | 285 | | | |
| Gly | Val | Phe | Glu | Glu | Asp | Ser | Gln | Ile | Asp | Ile | Ala | Thr | Val | Gln | Asp |
| | 290 | | | | | 295 | | | | | 300 | | | | |
| Met | Leu | Ser | Ser | His | His | Tyr | Lys | Ser | Phe | Lys | Val | Ser | Met | Ile | His |
| 305 | | | | | 310 | | | | | 315 | | | | | 320 |
| Arg | Leu | Arg | Phe | Thr | Thr | Asp | Val | Gln | Leu | Gly | Ile | Ser | Gly | Asp | Lys |
| | | | | 325 | | | | | 330 | | | | | 335 | |
| Val | Glu | Ile | Asp | Pro | Val | Thr | Asn | Gln | Lys | Ala | Ser | Thr | Lys | Phe | Trp |
| | | | 340 | | | | | 345 | | | | | 350 | | |
| Ile | Lys | Gln | Lys | Pro | Ile | Ser | Ile | Asp | Ser | Asp | Leu | Leu | Cys | Ala | Cys |
| | | 355 | | | | | 360 | | | | | 365 | | | |
| Asp | Leu | Ala | Glu | Glu | Lys | Ser | Pro | Ser | His | Ala | Ile | Phe | Lys | Leu | Thr |
| | 370 | | | | | 375 | | | | | 380 | | | | |
| Tyr | Leu | Ser | Asn | His | Asp | Tyr | Lys | His | Leu | Tyr | Phe | Glu | Ser | Asp | Ala |
| 385 | | | | | 390 | | | | | 395 | | | | | 400 |
| Ala | Thr | Val | Asn | Glu | Ile | Val | Leu | Lys | Val | Asn | Tyr | Ile | Leu | Glu | Ser |
| | | | | 405 | | | | | 410 | | | | | 415 | |
| Arg | Ala | Ser | Thr | Ala | Arg | Ala | Asp | Tyr | Phe | Ala | Gln | Lys | Lys | Ser | Gly |
| | | | 420 | | | | | 425 | | | | | 430 | | |

Arg ( 2 ) INFORMATION FOR SEQ ID NO:19:

( i ) SEQUENCE CHARACTERISTICS:
        ( A ) LENGTH: 3987 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..1498

( x i ) SEQUENCE DESCRIPTION: SEQ ID NO:19:

```
GGCGGCCGCG GCAGGGCGGG CGCCGCGCGG AGGCAGGGCG GGCGTATTCA ATGGAAGTGT      60
GTTACCAGCT GCCGGTACTG CCCCTGGACA GGCCGGTCCC CAGCACGTC  CTCAGCCGCC     120
GAGGAGCCAT CAGCTTCAGC TCCAGCTCCG CTCTCTTCGG CTGCCCCAAT CCCCGGCAGC     180
TCTCTCAGAG GCGTGGAGCT ATTTCCTATG ACAGTTCTGA TCAGACTGCA TTATACATTC     240
GTATGCTAGG AGATGTACGT GTAAGGAGCC GAGCAGGATT TGAATCAGAA AGAAGAGGTT     300
CTCACCCATA TATTGATTTT CGTATTTTCC ACTCTCAATC TGAAATTGAA GTGTCTGTCT     360
CTGCAAGGAA TATCAGAAGG CTACTAAGTT CCAGCGATA  TCTTAGATCT TCACGCTTTT     420
TTCGTGGTAC TGCGGTTTCA AATTCCCTAA ACATTTTAGA TGATGATTAT AATGGACAAG     480
CCAAGTGTAT GCTGGAAAAA GTTGGAAATT GGAATTTTGA TATCTTTCTA TTTGATAGAC     540
TAACAAATGG AAATAGTCTA GTAAGCTTAA CCTTTCATTT ATTTAGTCTT CATGGATTAA     600
TTGAGTACTT CCATTTAGAT ATGATGAAAC TTCGTAGATT TTTAGTTATG ATTCAAGAAG     660
ATTACCACAG TCAAAATCCT TACCATAACG CAGTCCACGC TGCGGATGTT ACTCAGGCCA     720
TGCACTGTTA CTTAAAGGAA CCTAAGCTTG CCAATTCTGT AACTCCTTGG GATATCTTGC     780
TGAGCTTAAT TGCAGCTGCC ACTCATGATC TGGATCATCC AGGTGTTAAT CAACCTTTCC     840
TTATTAAAAC TAACCATTAC TTGGCAACTT TATACAAGAA TACCTCAGTA CTGGAAAATC     900
ACCACTGGAG ATCTGCAGTG GGCTTATTGA GAGAATCAGG CTTATTCTCA CATCTGCCAT     960
TAGAAAGCAG GCAACAAATG GAGACACAGA TAGGTGCTCT GATACTAGCC ACAGACATCA    1020
GTCGCCAGAA TGAGTATCTG TCTTTGTTTA GGTCCCATTT GGATAGAGGT GATTTATGCC    1080
TAGAAGACAC CAGACACAGA CATTTGGTTT ACAGATGGC  TTTGAAATGT GCTGATATTT    1140
GTAACCCATG TCGGACGTGG GAATTAAGCA AGCAGTGGAG TGAAAAAGTA ACGGAGGAAT    1200
TCTTCCATCA AGGAGATATA GAAAAAAAT  ATCATTTGGG TGTGAGTCCA CTTTGCGATC    1260
GTCACACTGA ATCTATTGCC AACATCCAGA TTGGTTTTAT GACTTACCTA GTGGAGCCTT    1320
TATTTACAGA ATGGGCCAGG TTTTCCAATA CAAGGCTATC CCAGACAATG CTTGGACACG    1380
TGGGGCTGAA TAAAGCCAGC TGGAAGGGAC TGCAGAGAGA ACAGTCGAGC AGTGAGGACA    1440
CTGATGCTGC ATTTGAGTTG AACTCACAGT TATTACCTCA GGAAAATCGG TTATCATAAC    1500
CCCCAGAACC AGTGGGACAA ACTGCCTCCT GGAGGTTTTT AGAAATGTGA AATGGGGTCT    1560
TGAGGTGAGA GAACTTAACT CTTGACTGCC AAGGTTTCCA AGTGAGTGAT GCCAGCCAGC    1620
ATTATTTATT TCCAAGATTT CCTCTGTTGG ATCATTTGAA CCCACTTGTT AATTGCAAGA    1680
CCCGAACATA CAGCAATATG AATTTGGCTT TCATGTGAAA CCTTGAATAT NNAAAGCCCA    1740
GCAGGAGAGA ATCCGAAAGG AGTAACAAAG GAAGTTTTGA TATGTGCCAC GACTTTTTCA    1800
```

-continued

| | | | | | | |
|---|---|---|---|---|---|---|
| AAGCATCTAA | TCTTCAAAAC | GTCAAACTTG | AATTGTTCAG | CAACAATCTC | TTGGAATTTA | 1860 |
| ACCAGTCTGA | TGCAACAATG | TGTATCTTGT | ACCTTCCACT | AAGTTCTCTC | TGAGAAAATG | 1920 |
| GAAATGTGAA | GTGCCAGCC | TCTGCNTGCC | TCTGGCAAGA | CAATGTTTAC | AAATCAACTC | 1980 |
| TGAAAATATT | GGTTCTAAAT | TGCCTTGGAG | CATGATTGTG | AAGGAACCAC | TCAAACAAAT | 2040 |
| TTAAAGATCA | AACTTAGAC | TGCAGCTCTT | TCCCCCTGGT | TTGCCTTTTT | CTTCTTTGGA | 2100 |
| TGCCACCAAA | GCCTCCCATT | TGCTATAGTT | TTATTTCATG | CACTGGAAAC | TGAGCATTTA | 2160 |
| TCGTAGAGTA | CCGCCAAGCT | TTCACTCCAG | TGCCGTTTGG | CAATGCAATT | TTTTTAGCA | 2220 |
| ATTAGTTTTT | AATTTGGGGT | GGGAGGGGAA | GAACACCAAT | GTCCTAGCTG | TATTATGATT | 2280 |
| CTGCACTCAA | GACATTGCAT | GTTGTTTTCA | CTACTGTACA | CTTGACCTGC | ACATGCGAGA | 2340 |
| AAAAGGTGGA | ATGTTTAAAA | CACCATAATC | AGCTCAGNGT | ATTTGCCAAT | CTGAAATAAA | 2400 |
| AGTGGGATGG | GAGAGCGTGT | CCTTCAGATC | AAGGGTACTA | AAGTCCCTTT | CGCTGCAGTG | 2460 |
| AGTGAGAGGT | ATGTTGTGTG | TGAATGTACG | GATGTGTGTT | TGNTGNATG | TTTGTGCATG | 2520 |
| TGTGACNGTG | CATGTTATGT | TTCTCCATGT | GGGCAAAGAT | TTGAAANGTA | AGCTTTTATT | 2580 |
| TATTATTTTA | GAATGTGACA | TAATGAGCAG | CCACACTCGG | GGGAGGGGAA | GGTTGGTAGG | 2640 |
| TAAGCTGTAA | CAGATTGCTC | CAGTTGCCTT | AAACTATGCA | CATAGCTAAG | TGACCAAACT | 2700 |
| TCTTGTTTTG | ATTTGAAAAA | AGTGCATTGT | TTTCTTGTCC | CTCCCTTTGA | TGAAACGTTA | 2760 |
| CCCTTTGACG | GGCCTTTTGA | TGTGAACAGA | TGTTTTCTAG | GACAAACTAT | AAGGACTAAT | 2820 |
| TTTAAACTTC | AAACATTCCA | CTTTTGTAAT | TTGTTTTAAA | TTGTTTTATG | TATAGTAAGC | 2880 |
| ACAACTGTAA | TCTAGTTTTA | AGAGAAACCG | GTGCTTTCTT | TTAGTTCATT | TGTATTTCCC | 2940 |
| TTGTTACTGT | AAAAGACTGT | TTATTAATTG | TTTACAGTTT | GTTGCAACAG | CCATTTTCTT | 3000 |
| GGGAGAAAGC | TTGAGTGTAA | AGCCATTTGT | AAAAGGCTTT | GCCATACTCA | TTTTAATATG | 3060 |
| TGCCTGTTGC | TGTTAACTTT | TGATGAATAA | AAACCTATCT | TTTCATGAAA | CTTCTCTCTA | 3120 |
| TACAAATTGA | AATACATAAT | GCTTTCTGGT | TCTTCTTCAA | ACCAAAACTT | GTCAAATTCA | 3180 |
| TAGACAAGAT | AACAGTAAAA | CTGATGAAAG | TGTTCCATTG | TTGGTATACC | AGGAACAAGG | 3240 |
| TTATAGAGAT | GAAACTTCAA | AGCTTCACTC | TTCAGTAAGC | TATAAGCCAT | CTCTGTAAGA | 3300 |
| TTGATTCCAA | CTATTGCATA | AGAATACCCT | AATTTTGGAT | GATTTGAACG | GAAAGAATC | 3360 |
| TGATGAGCTT | CACTAGTGTA | ATTTTCACTG | AAATACACAA | GATTGATTAA | CCCAAGTATG | 3420 |
| CCCATGCCTC | TGAAGTCTGT | CTTGGGATCA | TCACCCTGAA | AACCAATTTC | AGCCCACTGC | 3480 |
| TTGGAGATTC | TAGCGTTTAA | CTTCTTCGTG | GGCATTAGAA | GATTCCAAAG | CTTCATGAGT | 3540 |
| AGCTCTTCAT | GCTGTAGGTT | ATCAGAATCA | TATGGCCTTT | TCCTCACACT | TTCTACATCC | 3600 |
| AAATACAGCT | GTTTATAACC | AGTTATCTGC | AGTAAGCACA | TCTTCATGCA | TATTTAAAA | 3660 |
| CTGGCATCCT | TCTCAGGGTT | AATATTCTTT | TCCTTCATAA | TATCATCTAC | ATATTTGTCC | 3720 |
| ACTTCACTCT | GAACAACATG | TGTCGCCTTC | TGTAAAACCT | TATTCTTGGA | GTATGTCAAG | 3780 |
| GAATTTTCTA | TCCTGTGTGT | CCTTTGTGCA | CCTACATAGG | TATCAAATAT | TCGCTGCAAT | 3840 |
| TCACACTTCC | CAGTCATCTG | TCGTAATAGC | CATTTCATCC | AAAATCGAAA | AAAGTGCCCA | 3900 |
| TAGAAGAACT | CCCACAAAGA | AATAAACATT | TTTTTTTCCT | CACAGGAGCG | GAAGAACTAG | 3960 |
| GGGGAGCAGG | AGCTGCAATG | CGGCCGC | | | | 3987 |

( 2 ) INFORMATION FOR SEQ ID NO:20:

( i ) SEQUENCE CHARACTERISTICS:
        ( A ) LENGTH: 498 amino acids
        ( B ) TYPE: amino acid ( C ) STRANDEDNESS: single
( D ) TOPOLOGY: linear ( x i ) SEQUENCE DESCRIPTION: SEQ ID NO:20:

```
Arg Pro Arg Gln Gly Gly Arg Arg Ala Glu Ala Gly Arg Ala Tyr Ser
1               5                   10                  15

Met Glu Val Cys Tyr Gln Leu Pro Val Leu Pro Leu Asp Arg Pro Val
            20                  25                  30

Pro Gln His Val Leu Ser Arg Arg Gly Ala Ile Ser Phe Ser Ser Ser
        35                  40                  45

Ser Ala Leu Phe Gly Cys Pro Asn Pro Arg Gln Leu Ser Gln Arg Arg
    50                  55                  60

Gly Ala Ile Ser Tyr Asp Ser Ser Asp Gln Thr Ala Leu Tyr Ile Arg
65                  70                  75                  80

Met Leu Gly Asp Val Arg Val Arg Ser Arg Ala Gly Phe Glu Ser Glu
                85                  90                  95

Arg Arg Gly Ser His Pro Tyr Ile Asp Phe Arg Ile Phe His Ser Gln
            100                 105                 110

Ser Glu Ile Glu Val Ser Val Ser Ala Arg Asn Ile Arg Arg Leu Leu
        115                 120                 125

Ser Phe Gln Arg Tyr Leu Arg Ser Ser Arg Phe Phe Arg Gly Thr Ala
    130                 135                 140

Val Ser Asn Ser Leu Asn Ile Leu Asp Asp Asp Tyr Asn Gly Gln Ala
145                 150                 155                 160

Lys Cys Met Leu Glu Lys Val Gly Asn Trp Asn Phe Asp Ile Phe Leu
                165                 170                 175

Phe Asp Arg Leu Thr Asn Gly Asn Ser Leu Val Ser Leu Thr Phe His
            180                 185                 190

Leu Phe Ser Leu His Gly Leu Ile Glu Tyr Phe His Leu Asp Met Met
        195                 200                 205

Lys Leu Arg Arg Phe Leu Val Met Ile Gln Glu Asp Tyr His Ser Gln
    210                 215                 220

Asn Pro Tyr His Asn Ala Val His Ala Ala Asp Val Thr Gln Ala Met
225                 230                 235                 240

His Cys Tyr Leu Lys Glu Pro Lys Leu Ala Asn Ser Val Thr Pro Trp
                245                 250                 255

Asp Ile Leu Leu Ser Leu Ile Ala Ala Ala Thr His Asp Leu Asp His
            260                 265                 270

Pro Gly Val Asn Gln Pro Phe Leu Ile Lys Thr Asn His Tyr Leu Ala
        275                 280                 285

Thr Leu Tyr Lys Asn Thr Ser Val Leu Glu Asn His His Trp Arg Ser
    290                 295                 300

Ala Val Gly Leu Leu Arg Glu Ser Gly Leu Phe Ser His Leu Pro Leu
305                 310                 315                 320

Glu Ser Arg Gln Gln Met Glu Thr Gln Ile Gly Ala Leu Ile Leu Ala
                325                 330                 335

Thr Asp Ile Ser Arg Gln Asn Glu Tyr Leu Ser Leu Phe Arg Ser His
            340                 345                 350

Leu Asp Arg Gly Asp Leu Cys Leu Glu Asp Thr Arg His Arg His Leu
        355                 360                 365

Val Leu Gln Met Ala Leu Lys Cys Ala Asp Ile Cys Asn Pro Cys Arg
    370                 375                 380

Thr Trp Glu Leu Ser Lys Gln Trp Ser Glu Lys Val Thr Glu Glu Phe
385                 390                 395                 400
```

| | | | | | | | | | | | | | | |
|---|---|---|---|---|---|---|---|---|---|---|---|---|---|---|
| Phe | His | Gln | Gly | Asp<br>405 | Ile | Glu | Lys | Lys | Tyr<br>410 | His | Leu | Gly | Val | Ser<br>415 | Pro |

| | | | | | | | | | | | | | | |
|---|---|---|---|---|---|---|---|---|---|---|---|---|---|---|
| Leu | Cys | Asp | Arg<br>420 | His | Thr | Glu | Ser | Ile<br>425 | Ala | Asn | Ile | Gln | Ile<br>430 | Gly | Phe |

| | | | | | | | | | | | | | | |
|---|---|---|---|---|---|---|---|---|---|---|---|---|---|---|
| Met | Thr | Tyr<br>435 | Leu | Val | Glu | Pro | Leu<br>440 | Phe | Thr | Glu | Trp | Ala<br>445 | Arg | Phe | Ser |

| | | | | | | | | | | | | | | |
|---|---|---|---|---|---|---|---|---|---|---|---|---|---|---|
| Asn | Thr<br>450 | Arg | Leu | Ser | Gln | Thr<br>455 | Met | Leu | Gly | His | Val<br>460 | Gly | Leu | Asn | Lys |

| | | | | | | | | | | | | | | |
|---|---|---|---|---|---|---|---|---|---|---|---|---|---|---|
| Ala<br>465 | Ser | Trp | Lys | Gly | Leu<br>470 | Gln | Arg | Glu | Gln | Ser<br>475 | Ser | Ser | Glu | Asp | Thr<br>480 |

| | | | | | | | | | | | | | | |
|---|---|---|---|---|---|---|---|---|---|---|---|---|---|---|
| Asp | Ala | Ala | Phe | Glu<br>485 | Leu | Asn | Ser | Gln | Leu<br>490 | Leu | Pro | Gln | Glu | Asn<br>495 | Arg |

Leu Ser ( 2 ) INFORMATION FOR SEQ ID NO:21:

( i ) SEQUENCE CHARACTERISTICS:
        ( A ) LENGTH: 3131 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1652
        ( D ) OTHER INFORMATION: /note="A shift in reading frame
            may occur at this residue."

( i x ) FEATURE:
        ( A ) NAME/KEY: CDS
        ( B ) LOCATION: join(743..1648, 1651..2661)

( x i ) SEQUENCE DESCRIPTION: SEQ ID NO:21:

| | | | | | |
|---|---|---|---|---|---|
| GCGGCCGCGC | GGCCTAGGCC | GCATCCCGGA | GCTGCAACTG | GTGGCCTTCC | CGGTGGCGGT | 60 |
| GGCGGCTGAG | GACGAGGCGT | TCCTGCCCGA | GCCCCTGGCC | CCGCGCGCGC | CCGCCGCCC | 120 |
| GCGTTCGCCG | CCCTCCTCGC | CCGTCTTCTT | CGCCAGCCCG | TCCCCAACTT | TCCGCAGACG | 180 |
| CCTTCGGCTT | CTCCGCAGCT | GCCAGGATTT | GGGCCGCCAG | GCTTGGGCTG | GGCTGGCTT | 240 |
| CGAGGCAGAG | AATGGGCCGA | CACCATCTCC | TGGCCGCAGC | CCCTGGACT | CGCAGGCGAG | 300 |
| CCCAGGACTC | GTGCTGCACG | CCGGGGCGCC | ACCAGCCAGC | GCCGGGAGTC | CTTCCTGTAC | 360 |
| CGCTCAGACA | GCGACTATGA | CATGTCACCC | AAGACCATGT | CCCGGAACTC | ATCGGTCACC | 420 |
| AGCGAGGCAC | AGTTGCTTCT | CTGCGGACCC | CTGACCTGCC | TCTGTCCTCA | ATCACAGGCA | 480 |
| CGCTGAAGAC | CTCATCGTAA | CACCATTTGC | TCAGGTGCTG | GCCAGCCTCC | GGAGCGTCCG | 540 |
| TAGCAACTTC | TCACTCCTGA | CCAATGTGCC | CGTTCCCAGT | AACAAGCGGT | CCCGCTGGGC | 600 |
| GGCCCCACCC | CTGTCTGCAA | GGCCACGCTG | TCAGACCTTC | TCAGTCACTA | CCCTGGCTGC | 660 |
| CCCTTCCTTA | GAAGAAACGT | GTCAGCAGTT | GGCCCGGGAG | ACTCTGGAGG | AGCTGGACTG | 720 |
| GTGTCTGGAG | CAGCTGGAGA | CC ATG CAG | ACC TAT CGC | TCT GTC AGC | GAG ATG | 772 |
| | | Met Gln<br>1 | Thr Tyr Arg<br>5 | Ser Val Ser | Glu Met<br>10 | |
| GCC TCG CAC | AAG TTC AAA | AGG ATG TTG | AAC CGT GAG | CTC ACA CAC | CTG | 820 |
| Ala Ser His | Lys Phe Lys<br>15 | Arg Met Leu | Asn Arg Glu<br>20 | Leu Thr His | Leu<br>25 | |
| TCA GAA ATG | AGC AGG TCC | GGA AAC CAG | GTC TCA GAG | TAC ATT TCC | ACA | 868 |
| Ser Glu Met | Ser Arg Ser<br>30 | Gly Asn Gln | Val Ser Glu<br>35 | Tyr Ile Ser | Thr<br>40 | |
| ACA TTC CTG | GAC AAA CAG | AAT GAA GTG | GAG ATC CCA | TCA CCC ACG | ATG | 916 |

```
Thr Phe Leu Asp Lys Gln Asn Glu Val Glu Ile Pro Ser Pro Thr Met
         45                  50                  55

AAG GAA CGA GAA AAA CAG CAA GCG CCG CGA CCA AGA CCC TCC CAG CCG          964
Lys Glu Arg Glu Lys Gln Gln Ala Pro Arg Pro Arg Pro Ser Gln Pro
         60                  65                  70

CCC CCG CCC CCT GTA CCA CAC TTA CAG CCC ATG TCC CAA ATC ACA GGG         1012
Pro Pro Pro Pro Val Pro His Leu Gln Pro Met Ser Gln Ile Thr Gly
 75                  80                  85                  90

TTG AAA AAG TTG ATG CAT AGT AAC AGC CTG AAC AAC TCT AAC ATT CCC         1060
Leu Lys Lys Leu Met His Ser Asn Ser Leu Asn Asn Ser Asn Ile Pro
                 95                  100                 105

CGA TTT GGG GTG AAG ACC GAT CAA GAA GAG CTC CTG GCC CAA GAA CTG         1108
Arg Phe Gly Val Lys Thr Asp Gln Glu Glu Leu Leu Ala Gln Glu Leu
             110                 115                 120

GAG AAC CTG AAC AAG TGG GGC CTG AAC ATC TTT TGC GTG TCG GAT TAC         1156
Glu Asn Leu Asn Lys Trp Gly Leu Asn Ile Phe Cys Val Ser Asp Tyr
         125                 130                 135

GCT GGA GGC CGC TCA CTC ACC TGC ATC ATG TAC ATG ATA TTC CAG GAG         1204
Ala Gly Gly Arg Ser Leu Thr Cys Ile Met Tyr Met Ile Phe Gln Glu
     140                 145                 150

CGG GAC CTG CTG AAG AAA TTC CGC ATC CCT GTG GAC ACG ATG GTG ACA         1252
Arg Asp Leu Leu Lys Lys Phe Arg Ile Pro Val Asp Thr Met Val Thr
155                 160                 165                 170

TAC ATG CTG ACG CTG GAG GAT CAC TAC CAC GCT GAC GTG GCC TAC CAT         1300
Tyr Met Leu Thr Leu Glu Asp His Tyr His Ala Asp Val Ala Tyr His
                 175                 180                 185

AAC AGC CTG CAC GCA GCT GAC GTG CTG CAG TCC ACC CAC GTA CTG CTG         1348
Asn Ser Leu His Ala Ala Asp Val Leu Gln Ser Thr His Val Leu Leu
             190                 195                 200

GCC ACG CCT GCA CTA GAT GCA GTG TTC ACG GAC CTG GAG ATT CTC GCC         1396
Ala Thr Pro Ala Leu Asp Ala Val Phe Thr Asp Leu Glu Ile Leu Ala
         205                 210                 215

GCC CTC TTC GCG GCT GCC ATC CAC GAT GTG GAT CAC CCT GGG GTC TCC         1444
Ala Leu Phe Ala Ala Ala Ile His Asp Val Asp His Pro Gly Val Ser
     220                 225                 230

AAC CAG TTC CTC ATC AAC ACC AAT TCG GAG CTG GCG CTC ATG TAC AAC         1492
Asn Gln Phe Leu Ile Asn Thr Asn Ser Glu Leu Ala Leu Met Tyr Asn
235                 240                 245                 250

GAT GAG TCG GTG CTC GAG AAT CAC CAC CTG GCC GTG GGC TTC AAG CTG         1540
Asp Glu Ser Val Leu Glu Asn His His Leu Ala Val Gly Phe Lys Leu
                 255                 260                 265

CTG CAG GAG GAC AAC TGC GAC ATC TTC CAG AAC CTC AGC AAG CGC CAG         1588
Leu Gln Glu Asp Asn Cys Asp Ile Phe Gln Asn Leu Ser Lys Arg Gln
             270                 275                 280

CGC AGA GCC TAC GCA AGA TGG TCA TCG ACA TGG TGC TGG CCA CGG ACA         1636
Arg Arg Ala Tyr Ala Arg Trp Ser Ser Thr Trp Cys Trp Pro Arg Thr
         285                 290                 295

TGT CCA AGC ACA TG ACC CTC CTG GCT GAC CTG AAG ACC ATG GTG GAG          1683
Cys Pro Ser Thr     Thr Leu Leu Ala Asp Leu Lys Thr Met Val Glu
     300                 305                 310

ACC AAG AAA GTG ACC AGC TCA GGG GTC CTC CTG CTA GAT AAC TAC TCC         1731
Thr Lys Lys Val Thr Ser Ser Gly Val Leu Leu Leu Asp Asn Tyr Ser
315                 320                 325

GAC CGC ATC CAG GTC CTC CGG AAC ATG GTG CAC TGT GCC GAC CTC AGC         1779
Asp Arg Ile Gln Val Leu Arg Asn Met Val His Cys Ala Asp Leu Ser
330                 335                 340                 345

AAC CCC ACC AAG CCG CTG GAG CTG TAC CGC CAG TGG ACA GAC CGC ATC         1827
Asn Pro Thr Lys Pro Leu Glu Leu Tyr Arg Gln Trp Thr Asp Arg Ile
             350                 355                 360

ATG GCC GAG TTC TTC CAG CAG GGT GAC CGA GAG CGC GAG CGT GGC ATG         1875
```

```
Met Ala Glu Phe Phe Gln Gln Gly Asp Arg Glu Arg Glu Arg Gly Met
            365                 370                 375

GAA ATC AGC CCC ATG TGT GAC AAG CAC ACT GCC TCC GTG GAG AAG TCT     1923
Glu Ile Ser Pro Met Cys Asp Lys His Thr Ala Ser Val Glu Lys Ser
        380                 385                 390

CAG GTG GGT TTT ATT GAC TAC ATT GTG CAC CCA TTG TGG GAG ACC TGG     1971
Gln Val Gly Phe Ile Asp Tyr Ile Val His Pro Leu Trp Glu Thr Trp
    395                 400                 405

GCG GAC CTT GTC CAC CCA GAT GCC CAG GAG ATC TTG GAC ACT TTG GAG     2019
Ala Asp Leu Val His Pro Asp Ala Gln Glu Ile Leu Asp Thr Leu Glu
410                 415                 420                 425

GAC AAC CGG GAC TGG TAC TAC AGC GCC ATC CGG CAG AGC CCA TCT CCG     2067
Asp Asn Arg Asp Trp Tyr Tyr Ser Ala Ile Arg Gln Ser Pro Ser Pro
                430                 435                 440

CCA CCC GAG GAG GAG TCA AGG GGG CCA GGC CAC CCA CCC CTG CCT GAC     2115
Pro Pro Glu Glu Glu Ser Arg Gly Pro Gly His Pro Pro Leu Pro Asp
            445                 450                 455

AAG TTC CAG TTT GAG CTG ACG CTG GAG GAG GAA GAG GAG GAA GAA ATA     2163
Lys Phe Gln Phe Glu Leu Thr Leu Glu Glu Glu Glu Glu Glu Glu Ile
        460                 465                 470

TCA ATG GCC CAG ATA CCG TGC ACA GCC CAA GAG GCA TTG ACT GAG CAG     2211
Ser Met Ala Gln Ile Pro Cys Thr Ala Gln Glu Ala Leu Thr Glu Gln
    475                 480                 485

GGA TTG TCA GGA GTC GAG GAA GCT CTG GAT GCA ACC ATA GCC TGG GAG     2259
Gly Leu Ser Gly Val Glu Glu Ala Leu Asp Ala Thr Ile Ala Trp Glu
490                 495                 500                 505

GCA TCC CCG GCC CAG GAG TCG TTG GAA GTT ATG GCA CAG GAA GCA TCC     2307
Ala Ser Pro Ala Gln Glu Ser Leu Glu Val Met Ala Gln Glu Ala Ser
                510                 515                 520

CTG GAG GCC GAG CTG GAG GCA GTG TAT TTG ACA CAG CAG GCA CAG TCC     2355
Leu Glu Ala Glu Leu Glu Ala Val Tyr Leu Thr Gln Gln Ala Gln Ser
            525                 530                 535

ACA GGC AGT GCA CCT GTG GCT CCG GAT GAG TTC TCG TCC CGG GAG GAA     2403
Thr Gly Ser Ala Pro Val Ala Pro Asp Glu Phe Ser Ser Arg Glu Glu
        540                 545                 550

TTC GTG GTT GCT GTA AGC CAC AGC AGC CCC TCT GCC CTG GCT CTT CAA     2451
Phe Val Val Ala Val Ser His Ser Ser Pro Ser Ala Leu Ala Leu Gln
    555                 560                 565

AGC CCC CTT CTC CCT GCT TGG AGG ACC CTG TCT GTT TCA GAG CAT GCC     2499
Ser Pro Leu Leu Pro Ala Trp Arg Thr Leu Ser Val Ser Glu His Ala
570                 575                 580                 585

CCG GGC CTC CCG GGC CTC CCC TCC ACG GCG GCC GAG GTG GAG GCC CAA     2547
Pro Gly Leu Pro Gly Leu Pro Ser Thr Ala Ala Glu Val Glu Ala Gln
                590                 595                 600

CGA GAG CAC CAG GCT GCC AAG AGG GCT TGC AGT GCC TGC GCA GGG ACA     2595
Arg Glu His Gln Ala Ala Lys Arg Ala Cys Ser Ala Cys Ala Gly Thr
            605                 610                 615

TTT GGG GAG GAC ACA TCC GCA CTC CCA GCT CCT GGT GGC GGG GGG TCA     2643
Phe Gly Glu Asp Thr Ser Ala Leu Pro Ala Pro Gly Gly Gly Gly Ser
        620                 625                 630

GGT GGA GAC CCT ACC TGATCCCCAG ACCTCTGTCC CTGTTCCCCT CCACTCCTCC     2698
Gly Gly Asp Pro Thr
        635

CCTCACTCCC CTGCTCCCCC GACCACCTCC TCCTCTGCCT CAAAGACTCT TGTCCTCTTG   2758

TCCCTCCTGA GATTTTTTTT TTTTTTTTT TTTTTTTTT TTTTACAACA CAAATGAATG     2818

GGCCATTTTA TTGATTTTTA CCTCCTAATA GTGGATACAG GTTGCTGTGG TTTCCAGCAG   2878

GATCTCAGAT GCAAAGGGAA GTGAAGAAAA CAGATGAATC CTAGGGTAC CCCGCCATGG    2938

AACCAAACAC CACGTCAACT GGAACTCTTC TTGCAAACGA AGGCTGAAGA TCAAGAATGA   2998
```

```
CATTCTCACA CCACAGCACA GCTTAAATAC TTCTTTGACA AAAATAATAA TAAATTATAT      3058

TTGACTCAGA AAATAAATTC TGTTCAGCAG AGTGACAGGA GGTAAAAATC AAATGAATGG      3118

GCAATGCGGC CGC                                                        3131
```

( 2 ) INFORMATION FOR SEQ ID NO:22:

( i ) SEQUENCE CHARACTERISTICS:
        ( A ) LENGTH: 638 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met Gln Thr Tyr Arg Ser Val Ser Glu Met Ala Ser His Lys Phe Lys
 1               5                  10                  15

Arg Met Leu Asn Arg Glu Leu Thr His Leu Ser Glu Met Ser Arg Ser
             20                  25                  30

Gly Asn Gln Val Ser Glu Tyr Ile Ser Thr Thr Phe Leu Asp Lys Gln
         35                  40                  45

Asn Glu Val Glu Ile Pro Ser Pro Thr Met Lys Glu Arg Glu Lys Gln
     50                  55                  60

Gln Ala Pro Arg Pro Arg Pro Ser Gln Pro Pro Pro Pro Pro Val Pro
 65                  70                  75                  80

His Leu Gln Pro Met Ser Gln Ile Thr Gly Leu Lys Lys Leu Met His
                 85                  90                  95

Ser Asn Ser Leu Asn Asn Ser Asn Ile Pro Arg Phe Gly Val Lys Thr
            100                 105                 110

Asp Gln Glu Glu Leu Leu Ala Gln Glu Leu Glu Asn Leu Asn Lys Trp
        115                 120                 125

Gly Leu Asn Ile Phe Cys Val Ser Asp Tyr Ala Gly Gly Arg Ser Leu
    130                 135                 140

Thr Cys Ile Met Tyr Met Ile Phe Gln Glu Arg Asp Leu Leu Lys Lys
145                 150                 155                 160

Phe Arg Ile Pro Val Asp Thr Met Val Thr Tyr Met Leu Thr Leu Glu
                165                 170                 175

Asp His Tyr His Ala Asp Val Ala Tyr His Asn Ser Leu His Ala Ala
            180                 185                 190

Asp Val Leu Gln Ser Thr His Val Leu Leu Ala Thr Pro Ala Leu Asp
        195                 200                 205

Ala Val Phe Thr Asp Leu Glu Ile Leu Ala Ala Leu Phe Ala Ala Ala
    210                 215                 220

Ile His Asp Val Asp His Pro Gly Val Ser Asn Gln Phe Leu Ile Asn
225                 230                 235                 240

Thr Asn Ser Glu Leu Ala Leu Met Tyr Asn Asp Glu Ser Val Leu Glu
                245                 250                 255

Asn His His Leu Ala Val Gly Phe Lys Leu Leu Gln Glu Asp Asn Cys
            260                 265                 270

Asp Ile Phe Gln Asn Leu Ser Lys Arg Gln Arg Arg Ala Tyr Ala Arg
        275                 280                 285

Trp Ser Ser Thr Trp Cys Trp Pro Arg Thr Cys Pro Ser Thr Thr Leu
    290                 295                 300

Leu Ala Asp Leu Lys Thr Met Val Glu Thr Lys Lys Val Thr Ser Ser
305                 310                 315                 320

Gly Val Leu Leu Leu Asp Asn Tyr Ser Asp Arg Ile Gln Val Leu Arg
```

```
                              325                          330                          335
Asn  Met  Val  His  Cys  Ala  Asp  Leu  Ser  Asn  Pro  Thr  Lys  Pro  Leu  Glu
               340                      345                     350

Leu  Tyr  Arg  Gln  Trp  Thr  Asp  Arg  Ile  Met  Ala  Glu  Phe  Phe  Gln  Gln
          355                      360                          365

Gly  Asp  Arg  Glu  Arg  Glu  Arg  Gly  Met  Glu  Ile  Ser  Pro  Met  Cys  Asp
          370                      375                     380

Lys  His  Thr  Ala  Ser  Val  Glu  Lys  Ser  Gln  Val  Gly  Phe  Ile  Asp  Tyr
385                      390                      395                          400

Ile  Val  His  Pro  Leu  Trp  Glu  Thr  Trp  Ala  Asp  Leu  Val  His  Pro  Asp
               405                      410                          415

Ala  Gln  Glu  Ile  Leu  Asp  Thr  Leu  Glu  Asp  Asn  Arg  Asp  Trp  Tyr  Tyr
               420                      425                     430

Ser  Ala  Ile  Arg  Gln  Ser  Pro  Ser  Pro  Pro  Glu  Glu  Ser  Arg
          435                      440                      445

Gly  Pro  Gly  His  Pro  Pro  Leu  Pro  Asp  Lys  Phe  Gln  Phe  Glu  Leu  Thr
     450                     455                      460

Leu  Glu  Glu  Glu  Glu  Glu  Glu  Ile  Ser  Met  Ala  Gln  Ile  Pro  Cys
465                      470                          475                     480

Thr  Ala  Gln  Glu  Ala  Leu  Thr  Glu  Gln  Gly  Leu  Ser  Gly  Val  Glu  Glu
               485                     490                          495

Ala  Leu  Asp  Ala  Thr  Ile  Ala  Trp  Glu  Ala  Ser  Pro  Ala  Gln  Glu  Ser
               500                     505                      510

Leu  Glu  Val  Met  Ala  Gln  Glu  Ala  Ser  Leu  Glu  Ala  Glu  Leu  Glu  Ala
               515                     520                          525

Val  Tyr  Leu  Thr  Gln  Gln  Ala  Gln  Ser  Thr  Gly  Ser  Ala  Pro  Val  Ala
     530                          535                     540

Pro  Asp  Glu  Phe  Ser  Ser  Arg  Glu  Glu  Phe  Val  Val  Ala  Val  Ser  His
545                     550                      555                          560

Ser  Ser  Pro  Ser  Ala  Leu  Ala  Leu  Gln  Ser  Pro  Leu  Leu  Pro  Ala  Trp
               565                     570                          575

Arg  Thr  Leu  Ser  Val  Ser  Glu  His  Ala  Pro  Gly  Leu  Pro  Gly  Leu  Pro
               580                     585                     590

Ser  Thr  Ala  Ala  Glu  Val  Glu  Ala  Gln  Arg  Glu  His  Gln  Ala  Ala  Lys
          595                     600                     605

Arg  Ala  Cys  Ser  Ala  Cys  Ala  Gly  Thr  Phe  Gly  Glu  Asp  Thr  Ser  Ala
     610                     615                     620

Leu  Pro  Ala  Pro  Gly  Gly  Gly  Gly  Ser  Gly  Gly  Asp  Pro  Thr
625                     630                     635
```

( 2 ) INFORMATION FOR SEQ ID NO:23:

( i ) SEQUENCE CHARACTERISTICS:
    ( A ) LENGTH: 3186 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 139..2348

( x i ) SEQUENCE DESCRIPTION: SEQ ID NO:23:

```
GCGGCCGCGG  CGGTGCAGCA  GAGGCGCCTC  GGGCAGGAGG  AGGGCGGCTT  CTGCGAGGGC     60

AGCCTGAGGT  ATTAAAAAGT  GTCAGCAAAC  TGCATTGAAT  AACAGACATC  CTAAGAGGGG    120
```

| | | | | | | | | | | | | | | | | |
|---|---|---|---|---|---|---|---|---|---|---|---|---|---|---|---|---|
| ATATTTCCA | CCTCTATA | ATG | AAG | AAA | AGC | AGG | AGT | GTG | ATG | ACG | GTG | ATG | | | | 171 |
| | | Met | Lys | Lys | Ser | Arg | Ser | Val | Met | Thr | Val | Met | | | | |
| | | 1 | | 5 | | | | | 10 | | | | | | | |
| GCT | GAT | GAT | AAT | GTT | AAA | GAT | TAT | TTT | GAA | TGT | AGC | TTG | AGT | AAA | TCC | 219 |
| Ala | Asp | Asp | Asn | Val | Lys | Asp | Tyr | Phe | Glu | Cys | Ser | Leu | Ser | Lys | Ser | |
| | | 15 | | | | 20 | | | | 25 | | | | | | |
| TAC | AGT | TCT | TCC | AGT | AAC | ACA | CTT | GGG | ATC | GAC | CTC | TGG | AGA | GGG | AGA | 267 |
| Tyr | Ser | Ser | Ser | Ser | Asn | Thr | Leu | Gly | Ile | Asp | Leu | Trp | Arg | Gly | Arg | |
| | 30 | | | | 35 | | | | 40 | | | | | | | |
| AGG | TGT | TGC | TCA | GGA | AAC | TTA | CAG | TTA | CCA | CCA | CTG | TCT | CAA | AGA | CAG | 315 |
| Arg | Cys | Cys | Ser | Gly | Asn | Leu | Gln | Leu | Pro | Pro | Leu | Ser | Gln | Arg | Gln | |
| | 45 | | | | 50 | | | | 55 | | | | | | | |
| AGT | GAA | AGG | GCA | AGG | ACT | CCT | GAG | GGA | GAT | GGT | ATT | TCC | AGG | CCG | ACC | 363 |
| Ser | Glu | Arg | Ala | Arg | Thr | Pro | Glu | Gly | Asp | Gly | Ile | Ser | Arg | Pro | Thr | |
| 60 | | | | 65 | | | | | 70 | | | | | 75 | | |
| ACA | CTG | CCT | TTG | ACA | ACG | CTT | CCA | AGC | ATT | GCT | ATT | ACA | ACT | GTA | AGC | 411 |
| Thr | Leu | Pro | Leu | Thr | Thr | Leu | Pro | Ser | Ile | Ala | Ile | Thr | Thr | Val | Ser | |
| | | | | 80 | | | | | 85 | | | | | 90 | | |
| CAG | GAG | TGC | TTT | GAT | GTG | GAA | AAT | GGC | CCT | TCC | CCA | GGT | CGG | AGT | CCA | 459 |
| Gln | Glu | Cys | Phe | Asp | Val | Glu | Asn | Gly | Pro | Ser | Pro | Gly | Arg | Ser | Pro | |
| | | | 95 | | | | | 100 | | | | | 105 | | | |
| CTG | GAT | CCC | CAG | GCC | AGC | TCT | TCC | GCT | GGG | CTG | GTA | CTT | CAC | GCC | ACC | 507 |
| Leu | Asp | Pro | Gln | Ala | Ser | Ser | Ser | Ala | Gly | Leu | Val | Leu | His | Ala | Thr | |
| | | | 110 | | | | | 115 | | | | | 120 | | | |
| TTT | CCT | GGG | CAC | AGC | CAG | CGC | AGA | GAG | TCA | TTT | CTC | TAC | AGA | TCA | GAC | 555 |
| Phe | Pro | Gly | His | Ser | Gln | Arg | Arg | Glu | Ser | Phe | Leu | Tyr | Arg | Ser | Asp | |
| | | 125 | | | | | 130 | | | | | 135 | | | | |
| AGC | GAC | TAT | GAC | TTG | TCA | CCA | AAG | GCG | ATG | TCG | AGA | AAC | TCT | TCT | CTT | 603 |
| Ser | Asp | Tyr | Asp | Leu | Ser | Pro | Lys | Ala | Met | Ser | Arg | Asn | Ser | Ser | Leu | |
| 140 | | | | | 145 | | | | | 150 | | | | | 155 | |
| CCA | AGC | GAG | CAA | CAC | GGC | GAT | GAC | TTG | ATT | GTA | ACT | CCT | TTT | GCC | CAG | 651 |
| Pro | Ser | Glu | Gln | His | Gly | Asp | Asp | Leu | Ile | Val | Thr | Pro | Phe | Ala | Gln | |
| | | | | 160 | | | | | 165 | | | | | 170 | | |
| GTC | CTT | GCC | AGC | TTG | CGA | AGT | GTG | AGA | AAC | AAC | TTC | ACT | ATA | CTG | ACA | 699 |
| Val | Leu | Ala | Ser | Leu | Arg | Ser | Val | Arg | Asn | Asn | Phe | Thr | Ile | Leu | Thr | |
| | | | 175 | | | | | 180 | | | | | 185 | | | |
| AAC | CTT | CAT | GGT | ACA | TCT | AAC | AAG | AGG | TCC | CCA | GCT | GCT | AGT | CAG | CCT | 747 |
| Asn | Leu | His | Gly | Thr | Ser | Asn | Lys | Arg | Ser | Pro | Ala | Ala | Ser | Gln | Pro | |
| | | | 190 | | | | | 195 | | | | | 200 | | | |
| CCT | GTC | TCC | AGA | GTC | AAC | CCA | CAA | GAA | GAA | TCT | TAT | CAA | AAA | TTA | GCA | 795 |
| Pro | Val | Ser | Arg | Val | Asn | Pro | Gln | Glu | Glu | Ser | Tyr | Gln | Lys | Leu | Ala | |
| | | 205 | | | | | 210 | | | | | 215 | | | | |
| ATG | GAA | ACG | CTG | GAG | GAA | TTA | GAC | TGG | TGT | TTA | GAC | CAG | CTA | GAG | ACC | 843 |
| Met | Glu | Thr | Leu | Glu | Glu | Leu | Asp | Trp | Cys | Leu | Asp | Gln | Leu | Glu | Thr | |
| 220 | | | | | 225 | | | | | 230 | | | | | 235 | |
| ATA | CAG | ACC | TAC | CGG | TCT | GTC | AGT | GAG | ATG | GCT | TCT | AAC | AAG | TTC | AAA | 891 |
| Ile | Gln | Thr | Tyr | Arg | Ser | Val | Ser | Glu | Met | Ala | Ser | Asn | Lys | Phe | Lys | |
| | | | | 240 | | | | | 245 | | | | | 250 | | |
| AGA | ATG | CTG | AAC | CGG | GAG | CTG | ACA | CAC | CTC | TCA | GAG | ATG | AGC | CGA | TCA | 939 |
| Arg | Met | Leu | Asn | Arg | Glu | Leu | Thr | His | Leu | Ser | Glu | Met | Ser | Arg | Ser | |
| | | | 255 | | | | | 260 | | | | | 265 | | | |
| GGG | AAC | CAG | GTG | TCT | GAA | TAC | ATT | TCA | AAT | ACT | TTC | TTA | GAC | AAG | CAG | 987 |
| Gly | Asn | Gln | Val | Ser | Glu | Tyr | Ile | Ser | Asn | Thr | Phe | Leu | Asp | Lys | Gln | |
| | | 270 | | | | | 275 | | | | | 280 | | | | |
| AAT | GAT | GTG | GAG | ATC | CCA | TCT | CCT | ACC | CAG | AAA | GAC | AGG | GAG | AAA | AAG | 1035 |
| Asn | Asp | Val | Glu | Ile | Pro | Ser | Pro | Thr | Gln | Lys | Asp | Arg | Glu | Lys | Lys | |
| | 285 | | | | | 290 | | | | | 295 | | | | | |
| AAA | AAG | CAG | CAG | CTC | ATG | ACC | CAG | ATA | AGT | GGA | GTG | AAG | AAA | TTA | ATG | 1083 |
| Lys | Lys | Gln | Gln | Leu | Met | Thr | Gln | Ile | Ser | Gly | Val | Lys | Lys | Leu | Met | |
| 300 | | | | | 305 | | | | | 310 | | | | | 315 | |

| | | | | | | | | | | | | | | | |
|---|---|---|---|---|---|---|---|---|---|---|---|---|---|---|---|
| CAT | AGT | TCA | AGC | CTA | AAC | AAT | ACA | AGC | ATC | TCA | CGC | TTT | GGA | GTC | AAC |
| His | Ser | Ser | Ser | Leu | Asn | Asn | Thr | Ser | Ile | Ser | Arg | Phe | Gly | Val | Asn |
| | | | | 320 | | | | | 325 | | | | | 330 | |

1131

| ACT | GAA | AAT | GAA | GAT | CAC | CTG | GCC | AAG | GAG | CTG | GAA | GAC | CTG | AAC | AAA |
|---|---|---|---|---|---|---|---|---|---|---|---|---|---|---|---|
| Thr | Glu | Asn | Glu | Asp | His | Leu | Ala | Lys | Glu | Leu | Glu | Asp | Leu | Asn | Lys |
| | | | 335 | | | | | 340 | | | | | 345 | | |

1179

| TGG | GGT | CTT | AAC | ATC | TTT | AAT | GTG | GCT | GGA | TAT | TCT | CAC | AAT | AGA | CCC |
|---|---|---|---|---|---|---|---|---|---|---|---|---|---|---|---|
| Trp | Gly | Leu | Asn | Ile | Phe | Asn | Val | Ala | Gly | Tyr | Ser | His | Asn | Arg | Pro |
| | | 350 | | | | | 355 | | | | | 360 | | | |

1227

| CTA | ACA | TGC | ATC | ATG | TAT | GCT | ATA | TTC | CAG | GAA | AGA | GAC | CTC | CTA | AAG |
|---|---|---|---|---|---|---|---|---|---|---|---|---|---|---|---|
| Leu | Thr | Cys | Ile | Met | Tyr | Ala | Ile | Phe | Gln | Glu | Arg | Asp | Leu | Leu | Lys |
| | 365 | | | | 370 | | | | | 375 | | | | | |

1275

| ACA | TTC | AGA | ATC | TCA | TCT | GAC | ACA | TTT | ATA | ACC | TAC | ATG | ATG | ACT | TTA |
|---|---|---|---|---|---|---|---|---|---|---|---|---|---|---|---|
| Thr | Phe | Arg | Ile | Ser | Ser | Asp | Thr | Phe | Ile | Thr | Tyr | Met | Met | Thr | Leu |
| 380 | | | | | 385 | | | | | 390 | | | | | 395 |

1323

| GAA | GAC | CAT | TAC | CAT | TCT | GAC | GTG | GCA | TAT | CAC | AAC | AGC | CTG | CAC | GCT |
|---|---|---|---|---|---|---|---|---|---|---|---|---|---|---|---|
| Glu | Asp | His | Tyr | His | Ser | Asp | Val | Ala | Tyr | His | Asn | Ser | Leu | His | Ala |
| | | | | 400 | | | | | 405 | | | | | 410 | |

1371

| GCT | GAT | GTA | GCC | CAG | TCG | ACC | CAT | GTT | CTC | CTT | TCT | ACA | CCA | GCA | TTA |
|---|---|---|---|---|---|---|---|---|---|---|---|---|---|---|---|
| Ala | Asp | Val | Ala | Gln | Ser | Thr | His | Val | Leu | Leu | Ser | Thr | Pro | Ala | Leu |
| | | | 415 | | | | | 420 | | | | | 425 | | |

1419

| GAC | GCT | GTC | TTC | ACA | GAT | TTG | GAG | ATC | CTG | GCT | GCC | ATT | TTT | GCA | GCT |
|---|---|---|---|---|---|---|---|---|---|---|---|---|---|---|---|
| Asp | Ala | Val | Phe | Thr | Asp | Leu | Glu | Ile | Leu | Ala | Ala | Ile | Phe | Ala | Ala |
| | | 430 | | | | | 435 | | | | | 440 | | | |

1467

| GCC | ATC | CAT | GAC | GTT | GAT | CAT | CCT | GGA | GTC | TCC | AAT | CAG | TTT | CTC | ATC |
|---|---|---|---|---|---|---|---|---|---|---|---|---|---|---|---|
| Ala | Ile | His | Asp | Val | Asp | His | Pro | Gly | Val | Ser | Asn | Gln | Phe | Leu | Ile |
| 445 | | | | | 450 | | | | | 455 | | | | | |

1515

| AAC | ACA | AAT | TCA | GAA | CTT | GCT | TTG | ATG | TAT | AAT | GAT | GAA | TCT | GTG | TTG |
|---|---|---|---|---|---|---|---|---|---|---|---|---|---|---|---|
| Asn | Thr | Asn | Ser | Glu | Leu | Ala | Leu | Met | Tyr | Asn | Asp | Glu | Ser | Val | Leu |
| 460 | | | | | 465 | | | | | 470 | | | | | 475 |

1563

| GAA | AAT | CAT | CAC | CTT | GCT | GTG | GGT | TTC | AAA | CTG | CTG | CAA | GAA | GAA | CAC |
|---|---|---|---|---|---|---|---|---|---|---|---|---|---|---|---|
| Glu | Asn | His | His | Leu | Ala | Val | Gly | Phe | Lys | Leu | Leu | Gln | Glu | Glu | His |
| | | | | 480 | | | | | 485 | | | | | 490 | |

1611

| TGT | GAC | ATC | TTC | ATG | AAT | CTC | ACC | AAG | AAG | CAG | CGT | CAG | ACA | CTC | AGG |
|---|---|---|---|---|---|---|---|---|---|---|---|---|---|---|---|
| Cys | Asp | Ile | Phe | Met | Asn | Leu | Thr | Lys | Lys | Gln | Arg | Gln | Thr | Leu | Arg |
| | | | 495 | | | | | 500 | | | | | 505 | | |

1659

| AAG | ATG | GTT | ATT | GAC | ATG | GTG | TTA | GCA | ACT | GAT | ATG | TCT | AAA | CAT | ATG |
|---|---|---|---|---|---|---|---|---|---|---|---|---|---|---|---|
| Lys | Met | Val | Ile | Asp | Met | Val | Leu | Ala | Thr | Asp | Met | Ser | Lys | His | Met |
| | | 510 | | | | | 515 | | | | | 520 | | | |

1707

| AGC | CTG | CTG | GCA | GAC | CTG | AAG | ACA | ATG | GTA | GAA | ACG | AAG | AAA | GTT | ACA |
|---|---|---|---|---|---|---|---|---|---|---|---|---|---|---|---|
| Ser | Leu | Leu | Ala | Asp | Leu | Lys | Thr | Met | Val | Glu | Thr | Lys | Lys | Val | Thr |
| | 525 | | | | | 530 | | | | | 535 | | | | |

1755

| AGT | TCA | GGC | GTT | CTT | CTC | CTA | GAC | AAC | TAT | ACC | GAT | CGC | ATT | CAG | GTC |
|---|---|---|---|---|---|---|---|---|---|---|---|---|---|---|---|
| Ser | Ser | Gly | Val | Leu | Leu | Leu | Asp | Asn | Tyr | Thr | Asp | Arg | Ile | Gln | Val |
| 540 | | | | | 545 | | | | | 550 | | | | | 555 |

1803

| CTT | CGC | AAC | ATG | GTA | CAC | TGT | GCA | GAC | CTG | AGC | AAC | CCC | ACC | AAG | TCC |
|---|---|---|---|---|---|---|---|---|---|---|---|---|---|---|---|
| Leu | Arg | Asn | Met | Val | His | Cys | Ala | Asp | Leu | Ser | Asn | Pro | Thr | Lys | Ser |
| | | | | 560 | | | | | 565 | | | | | 570 | |

1851

| TTG | GAA | TTG | TAT | CGG | CAA | TGG | ACA | GAC | CGC | ATC | ATG | GAG | GAA | TTT | TTC |
|---|---|---|---|---|---|---|---|---|---|---|---|---|---|---|---|
| Leu | Glu | Leu | Tyr | Arg | Gln | Trp | Thr | Asp | Arg | Ile | Met | Glu | Glu | Phe | Phe |
| | | | 575 | | | | | 580 | | | | | 585 | | |

1899

| CAG | CAG | GGA | GAC | AAA | GAG | CGG | GAG | AGG | GGA | ATG | GAA | ATT | AGC | CCA | ATG |
|---|---|---|---|---|---|---|---|---|---|---|---|---|---|---|---|
| Gln | Gln | Gly | Asp | Lys | Glu | Arg | Glu | Arg | Gly | Met | Glu | Ile | Ser | Pro | Met |
| | | 590 | | | | | 595 | | | | | 600 | | | |

1947

| TGT | GAT | AAA | CAC | ACA | GCT | TCT | GTG | GAA | AAA | TCC | CAG | GTT | GGT | TTC | ATC |
|---|---|---|---|---|---|---|---|---|---|---|---|---|---|---|---|
| Cys | Asp | Lys | His | Thr | Ala | Ser | Val | Glu | Lys | Ser | Gln | Val | Gly | Phe | Ile |
| 605 | | | | | 610 | | | | | 615 | | | | | |

1995

| GAC | TAC | ATT | GTC | CAT | CCA | TTG | TGG | GAG | ACA | TGG | GCA | GAT | TTG | GTA | CAG |
|---|---|---|---|---|---|---|---|---|---|---|---|---|---|---|---|
| Asp | Tyr | Ile | Val | His | Pro | Leu | Trp | Glu | Thr | Trp | Ala | Asp | Leu | Val | Gln |
| 620 | | | | | 625 | | | | | 630 | | | | | 635 |

2043

| | | | | | | | | | | | | | | | | |
|---|---|---|---|---|---|---|---|---|---|---|---|---|---|---|---|---|
| CCT | GAT | GCT | CAG | GAC | ATT | CTC | GAT | ACC | TTA | GAA | GAT | AAC | AGG | AAC | TGG | 2091 |
| Pro | Asp | Ala | Gln | Asp | Ile | Leu | Asp | Thr | Leu | Glu | Asp | Asn | Arg | Asn | Trp | |
| | | | 640 | | | | | 645 | | | | | 650 | | | |
| TAT | CAG | AGC | ATG | ATA | CCT | CAA | AGT | CCC | TCA | CCA | CCA | CTG | GAC | GAG | CAG | 2139 |
| Tyr | Gln | Ser | Met | Ile | Pro | Gln | Ser | Pro | Ser | Pro | Pro | Leu | Asp | Glu | Gln | |
| | | | 655 | | | | | 660 | | | | | 665 | | | |
| AAC | AGG | GAC | TGC | CAG | GGT | CTG | ATG | GAG | AAG | TTT | CAG | TTT | GAA | CTG | ACT | 2187 |
| Asn | Arg | Asp | Cys | Gln | Gly | Leu | Met | Glu | Lys | Phe | Gln | Phe | Glu | Leu | Thr | |
| | | 670 | | | | | 675 | | | | | 680 | | | | |
| CTC | GAT | GAG | GAA | GAT | TCT | GAA | GGA | CCT | GAG | AAG | GAG | GGA | GAG | GGA | CAC | 2235 |
| Leu | Asp | Glu | Glu | Asp | Ser | Glu | Gly | Pro | Glu | Lys | Glu | Gly | Glu | Gly | His | |
| | 685 | | | | | 690 | | | | | 695 | | | | | |
| AGC | TAT | TTC | AGC | AGC | ACA | AAG | ACG | CTT | TGT | GTG | ATT | GAT | CCA | GAA | AAC | 2283 |
| er | Tyr | Phe | Ser | Ser | Thr | Lys | Thr | Leu | Cys | Val | Ile | Asp | Pro | Glu | Asn | |
| 700 | | | | | 705 | | | | | 710 | | | | | 715 | |
| AGA | GAT | TCC | CTG | GGA | GAG | ACT | GAC | ATA | GAC | ATT | GCA | ACA | GAA | GAC | AAG | 2331 |
| Arg | Asp | Ser | Leu | Gly | Glu | Thr | Asp | Ile | Asp | Ile | Ala | Thr | Glu | Asp | Lys | |
| | | | 720 | | | | | 725 | | | | | 730 | | | |
| TCC | CCC | GTG | GAT | ACA | TA ATCCCCTCT | CCCTGTGGAG | ATGAACATTC | | | | | | | | | 2378 |
| Ser | Pro | Val | Asp | Thr | | | | | | | | | | | | |
| | | | 735 | | | | | | | | | | | | | |

| | | | | | |
|---|---|---|---|---|---|
| TATCCTTGAT | GAGCATGCCA | GCTATGTGGT | AGGGCCAGCC | CACCATGGGG | GCCAAGACCT | 2438 |
| GCACAGGACA | AGGGCCACCT | GGCCTTTCAG | TTACTTGAGT | TTGGAGTCAG | AAAGCAAGAC | 2498 |
| CAGGAAGCAA | ATAGCAGCTC | AGGAAATCCC | ACGGTTGACT | TGCCTTGATG | GCAAGCTTGG | 2558 |
| TGGAGAGGGC | TGAAGCTGTT | GCTGGGGGCC | GATTCTGATC | AAGACACATG | GCTTGAAAAT | 2618 |
| GGAAGACACA | AAACTGAGAG | ATCATTCTGC | ACTAAGTTTC | GGGAACTTAT | CCCCGACAGT | 2678 |
| GACTGAACTC | ACTGACTAAT | AACTTCATTT | ATGAATCTTC | TCACTTGTCC | CTTTGTCTGC | 2738 |
| CAACCTGTGT | GCCTTTTTTG | TAAAACATTT | TCATGTCTTT | AAAATGCCTG | TTGAATACCT | 2798 |
| GGAGTTTAGT | ATCAACTTCT | ACACAGATAA | GCTTTCAAAG | TTGACAAACT | TTTTTGACTC | 2858 |
| TTTCTGGAAA | AGGGAAAGAA | AATAGTCTTC | CTTCTTTCTT | GGGCAATATC | CTTCACTTTA | 2918 |
| CTACAGTTAC | TTTTGCAAAC | AGACAGAAAG | GATACACTTC | TAACCACATT | TTACTTCCTT | 2978 |
| CCCCTGTTGT | CCAGTCCAAC | TCCACAGTCA | CTCTTAAAAC | TTCTCTCTGT | TTGCCTGCCT | 3038 |
| CCAACAGTAC | TTTTAACTTT | TTGCTGTAAA | CAGAATAAAA | TTGAACAAAT | TAGGGGGTAG | 3098 |
| AAAGGAGCAG | TGGTGTCGTT | CACCGTGAGA | GTCTGCATAG | AACTCAGCAG | TGTGCCCTGC | 3158 |
| TGTGTCTTGG | ACCCTGCAAT | GCGGCCGC | | | | 3186 |

( 2 ) INFORMATION FOR SEQ ID NO:24:

( i ) SEQUENCE CHARACTERISTICS:
        ( A ) LENGTH: 736 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| | | | | | | | | | | | | | | |
|---|---|---|---|---|---|---|---|---|---|---|---|---|---|---|
| Met | Lys | Lys | Ser | Arg | Ser | Val | Met | Thr | Val | Met | Ala | Asp | Asp | Asn | Val |
| 1 | | | | 5 | | | | | 10 | | | | | 15 | |
| Lys | Asp | Tyr | Phe | Glu | Cys | Ser | Leu | Ser | Lys | Ser | Tyr | Ser | Ser | Ser | Ser |
| | | | 20 | | | | | 25 | | | | | 30 | | |
| Asn | Thr | Leu | Gly | Ile | Asp | Leu | Trp | Arg | Gly | Arg | Arg | Cys | Cys | Ser | Gly |
| | | 35 | | | | | 40 | | | | | 45 | | | |
| Asn | Leu | Gln | Leu | Pro | Pro | Leu | Ser | Gln | Arg | Gln | Ser | Glu | Arg | Ala | Arg |
| | 50 | | | | | 55 | | | | | 60 | | | | |

| | | | | | | | | | | | | | | | |
|---|---|---|---|---|---|---|---|---|---|---|---|---|---|---|---|
| Thr | Pro | Glu | Gly | Asp | Gly | Ile | Ser | Arg | Pro | Thr | Thr | Leu | Pro | Leu | Thr |
| 65 | | | | 70 | | | | | 75 | | | | | | 80 |
| Thr | Leu | Pro | Ser | Ile | Ala | Ile | Thr | Thr | Val | Ser | Gln | Glu | Cys | Phe | Asp |
| | | | | 85 | | | | | 90 | | | | | 95 | |
| Val | Glu | Asn | Gly | Pro | Ser | Pro | Gly | Arg | Ser | Pro | Leu | Asp | Pro | Gln | Ala |
| | | | 100 | | | | | 105 | | | | | 110 | | |
| Ser | Ser | Ser | Ala | Gly | Leu | Val | Leu | His | Ala | Thr | Phe | Pro | Gly | His | Ser |
| | | 115 | | | | 120 | | | | | | 125 | | | |
| Gln | Arg | Arg | Glu | Ser | Phe | Leu | Tyr | Arg | Ser | Asp | Ser | Asp | Tyr | Asp | Leu |
| | 130 | | | | | 135 | | | | | 140 | | | | |
| Ser | Pro | Lys | Ala | Met | Ser | Arg | Asn | Ser | Ser | Leu | Pro | Ser | Glu | Gln | His |
| 145 | | | | | 150 | | | | | 155 | | | | | 160 |
| Gly | Asp | Asp | Leu | Ile | Val | Thr | Pro | Phe | Ala | Gln | Val | Leu | Ala | Ser | Leu |
| | | | | 165 | | | | | 170 | | | | | 175 | |
| Arg | Ser | Val | Arg | Asn | Asn | Phe | Thr | Ile | Leu | Thr | Asn | Leu | His | Gly | Thr |
| | | | 180 | | | | | 185 | | | | | 190 | | |
| Ser | Asn | Lys | Arg | Ser | Pro | Ala | Ala | Ser | Gln | Pro | Pro | Val | Ser | Arg | Val |
| | | | 195 | | | | | 200 | | | | | 205 | | |
| Asn | Pro | Gln | Glu | Glu | Ser | Tyr | Gln | Lys | Leu | Ala | Met | Glu | Thr | Leu | Glu |
| | 210 | | | | | 215 | | | | | 220 | | | | |
| Glu | Leu | Asp | Trp | Cys | Leu | Asp | Gln | Leu | Glu | Thr | Ile | Gln | Thr | Tyr | Arg |
| 225 | | | | | 230 | | | | | 235 | | | | | 240 |
| Ser | Val | Ser | Glu | Met | Ala | Ser | Asn | Lys | Phe | Lys | Arg | Met | Leu | Asn | Arg |
| | | | | 245 | | | | | 250 | | | | | 255 | |
| Glu | Leu | Thr | His | Leu | Ser | Glu | Met | Ser | Arg | Ser | Gly | Asn | Gln | Val | Ser |
| | | | 260 | | | | | 265 | | | | | 270 | | |
| Glu | Tyr | Ile | Ser | Asn | Thr | Phe | Leu | Asp | Lys | Gln | Asn | Asp | Val | Glu | Ile |
| | | 275 | | | | | 280 | | | | | 285 | | | |
| Pro | Ser | Pro | Thr | Gln | Lys | Asp | Arg | Glu | Lys | Lys | Lys | Lys | Gln | Gln | Leu |
| | 290 | | | | | 295 | | | | | 300 | | | | |
| Met | Thr | Gln | Ile | Ser | Gly | Val | Lys | Lys | Leu | Met | His | Ser | Ser | Ser | Leu |
| 305 | | | | | 310 | | | | | 315 | | | | | 320 |
| Asn | Asn | Thr | Ser | Ile | Ser | Arg | Phe | Gly | Val | Asn | Thr | Glu | Asn | Glu | Asp |
| | | | | 325 | | | | | 330 | | | | | 335 | |
| His | Leu | Ala | Lys | Glu | Leu | Glu | Asp | Leu | Asn | Lys | Trp | Gly | Leu | Asn | Ile |
| | | | 340 | | | | | 345 | | | | | 350 | | |
| Phe | Asn | Val | Ala | Gly | Tyr | Ser | His | Asn | Arg | Pro | Leu | Thr | Cys | Ile | Met |
| | | 355 | | | | | 360 | | | | | 365 | | | |
| Tyr | Ala | Ile | Phe | Gln | Glu | Arg | Asp | Leu | Leu | Lys | Thr | Phe | Arg | Ile | Ser |
| | 370 | | | | | 375 | | | | | 380 | | | | |
| Ser | Asp | Thr | Phe | Ile | Thr | Tyr | Met | Met | Thr | Leu | Glu | Asp | His | Tyr | His |
| 385 | | | | | 390 | | | | | 395 | | | | | 400 |
| Ser | Asp | Val | Ala | Tyr | His | Asn | Ser | Leu | His | Ala | Ala | Asp | Val | Ala | Gln |
| | | | | 405 | | | | | 410 | | | | | 415 | |
| Ser | Thr | His | Val | Leu | Leu | Ser | Thr | Pro | Ala | Leu | Asp | Ala | Val | Phe | Thr |
| | | | 420 | | | | | 425 | | | | | 430 | | |
| Asp | Leu | Glu | Ile | Leu | Ala | Ala | Ile | Phe | Ala | Ala | Ala | Ile | His | Asp | Val |
| | | 435 | | | | | 440 | | | | | 445 | | | |
| Asp | His | Pro | Gly | Val | Ser | Asn | Gln | Phe | Leu | Ile | Asn | Thr | Asn | Ser | Glu |
| | 450 | | | | | 455 | | | | | 460 | | | | |
| Leu | Ala | Leu | Met | Tyr | Asn | Asp | Glu | Ser | Val | Leu | Glu | Asn | His | His | Leu |
| 465 | | | | | 470 | | | | | 475 | | | | | 480 |
| Ala | Val | Gly | Phe | Lys | Leu | Leu | Gln | Glu | Glu | His | Cys | Asp | Ile | Phe | Met |

|  |  |  |  | 485 |  |  |  |  | 490 |  |  |  |  | 495 |  |
|---|---|---|---|---|---|---|---|---|---|---|---|---|---|---|---|
| Asn | Leu | Thr | Lys | Lys | Gln | Arg | Gln | Thr | Leu | Arg | Lys | Met | Val | Ile | Asp |
|  |  |  | 500 |  |  |  |  | 505 |  |  |  | 510 |  |  |  |
| Met | Val | Leu | Ala | Thr | Asp | Met | Ser | Lys | His | Met | Ser | Leu | Leu | Ala | Asp |
|  |  |  | 515 |  |  |  |  | 520 |  |  |  | 525 |  |  |  |
| Leu | Lys | Thr | Met | Val | Glu | Thr | Lys | Lys | Val | Thr | Ser | Ser | Gly | Val | Leu |
|  |  |  | 530 |  |  |  |  | 535 |  |  |  | 540 |  |  |  |
| Leu | Leu | Asp | Asn | Tyr | Thr | Asp | Arg | Ile | Gln | Val | Leu | Arg | Asn | Met | Val |
| 545 |  |  |  |  | 550 |  |  |  |  | 555 |  |  |  |  | 560 |
| His | Cys | Ala | Asp | Leu | Ser | Asn | Pro | Thr | Lys | Ser | Leu | Glu | Leu | Tyr | Arg |
|  |  |  |  | 565 |  |  |  |  | 570 |  |  |  |  | 575 |  |
| Gln | Trp | Thr | Asp | Arg | Ile | Met | Glu | Glu | Phe | Phe | Gln | Gln | Gly | Asp | Lys |
|  |  |  |  | 580 |  |  |  |  | 585 |  |  |  |  | 590 |  |
| Glu | Arg | Glu | Arg | Gly | Met | Glu | Ile | Ser | Pro | Met | Cys | Asp | Lys | His | Thr |
|  |  |  | 595 |  |  |  |  | 600 |  |  |  | 605 |  |  |  |
| Ala | Ser | Val | Glu | Lys | Ser | Gln | Val | Gly | Phe | Ile | Asp | Tyr | Ile | Val | His |
|  |  |  | 610 |  |  |  |  | 615 |  |  |  | 620 |  |  |  |
| Pro | Leu | Trp | Glu | Thr | Trp | Ala | Asp | Leu | Val | Gln | Pro | Asp | Ala | Gln | Asp |
| 625 |  |  |  |  | 630 |  |  |  |  | 635 |  |  |  |  | 640 |
| Ile | Leu | Asp | Thr | Leu | Glu | Asp | Asn | Arg | Asn | Trp | Tyr | Gln | Ser | Met | Ile |
|  |  |  |  | 645 |  |  |  |  | 650 |  |  |  |  | 655 |  |
| Pro | Gln | Ser | Pro | Ser | Pro | Pro | Leu | Asp | Glu | Gln | Asn | Arg | Asp | Cys | Gln |
|  |  |  |  | 660 |  |  |  |  | 665 |  |  |  |  | 670 |  |
| Gly | Leu | Met | Glu | Lys | Phe | Gln | Phe | Glu | Leu | Thr | Leu | Asp | Glu | Glu | Asp |
|  |  |  | 675 |  |  |  |  | 680 |  |  |  | 685 |  |  |  |
| Ser | Glu | Gly | Pro | Glu | Lys | Glu | Gly | Glu | Gly | His | Ser | Tyr | Phe | Ser | Ser |
|  |  |  | 690 |  |  |  |  | 695 |  |  |  | 700 |  |  |  |
| Thr | Lys | Thr | Leu | Cys | Val | Ile | Asp | Pro | Glu | Asn | Arg | Asp | Ser | Leu | Gly |
| 705 |  |  |  |  | 710 |  |  |  |  | 715 |  |  |  |  | 720 |
| Glu | Thr | Asp | Ile | Asp | Ile | Ala | Thr | Glu | Asp | Lys | Ser | Pro | Val | Asp | Thr |
|  |  |  |  | 725 |  |  |  |  | 730 |  |  |  |  | 735 |  |

(2) INFORMATION FOR SEQ ID NO:25:

(i) SEQUENCE CHARACTERISTICS:
        (A) LENGTH: 1276 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..504

(xi) SEQUENCE DESCRIPTION: SEQ ID NO:25:

| GCGGCCGCAT | TGCGTGGTGG | CGGCGGCCGA | GCCTCGCTTT | GAGAGACAGA | ATGGACAGCA | 60 |
|---|---|---|---|---|---|---|
| AATTATGGAT | GAACCTATGG | GAGAGGAGGA | GATTAACCCA | CAAACTGAAG | AAGTCAGTAT | 120 |
| CAAAGAAATT | GCAATCACAC | ATCATGTAAA | GGAAGGACAT | GAAAAGGCAG | ATCCTTCCCA | 180 |
| GTTTGAACTT | TTAAAAGTAT | TAGGGCAGGG | ATCATTTGGA | AAGGTTTTCT | TAGTTAAAAA | 240 |
| AATCTCAGGC | TCTGATGCTA | GGCAGCTTTA | TGCCATGAAG | GTATTGAAGA | AGGCCACACT | 300 |
| GAAAGTTCGA | GACCGAGTTC | GGACAAAAAT | GGAACGTGAT | ATCTTGGTAG | AGGTTAATCA | 360 |
| TCCTTTTATT | GTCAAGTTGC | ATTATCTTTT | CAAACTGAAG | GGAAGTTGTA | TCTTATTTGG | 420 |
| ATTTTCTCAG | GGGAGGAGAT | TTGTTTACAC | GCTTATCCAA | AGAGGTGATG | TTCACAGAAG | 480 |

```
AAGATGTCAA ATTCTACCTG GCTGAACTTG CACTTGCTTT AGACCATCTA CNTAGCCTGG      540

GAATAATTTA TAGAGACTTA AAACCAGAAA ATATCTTCTT GATGAAGAAG GTCACATCAA      600

GTTAACAGAT TTCGGCCTAA GTAAAGAGTC TATTGACCAT GAAAAGAAGG CATATCTTTT      660

TGTGGAACTG TGGAGTATAT GGCTCCAGAA GTAGTTAATC GTCGAGGTCA TACTCAGAGT      720

GCTGACTGGT GGTCTTTTGG TGTGTTAATG TTTGAAATGC TTACTGGTAC CACTCCCTTT      780

CCAAGGAAAA GATCGAAAAG AAACAATGAC TATGATTCTT AAAGCCAAAA CTTGGAATGC      840

CACAGTTTTT GAGTCCTGAA GCGCAGAGTC TTTTACGAAT GCTTTMAAG CGAAATCCTG      900

CAAACAGATT AGGTGCAGGA CCAGATGGAG TTGAAGAAAT TAAAAGACAT TCATTTTTCT      960

CAACGATAGA CTGGAATAAA CTGTATAGAG AGAAATTCAT CCGCCATTTA AACCTGCAAC     1020

GGGCAGGCCT GAAGATACAT TCTATTTTGA TCCTGAGTTT ACTGCAAAAA CTCCCAAAGA     1080

TTCACCTGGC ATTCCACCTA GTGCTAATGC ACATCAGCTT TTTCGGGGGT TTAGTTTTGT     1140

TGCTATTACC TCAGATGATG AAAGCCAAGC TATGCAGACA GTTGGTGTAC ATTCAATTGT     1200

TCAGCAGTTA CACAGGAACA GTATNCAGTT TACTGATGGA TATGAAGTAA AAGAAGATAT     1260

TGGAGTTGGC TCCTAC                                                     1276
```

(2) INFORMATION FOR SEQ ID NO:26:

(i) SEQUENCE CHARACTERISTICS:
        (A) LENGTH: 167 amino acids
        (B) TYPE: amino acid
        (C) STRANDEDNESS: single
        (D) TOPOLOGY: linear (xi) SEQUENCE DESCRIPTION: SEQ ID NO:26:

```
Arg Pro His Cys Val Val Ala Ala Ala Glu Pro Arg Phe Glu Arg Gln
 1               5                  10                  15

Asn Gly Gln Gln Ile Met Asp Glu Pro Met Gly Glu Glu Ile Asn
                20                  25                  30

Pro Gln Thr Glu Glu Val Ser Ile Lys Glu Ile Ala Ile Thr His His
            35                  40                  45

Val Lys Glu Gly His Glu Lys Ala Asp Pro Ser Gln Phe Glu Leu Leu
 50                  55                  60

Lys Val Leu Gly Gln Gly Ser Phe Gly Lys Val Phe Leu Val Lys Lys
 65                  70                  75                  80

Ile Ser Gly Ser Asp Ala Arg Gln Leu Tyr Ala Met Lys Val Leu Lys
                85                  90                  95

Lys Ala Thr Leu Lys Val Arg Asp Arg Val Arg Thr Lys Met Glu Arg
            100                 105                 110

Asp Ile Leu Val Glu Val Asn His Pro Phe Ile Val Lys Leu His Tyr
            115                 120                 125

Leu Phe Lys Leu Lys Gly Ser Cys Ile Leu Phe Gly Phe Ser Gln Gly
            130                 135                 140

Arg Arg Phe Val Tyr Thr Leu Ile Gln Arg Gly Asp Val His Arg Arg
145                 150                 155                 160

Arg Cys Gln Ile Leu Pro Gly
                165
```

(2) INFORMATION FOR SEQ ID NO:27:

(i) SEQUENCE CHARACTERISTICS:
        (A) LENGTH: 2384 base pairs
        (B) TYPE: nucleic acid
        (C) STRANDEDNESS: single
        (D) TOPOLOGY: linear ( i i ) MOLECULE TYPE: cDNA ( i x ) FEATURE:
    ( A ) NAME/KEY: CDS
    ( B ) LOCATION: join(1..1539, 1859..2383)

( x i ) SEQUENCE DESCRIPTION: SEQ ID NO:27:

```
GCG GCC GCA TTC GGG GAC AGC GGC GGG CGG CTG GGA CGG CGG GTG CGG      48
Ala Ala Ala Phe Gly Asp Ser Gly Gly Arg Leu Gly Arg Arg Val Arg
 1               5                  10                  15

CGG GGC CGA GCC CGC ACG ATG CCT CAC TTC ACC GTG GTG CCA GTG GAC      96
Arg Gly Arg Ala Arg Thr Met Pro His Phe Thr Val Val Pro Val Asp
             20                  25                  30

GGG CCG AGG CGC GGC GAC TAT GAC AAC CTC GAG GGG CTC AGT TGG GTG     144
Gly Pro Arg Arg Gly Asp Tyr Asp Asn Leu Glu Gly Leu Ser Trp Val
         35                  40                  45

GAC TAC GGG GAG CGC GCC GAG CTG GAT GAC TCG GAC GGA CAT GGC AAC     192
Asp Tyr Gly Glu Arg Ala Glu Leu Asp Asp Ser Asp Gly His Gly Asn
     50                  55                  60

CAC AGA GAG AGC AGC CCT TTT CTT TCC CCC TTG GAG GCT TCC AGA GGA     240
His Arg Glu Ser Ser Pro Phe Leu Ser Pro Leu Glu Ala Ser Arg Gly
 65                  70                  75                  80

ATT GAC TAC TAT GAC AGG AAC CTG GCA CTG TTT GAG GAA GAG CTG GAC     288
Ile Asp Tyr Tyr Asp Arg Asn Leu Ala Leu Phe Glu Glu Glu Leu Asp
                 85                  90                  95

ATC CGC CCA AAG GTA TCG TCT CTT CTG GGA AAG CTC GTC AGC TAC ACC     336
Ile Arg Pro Lys Val Ser Ser Leu Leu Gly Lys Leu Val Ser Tyr Thr
            100                 105                 110

AAC CTC ACC CAG GGC GCC AAA GAG CAT GAG GAG GCC GAG AGT GGG GAG     384
Asn Leu Thr Gln Gly Ala Lys Glu His Glu Glu Ala Glu Ser Gly Glu
        115                 120                 125

GGC ACC CGC CGG AGG GCA GCC GAG GCA CCC AGC ATG GGC ACC CTC ATG     432
Gly Thr Arg Arg Arg Ala Ala Glu Ala Pro Ser Met Gly Thr Leu Met
    130                 135                 140

GGG GTG TAC CTG CCC TGC CTG CAG AAT ATC TTT GGG GTT ATC CTC TTC     480
Gly Val Tyr Leu Pro Cys Leu Gln Asn Ile Phe Gly Val Ile Leu Phe
145                 150                 155                 160

CTG CGG CTG ACC TGG ATG GTG GGC ACA GCA GGT GTG CTA CAG GCC CTC     528
Leu Arg Leu Thr Trp Met Val Gly Thr Ala Gly Val Leu Gln Ala Leu
                165                 170                 175

CTC ATC GTG CTT ATC TGC TGC TGT TGT ACC CTG CTG ACG GCC ATC TCC     576
Leu Ile Val Leu Ile Cys Cys Cys Cys Thr Leu Leu Thr Ala Ile Ser
            180                 185                 190

ATG AGT GCC ATC GCC ACC AAC GGT GTG GTT CCA GCT GGG GGC TCC TAT     624
Met Ser Ala Ile Ala Thr Asn Gly Val Val Pro Ala Gly Gly Ser Tyr
        195                 200                 205

TTC ATG ATC TCT CGT TCA CTG GGG CCA GAA TTT GGA GGT GCT GTG GGC     672
Phe Met Ile Ser Arg Ser Leu Gly Pro Glu Phe Gly Gly Ala Val Gly
    210                 215                 220

CTG TGC TTC TAC CTG GGA ACA ACA TTC GCA GCA GCC ATG TAC ATC CTG     720
Leu Cys Phe Tyr Leu Gly Thr Thr Phe Ala Ala Ala Met Tyr Ile Leu
225                 230                 235                 240

GGG GCC ATC GAG ATC TTG CTG ACC TAC ATT GCC CCA CCA GCT GCC ATT     768
Gly Ala Ile Glu Ile Leu Leu Thr Tyr Ile Ala Pro Pro Ala Ala Ile
                245                 250                 255

TTT TAC CCA TCG GGT GCT CAT GAC ACG TCG AAT GCC ACT TTG AAC AAT     816
Phe Tyr Pro Ser Gly Ala His Asp Thr Ser Asn Ala Thr Leu Asn Asn
            260                 265                 270

ATG CGT GTG TAT GGG ACC ATT TTC CTG GCC TTC ATG ACC CTG GTG GTG     864
Met Arg Val Tyr Gly Thr Ile Phe Leu Ala Phe Met Thr Leu Val Val
        275                 280                 285
```

| | | | | | | | | | | | | | | | | |
|---|---|---|---|---|---|---|---|---|---|---|---|---|---|---|---|---|
| TTT | GTG | GGG | GTC | AAG | TAT | GTG | AAC | AAA | TTT | GCC | TCG | CTC | TTC | CTG | GCC | 912 |
| Phe | Val | Gly | Val | Lys | Tyr | Val | Asn | Lys | Phe | Ala | Ser | Leu | Phe | Leu | Ala | |
| | 290 | | | | | 295 | | | | 300 | | | | | | |
| TGT | GTG | ATC | ATC | TCC | ATC | CTC | TCC | ATC | TAT | GCT | GGG | GGC | ATA | AAG | TCT | 960 |
| Cys | Val | Ile | Ile | Ser | Ile | Leu | Ser | Ile | Tyr | Ala | Gly | Gly | Ile | Lys | Ser | |
| 305 | | | | | 310 | | | | | 315 | | | | | 320 | |
| ATA | TTT | GAC | CCT | CCC | GTG | TTT | CCG | GTA | TGC | ATG | CTG | GGC | AAC | AGG | ACC | 1008 |
| Ile | Phe | Asp | Pro | Pro | Val | Phe | Pro | Val | Cys | Met | Leu | Gly | Asn | Arg | Thr | |
| | | | | 325 | | | | | 330 | | | | | 335 | | |
| CTG | TCC | CGG | GAC | CAG | TTT | GAC | ATC | TGT | GCC | AAG | ACA | GCT | GTA | GTG | GAC | 1056 |
| Leu | Ser | Arg | Asp | Gln | Phe | Asp | Ile | Cys | Ala | Lys | Thr | Ala | Val | Val | Asp | |
| | | | 340 | | | | | 345 | | | | | 350 | | | |
| AAT | GAG | ACA | GTG | GCC | ACC | CAG | CTA | TGG | AGT | TTC | TTC | TGC | CAC | AGC | CCC | 1104 |
| Asn | Glu | Thr | Val | Ala | Thr | Gln | Leu | Trp | Ser | Phe | Phe | Cys | His | Ser | Pro | |
| | | 355 | | | | | 360 | | | | | 365 | | | | |
| AAC | CTT | ACG | ACC | GAC | TCC | TGT | GAC | CCC | TAC | TTC | ATG | CTC | AAC | AAT | GTG | 1152 |
| Asn | Leu | Thr | Thr | Asp | Ser | Cys | Asp | Pro | Tyr | Phe | Met | Leu | Asn | Asn | Val | |
| | 370 | | | | | 375 | | | | | 380 | | | | | |
| ACC | GAG | ATC | CCT | GGC | ATC | CCC | GGG | GCA | GCT | GCT | GGT | GTG | CTC | CAG | GAA | 1200 |
| Thr | Glu | Ile | Pro | Gly | Ile | Pro | Gly | Ala | Ala | Ala | Gly | Val | Leu | Gln | Glu | |
| 385 | | | | | 390 | | | | | 395 | | | | | 400 | |
| AAC | CTG | TGG | AGC | GCC | TAC | CTG | GAG | AAG | GGT | GAC | ATC | GTG | GAG | AAG | CAT | 1248 |
| Asn | Leu | Trp | Ser | Ala | Tyr | Leu | Glu | Lys | Gly | Asp | Ile | Val | Glu | Lys | His | |
| | | | | 405 | | | | | 410 | | | | | 415 | | |
| GGG | CTG | CCC | TCC | GCA | GAT | GCC | CCG | AGC | CTG | AAG | GAG | AGC | CTG | CCT | CTG | 1296 |
| Gly | Leu | Pro | Ser | Ala | Asp | Ala | Pro | Ser | Leu | Lys | Glu | Ser | Leu | Pro | Leu | |
| | | | 420 | | | | | 425 | | | | | 430 | | | |
| TAC | GTG | GTC | GCT | GAC | ATC | GCC | ACA | TCC | TTC | ACC | GTG | CTG | GTC | GGC | ATC | 1344 |
| Tyr | Val | Val | Ala | Asp | Ile | Ala | Thr | Ser | Phe | Thr | Val | Leu | Val | Gly | Ile | |
| | | 435 | | | | | 440 | | | | | 445 | | | | |
| TTC | TTC | CCT | TCT | GTA | ACA | GGT | ATG | GCG | ATG | GTG | TCA | GCA | GGA | ACT | TGG | 1392 |
| Phe | Phe | Pro | Ser | Val | Thr | Gly | Met | Ala | Met | Val | Ser | Ala | Gly | Thr | Trp | |
| | 450 | | | | | 455 | | | | | 460 | | | | | |
| TGG | TGG | GCA | CAC | TGG | CCT | GGC | CTT | CAC | CCT | GGG | TCA | TCG | TCA | TCG | GCT | 1440 |
| Trp | Trp | Ala | His | Trp | Pro | Gly | Leu | His | Pro | Gly | Ser | Ser | Ser | Ser | Ala | |
| 465 | | | | | 470 | | | | | 475 | | | | | 480 | |
| CCT | TCT | TTT | CAA | CGT | GTG | GCG | CTG | GCC | TCC | AGA | GCC | TCA | CAG | GGG | CAC | 1488 |
| Pro | Ser | Phe | Gln | Arg | Val | Ala | Leu | Ala | Ser | Arg | Ala | Ser | Gln | Gly | His | |
| | | | | 485 | | | | | 490 | | | | | 495 | | |
| CAC | GCC | TAT | TGC | AGG | CCA | TTG | CCA | AGG | ACA | ACA | TCA | TCC | CCT | TCC | TCC | 1536 |
| His | Ala | Tyr | Cys | Arg | Pro | Leu | Pro | Arg | Thr | Thr | Ser | Ser | Pro | Ser | Ser | |
| | | | 500 | | | | | 505 | | | | | 510 | | | |
| GGG | TGAGCCCCTC | TGCACTCCCC | CATGGCCTGG | CTGCTCCCAG | GCCCTCGCCC | | | | | | | | | | | 1589 |
| Gly | | | | | | | | | | | | | | | | |
| GGCTGGGGAG | AGAGATAGGG | AACACAGATG | CAGCACGTCC | TGCCCTTATT | GCCCCCGGGC | | | | | | | | | | | 1649 |
| CAGGCGGCCA | TCCATGAGGA | GCTACTGAGA | AGTGCCCTGG | GCCTGGCACT | CACCTGGGCC | | | | | | | | | | | 1709 |
| TGGAGCTGCC | TGGACCCAGA | ATCTTCATGG | CCTGTTTAGG | GCTCATCCAA | AGGAGAGAGG | | | | | | | | | | | 1769 |
| CCTGGTGAGG | TGGAATCAGG | GAGACTGGTG | ACACCCATAG | GGATAGACAC | AGGGGCGGCC | | | | | | | | | | | 1829 |
| TGAGCCCCCA | AGGCGGGCCC | TGGGGGTGA | GGG | AGG | CCA | GGC | TGG | GGT | CTG | GGG | | | | | | 1882 |
| | | | | Gly | Arg | Pro | Gly | Trp | Gly | Leu | Gly | | | | | |
| | | | | | | 515 | | | | | 520 | | | | | |
| CCC | AAG | GTG | TGG | AAT | GGG | GGT | GAC | AGG | ACC | CAG | CTT | CCT | TCC | TGG | TGC | 1930 |
| Pro | Lys | Val | Trp | Asn | Gly | Gly | Asp | Arg | Thr | Gln | Leu | Pro | Ser | Trp | Cys | |
| | | | | 525 | | | | 530 | | | | | 535 | | | |
| ACA | CAG | GTG | TTT | GGC | CAC | GGG | AAG | GTG | AAT | GGT | GAA | CCC | ACA | TGG | GCA | 1978 |
| Thr | Gln | Val | Phe | Gly | His | Gly | Lys | Val | Asn | Gly | Glu | Pro | Thr | Trp | Ala | |
| | | 540 | | | | | 545 | | | | | 550 | | | | |

| | | | | | | | | | | | | | | | | |
|---|---|---|---|---|---|---|---|---|---|---|---|---|---|---|---|---|
| CTC | CTC | CTG | ACG | GCA | CTC | ATC | GCC | GAG | CTG | GGC | ATC | CTC | ATC | GCC | TCC | 2026 |
| Leu | Leu | Leu | Thr | Ala | Leu | Ile | Ala | Glu | Leu | Gly | Ile | Leu | Ile | Ala | Ser | |
| | | 555 | | | | 560 | | | | 565 | | | | | | |
| CTC | GAC | ATG | GTG | GCC | CCC | ATC | TTA | TCC | ATG | TTC | TTT | CTG | ATG | TGC | TAC | 2074 |
| Leu | Asp | Met | Val | Ala | Pro | Ile | Leu | Ser | Met | Phe | Phe | Leu | Met | Cys | Tyr | |
| 570 | | | | | 575 | | | | | 580 | | | | | 585 | |
| CTG | TTC | GTG | AAC | CTC | GCC | TGT | GCG | GTG | CAG | ACA | CTC | CTG | AGG | ACC | CCC | 2122 |
| Leu | Phe | Val | Asn | Leu | Ala | Cys | Ala | Val | Gln | Thr | Leu | Leu | Arg | Thr | Pro | |
| | | | | 590 | | | | | 595 | | | | | 600 | | |
| AAC | TGG | CGG | CCC | CGG | TTC | AAG | TAC | TAT | CAC | TGG | GCG | CTG | TCC | TTC | CTG | 2170 |
| Asn | Trp | Arg | Pro | Arg | Phe | Lys | Tyr | Tyr | His | Trp | Ala | Leu | Ser | Phe | Leu | |
| | | | | 605 | | | | | 610 | | | | | 615 | | |
| GGC | ATG | AGT | CTC | TGC | CTG | GCC | CTT | ATG | TTT | GTC | TCC | TCC | TGG | TAC | TAT | 2218 |
| Gly | Met | Ser | Leu | Cys | Leu | Ala | Leu | Met | Phe | Val | Ser | Ser | Trp | Tyr | Tyr | |
| | | | 620 | | | | | 625 | | | | | 630 | | | |
| GCC | CTG | GTG | GCC | ATG | CTC | ATC | GCC | GGC | ATG | ATC | TAC | AAA | TAC | ATC | GAG | 2266 |
| Ala | Leu | Val | Ala | Met | Leu | Ile | Ala | Gly | Met | Ile | Tyr | Lys | Tyr | Ile | Glu | |
| | | 635 | | | | | 640 | | | | | 645 | | | | |
| TAC | CAA | GGG | GCT | GAG | AAG | GAG | TGG | GGT | GAC | GGG | ATC | CGA | GGC | CTG | TCC | 2314 |
| Tyr | Gln | Gly | Ala | Glu | Lys | Glu | Trp | Gly | Asp | Gly | Ile | Arg | Gly | Leu | Ser | |
| 650 | | | | | 655 | | | | | 660 | | | | | 665 | |
| CTG | AGC | GCT | GCC | CGC | TAC | GCG | CTG | TTG | CGG | CTG | GAG | GAG | GGG | CCT | CCT | 2362 |
| Leu | Ser | Ala | Ala | Arg | Tyr | Ala | Leu | Leu | Arg | Leu | Glu | Glu | Gly | Pro | Pro | |
| | | | | 670 | | | | | 675 | | | | | 680 | | |
| CAC | ACC | AAG | AAC | TGG | CGG | CCG | C | | | | | | | | | 2384 |
| His | Thr | Lys | Asn | Trp | Arg | Pro | | | | | | | | | | |
| | | | | 685 | | | | | | | | | | | | |

( 2 ) INFORMATION FOR SEQ ID NO:28:

( i ) SEQUENCE CHARACTERISTICS:
        ( A ) LENGTH: 688 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| | | | | | | | | | | | | | | |
|---|---|---|---|---|---|---|---|---|---|---|---|---|---|---|
| Ala | Ala | Ala | Phe | Gly | Asp | Ser | Gly | Gly | Arg | Leu | Gly | Arg | Arg | Val | Arg |
| 1 | | | | 5 | | | | | 10 | | | | | 15 | |
| Arg | Gly | Arg | Ala | Arg | Thr | Met | Pro | His | Phe | Thr | Val | Val | Pro | Val | Asp |
| | | | 20 | | | | | 25 | | | | | 30 | | |
| Gly | Pro | Arg | Arg | Gly | Asp | Tyr | Asp | Asn | Leu | Glu | Gly | Leu | Ser | Trp | Val |
| | | 35 | | | | | 40 | | | | | 45 | | | |
| Asp | Tyr | Gly | Glu | Arg | Ala | Glu | Leu | Asp | Asp | Ser | Asp | Gly | His | Gly | Asn |
| 50 | | | | | 55 | | | | | 60 | | | | | |
| His | Arg | Glu | Ser | Ser | Pro | Phe | Leu | Ser | Pro | Leu | Glu | Ala | Ser | Arg | Gly |
| 65 | | | | 70 | | | | | 75 | | | | | 80 | |
| Ile | Asp | Tyr | Tyr | Asp | Arg | Asn | Leu | Ala | Leu | Phe | Glu | Glu | Glu | Leu | Asp |
| | | | 85 | | | | | 90 | | | | | 95 | | |
| Ile | Arg | Pro | Lys | Val | Ser | Ser | Leu | Leu | Gly | Lys | Leu | Val | Ser | Tyr | Thr |
| | | | 100 | | | | | 105 | | | | | 110 | | |
| Asn | Leu | Thr | Gln | Gly | Ala | Lys | Glu | His | Glu | Glu | Ala | Glu | Ser | Gly | Glu |
| | | 115 | | | | | 120 | | | | | 125 | | | |
| Gly | Thr | Arg | Arg | Arg | Ala | Ala | Glu | Ala | Pro | Ser | Met | Gly | Thr | Leu | Met |
| | | 130 | | | | | 135 | | | | | 140 | | | |
| Gly | Val | Tyr | Leu | Pro | Cys | Leu | Gln | Asn | Ile | Phe | Gly | Val | Ile | Leu | Phe |
| 145 | | | | | 150 | | | | | 155 | | | | | 160 |
| Leu | Arg | Leu | Thr | Trp | Met | Val | Gly | Thr | Ala | Gly | Val | Leu | Gln | Ala | Leu |
| | | | | 165 | | | | | 170 | | | | | 175 | |

```
Leu Ile Val Leu Ile Cys Cys Cys Cys Thr Leu Leu Thr Ala Ile Ser
        180             185                 190
Met Ser Ala Ile Ala Thr Asn Gly Val Val Pro Ala Gly Gly Ser Tyr
        195             200             205
Phe Met Ile Ser Arg Ser Leu Gly Pro Glu Phe Gly Gly Ala Val Gly
    210             215             220
Leu Cys Phe Tyr Leu Gly Thr Thr Phe Ala Ala Ala Met Tyr Ile Leu
225             230             235                 240
Gly Ala Ile Glu Ile Leu Leu Thr Tyr Ile Ala Pro Pro Ala Ala Ile
            245             250             255
Phe Tyr Pro Ser Gly Ala His Asp Thr Ser Asn Ala Thr Leu Asn Asn
            260             265             270
Met Arg Val Tyr Gly Thr Ile Phe Leu Ala Phe Met Thr Leu Val Val
        275             280             285
Phe Val Gly Val Lys Tyr Val Asn Lys Phe Ala Ser Leu Phe Leu Ala
    290             295             300
Cys Val Ile Ile Ser Ile Leu Ser Ile Tyr Ala Gly Gly Ile Lys Ser
305             310             315                 320
Ile Phe Asp Pro Pro Val Phe Pro Val Cys Met Leu Gly Asn Arg Thr
            325             330             335
Leu Ser Arg Asp Gln Phe Asp Ile Cys Ala Lys Thr Ala Val Val Asp
            340             345             350
Asn Glu Thr Val Ala Thr Gln Leu Trp Ser Phe Phe Cys His Ser Pro
        355             360             365
Asn Leu Thr Thr Asp Ser Cys Asp Pro Tyr Phe Met Leu Asn Asn Val
370             375             380
Thr Glu Ile Pro Gly Ile Pro Gly Ala Ala Ala Gly Val Leu Gln Glu
385             390             395                 400
Asn Leu Trp Ser Ala Tyr Leu Glu Lys Gly Asp Ile Val Glu Lys His
            405             410             415
Gly Leu Pro Ser Ala Asp Ala Pro Ser Leu Lys Glu Ser Leu Pro Leu
            420             425             430
Tyr Val Val Ala Asp Ile Ala Thr Ser Phe Thr Val Leu Val Gly Ile
        435             440             445
Phe Phe Pro Ser Val Thr Gly Met Ala Met Val Ser Ala Gly Thr Trp
    450             455             460
Trp Trp Ala His Trp Pro Gly Leu His Pro Gly Ser Ser Ser Ser Ala
465             470             475                 480
Pro Ser Phe Gln Arg Val Ala Leu Ala Ser Arg Ala Ser Gln Gly His
            485             490             495
His Ala Tyr Cys Arg Pro Leu Pro Arg Thr Thr Ser Ser Pro Ser Ser
            500             505             510
Gly Gly Arg Pro Gly Trp Gly Leu Gly Pro Lys Val Trp Asn Gly Gly
            515             520             525
Asp Arg Thr Gln Leu Pro Ser Trp Cys Thr Gln Val Phe Gly His Gly
        530             535             540
Lys Val Asn Gly Glu Pro Thr Trp Ala Leu Leu Leu Thr Ala Leu Ile
545             550             555             560
Ala Glu Leu Gly Ile Leu Ile Ala Ser Leu Asp Met Val Ala Pro Ile
            565             570             575
Leu Ser Met Phe Phe Leu Met Cys Tyr Leu Phe Val Asn Leu Ala Cys
            580             585             590
Ala Val Gln Thr Leu Leu Arg Thr Pro Asn Trp Arg Pro Arg Phe Lys
```

-continued

```
                595                            600                              605
Tyr  Tyr  His  Trp  Ala  Leu  Ser  Phe  Leu  Gly  Met  Ser  Leu  Cys  Leu  Ala
     610                           615                      620
Leu  Met  Phe  Val  Ser  Ser  Trp  Tyr  Tyr  Ala  Leu  Val  Ala  Met  Leu  Ile
625                      630                      635                           640
Ala  Gly  Met  Ile  Tyr  Lys  Tyr  Ile  Glu  Tyr  Gln  Gly  Ala  Glu  Lys  Glu
                645                      650                           655
Trp  Gly  Asp  Gly  Ile  Arg  Gly  Leu  Ser  Leu  Ser  Ala  Ala  Arg  Tyr  Ala
               660                      665                 670
Leu  Leu  Arg  Leu  Glu  Glu  Gly  Pro  Pro  His  Thr  Lys  Asn  Trp  Arg  Pro
     675                          680                      685
```

( 2 ) INFORMATION FOR SEQ ID NO:29:

( i ) SEQUENCE CHARACTERISTICS:
        ( A ) LENGTH: 1675 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 492..1330

( x i ) SEQUENCE DESCRIPTION: SEQ ID NO:29:

```
AAGCTTGCGG  CCGCATTGCG  AGAACGAGAA  CGGGAGCGAG  AGAGAGAGCG  AGAGAGGGAA         60

CGGGAGCGAG  AAAGAGAAAA  AGACAAAAAA  CGGGACCGAG  AAGAAGATGA  GAAGATGCA         120

TACGAACGAA  GAAAACTTGA  AAGAAAACTC  CGAGAGAAAG  AAGCTGCTTA  TCAAGAGCGC         180

CTTAAGAATT  GGGAAATCAG  AGAACGAAAG  AAAACCCGGG  AATATGAGAA  AGAAGCTGAA         240

AGAGAAGAAG  AAAGAAGAAG  AGAAATGGCC  AAAGAAGCTA  AACGACTAAA  AGAATTCTTA         300

GAAGACTATG  ATGATGATAG  AGATGACCCC  AAATATTACA  GAGGAAGTGC  TCTTCAGAAA         360

AGGTTGCGTG  ATAGAGAAAA  GGAAATGGAA  GCAGATGAAC  GAGATAGGAA  GAGAGAGAAG         420

GAGGAGCTTG  AGGAAATCAG  GCAGCGCTTC  TGGCAGAAGG  GCATCCAGAT  CCAGATGCAG         480

AGCTCCAGAG  G ATG GAA CAA GAG GCT GAG AGG CGC AGG CAG CCA CAA ATA             530
            Met Glu Gln Glu Ala Glu Arg Arg Arg Gln Pro Gln Ile
             1               5                        10

AAG CAA GAG CCA GAA TCA GAA GAG GAG GAA GAA GAA AAG CAA GAA AAA               578
Lys Gln Glu Pro Glu Ser Glu Glu Glu Glu Glu Glu Lys Gln Glu Lys
 15                  20                       25

GAA GAA AAA CGA GAA GAA CCC ATG GAA GAG GAA GAG GAG CCA GAG CAA               626
Glu Glu Lys Arg Glu Glu Pro Met Glu Glu Glu Glu Glu Pro Glu Gln
 30                      35                          40                  45

AAG CCT TGT CTG AAA CCT ACT CTG AGG CCC ATC AGC TCT GCT CCA TCT               674
Lys Pro Cys Leu Lys Pro Thr Leu Arg Pro Ile Ser Ser Ala Pro Ser
                 50                      55                      60

GTT TCC TCT GCC AGT GGC AAT GCA ACA CCT AAC ACT CCT GGG GAT GAG               722
Val Ser Ser Ala Ser Gly Asn Ala Thr Pro Asn Thr Pro Gly Asp Glu
                 65                      70                      75

TCT CCC TGT GGT ATT ATT ATT CCT CAT GAA AAC TCA CCA GAT CAA CAG               770
Ser Pro Cys Gly Ile Ile Ile Pro His Glu Asn Ser Pro Asp Gln Gln
             80                      85                      90

CAA CCT GAG GAG CAT AGG CCA AAA ATA GGA CTA AGT CTT AAA CTG GGT               818
Gln Pro Glu Glu His Arg Pro Lys Ile Gly Leu Ser Leu Lys Leu Gly
         95                      100                     105

GCT TCC AAT AGT CCT GGT CAG CCT AAT TCT GTG AAG AGA AAG AAA CTA               866
Ala Ser Asn Ser Pro Gly Gln Pro Asn Ser Val Lys Arg Lys Lys Leu
```

| | | | | | | | | | | | | | | | | |
|---|---|---|---|---|---|---|---|---|---|---|---|---|---|---|---|---|
| | 110 | | | | 115 | | | | | 120 | | | | | 125 | |
| CCT | GTA | GAT | AGT | GTC | TTT | AAC | AAA | TTT | GAG | GAT | GAA | GAC | AGT | GAT | GAC | 914 |
| Pro | Val | Asp | Ser | Val | Phe | Asn | Lys | Phe | Glu | Asp | Glu | Asp | Ser | Asp | Asp | |
| | | | 130 | | | | | 135 | | | | | 140 | | | |
| GTA | CCC | CGA | AAA | AGG | AAA | CTG | GTT | CCC | TTG | GAT | TAT | GGT | GAA | GAT | GAT | 962 |
| Val | Pro | Arg | Lys | Arg | Lys | Leu | Val | Pro | Leu | Asp | Tyr | Gly | Glu | Asp | Asp | |
| | | | 145 | | | | | 150 | | | | | 155 | | | |
| AAA | AAT | GCA | ACC | AAA | GGC | ACT | GTA | AAC | ACT | GAA | GAA | AAG | CGT | AAA | CAC | 1010 |
| Lys | Asn | Ala | Thr | Lys | Gly | Thr | Val | Asn | Thr | Glu | Glu | Lys | Arg | Lys | His | |
| | | | 160 | | | | 165 | | | | | 170 | | | | |
| ATT | AAG | AGT | CTC | ATT | GAG | AAA | ATC | CCT | ACA | GCC | AAA | CCT | GAG | CTC | TTC | 1058 |
| Ile | Lys | Ser | Leu | Ile | Glu | Lys | Ile | Pro | Thr | Ala | Lys | Pro | Glu | Leu | Phe | |
| | 175 | | | | | 180 | | | | | 185 | | | | | |
| GCT | TAT | CCC | CTG | GAT | TGG | TCT | ATT | GTG | GAT | TCT | ATA | CTG | ATG | GAA | CGT | 1106 |
| Ala | Tyr | Pro | Leu | Asp | Trp | Ser | Ile | Val | Asp | Ser | Ile | Leu | Met | Glu | Arg | |
| 190 | | | | | 195 | | | | | 200 | | | | | 205 | |
| CGA | ATT | AGA | CCA | TGG | ATT | AAT | AAG | AAA | ATC | ATA | GAA | TAT | ATA | GGT | GAA | 1154 |
| Arg | Ile | Arg | Pro | Trp | Ile | Asn | Lys | Lys | Ile | Ile | Glu | Tyr | Ile | Gly | Glu | |
| | | | | 210 | | | | | 215 | | | | | 220 | | |
| GAA | GAA | GCT | ACA | TTA | GTT | GAT | TTT | GTT | TGT | TCT | AAG | GTT | ATG | GCT | CAT | 1202 |
| Glu | Glu | Ala | Thr | Leu | Val | Asp | Phe | Val | Cys | Ser | Lys | Val | Met | Ala | His | |
| | | | 225 | | | | | 230 | | | | | 235 | | | |
| AGT | TCA | CCC | CAG | AGC | ATT | TTA | GAT | GAT | GTT | GCC | ATG | GTA | CTT | GAT | GAA | 1250 |
| Ser | Ser | Pro | Gln | Ser | Ile | Leu | Asp | Asp | Val | Ala | Met | Val | Leu | Asp | Glu | |
| | | | 240 | | | | | 245 | | | | | 250 | | | |
| GAA | GCA | GAA | GTT | TTT | ATA | GTC | AAA | ATG | TGG | AGA | TTA | TTG | ATA | TAT | GAA | 1298 |
| Glu | Ala | Glu | Val | Phe | Ile | Val | Lys | Met | Trp | Arg | Leu | Leu | Ile | Tyr | Glu | |
| | 255 | | | | | 260 | | | | | 265 | | | | | |
| ACA | GAA | GCC | AAG | AAA | ATT | GGT | CTT | GTG | AAG | TA AAACTTTTA TATTTAGAGT | | | | | | 1350 |
| Thr | Glu | Ala | Lys | Lys | Ile | Gly | Leu | Val | Lys | | | | | | | |
| 270 | | | | | 275 | | | | | | | | | | | |

| | | | | |
|---|---|---|---|---|
| TCCATTTCAG | ATTTCTTCTT | TGCCACCCTT | TTAAGGACTT | TGAATTTTTC TTTGTCTTTG | 1410 |
| AAGACATTGT | GAGATCTGTA | ATTTTTTTT | TTTGTAGAAA | ATGTGAATTT TTTGGTCCTC | 1470 |
| TAATTTGTTG | TTGCCCTGTG | TACTCCCTTG | GTTGTAAAGT | CATCTGAATC CTTGGTTCTC | 1530 |
| TTTATACTCA | CCAGGTACAA | ATTACTGGTA | TGTTTTATAA | GCCGCAGCTA CTGTACACAG | 1590 |
| CCTATCTGAT | ATAATCTTGT | TCTGCTGATT | TGTTTCTTGT | AAATATTAAA ACGACTCCCC | 1650 |
| AATTAAAAAA | AAAAAATGCG | GCCGC | | | 1675 |

( 2 ) INFORMATION FOR SEQ ID NO:30:

( i ) SEQUENCE CHARACTERISTICS:
        ( A ) LENGTH: 279 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| | | | | | | | | | | | | | | | |
|---|---|---|---|---|---|---|---|---|---|---|---|---|---|---|---|
| Met | Glu | Gln | Glu | Ala | Glu | Arg | Arg | Arg | Gln | Pro | Gln | Ile | Lys | Gln | Glu |
| 1 | | | | 5 | | | | | 10 | | | | | 15 | |
| Pro | Glu | Ser | Glu | Glu | Glu | Glu | Glu | Lys | Gln | Glu | Lys | Glu | Glu | Lys | |
| | | | 20 | | | | | 25 | | | | | 30 | | |
| Arg | Glu | Glu | Pro | Met | Glu | Glu | Glu | Glu | Pro | Glu | Gln | Lys | Pro | Cys | |
| | | 35 | | | | | 40 | | | | | 45 | | | |
| Leu | Lys | Pro | Thr | Leu | Arg | Pro | Ile | Ser | Ser | Ala | Pro | Ser | Val | Ser | Ser |
| | 50 | | | | | 55 | | | | | 60 | | | | |
| Ala | Ser | Gly | Asn | Ala | Thr | Pro | Asn | Thr | Pro | Gly | Asp | Glu | Ser | Pro | Cys |
| 65 | | | | | 70 | | | | | 75 | | | | | 80 |

```
Gly Ile Ile Ile Pro His Glu Asn Ser Pro Asp Gln Gln Pro Glu
            85                  90                  95

Glu His Arg Pro Lys Ile Gly Leu Ser Leu Lys Leu Gly Ala Ser Asn
            100                 105                 110

Ser Pro Gly Gln Pro Asn Ser Val Lys Arg Lys Lys Leu Pro Val Asp
            115                 120                 125

Ser Val Phe Asn Lys Phe Glu Asp Glu Asp Ser Asp Asp Val Pro Arg
        130                 135                 140

Lys Arg Lys Leu Val Pro Leu Asp Tyr Gly Glu Asp Asp Lys Asn Ala
145                 150                 155                 160

Thr Lys Gly Thr Val Asn Thr Glu Glu Lys Arg Lys His Ile Lys Ser
            165                 170                 175

Leu Ile Glu Lys Ile Pro Thr Ala Lys Pro Glu Leu Phe Ala Tyr Pro
            180                 185                 190

Leu Asp Trp Ser Ile Val Asp Ser Ile Leu Met Glu Arg Arg Ile Arg
            195                 200                 205

Pro Trp Ile Asn Lys Lys Ile Ile Glu Tyr Ile Gly Glu Glu Glu Ala
        210                 215                 220

Thr Leu Val Asp Phe Val Cys Ser Lys Val Met Ala His Ser Ser Pro
225                 230                 235                 240

Gln Ser Ile Leu Asp Asp Val Ala Met Val Leu Asp Glu Glu Ala Glu
            245                 250                 255

Val Phe Ile Val Lys Met Trp Arg Leu Leu Ile Tyr Glu Thr Glu Ala
            260                 265                 270

Lys Lys Ile Gly Leu Val Lys
            275
```

( 2 ) INFORMATION FOR SEQ ID NO:31:

( i ) SEQUENCE CHARACTERISTICS:
    ( A ) LENGTH: 3073 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 3..1111

( x i ) SEQUENCE DESCRIPTION: SEQ ID NO:31:

```
GC GGC CGC GCG CCG CAT TCG GAG AGC GGA CCC CAG AGA GCC CTG AGC        47
   Gly Arg Ala Pro His Ser Glu Ser Gly Pro Gln Arg Ala Leu Ser
    1               5                  10                  15

AGC CCC ACC GCC GCC GCC GGC CTA GTT ACC ATC ACA CCC CGG GAG GAG       95
Ser Pro Thr Ala Ala Ala Gly Leu Val Thr Ile Thr Pro Arg Glu Glu
                20                  25                  30

CCG CAG CTG CCG CAG CCG GCC CCA GTC ACC ATC ACC GCA ACC ATG AGC      143
Pro Gln Leu Pro Gln Pro Ala Pro Val Thr Ile Thr Ala Thr Met Ser
            35                  40                  45

AGC GAG GCC GAG ACC CAG CAG CCG CCC GCC GCC CCC CCC GCC GCC CCC      191
Ser Glu Ala Glu Thr Gln Gln Pro Pro Ala Ala Pro Pro Ala Ala Pro
        50                  55                  60

GCC CTC AGC GCC GCC GAC ACC AAG CCC GGC ACT ACG GGC AGC GGC GCA      239
Ala Leu Ser Ala Ala Asp Thr Lys Pro Gly Thr Thr Gly Ser Gly Ala
65                  70                  75

GGG AGC GGT GGC CCG GGC GGC CTC ACA TCG GCG GCG CCT GCC GGC GGG      287
Gly Ser Gly Gly Pro Gly Gly Leu Thr Ser Ala Ala Pro Ala Gly Gly
 80                  85                  90                  95
```

| | | | | | | | | | | | | | | | | |
|---|---|---|---|---|---|---|---|---|---|---|---|---|---|---|---|---|
| GAC | AAG | AAG | GTC | ATC | GCA | ACG | AAG | GTT | TTG | GGA | ACA | GTA | AAA | TGG | TTC | 335 |
| Asp | Lys | Lys | Val | Ile | Ala | Thr | Lys | Val | Leu | Gly | Thr | Val | Lys | Trp | Phe | |
| | | | 100 | | | | | | 105 | | | | | 110 | | |
| AAT | GTA | AGG | AAC | GGA | TAT | GGT | TTC | ATC | AAC | AGG | AAT | GAC | ACC | AAG | GAA | 383 |
| Asn | Val | Arg | Asn | Gly | Tyr | Gly | Phe | Ile | Asn | Arg | Asn | Asp | Thr | Lys | Glu | |
| | | | | 115 | | | | | 120 | | | | | 125 | | |
| GAT | GTA | TTT | GTA | CAC | CAG | ACT | GCC | ATA | AAG | AAG | AAT | AAC | CCC | AGG | AAG | 431 |
| Asp | Val | Phe | Val | His | Gln | Thr | Ala | Ile | Lys | Lys | Asn | Asn | Pro | Arg | Lys | |
| | | | 130 | | | | | 135 | | | | | 140 | | | |
| TAC | CTT | CGC | AGT | GTA | GGA | GAT | GGA | GAG | ACT | GTG | GAG | TTT | GAT | GTT | GTT | 479 |
| Tyr | Leu | Arg | Ser | Val | Gly | Asp | Gly | Glu | Thr | Val | Glu | Phe | Asp | Val | Val | |
| | 145 | | | | | 150 | | | | | 155 | | | | | |
| GAA | GGA | GAA | AAG | GGT | GCG | GAG | GCA | GCA | AAT | GTT | ACA | GGT | CCT | GGT | GGT | 527 |
| Glu | Gly | Glu | Lys | Gly | Ala | Glu | Ala | Ala | Asn | Val | Thr | Gly | Pro | Gly | Gly | |
| 160 | | | | | 165 | | | | | 170 | | | | | 175 | |
| GTT | CCA | GTT | CAA | GGC | AGT | AAA | TAT | GCA | GCA | GAC | CGT | AAC | CAT | TAT | AGA | 575 |
| Val | Pro | Val | Gln | Gly | Ser | Lys | Tyr | Ala | Ala | Asp | Arg | Asn | His | Tyr | Arg | |
| | | | | 180 | | | | | 185 | | | | | 190 | | |
| CGC | TAT | CCA | CGT | CGT | AGG | GGT | CCT | CCA | CGC | AAT | TAC | CAG | CAA | AAT | TAC | 623 |
| Arg | Tyr | Pro | Arg | Arg | Arg | Gly | Pro | Pro | Arg | Asn | Tyr | Gln | Gln | Asn | Tyr | |
| | | | 195 | | | | | 200 | | | | | 205 | | | |
| CAG | AAT | AGT | GAG | AGT | GGG | GAA | AAG | AAC | GAG | GGA | TCG | GAG | AGT | GCT | CCC | 671 |
| Gln | Asn | Ser | Glu | Ser | Gly | Glu | Lys | Asn | Glu | Gly | Ser | Glu | Ser | Ala | Pro | |
| | | 210 | | | | | 215 | | | | | 220 | | | | |
| GAA | GGC | CAG | GCC | CAA | CAA | CGC | CGG | CCC | TAC | CGC | AGG | CGA | AGG | TTC | CCA | 719 |
| Glu | Gly | Gln | Ala | Gln | Gln | Arg | Arg | Pro | Tyr | Arg | Arg | Arg | Arg | Phe | Pro | |
| | 225 | | | | | 230 | | | | | 235 | | | | | |
| CCT | TAC | TAC | ATG | CGG | AGA | CCC | TAT | GGG | CGT | CGA | CCA | CAG | TAT | TCC | AAC | 767 |
| Pro | Tyr | Tyr | Met | Arg | Arg | Pro | Tyr | Gly | Arg | Arg | Pro | Gln | Tyr | Ser | Asn | |
| 240 | | | | | 245 | | | | | 250 | | | | | 255 | |
| CCT | CCT | GTG | CAG | GGA | GAA | GTG | ATG | GAG | GGT | GCT | GAC | AAC | CAG | GGT | GCA | 815 |
| Pro | Pro | Val | Gln | Gly | Glu | Val | Met | Glu | Gly | Ala | Asp | Asn | Gln | Gly | Ala | |
| | | | | 260 | | | | | 265 | | | | | 270 | | |
| GGA | GAA | CAA | GGT | AGA | CCA | GTG | AGG | CAG | AAT | ATG | TAT | CGG | GGA | TAT | AGA | 863 |
| Gly | Glu | Gln | Gly | Arg | Pro | Val | Arg | Gln | Asn | Met | Tyr | Arg | Gly | Tyr | Arg | |
| | | | 275 | | | | | 280 | | | | | 285 | | | |
| CCA | CGA | TTC | CGC | AGG | GGC | CCT | CCT | CGC | CAA | AGA | CAG | CCT | AGA | GAG | GAC | 911 |
| Pro | Arg | Phe | Arg | Arg | Gly | Pro | Pro | Arg | Gln | Arg | Gln | Pro | Arg | Glu | Asp | |
| | | 290 | | | | | 295 | | | | | 300 | | | | |
| GGC | AAT | GAA | GAA | GAT | AAA | GAA | AAT | CAA | GGA | GAT | GAG | ACC | CAA | GGT | CAG | 959 |
| Gly | Asn | Glu | Glu | Asp | Lys | Glu | Asn | Gln | Gly | Asp | Glu | Thr | Gln | Gly | Gln | |
| | 305 | | | | | 310 | | | | | 315 | | | | | |
| CAG | CCA | CCT | CAA | CGT | CGG | TAC | CGC | CGC | AAC | TTC | AAT | TAC | CGA | CGC | AGA | 1007 |
| Gln | Pro | Pro | Gln | Arg | Arg | Tyr | Arg | Arg | Asn | Phe | Asn | Tyr | Arg | Arg | Arg | |
| 320 | | | | | 325 | | | | | 330 | | | | | 335 | |
| CGC | CCA | GAA | AAC | CCT | AAA | CCA | CAA | GAT | GGC | AAA | GAG | ACA | AAA | GCA | GCC | 1055 |
| Arg | Pro | Glu | Asn | Pro | Lys | Pro | Gln | Asp | Gly | Lys | Glu | Thr | Lys | Ala | Ala | |
| | | | | 340 | | | | | 345 | | | | | 350 | | |
| GAT | CCA | CCA | GCT | GAG | AAT | TCG | TCC | GCT | CCC | GAG | GCT | GAG | CAG | GGC | GGG | 1103 |
| Asp | Pro | Pro | Ala | Glu | Asn | Ser | Ser | Ala | Pro | Glu | Ala | Glu | Gln | Gly | Gly | |
| | | | 355 | | | | | 360 | | | | | 365 | | | |
| GCT | GAG | TA AATGCCGGCT | | TACCATCTCT | | ACCATCATCC | | GGTTTAGTCA | | TCCAACAAGA | | | | | | 1161 |
| Ala | Glu | | | | | | | | | | | | | | | |

AGAAATATGA AATTCCAGCA ATAAGAAATG AACAAAAGAT TGGAGCTGAA GACCTAAAGT 1221

GCTTGCTTTT TGCCCGTTGA CCAGATAAAT AGAACTATCT GCATTATCTA TGCAGCATGG 1281

GGTTTTTATT ATTTTTACCT AAAGACGTCT CTTTTTGGTA ATAACAAACG TGTTTTTAA 1341

AAAAGCCTGG TTTTTCTCAA TACGCCTTTA AAGGTTTTTA AATTGTTTCA TATCTGGTCA 1401

```
AGTTGAGATT TTTAAGAACT TCATTTTTAA TTTGTAATAA AAGTTTACAA CTTGATTTTT      1461

TCAAAAAAGT CAACAAACTG CAAGCACCTG TTAATAAAGG TCTTAAATAA TTGTCTTTGT      1521

GTAAAAAAAA AAAAAAAAAA AAAAAAAAAA AAAAAAAAAG CTTGGTATTC ATTACTTCAT      1581

GTATATCAAG CACAGCAGTA AAACAAAAAC CCATGTATTT AACTTTTTTT TAGGATTTTT      1641

GCTTTTGTGA TTTTTTTTTT TTTTTTTTTG ATACTTGCCT AACATGCATG TGCTGTAAAA      1701

ATAGTTAACA GGGAAATAAC TTGAGATGAT GGCTAGCTTT GTTTAATGTC TTATGAAATT      1761

TTCATGAACA ATCCAAGCAT AATTGTTAAG AACACGTGTA TTAAATTCAT GTAAGTGGAA      1821

TAAAAGTTTT ATGAATGGAC TTTTCAACTA CTTTCTCTAC AGCTTTTCAT GTAAATTAGT      1881

CTTGGTTCTG AAACTTCTCT AAAGGAAATT GTACATTTTT TGAAATTTAT TCCTTATTCC      1941

CTCTTGGCAG CTAATGGGCT CTTACCAAGT TTAAACACAA AATTTATCAT AACAAAAATA      2001

CTACTAATAT AACTACTGTT TCCATGTCCC ATGATCCCCT CTCTTCCTCC CCACCCTGAA      2061

AAAAATGAGT TCCTATTTTT TCTGGGAGAG GGGGGGATTG ATTAGAAAAA ATGTAGTGT       2121

GTTCCATTTA AAATTTTGGC ATATGGCATT TTCTAACTTA GGAAGCCACA ATGTTCTTGG      2181

CCCATCATGA CATTGGGTAG CATTAACTGT AAGTTTGTG CTTCCAAATC ACTTTTGGT       2241

TTTTAAGAAT TTCTTGATAC TCTTATAGCC TGCCTTCAAT TTTGATCCTT TATTCTTTCT     2301

ATTTGTCAGG TGCACAAGAT TACCTTCCTG TTTTAGCCTT CTGTCTTGTC ACCAACCATT     2361

CTTACTTGGT GGCCATGTAC TTGGAAAAAG GCCGCATGAT CTTTCTGGCT CCACTCAGTG     2421

TCTAAGGCAC CCTGCTTCCT TTGCTTGCAT CCCACAGACT ATTTCCCTCA TCCTATTTAC     2481

TGCAGCAAAT CTCTCCTTAG TTGATGAGAC TGTGTTATC TCCCTTTAAA ACCCTACCTA      2541

TCCTGAATGG TCTGTCATTG TCTGCCTTTA AAATCCTTCC TCTTTCTTCC TCCTCTATTC     2601

TCTAAATAAT GATGGGGCTA AGTTATACCC AAAGCTCACT TTACAAAATA TTTCCTCAGT     2661

ACTTTGCAGA AAACACCAAA CAAAAATGCC ATTTTAAAAA AGGTGTATTT TTTCTTTTAG     2721

AATGTAAGCT CCTCAAGAGC AGGGACAATG TTTTCTGTAT GTTCTATTGT GCCTAGTACA     2781

CTGTAAATGC TCAATGAATA TTATCCCTAA TACCTGCCAC CCCACTCTTA ATCAGTGGTG     2841

GAAGAACGGT CTCAGAACTG TTTGTTCAA TTGGCCATTT AAGTTAGTA GTAAAAGACT       2901

GGTTAATGAT AACAATGCAT CGTAAAACCT TCAGAAGGAA AGGAGAATGT TTTGTGGACC     2961

ACTTTGGTTT TCTTTTTTGC GTGTGGCAGT TTTAAGTTAT TAGTTTTAA AATCAGTACT      3021

TTTTAATGGA AACAACTTGA CCAAAAATTT GTCACAGAAT TTTGGCGGCC GC             3073
```

(2) INFORMATION FOR SEQ ID NO:32:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:32:

```
Gly Arg Ala Pro His Ser Glu Ser Gly Pro Gln Arg Ala Leu Ser Ser
 1               5                  10                  15

Pro Thr Ala Ala Ala Gly Leu Val Thr Ile Thr Pro Arg Glu Glu Pro
            20                  25                  30

Gln Leu Pro Gln Pro Ala Pro Val Thr Ile Thr Ala Thr Met Ser Ser
        35                  40                  45

Glu Ala Glu Thr Gln Gln Pro Pro Ala Ala Pro Pro Ala Ala Pro Ala
    50                  55                  60
```

| | | | | | | | | | | | | | | | |
|---|---|---|---|---|---|---|---|---|---|---|---|---|---|---|---|
|Leu|Ser|Ala|Ala|Asp|Thr|Lys|Pro|Gly|Thr|Thr|Gly|Ser|Gly|Ala|Gly|
|65| | | |  |70| | | | |75| | | | |80|
|Ser|Gly|Gly|Pro|Gly|Gly|Leu|Thr|Ser|Ala|Ala|Pro|Ala|Gly|Gly|Asp|
| | | | |85| | | | |90| | | | |95| |
|Lys|Lys|Val|Ile|Ala|Thr|Lys|Val|Leu|Gly|Thr|Val|Lys|Trp|Phe|Asn|
| | | |100| | | | |105| | | | |110| | |
|Val|Arg|Asn|Gly|Tyr|Gly|Phe|Ile|Asn|Arg|Asn|Asp|Thr|Lys|Glu|Asp|
| | |115| | | | |120| | | | |125| | | |
|Val|Phe|Val|His|Gln|Thr|Ala|Ile|Lys|Lys|Asn|Asn|Pro|Arg|Lys|Tyr|
| |130| | | | |135| | | | |140| | | | |
|Leu|Arg|Ser|Val|Gly|Asp|Gly|Glu|Thr|Val|Glu|Phe|Asp|Val|Val|Glu|
|145| | | | |150| | | | |155| | | | |160|
|Gly|Glu|Lys|Gly|Ala|Glu|Ala|Ala|Asn|Val|Thr|Gly|Pro|Gly|Gly|Val|
| | | | |165| | | | |170| | | | |175| |
|Pro|Val|Gln|Gly|Ser|Lys|Tyr|Ala|Ala|Asp|Arg|Asn|His|Tyr|Arg|Arg|
| | | |180| | | | |185| | | | |190| | |
|Tyr|Pro|Arg|Arg|Arg|Gly|Pro|Pro|Arg|Asn|Tyr|Gln|Gln|Asn|Tyr|Gln|
| | |195| | | | |200| | | | |205| | | |
|Asn|Ser|Glu|Ser|Gly|Glu|Lys|Asn|Glu|Gly|Ser|Glu|Ser|Ala|Pro|Glu|
| |210| | | | |215| | | | |220| | | | |
|Gly|Gln|Ala|Gln|Gln|Arg|Arg|Pro|Tyr|Arg|Arg|Arg|Arg|Phe|Pro|Pro|
|225| | | | |230| | | | |235| | | | |240|
|Tyr|Tyr|Met|Arg|Arg|Pro|Tyr|Gly|Arg|Arg|Pro|Gln|Tyr|Ser|Asn|Pro|
| | | | |245| | | | |250| | | | |255| |
|Pro|Val|Gln|Gly|Glu|Val|Met|Glu|Gly|Ala|Asp|Asn|Gln|Gly|Ala|Gly|
| | | |260| | | | |265| | | | |270| | |
|Glu|Gln|Gly|Arg|Pro|Val|Arg|Gln|Asn|Met|Tyr|Arg|Gly|Tyr|Arg|Pro|
| | |275| | | | |280| | | | |285| | | |
|Arg|Phe|Arg|Arg|Gly|Pro|Pro|Arg|Gln|Arg|Gln|Pro|Arg|Glu|Asp|Gly|
| |290| | | | |295| | | | |300| | | | |
|Asn|Glu|Glu|Asp|Lys|Glu|Asn|Gln|Gly|Asp|Glu|Thr|Gln|Gly|Gln|Gln|
|305| | | | |310| | | | |315| | | | |320|
|Pro|Pro|Gln|Arg|Arg|Tyr|Arg|Arg|Asn|Phe|Asn|Tyr|Arg|Arg|Arg|Arg|
| | | | |325| | | | |330| | | | |335| |
|Pro|Glu|Asn|Pro|Lys|Pro|Gln|Asp|Gly|Lys|Glu|Thr|Lys|Ala|Ala|Asp|
| | | |340| | | | |345| | | | |350| | |
|Pro|Pro|Ala|Glu|Asn|Ser|Ser|Ala|Pro|Glu|Ala|Glu|Gln|Gly|Gly|Ala|
| | |355| | | | |360| | | | |365| | | |
|Glu| | | | | | | | | | | | | | | |

( 2 ) INFORMATION FOR SEQ ID NO:33:

( i ) SEQUENCE CHARACTERISTICS:
        ( A ) LENGTH: 1811 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

```
GAATTCCTGG TAGGGCCAGC CCACCATGGG GGCCAAGACC TGCACAGGAC AAGGGCCACC      60

TGGCCTTTCA GTTACTTGAG TTTGGAGTCA GAAAGCAAGA CCAGGAAGCA AATAGCAGCT     120

CAGGAAATCC CACGGTTGAC TTGCCTTGAT GGCAAGCTTG GTGGAGAGGG CTGAAGCTGT     180

TGCTGGGGGC CGATTCTGAT CAAGACACAT GGCTTGAAAA TGGAAGACAC AAAACTGAGA     240
```

| | | | | | |
|---|---|---|---|---|---|
| GATCATTCTG | CACTAAGTTT | CGGGAACTTA | TCCCCGACAG | TGACTGAACT | CACTGACTAA | 300
| TAACTTCATT | TATGAATCTT | CTCCCTTGTC | CCTTTGTCTG | CCAACCTGTG | TGCCTTTTTT | 360
| GTAAACATT | TTCATGTCTT | TAAAATGCCT | GTTGAATACC | TGGAGTTTAG | TATCAACTTC | 420
| TACACAGATA | AGCTTTCAAA | GTTGACAAAC | TTTTTGACT | CTTTCTGGAA | AAGGGAAAGA | 480
| AAATAGTCTT | CCTTCTTTCT | TGGGCAATAT | CCTTCACTTT | ACTACAGTTA | CTTTTGCAAA | 540
| CAGACAGAAA | GGATACACTT | CTAACCACAT | TTTACTTCCT | TCCCCTGTTG | TCCAGTCCAA | 600
| CTCCACAGTC | ACTCTTAAAA | CTTCTCTCTG | TTTGCCTGCC | TCCAACAGTA | CTTTTAACTT | 660
| TTTGCTGTAA | ACAGAATAAA | ATTGAACAAA | TTAGGGGGTA | GAAAGGAGCA | GTGGTGTCGT | 720
| TCACCGTGAG | AGTCTGCATA | GAACTCAGCA | GTGTGCCCTG | CTGTGTCTTG | GACCCTGCCC | 780
| CCCACAGGAG | TTGTACAGTC | CCTGGCCCTG | TTCCCTACCT | CCTCTCTTCA | CCCCGTTAGG | 840
| CTGTTTTCAA | TGTAATGCTG | CCGTCCTTCT | CTTGCACTGC | CTTCTGCGCT | AACACCTCCA | 900
| TTCCTGTTTA | TAACCGTGTA | TTTATTACTT | AATGTATATA | ATGTAATGTT | TTGTAAGTTA | 960
| TTAATTTATA | TATCTAACAT | TGCCTGCCAA | TGGTGGTGTT | AAATTTGTGT | AGAAAACTCT | 1020
| GCCTAAGAGT | TACGACTTTT | TCTTGTAATG | TTTTGTATTG | TGTATTATAT | AACCCAAACG | 1080
| TCACTTAGTA | GAGACATATG | GCCCCCTTGG | CAGAGAGGAC | AGGGGTGGGC | TTTTGTTCAA | 1140
| AGGGTCTGCC | CTTTCCCTGC | CTGAGTTGCT | ACTTCTGCAC | AACCCCTTTA | TGAACCAGTT | 1200
| TTGGAAACAA | TATTCTCACA | TTAGATACTA | AATGGTTTAT | ACTGAGCTTT | TACTTTTGTA | 1260
| TAGCTTGATA | GGGGCAGGGG | GCAATGGGAT | GTAGTTTTTA | CCCAGGTTCT | ATCCAAATCT | 1320
| ATGTGGGCAT | GAGTTGGGTT | ATAACTGGAT | CCTACTATCA | TTGTGGCTTT | GGTTCAAAAG | 1380
| GAAACACTAC | ATTTGCTCAC | AGATGATTCT | TCTGAATGCT | CCCGAACTAC | TGACTTTGAA | 1440
| GAGGTAGCCT | CCTGCCTGCC | ATTAAGCAGG | AATGTCATGT | TCCAGTTCAT | TACAAAAGAA | 1500
| AACAATAAAA | CAATGTGAAT | TTTTATAATA | AAATGTGAAC | TGATGTAGCA | AATTACGCAA | 1560
| ATGTGAAGCC | TCTTCTGATA | ACACTTGTTA | GGCCTCTTAC | TGATGTCAGT | TTCAGTTTGT | 1620
| AAAATATGTT | TCATGCTTTC | AGTTCAGCAT | TGTGACTCAG | TAATTACAGA | AAATGGCACA | 1680
| AATGTGCATG | ACCAATGGGT | TTGTATGTCT | ATGAACACTG | CATTGTTTCA | GGTGGACATT | 1740
| TTATCATTTT | CAAATGTTTC | TCACAATGTA | TGTTATAGTA | TTATTATTAT | ATATTGTGTT | 1800
| CAAATGCATT | C | | | | | 1811

( 2 ) INFORMATION FOR SEQ ID NO:34:

( i ) SEQUENCE CHARACTERISTICS:
    ( A ) LENGTH: 1672 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:34:

| | | | | | |
|---|---|---|---|---|---|
| GAATTCCCCA | CCATGGGGGC | CAAGACCTGC | ACAGGACAAG | GCCACCTGGC | CTTTCAGTTA | 60
| CTTGAGTTTG | GAGTCAGAAA | GCAAGACCAG | GAAGCAAATA | GCAGCTCAGG | AAATCCCACG | 120
| GTTGACTTGC | CTTGATGGCA | AGCTTGGTGG | AGAGGGCTGA | AGCTGTTGCT | GGGGGCCGTT | 180
| CTGATCAAGA | CACATGGCTT | GAAAATGGAA | GACACAAAAC | TGAGAGATCA | TTCTGCACTA | 240
| AGTTTCGGGA | ACTTATCCCC | GACAGTGACT | GAACTCACTG | ACTAATAACT | TCATTTATGA | 300
| ATCTTCTCCC | TTGTCCCTTT | GTCTGCCAAC | CTGTGTGCCT | TTTTGTAAA | ACATTTCAGT | 360
| CTTTAAAATG | CCTGTTGAAT | ACCTGGAGTT | AGATCAACTT | CTACACAGAT | AAGCTTTCAA | 420

| | | | | | |
|---|---|---|---|---|---|
| AGTTGACAAA | CTTTTTTGAC | TCTTCTGGAA | AAGGGAAAGA | AAATAGTCTT | CCTTCTTTCT | 480 |
| TGGGCAATAT | CCTTCACTTT | ACTACAGTTA | CTTTTGCAAA | CAGACAGAAA | GGATACACTT | 540 |
| CTAACCACAT | TTTACTTCCT | TCCCCTGTTG | TCCAGTCCAA | CTCCACAGTC | ACTCTTAAAA | 600 |
| CTTCTCTCTG | TTTGCCTGCC | TCCAACAGTA | CTTTTAACTT | TTAACTTTTT | GCTGTAAACA | 660 |
| GAATAAAATT | GAACAAATTA | GGGGGTAGAA | AGGAGCAGTG | GTGTCGTTCA | CCGTGAGAGT | 720 |
| CTGCATAGAA | CTCAGCAGTG | TGCCCTGCTG | TGTCTTGGAC | CCTGCCCCCC | ACAGGAGTTG | 780 |
| TACAGTCCCT | GGCCCTGTTC | CCTACCTCCT | CTCTTCACCC | CGTTAGGCTG | TTTTCAATGT | 840 |
| AATGCTGCCG | TCCTTCTCTT | GCACTGCCTT | CTGCGCTAAC | ACCTCCATTC | CTGTTTATAA | 900 |
| CCGTGTATTT | ATTACTTAAT | GTATATAATG | TAATGTTTTG | TAAGTTATTA | ATTTATATAT | 960 |
| CTAACATTGC | CTGCCAATGG | TGGTGTTAAA | TTTGTGTAGA | AAACTCTGCC | TAAGAGTTAC | 1020 |
| GACTTTTTCT | TGTAATGTTT | TGTATTGTGT | ATTATATAAC | CCAAACGTCA | CTTAGTAGAG | 1080 |
| ACATATGGCC | CCCTTGGCAG | AGAGGACAGG | GGTGGGCTTT | TGTTCAAAGG | GTCTGCCCTT | 1140 |
| TCCCTGCCTG | AGTTGCTACT | TCTGCACAAC | CCCTTTATGA | ACCAGTTTG | GAAACAATAT | 1200 |
| TCTCACATTA | GATACTAAAT | GGTTTATACT | GAGCTTTTAC | TTTTGTATAG | CTTGATAGGG | 1260 |
| GCAGGGGGCA | ATGGGATGTA | GTTTTACCC | AGGTTCTATC | CAAATCTATG | TGGGCATGAG | 1320 |
| TTGGGTTATA | ACTGGATCCT | ACTATCATTG | TGGCTTTGGT | TCAAAGGAA | ACACTACATT | 1380 |
| TGCTCACAGA | TGATTCTTCT | GAATGCTCCC | GAACTACTGA | CTTTGAAGAG | GTAGCCTCCT | 1440 |
| GCCTGCCATT | AAGCAGGAAT | GTCATGTTCC | AGTTCATTAC | AAAAGAAAAC | AATAAAACAA | 1500 |
| TGTGAATTTT | TATAATAAAA | TGTGAACTGA | TGTAGCAAAT | TACGCAAATG | TGAAGCCTCT | 1560 |
| TCTGATAACA | CTTGTTAGGC | CTCTTACTGA | TGTCAGTTTC | AGTTTGTAAA | ATATGTTTCA | 1620 |
| TGCTTTCAGT | TCAGCATTGT | GACTCAGTAA | TTACAGAAAA | AAAAAAGAAT | TC | 1672 |

( 2 ) INFORMATION FOR SEQ ID NO:35:

( i ) SEQUENCE CHARACTERISTICS:
        ( A ) LENGTH: 1649 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 210..1018

( x i ) SEQUENCE DESCRIPTION: SEQ ID NO:35:

```
GAATTCCTTC TGACGTGGCA TATCACAACA GCCTGCACGC TGCTGATGTA GCCCAGTCGA      60

CCCATGTTCT CCTTTCTACA CCAGCATTAG ACGCTGTCTT CACAGATTTG GAAATCCTGG     120

CTGCCATTTT TGCAGCTGCC ATCCATGACG TTGATCATCC TGGAGTCTCC AATCAGTTTC     180

TCATCAACAC AAATTCAGAA CTTGCTTTG ATG TAT AAT GAT GAA TCT GTG TTG      233
                                 Met Tyr Asn Asp Glu Ser Val Leu
                                   1               5

GAA AAT CAT CAC CTT GCT GTG GGT TTC AAA CTG CTG CAA GAA GAA CAC      281
Glu Asn His His Leu Ala Val Gly Phe Lys Leu Leu Gln Glu Glu His
         10              15                  20

TGT GAC ATC TTC ATG AAT CTC ACC AAG AAG CAG CGT CAG ACA CTC AGG      329
Cys Asp Ile Phe Met Asn Leu Thr Lys Lys Gln Arg Gln Thr Leu Arg
 25              30                  35                  40

AAG ATG GTT ATT GAC ATG GTG TTA GCA ACT GAT ATG TCT AAA CAT ATG      377
Lys Met Val Ile Asp Met Val Leu Ala Thr Asp Met Ser Lys His Met
```

| | | | | | | | | | | | | | | | | |
|---|---|---|---|---|---|---|---|---|---|---|---|---|---|---|---|---|
| | | | | 45 | | | | | 50 | | | | | 55 | | |
| AGC | CTG | CTG | GCA | GAC | CTG | AAG | ACA | ATG | GTA | GAA | ACG | AAG | AAA | GTT | ACA | 425 |
| Ser | Leu | Leu | Ala | Asp | Leu | Lys | Thr | Met | Val | Glu | Thr | Lys | Lys | Val | Thr | |
| | | | 60 | | | | | 65 | | | | | 70 | | | |
| AGT | TCA | GGC | GTT | CTT | CTC | CTA | GAC | AAC | TAT | ACC | GAT | CGC | ATT | CAG | GTC | 473 |
| Ser | Ser | Gly | Val | Leu | Leu | Leu | Asp | Asn | Tyr | Thr | Asp | Arg | Ile | Gln | Val | |
| | | 75 | | | | | 80 | | | | | 85 | | | | |
| CTT | CGC | AAC | ATG | GTA | CAC | TGT | GCA | GAC | CTG | AGC | AAC | CCC | ACC | AAG | TCC | 521 |
| Leu | Arg | Asn | Met | Val | His | Cys | Ala | Asp | Leu | Ser | Asn | Pro | Thr | Lys | Ser | |
| | 90 | | | | | 95 | | | | | 100 | | | | | |
| TTG | GAA | TTG | TAT | CGG | CAA | TGG | ACA | GAC | CGC | ATC | ATG | GAG | GAA | TTT | TTC | 569 |
| Leu | Glu | Leu | Tyr | Arg | Gln | Trp | Thr | Asp | Arg | Ile | Met | Glu | Glu | Phe | Phe | |
| 105 | | | | | 110 | | | | | 115 | | | | | 120 | |
| CAG | CAG | GGA | GAC | AAA | GAG | CGG | GAG | AGG | GGA | ATG | GAA | ATT | AGC | CCA | ATG | 617 |
| Gln | Gln | Gly | Asp | Lys | Glu | Arg | Glu | Arg | Gly | Met | Glu | Ile | Ser | Pro | Met | |
| | | | 125 | | | | | 130 | | | | | 135 | | | |
| TGT | GAT | AAA | CAC | ACA | GCT | TCT | GTG | GAA | AAA | TCC | CAG | GTT | GGT | TTC | ATC | 665 |
| Cys | Asp | Lys | His | Thr | Ala | Ser | Val | Glu | Lys | Ser | Gln | Val | Gly | Phe | Ile | |
| | | 140 | | | | | 145 | | | | | 150 | | | | |
| GAC | TAC | ATT | GTC | CAT | CCA | TTG | TGG | GAG | ACA | TGG | GCA | GAT | TTG | GTA | CAG | 713 |
| Asp | Tyr | Ile | Val | His | Pro | Leu | Trp | Glu | Thr | Trp | Ala | Asp | Leu | Val | Gln | |
| | 155 | | | | | 160 | | | | | 165 | | | | | |
| CCT | GAT | GCT | CAG | GAC | ATT | CTC | GAT | ACC | TTA | GAA | GAT | AAC | AGG | AAC | TGG | 761 |
| Pro | Asp | Ala | Gln | Asp | Ile | Leu | Asp | Thr | Leu | Glu | Asp | Asn | Arg | Asn | Trp | |
| 170 | | | | | 175 | | | | | 180 | | | | | | |
| TAT | CAG | AGC | ATG | ATA | CCT | CAA | AGT | CCC | TCA | CCA | CCA | CTG | GAC | GAG | CAG | 809 |
| Tyr | Gln | Ser | Met | Ile | Pro | Gln | Ser | Pro | Ser | Pro | Pro | Leu | Asp | Glu | Gln | |
| 185 | | | | | 190 | | | | | 195 | | | | | 200 | |
| AAC | AGG | GAC | TGC | CAG | GGT | CTG | ATG | GAG | AAG | TTT | CAG | TTT | GAA | CTG | ACT | 857 |
| Asn | Arg | Asp | Cys | Gln | Gly | Leu | Met | Glu | Lys | Phe | Gln | Phe | Glu | Leu | Thr | |
| | | | 205 | | | | | 210 | | | | | 215 | | | |
| CTC | GAT | GAG | GAA | GAT | TCT | GAA | GGA | CCT | GAG | AAG | GAG | GGA | GAG | GGA | CAC | 905 |
| Leu | Asp | Glu | Glu | Asp | Ser | Glu | Gly | Pro | Glu | Lys | Glu | Gly | Glu | Gly | His | |
| | | 220 | | | | | 225 | | | | | 230 | | | | |
| AGC | TAT | TTC | AGC | AGC | ACA | AAG | ACG | CTT | TGT | GTG | ATT | GAT | CCA | GAA | AAC | 953 |
| Ser | Tyr | Phe | Ser | Ser | Thr | Lys | Thr | Leu | Cys | Val | Ile | Asp | Pro | Glu | Asn | |
| | 235 | | | | | 240 | | | | | 245 | | | | | |
| AGA | GAT | TCC | CTG | GGA | GAG | ACT | GAC | ATA | GAC | ATT | GCA | ACA | GAA | GAC | AAG | 1001 |
| Arg | Asp | Ser | Leu | Gly | Glu | Thr | Asp | Ile | Asp | Ile | Ala | Thr | Glu | Asp | Lys | |
| 250 | | | | | 255 | | | | | 260 | | | | | | |
| TCC | CCC | GTG | GAT | ACA | TA | ATCCCCCTCT | CCCTGTGGAG | ATGAACATTC | | | | | | | | 1048 |
| Ser | Pro | Val | Asp | Thr | | | | | | | | | | | | |
| 265 | | | | | | | | | | | | | | | | |

| | |
|---|---|
| TATCCTTGAT GAGCATGCCA GCTATGTGGT AGGGCCAGCC CACCATGGGG GCCAAGACCT | 1108 |
| GCACAGGACA AGGGCCACCT GGCCTTTCAG TTACTTGAGT TTGGAGTCAG AAAGCAAGAC | 1168 |
| CAGGAAGCAA ATAGCAGCTC AGGAAATCCC ACGGTTGACT TGCCTTGATG CAAGCTTGG | 1228 |
| TGGAGAGGGC TGAAGCTGTT GCTGGGGGCC GATTCTGATC AAGACACATG GCTTGAAAAT | 1288 |
| GGAAGACACA AAACCGAGAG ATCATTCTGC ACTAAGTTTC GGGAACTTAT CCCCGACAGT | 1348 |
| GACTGAACTC ACTGACTAAT AACTTCATTT ATGAATCTTC TCCCTTGTCC CTTTGTCTGC | 1408 |
| CAACCTGTGT GCCTTTTTTG TAAAACATTT TCATGTCTTT AAAATGCCTG TTGAATACCT | 1468 |
| GGAGTTTAGT ATCAACTTCT ACACAGATAA GCTTTCAAAG TTGACAAACT TTTTGACTC | 1528 |
| TTTCTGGAAA AGGGAAAGAA AATAGTCTTC CTTCTTTCTT GGGCAATATC CTTCACTTTA | 1588 |
| CTACAGTTAC TTTTGCAAAC AGACAGAAAG GATACACTTC TAACCACATT TTACGGAATT | 1648 |
| C | 1649 |

( 2 ) INFORMATION FOR SEQ ID NO:36:

( i ) SEQUENCE CHARACTERISTICS:
    ( A ) LENGTH: 269 amino acids
    ( B ) TYPE: amino acid
    ( D ) TOPOLOGY: linear ( i i ) MOLECULE TYPE: protein ( x i ) SEQUENCE DESCRIPTION: SEQ ID NO:36:

```
Met Tyr Asn Asp Glu Ser Val Leu Glu Asn His His Leu Ala Val Gly
 1               5                  10                  15

Phe Lys Leu Leu Gln Glu Glu His Cys Asp Ile Phe Met Asn Leu Thr
             20                  25                  30

Lys Lys Gln Arg Gln Thr Leu Arg Lys Met Val Ile Asp Met Val Leu
         35                  40                  45

Ala Thr Asp Met Ser Lys His Met Ser Leu Leu Ala Asp Leu Lys Thr
     50                  55                  60

Met Val Glu Thr Lys Lys Val Thr Ser Ser Gly Val Leu Leu Leu Asp
 65                  70                  75                  80

Asn Tyr Thr Asp Arg Ile Gln Val Leu Arg Asn Met Val His Cys Ala
                 85                  90                  95

Asp Leu Ser Asn Pro Thr Lys Ser Leu Glu Leu Tyr Arg Gln Trp Thr
            100                 105                 110

Asp Arg Ile Met Glu Glu Phe Phe Gln Gln Gly Asp Lys Glu Arg Glu
        115                 120                 125

Arg Gly Met Glu Ile Ser Pro Met Cys Asp Lys His Thr Ala Ser Val
    130                 135                 140

Glu Lys Ser Gln Val Gly Phe Ile Asp Tyr Ile Val His Pro Leu Trp
145                 150                 155                 160

Glu Thr Trp Ala Asp Leu Val Gln Pro Asp Ala Gln Asp Ile Leu Asp
                165                 170                 175

Thr Leu Glu Asp Asn Arg Asn Trp Tyr Gln Ser Met Ile Pro Gln Ser
            180                 185                 190

Pro Ser Pro Pro Leu Asp Glu Gln Asn Arg Asp Cys Gln Gly Leu Met
        195                 200                 205

Glu Lys Phe Gln Phe Glu Leu Thr Leu Asp Glu Glu Asp Ser Glu Gly
    210                 215                 220

Pro Glu Lys Glu Gly Glu Gly His Ser Tyr Phe Ser Ser Thr Lys Thr
225                 230                 235                 240

Leu Cys Val Ile Asp Pro Glu Asn Arg Asp Ser Leu Gly Glu Thr Asp
                245                 250                 255

Ile Asp Ile Ala Thr Glu Asp Lys Ser Pro Val Asp Thr
            260                 265
```

( 2 ) INFORMATION FOR SEQ ID NO:37:

( i ) SEQUENCE CHARACTERISTICS:
    ( A ) LENGTH: 609 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 2..606

( x i ) SEQUENCE DESCRIPTION: SEQ ID NO:37:

```
G AAT TCC AAC ATT CCC CGA TTT GGG GTG AAG ACC GAT CAA GAA GAG         46
  Asn Ser Asn Ile Pro Arg Phe Gly Val Lys Thr Asp Gln Glu Glu
   1               5                  10                  15

CTC CTG GCC CAA GAA CTG GAG AAC CTG AAC AAG TGG GGC CTG AAC ATC       94
Leu Leu Ala Gln Glu Leu Glu Asn Leu Asn Lys Trp Gly Leu Asn Ile
                20                  25                  30

TTT TGC GTG TCG GAT TAC GCT GGA GGC CGC TCA CTC ACC TGC ATC ATG      142
Phe Cys Val Ser Asp Tyr Ala Gly Gly Arg Ser Leu Thr Cys Ile Met
            35                  40                  45

TAC ATG ATA TTC CAG GAG CGG GAC CTG CTG AAG AAA TTC CGC ATC CCT      190
Tyr Met Ile Phe Gln Glu Arg Asp Leu Leu Lys Lys Phe Arg Ile Pro
        50                  55                  60

GTG GAC ACG ATG GTG ACA TAC ATG CTG ACG CTG GAG GAT CAC TAC CAC      238
Val Asp Thr Met Val Thr Tyr Met Leu Thr Leu Glu Asp His Tyr His
    65                  70                  75

GCT GAC GTG GCC TAC CAT AAC AGC CTG CAC GCA GCT GAC GTG CTG CAG      286
Ala Asp Val Ala Tyr His Asn Ser Leu His Ala Ala Asp Val Leu Gln
 80                  85                  90                  95

TCC ACC CAC GTA CTG CTG GCC ACG CCT GCA CTA GAT GCA GTG TTC ACG      334
Ser Thr His Val Leu Leu Ala Thr Pro Ala Leu Asp Ala Val Phe Thr
                100                 105                 110

GAC CTG GAG ATT CTC GCC GCC CTC TTC GCG GCT GCC ATC CAC GAT GTG      382
Asp Leu Glu Ile Leu Ala Ala Leu Phe Ala Ala Ala Ile His Asp Val
            115                 120                 125

GAT CAC CCT GGG GTC TCC AAC CAG TTC CTC ATC AAC ACC AAT TCG GAG      430
Asp His Pro Gly Val Ser Asn Gln Phe Leu Ile Asn Thr Asn Ser Glu
        130                 135                 140

CTG GCG CTC ATG TAC AAC GAT GAG TCG GTG CTC GAG AAT CAC CAC CTG      478
Leu Ala Leu Met Tyr Asn Asp Glu Ser Val Leu Glu Asn His His Leu
    145                 150                 155

GCC GTG GGC TTC AAG CTG CTG CAG GAG GAC AAC TGC GAC ATC TTC CAG      526
Ala Val Gly Phe Lys Leu Leu Gln Glu Asp Asn Cys Asp Ile Phe Gln
160                 165                 170                 175

AAC CTC AGC AAG CGC CAG CGG CAG AGC TAC GCA AGA TGG TCA TCG ACA      574
Asn Leu Ser Lys Arg Gln Arg Gln Ser Tyr Ala Arg Trp Ser Ser Thr
                180                 185                 190

TGG TGC TGG CCA CGG ACA TGT CCA AGC ACA TG ACC                       609
Trp Cys Trp Pro Arg Thr Cys Pro Ser Thr
            195                 200
```

( 2 ) INFORMATION FOR SEQ ID NO:38:

( i ) SEQUENCE CHARACTERISTICS:
        ( A ) LENGTH: 201 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Asn Ser Asn Ile Pro Arg Phe Gly Val Lys Thr Asp Gln Glu Glu Leu
 1               5                  10                  15

Leu Ala Gln Glu Leu Glu Asn Leu Asn Lys Trp Gly Leu Asn Ile Phe
            20                  25                  30

Cys Val Ser Asp Tyr Ala Gly Gly Arg Ser Leu Thr Cys Ile Met Tyr
        35                  40                  45

Met Ile Phe Gln Glu Arg Asp Leu Leu Lys Lys Phe Arg Ile Pro Val
    50                  55                  60

Asp Thr Met Val Thr Tyr Met Leu Thr Leu Glu Asp His Tyr His Ala
65                  70                  75                  80

Asp Val Ala Tyr His Asn Ser Leu His Ala Ala Asp Val Leu Gln Ser
```

|  |  |  |  |  |  |  | 85 |  |  |  |  | 90 |  |  |  |  | 95 |  |  |
|---|---|---|---|---|---|---|---|---|---|---|---|---|---|---|---|---|---|---|---|
| Thr | His | Val | Leu | Leu | Ala | Thr | Pro | Ala | Leu | Asp | Ala | Val | Phe | Thr | Asp |
|  |  |  | 100 |  |  |  | 105 |  |  |  | 110 |

Thr His Val Leu Leu Ala Thr Pro Ala Leu Asp Ala Val Phe Thr Asp
              100               105              110

Leu Glu Ile Leu Ala Ala Leu Phe Ala Ala Ala Ile His Asp Val Asp
             115              120             125

His Pro Gly Val Ser Asn Gln Phe Leu Ile Asn Thr Asn Ser Glu Leu
         130             135             140

Ala Leu Met Tyr Asn Asp Glu Ser Val Leu Glu Asn His His Leu Ala
145             150              155                     160

Val Gly Phe Lys Leu Leu Gln Glu Asp Asn Cys Asp Ile Phe Gln Asn
                 165             170              175

Leu Ser Lys Arg Gln Arg Gln Ser Tyr Ala Arg Trp Ser Ser Thr Trp
             180             185             190

Cys Trp Pro Arg Thr Cys Pro Ser Thr
         195             200

(2) INFORMATION FOR SEQ ID NO:39:

(i) SEQUENCE CHARACTERISTICS:
      (A) LENGTH: 1230 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 3..1156

(xi) SEQUENCE DESCRIPTION: SEQ ID NO:39:

```
AC ATG GTG CAC TGT GCC GAC CTC AGC AAC CCC ACC AAG CCG CTG GAG           47
   Met Val His Cys Ala Asp Leu Ser Asn Pro Thr Lys Pro Leu Glu
   1               5                  10                  15

CTG TAC CGC CAG TGG ACA GAC CGC ATC ATG GCC GAG TTC TTC CAG CAG          95
Leu Tyr Arg Gln Trp Thr Asp Arg Ile Met Ala Glu Phe Phe Gln Gln
             20                  25                  30

GGT GAC CGA GAG CGC GAG CGT GGC ATG GAA ATC AGC CCC ATG TGT GAC         143
Gly Asp Arg Glu Arg Glu Arg Gly Met Glu Ile Ser Pro Met Cys Asp
         35                  40                  45

AAG CAC ACT GCC TCC GTG GAG AAG TCT CAG GTG GGT TTT ATT GAC TAC         191
Lys His Thr Ala Ser Val Glu Lys Ser Gln Val Gly Phe Ile Asp Tyr
        50                  55                  60

ATT GTG CAC CCA TTG TGG GAG ACC TGG GCG GAC CTT GTC CAC CCA GAT         239
Ile Val His Pro Leu Trp Glu Thr Trp Ala Asp Leu Val His Pro Asp
    65                  70                  75

GCC CAG GAG ATC TTG GAC ACT TTG GAG GAC AAC CGG GAC TGG TAC TAC         287
Ala Gln Glu Ile Leu Asp Thr Leu Glu Asp Asn Arg Asp Trp Tyr Tyr
80                  85                  90                  95

AGC GCC ATC CGG CAG AGC CCA TCT CCG CCA CCC GAG GAG GAG TCA AGG         335
Ser Ala Ile Arg Gln Ser Pro Ser Pro Pro Pro Glu Glu Glu Ser Arg
                100                 105                 110

GGG CCA GGC CAC CCA CCC CTG CCT GAC AAG TTC CAG TTT GAC GTG ACG         383
Gly Pro Gly His Pro Pro Leu Pro Asp Lys Phe Gln Phe Asp Val Thr
            115                 120                 125

CTG GAG GAG GAA GAG GAG GAA GAA ATA TCA ATG GCC CAG ATA CCG TGC         431
Leu Glu Glu Glu Glu Glu Glu Glu Ile Ser Met Ala Gln Ile Pro Cys
        130                 135                 140

ACA GCC CAA GAG GCA TTG ACT GCG CAG GGA TTG TCA GGA GTC GAG GAA         479
Thr Ala Gln Glu Ala Leu Thr Ala Gln Gly Leu Ser Gly Val Glu Glu
145                 150                 155
```

```
GCT CTG GAT GCA ACC ATA GCC TGG GAG GCA TCC CCG GCC CAG GAG TCG      527
Ala Leu Asp Ala Thr Ile Ala Trp Glu Ala Ser Pro Ala Gln Glu Ser
160                 165                 170                 175

TTG GAA GTT ATG GCA CAG GAA GCA TCC CTG GAG GCC GAG CTG GAG GCA      575
Leu Glu Val Met Ala Gln Glu Ala Ser Leu Glu Ala Glu Leu Glu Ala
                180                 185                 190

GNG TAT TTG ACA CAG CAG GCA CAG TCC ACA GGC AGT GCA CCT GTG GCT      623
Val Tyr Leu Thr Gln Gln Ala Gln Ser Thr Gly Ser Ala Pro Val Ala
            195                 200                 205

CCG GAT GAG TTC TCG TCC CGG GAG GAA TTC GTG GTT GCT GTA AGC CAC      671
Pro Asp Glu Phe Ser Ser Arg Glu Glu Phe Val Val Ala Val Ser His
        210                 215                 220

AGC AGC CCC TCT GCC CTG GCT CTT CAA AGC CCC CTT CTC CCT GCT TGG      719
Ser Ser Pro Ser Ala Leu Ala Leu Gln Ser Pro Leu Leu Pro Ala Trp
    225                 230                 235

AGG ACC CTG TCT GTT TCA GAG CAT GCC CCG GGC CTC CCG GCC TCC CCT      767
Arg Thr Leu Ser Val Ser Glu His Ala Pro Gly Leu Pro Ala Ser Pro
240                 245                 250                 255

CCA CGG CGG CCT AGG TGG AAC GAG AGC ACC AGG CTG CCA AGA GGG CTT      815
Pro Arg Arg Pro Arg Trp Asn Glu Ser Thr Arg Leu Pro Arg Gly Leu
                260                 265                 270

GCA GTG CCT GCG CAG GGA CAT TTG GGG AGG ACA CAT CCG CAC TCC CAG      863
Ala Val Pro Ala Gln Gly His Leu Gly Arg Thr His Pro His Ser Gln
            275                 280                 285

CTC CTG GTG GCG GGG GGT CAG GTG GAG ACC CTA CCT GAT CCC CAG ACC      911
Leu Leu Val Ala Gly Gly Gln Val Glu Thr Leu Pro Asp Pro Gln Thr
        290                 295                 300

TCT GTC CCT GTT CCC CTC CAC TCC TCC CCT CAC TCC CCT GCT CCC CCG      959
Ser Val Pro Val Pro Leu His Ser Ser Pro His Ser Pro Ala Pro Pro
    305                 310                 315

ACC ACC TCC TCC TCT GCC TCA AAG ACT CTT GTC CTC TTG TCC CTC CTG     1007
Thr Thr Ser Ser Ser Ala Ser Lys Thr Leu Val Leu Leu Ser Leu Leu
320                 325                 330                 335

AGA AAA AAG AAA ACG AAA AGT GGG GTT TTT TTC TGT TTT CTT TTT TTC     1055
Arg Lys Lys Lys Thr Lys Ser Gly Val Phe Phe Cys Phe Leu Phe Phe
                340                 345                 350

CCC TTT CCC CCT GCC CCC ACC CAC GGG GCC TTT TTT TGG AGG TGG GGG     1103
Pro Phe Pro Pro Ala Pro Thr His Gly Ala Phe Phe Trp Arg Trp Gly
            355                 360                 365

CTG GGG AAT GAG GGG CTG AGG TCC CGG AAG GGA TTT TAT TTT TTT GAA     1151
Leu Gly Asn Glu Gly Leu Arg Ser Arg Lys Gly Phe Tyr Phe Phe Glu
        370                 375                 380

TTT TA ATTGTAACAT TTTTAGAAAA AGAACAAAAA AAGAAAAAAA AAAGAAAGAA       1206
Phe

ACACAAAAAA AAAAAAAGGA ATTC                                          1230

( 2 ) INFORMATION FOR SEQ ID NO:40:

( i ) SEQUENCE CHARACTERISTICS:
                ( A ) LENGTH: 384 amino acids
                ( B ) TYPE: amino acid
                ( D ) TOPOLOGY: linear ( i i ) MOLECULE TYPE: protein ( x i ) SEQUENCE DESCRIPTION: SEQ ID NO:40:

Met Val His Cys Ala Asp Leu Ser Asn Pro Thr Lys Pro Leu Glu Leu
1               5                   10                  15

Tyr Arg Gln Trp Thr Asp Arg Ile Met Ala Glu Phe Phe Gln Gln Gly
                20                  25                  30

Asp Arg Glu Arg Glu Arg Gly Met Glu Ile Ser Pro Met Cys Asp Lys
```

|     |     |     |     | 35  |     |     |     |     | 40  |     |     |     |     | 45  |     |
| --- | --- | --- | --- | --- | --- | --- | --- | --- | --- | --- | --- | --- | --- | --- | --- |
| His | Thr | Ala | Ser | Val | Glu | Lys | Ser | Gln | Val | Gly | Phe | Ile | Asp | Tyr | Ile |
|     | 50  |     |     |     |     | 55  |     |     |     |     | 60  |     |     |     |     |
| Val | His | Pro | Leu | Trp | Glu | Thr | Trp | Ala | Asp | Leu | Val | His | Pro | Asp | Ala |
| 65  |     |     |     |     | 70  |     |     |     |     | 75  |     |     |     |     | 80  |
| Gln | Glu | Ile | Leu | Asp | Thr | Leu | Glu | Asp | Asn | Arg | Asp | Trp | Tyr | Tyr | Ser |
|     |     |     |     | 85  |     |     |     |     | 90  |     |     |     |     | 95  |     |
| Ala | Ile | Arg | Gln | Ser | Pro | Ser | Pro | Pro | Glu | Glu | Glu | Ser | Arg | Gly |     |
|     |     |     | 100 |     |     |     |     | 105 |     |     |     | 110 |     |     |     |
| Pro | Gly | His | Pro | Pro | Leu | Pro | Asp | Lys | Phe | Gln | Phe | Asp | Val | Thr | Leu |
|     |     | 115 |     |     |     |     | 120 |     |     |     |     | 125 |     |     |     |
| Glu | Glu | Glu | Glu | Glu | Glu | Ile | Ser | Met | Ala | Gln | Ile | Pro | Cys | Thr |     |
|     | 130 |     |     |     |     | 135 |     |     |     |     | 140 |     |     |     |     |
| Ala | Gln | Glu | Ala | Leu | Thr | Ala | Gln | Gly | Leu | Ser | Gly | Val | Glu | Glu | Ala |
| 145 |     |     |     |     | 150 |     |     |     |     | 155 |     |     |     |     | 160 |
| Leu | Asp | Ala | Thr | Ile | Ala | Trp | Glu | Ala | Ser | Pro | Ala | Gln | Glu | Ser | Leu |
|     |     |     |     | 165 |     |     |     |     | 170 |     |     |     |     | 175 |     |
| Glu | Val | Met | Ala | Gln | Glu | Ala | Ser | Leu | Glu | Ala | Glu | Leu | Glu | Ala | Val |
|     |     |     | 180 |     |     |     |     | 185 |     |     |     |     | 190 |     |     |
| Tyr | Leu | Thr | Gln | Gln | Ala | Gln | Ser | Thr | Gly | Ser | Ala | Pro | Val | Ala | Pro |
|     |     | 195 |     |     |     |     | 200 |     |     |     |     | 205 |     |     |     |
| Asp | Glu | Phe | Ser | Ser | Arg | Glu | Glu | Phe | Val | Val | Ala | Val | Ser | His | Ser |
|     | 210 |     |     |     |     | 215 |     |     |     |     | 220 |     |     |     |     |
| Ser | Pro | Ser | Ala | Leu | Ala | Leu | Gln | Ser | Pro | Leu | Leu | Pro | Ala | Trp | Arg |
| 225 |     |     |     |     | 230 |     |     |     |     | 235 |     |     |     |     | 240 |
| Thr | Leu | Ser | Val | Ser | Glu | His | Ala | Pro | Gly | Leu | Pro | Ala | Ser | Pro | Pro |
|     |     |     |     | 245 |     |     |     |     | 250 |     |     |     |     | 255 |     |
| Arg | Arg | Pro | Arg | Trp | Asn | Glu | Ser | Thr | Arg | Leu | Pro | Arg | Gly | Leu | Ala |
|     |     |     | 260 |     |     |     |     | 265 |     |     |     |     | 270 |     |     |
| Val | Pro | Ala | Gln | Gly | His | Leu | Gly | Arg | Thr | His | Pro | His | Ser | Gln | Leu |
|     |     | 275 |     |     |     |     | 280 |     |     |     |     | 285 |     |     |     |
| Leu | Val | Ala | Gly | Gly | Gln | Val | Glu | Thr | Leu | Pro | Asp | Pro | Gln | Thr | Ser |
|     | 290 |     |     |     |     | 295 |     |     |     |     | 300 |     |     |     |     |
| Val | Pro | Val | Pro | Leu | His | Ser | Ser | Pro | His | Ser | Pro | Ala | Pro | Pro | Thr |
| 305 |     |     |     |     | 310 |     |     |     |     | 315 |     |     |     |     | 320 |
| Thr | Ser | Ser | Ser | Ala | Ser | Lys | Thr | Leu | Val | Leu | Leu | Ser | Leu | Leu | Arg |
|     |     |     |     | 325 |     |     |     |     | 330 |     |     |     |     | 335 |     |
| Lys | Lys | Lys | Thr | Lys | Ser | Gly | Val | Phe | Phe | Cys | Phe | Leu | Phe | Phe | Pro |
|     |     |     | 340 |     |     |     |     | 345 |     |     |     |     | 350 |     |     |
| Phe | Pro | Pro | Ala | Pro | Thr | His | Gly | Ala | Phe | Phe | Trp | Arg | Trp | Gly | Leu |
|     |     | 355 |     |     |     |     | 360 |     |     |     |     | 365 |     |     |     |
| Gly | Asn | Glu | Gly | Leu | Arg | Ser | Arg | Lys | Gly | Phe | Tyr | Phe | Phe | Glu | Phe |
|     |     | 370 |     |     |     |     | 375 |     |     |     |     | 380 |     |     |     |

( 2 ) INFORMATION FOR SEQ ID NO:41:

( i ) SEQUENCE CHARACTERISTICS:
        ( A ) LENGTH: 798 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 3..798

( x i ) SEQUENCE DESCRIPTION: SEQ ID NO:41:

| | | | | | | | | | | | | | | | |
|---|---|---|---|---|---|---|---|---|---|---|---|---|---|---|---|
| GA | ATT | CCT | CTG | ACT | AAT | TCA | AGT | ATC | CCA | AGG | TTT | GGA | GTT | AAA | ACT | 47
| | Ile | Pro | Leu | Thr | Asn | Ser | Ser | Ile | Pro | Arg | Phe | Gly | Val | Lys | Thr |
| | 1 | | | 5 | | | | | 10 | | | | | 15 | |

| GAA | CAA | GAA | GAT | GTC | CTT | GCC | AAG | GAA | CTA | GAA | GAT | GTG | AAC | AAA | TGG | 95
|---|---|---|---|---|---|---|---|---|---|---|---|---|---|---|---|---|
| Glu | Gln | Glu | Asp | Val | Leu | Ala | Lys | Glu | Leu | Glu | Asp | Val | Asn | Lys | Trp |
| | | | | 20 | | | | 25 | | | | | 30 | | |

| GGT | CTT | CAT | GTT | TTC | AGA | ATA | GCA | GAG | TTG | TCT | GGT | AAC | CGG | CCC | TTG | 143
|---|---|---|---|---|---|---|---|---|---|---|---|---|---|---|---|---|
| Gly | Leu | His | Val | Phe | Arg | Ile | Ala | Glu | Leu | Ser | Gly | Asn | Arg | Pro | Leu |
| | | | 35 | | | | | 40 | | | | | 45 | | |

| ACT | GTT | ATC | ATG | CAC | ACC | ATT | TTT | CAG | GAA | CGG | GAT | TTA | TTA | AAA | ACA | 191
|---|---|---|---|---|---|---|---|---|---|---|---|---|---|---|---|---|
| Thr | Val | Ile | Met | His | Thr | Ile | Phe | Gln | Glu | Arg | Asp | Leu | Leu | Lys | Thr |
| | | 50 | | | | | 55 | | | | | 60 | | | |

| TTT | AAA | ATT | CCA | GTA | GAT | ACT | TTA | ATT | ACA | TAT | CTT | ATG | ACT | CTC | GAA | 239
|---|---|---|---|---|---|---|---|---|---|---|---|---|---|---|---|---|
| Phe | Lys | Ile | Pro | Val | Asp | Thr | Leu | Ile | Thr | Tyr | Leu | Met | Thr | Leu | Glu |
| | 65 | | | | 70 | | | | | 75 | | | | | |

| GAC | CAT | TAC | CAT | GCT | GAT | GTG | GCC | TAT | CAC | AAC | AAT | ATC | CAT | GCT | GCA | 287
|---|---|---|---|---|---|---|---|---|---|---|---|---|---|---|---|---|
| Asp | His | Tyr | His | Ala | Asp | Val | Ala | Tyr | His | Asn | Asn | Ile | His | Ala | Ala |
| 80 | | | | | 85 | | | | | 90 | | | | | 95 |

| GAT | GTT | GTC | CAG | TCT | ACT | CAT | GTG | CTA | TTA | TCT | ACA | CCT | GCT | TTG | GAG | 335
|---|---|---|---|---|---|---|---|---|---|---|---|---|---|---|---|---|
| Asp | Val | Val | Gln | Ser | Thr | His | Val | Leu | Leu | Ser | Thr | Pro | Ala | Leu | Glu |
| | | | 100 | | | | | 105 | | | | | 110 | | |

| GCT | GTG | TTT | ACA | GAT | TTG | GAG | ATT | CTT | GCA | GCA | ATT | TTT | GCC | AGT | GCA | 383
|---|---|---|---|---|---|---|---|---|---|---|---|---|---|---|---|---|
| Ala | Val | Phe | Thr | Asp | Leu | Glu | Ile | Leu | Ala | Ala | Ile | Phe | Ala | Ser | Ala |
| | | 115 | | | | | 120 | | | | | 125 | | | |

| ATA | CAT | GAT | GTA | GAT | CAT | CCT | GGT | GTG | TCC | AAT | CAA | TTT | CTG | ATC | AAT | 431
|---|---|---|---|---|---|---|---|---|---|---|---|---|---|---|---|---|
| Ile | His | Asp | Val | Asp | His | Pro | Gly | Val | Ser | Asn | Gln | Phe | Leu | Ile | Asn |
| | | 130 | | | | | 135 | | | | | 140 | | | |

| ACA | AAC | TCT | GAA | CTT | GCC | TTG | ATG | TAC | AAT | GAT | TCC | TCA | GTC | TTA | GAG | 479
|---|---|---|---|---|---|---|---|---|---|---|---|---|---|---|---|---|
| Thr | Asn | Ser | Glu | Leu | Ala | Leu | Met | Tyr | Asn | Asp | Ser | Ser | Val | Leu | Glu |
| | 145 | | | | | 150 | | | | | 155 | | | | |

| AAC | CAT | CAT | TTG | GCT | GTG | GGC | TTT | AAA | TTG | CTT | CAG | GAA | GAA | AAC | TGT | 527
|---|---|---|---|---|---|---|---|---|---|---|---|---|---|---|---|---|
| Asn | His | His | Leu | Ala | Val | Gly | Phe | Lys | Leu | Leu | Gln | Glu | Glu | Asn | Cys |
| 160 | | | | | 165 | | | | | 170 | | | | | 175 |

| GAC | ATT | TTC | CAG | AAT | TTG | ACC | AAA | AAA | CAA | AGA | CAA | TCT | TTA | AGG | AAA | 575
|---|---|---|---|---|---|---|---|---|---|---|---|---|---|---|---|---|
| Asp | Ile | Phe | Gln | Asn | Leu | Thr | Lys | Lys | Gln | Arg | Gln | Ser | Leu | Arg | Lys |
| | | | | 180 | | | | | 185 | | | | | 190 | |

| ATG | GTC | ATT | GAC | ATC | GTA | CTT | GCA | ACA | GAT | ATG | TCA | AAA | CAC | ATG | AAT | 623
|---|---|---|---|---|---|---|---|---|---|---|---|---|---|---|---|---|
| Met | Val | Ile | Asp | Ile | Val | Leu | Ala | Thr | Asp | Met | Ser | Lys | His | Met | Asn |
| | | | 195 | | | | | 200 | | | | | 205 | | |

| CTA | CTG | GCT | GAT | TTG | AAG | ACT | ATG | GTT | GAA | ACT | AAG | AAA | GTG | ACA | AGC | 671
|---|---|---|---|---|---|---|---|---|---|---|---|---|---|---|---|---|
| Leu | Leu | Ala | Asp | Leu | Lys | Thr | Met | Val | Glu | Thr | Lys | Lys | Val | Thr | Ser |
| | | 210 | | | | | 215 | | | | | 220 | | | |

| TCT | GGA | GTT | CTT | CTT | CTT | GAT | AAT | TAT | TCC | GAT | AGG | ATT | CAG | GTT | CTT | 719
|---|---|---|---|---|---|---|---|---|---|---|---|---|---|---|---|---|
| Ser | Gly | Val | Leu | Leu | Leu | Asp | Asn | Tyr | Ser | Asp | Arg | Ile | Gln | Val | Leu |
| | 225 | | | | | 230 | | | | | 235 | | | | |

| CAG | AAT | ATG | GTG | CAC | TGT | GCA | GAT | CTG | AGC | AAC | CCA | ACA | AAG | CCT | CTC | 767
|---|---|---|---|---|---|---|---|---|---|---|---|---|---|---|---|---|
| Gln | Asn | Met | Val | His | Cys | Ala | Asp | Leu | Ser | Asn | Pro | Thr | Lys | Pro | Leu |
| 240 | | | | | 245 | | | | | 250 | | | | | 255 |

| CAG | CTG | TAC | CGC | CAG | TGG | ACG | GAC | GGA | ATT | C | | | | | | 798
|---|---|---|---|---|---|---|---|---|---|---|---|---|---|---|---|---|
| Gln | Leu | Tyr | Arg | Gln | Trp | Thr | Asp | Gly | Ile | | | | | | |
| | | | | 260 | | | | | 265 | | | | | | |

( 2 ) INFORMATION FOR SEQ ID NO:42:

( i ) SEQUENCE CHARACTERISTICS:
  ( A ) LENGTH: 265 amino acids
  ( B ) TYPE: amino acid
  ( D ) TOPOLOGY: linear ( i i ) MOLECULE TYPE: protein ( x i ) SEQUENCE DESCRIPTION: SEQ ID NO:42:

| Ile | Pro | Leu | Thr | Asn | Ser | Ser | Ile | Pro | Arg | Phe | Gly | Val | Lys | Thr | Glu |
|---|---|---|---|---|---|---|---|---|---|---|---|---|---|---|---|
| 1 | | | | 5 | | | | | 10 | | | | | 15 | |
| Gln | Glu | Asp | Val | Leu | Ala | Lys | Glu | Leu | Glu | Asp | Val | Asn | Lys | Trp | Gly |
| | | | 20 | | | | | 25 | | | | | 30 | | |
| Leu | His | Val | Phe | Arg | Ile | Ala | Glu | Leu | Ser | Gly | Asn | Arg | Pro | Leu | Thr |
| | | 35 | | | | | 40 | | | | | 45 | | | |
| Val | Ile | Met | His | Thr | Ile | Phe | Gln | Glu | Arg | Asp | Leu | Leu | Lys | Thr | Phe |
| | 50 | | | | | 55 | | | | | 60 | | | | |
| Lys | Ile | Pro | Val | Asp | Thr | Leu | Ile | Thr | Tyr | Leu | Met | Thr | Leu | Glu | Asp |
| 65 | | | | | 70 | | | | | 75 | | | | | 80 |
| His | Tyr | His | Ala | Asp | Val | Ala | Tyr | His | Asn | Asn | Ile | His | Ala | Ala | Asp |
| | | | | 85 | | | | | 90 | | | | | 95 | |
| Val | Val | Gln | Ser | Thr | His | Val | Leu | Leu | Ser | Thr | Pro | Ala | Leu | Glu | Ala |
| | | | | 100 | | | | | 105 | | | | | 110 | |
| Val | Phe | Thr | Asp | Leu | Glu | Ile | Leu | Ala | Ala | Ile | Phe | Ala | Ser | Ala | Ile |
| | | | 115 | | | | | 120 | | | | | 125 | | |
| His | Asp | Val | Asp | His | Pro | Gly | Val | Ser | Asn | Gln | Phe | Leu | Ile | Asn | Thr |
| | 130 | | | | | 135 | | | | | 140 | | | | |
| Asn | Ser | Glu | Leu | Ala | Leu | Met | Tyr | Asn | Asp | Ser | Ser | Val | Leu | Glu | Asn |
| 145 | | | | | 150 | | | | | 155 | | | | | 160 |
| His | His | Leu | Ala | Val | Gly | Phe | Lys | Leu | Leu | Gln | Glu | Glu | Asn | Cys | Asp |
| | | | | 165 | | | | | 170 | | | | | 175 | |
| Ile | Phe | Gln | Asn | Leu | Thr | Lys | Lys | Gln | Arg | Gln | Ser | Leu | Arg | Lys | Met |
| | | | 180 | | | | | 185 | | | | | 190 | | |
| Val | Ile | Asp | Ile | Val | Leu | Ala | Thr | Asp | Met | Ser | Lys | His | Met | Asn | Leu |
| | | 195 | | | | | 200 | | | | | 205 | | | |
| Leu | Ala | Asp | Leu | Lys | Thr | Met | Val | Glu | Thr | Lys | Lys | Val | Thr | Ser | Ser |
| 210 | | | | | 215 | | | | | 220 | | | | | |
| Gly | Val | Leu | Leu | Leu | Asp | Asn | Tyr | Ser | Asp | Arg | Ile | Gln | Val | Leu | Gln |
| 225 | | | | | 230 | | | | | 235 | | | | | 240 |
| Asn | Met | Val | His | Cys | Ala | Asp | Leu | Ser | Asn | Pro | Thr | Lys | Pro | Leu | Gln |
| | | | | 245 | | | | | 250 | | | | | 255 | |
| Leu | Tyr | Arg | Gln | Trp | Thr | Asp | Gly | Ile | | | | | | | |
| | | | 260 | | | | | 265 | | | | | | | |

( 2 ) INFORMATION FOR SEQ ID NO:43:

( i ) SEQUENCE CHARACTERISTICS:
        ( A ) LENGTH: 1902 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 97..1256

( x i ) SEQUENCE DESCRIPTION: SEQ ID NO:43:

```
GAATTCCTTT GTTCACATCT TCTAGTTCCT TGGCAAGGAC ATCTTCATGT TTTCAGAATA         60

GCAGAGTTGT CTGGTAACCG GCCCTTGACT GTTATC ATG CAC ACC ATT TTT CAG         114
                                        Met His Thr Ile Phe Gln
                                         1                   5

GAA CGG GAT TTA TTA AAA ACA TTT AAA ATT CCA GTA GAT ACT TTA ATT         162
Glu Arg Asp Leu Leu Lys Thr Phe Lys Ile Pro Val Asp Thr Leu Ile
         10                  15                  20
```

| | | | | | | | | | | | | | | | | |
|---|---|---|---|---|---|---|---|---|---|---|---|---|---|---|---|---|
| ACA | TAT | CTT | ATG | ACT | CTC | GAA | GAC | CAT | TAC | CAT | GCT | GAT | GTG | GCC | TAT | 210 |
| Thr | Tyr | Leu | Met | Thr | Leu | Glu | Asp | His | Tyr | His | Ala | Asp | Val | Ala | Tyr | |
| | | 25 | | | | 30 | | | | | 35 | | | | | |
| CAC | AAC | AAT | ATC | CAT | GCT | GCA | GAT | GTT | GTC | CAG | TCT | ACT | CAT | GTG | CTA | 258 |
| His | Asn | Asn | Ile | His | Ala | Ala | Asp | Val | Val | Gln | Ser | Thr | His | Val | Leu | |
| | | 40 | | | | 45 | | | | | 50 | | | | | |
| TTA | TCT | ACA | CCT | GCT | TTG | GAG | GCT | GTG | TTT | ACA | GAT | TTG | GAG | ATT | CTT | 306 |
| Leu | Ser | Thr | Pro | Ala | Leu | Glu | Ala | Val | Phe | Thr | Asp | Leu | Glu | Ile | Leu | |
| 55 | | | | | 60 | | | | | 65 | | | | | 70 | |
| GCA | GCA | ATT | TTT | GCC | AGT | GCA | ATA | CAT | GAT | GTA | GAT | CAT | CCT | GGT | GTG | 354 |
| Ala | Ala | Ile | Phe | Ala | Ser | Ala | Ile | His | Asp | Val | Asp | His | Pro | Gly | Val | |
| | | | | 75 | | | | 80 | | | | | 85 | | | |
| TCC | AAT | CAA | TTT | CTG | ATC | AAT | ACA | AAC | TCT | GAA | CTT | GCC | TTG | ATG | TAC | 402 |
| Ser | Asn | Gln | Phe | Leu | Ile | Asn | Thr | Asn | Ser | Glu | Leu | Ala | Leu | Met | Tyr | |
| | | 90 | | | | 95 | | | | | 100 | | | | | |
| AAT | GAT | TCC | TCA | GTC | TTA | GAG | AAC | CAT | CAT | TTG | GCT | GTG | GGC | TTT | AAA | 450 |
| Asn | Asp | Ser | Ser | Val | Leu | Glu | Asn | His | His | Leu | Ala | Val | Gly | Phe | Lys | |
| | | 105 | | | | 110 | | | | | 115 | | | | | |
| TTG | CTT | CAG | GAA | GAA | AAC | TGT | GAC | ATT | TTC | CAG | AAT | TTG | ACC | AAA | AAA | 498 |
| Leu | Leu | Gln | Glu | Glu | Asn | Cys | Asp | Ile | Phe | Gln | Asn | Leu | Thr | Lys | Lys | |
| | | 120 | | | | 125 | | | | | 130 | | | | | |
| CAA | AGA | CAA | TCT | TTA | AGG | AAA | ATG | GTC | ATT | GAC | ATC | GTA | CTT | GCA | ACA | 546 |
| Gln | Arg | Gln | Ser | Leu | Arg | Lys | Met | Val | Ile | Asp | Ile | Val | Leu | Ala | Thr | |
| 135 | | | | | 140 | | | | | 145 | | | | | 150 | |
| GAT | ATG | TCA | AAA | CAC | ATG | AAT | CTA | CTG | GCT | GAT | TTG | AAG | ACT | ATG | GTT | 594 |
| Asp | Met | Ser | Lys | His | Met | Asn | Leu | Leu | Ala | Asp | Leu | Lys | Thr | Met | Val | |
| | | | | 155 | | | | 160 | | | | | 165 | | | |
| GAA | ACT | AAG | AAA | GTG | ACA | AGC | TCT | GGA | GTT | CTT | CTT | CTT | GAT | AAT | TAT | 642 |
| Glu | Thr | Lys | Lys | Val | Thr | Ser | Ser | Gly | Val | Leu | Leu | Leu | Asp | Asn | Tyr | |
| | | | 170 | | | | | 175 | | | | | 180 | | | |
| TCC | GAT | AGG | ATT | CAG | GTT | CTT | CAG | AAT | ATG | GTG | CAC | TGT | GCA | GAT | CTG | 690 |
| Ser | Asp | Arg | Ile | Gln | Val | Leu | Gln | Asn | Met | Val | His | Cys | Ala | Asp | Leu | |
| | | | 185 | | | | | 190 | | | | | 195 | | | |
| AGC | AAC | CCA | ACA | AAG | CCT | CTC | CAG | CTG | TAC | CGC | CAG | TGG | ACG | GAC | CGG | 738 |
| Ser | Asn | Pro | Thr | Lys | Pro | Leu | Gln | Leu | Tyr | Arg | Gln | Trp | Thr | Asp | Arg | |
| | | 200 | | | | 205 | | | | | 210 | | | | | |
| ATA | ATG | GAG | GAG | TTC | TTC | CGC | CAA | GGA | GAC | CGA | GAG | AGG | GAA | CGT | GGC | 786 |
| Ile | Met | Glu | Glu | Phe | Phe | Arg | Gln | Gly | Asp | Arg | Glu | Arg | Glu | Arg | Gly | |
| 215 | | | | | 220 | | | | | 225 | | | | | 230 | |
| ATG | GAG | ATA | AGC | CCC | ATG | TGT | GAC | AAG | CAC | AAT | GCT | TCC | GTG | GAA | AAA | 834 |
| Met | Glu | Ile | Ser | Pro | Met | Cys | Asp | Lys | His | Asn | Ala | Ser | Val | Glu | Lys | |
| | | | | 235 | | | | 240 | | | | | 245 | | | |
| TCA | CAG | GTG | GGC | TTC | ATA | GAC | TAT | ATT | GTT | CAT | CCC | CTC | TGG | GAG | ACA | 882 |
| Ser | Gln | Val | Gly | Phe | Ile | Asp | Tyr | Ile | Val | His | Pro | Leu | Trp | Glu | Thr | |
| | | | 250 | | | | | 255 | | | | | 260 | | | |
| TGG | GCA | GAC | CTC | GTC | CAC | CCT | GAC | GCC | CAG | GAT | ATT | TTG | GAC | ACT | TTG | 930 |
| Trp | Ala | Asp | Leu | Val | His | Pro | Asp | Ala | Gln | Asp | Ile | Leu | Asp | Thr | Leu | |
| | | 265 | | | | 270 | | | | | 275 | | | | | |
| GAG | GAC | AAT | CGT | GAA | TGG | TAC | CAG | AGC | ACA | ATC | CCT | CAG | AGC | CCC | TCT | 978 |
| Glu | Asp | Asn | Arg | Glu | Trp | Tyr | Gln | Ser | Thr | Ile | Pro | Gln | Ser | Pro | Ser | |
| 280 | | | | | 285 | | | | | 290 | | | | | | |
| CCT | GCA | CCT | GAT | GAC | CCA | GAG | GAG | GGC | CGG | CAG | GGT | CAA | ACT | GAG | AAA | 1026 |
| Pro | Ala | Pro | Asp | Asp | Pro | Glu | Glu | Gly | Arg | Gln | Gly | Gln | Thr | Glu | Lys | |
| 295 | | | | | 300 | | | | | 305 | | | | | 310 | |
| TTC | CAG | TTT | GAA | CTA | ACT | TTA | GAG | GAA | GAT | GGT | GAG | TCA | GAC | ACG | GAA | 1074 |
| Phe | Gln | Phe | Glu | Leu | Thr | Leu | Glu | Glu | Asp | Gly | Glu | Ser | Asp | Thr | Glu | |
| | | | | 315 | | | | 320 | | | | | 325 | | | |
| AAG | GAC | AGT | GGC | AGT | CAA | GTG | GAA | GAA | GAC | ACT | AGC | TGC | AGT | GAC | TCC | 1122 |
| Lys | Asp | Ser | Gly | Ser | Gln | Val | Glu | Glu | Asp | Thr | Ser | Cys | Ser | Asp | Ser | |
| | | | 330 | | | | | 335 | | | | | 340 | | | |

| | | | | | | | | | | | | | | | |
|---|---|---|---|---|---|---|---|---|---|---|---|---|---|---|---|
| AAG | ACT | CTT | TGT | ACT | CAA | GAC | TCA | GAG | TCT | ACT | GAA | ATT | CCC | CTT | GAT | 1170
| Lys | Thr | Leu | Cys | Thr | Gln | Asp | Ser | Glu | Ser | Thr | Glu | Ile | Pro | Leu | Asp |
| | | 345 | | | | 350 | | | | | 355 | | | | |
| GAA | CAG | GTT | GAA | GAG | GAG | GCA | GTA | GGG | GAA | GAA | GAG | GAA | AGC | CAG | CCT | 1218
| Glu | Gln | Val | Glu | Glu | Glu | Ala | Val | Gly | Glu | Glu | Glu | Glu | Ser | Gln | Pro |
| | 360 | | | | | 365 | | | | | 370 | | | | |
| GAA | GCC | TGT | GTC | ATA | GAT | GAT | CGT | TCT | CCT | GAC | ACG | TA ACAGTGCAAA | | | | 1266
| Glu | Ala | Cys | Val | Ile | Asp | Asp | Arg | Ser | Pro | Asp | Thr | | | | |
| 375 | | | | | 380 | | | | | 385 | | | | | |

| | | | | |
|---|---|---|---|---|
| AACTTTCATG | CCTTTTTTT | TTTTAAGTAG | AAAAATTGTT | TCCAAAGTGC ATGTCACATG | 1326
| CCACAACCAC | GGTCACACCT | CACTGTCATC | TGCCAGGACG | TTTGTTGAAC AAAACTGACC | 1386
| TTGACTACTC | AGTCCAGCGC | TCAGGAATAT | CGTAACCAGT | TTTTTCACCT CCATGTCATC | 1446
| CGAGCAAGGT | GGACATCTTC | ACGAACAGCG | TTTTTAACAA | GATTTCAGCT TGGTAGAGCT | 1506
| GACAAAGCAG | ATAAAATCTA | CTCCAAATTA | TTTTCAAGAG | AGTGTGACTC ATCAGGCAGC | 1566
| CCAAAAGTTT | ATTGGACTTG | GGGTTTCTAT | TCCTTTTTAT | TTGTTTGCAA TATTTTCAGA | 1626
| AGAAAGGCAT | TGCACAGAGT | GAACTTAATG | GACGAAGCAA | CAAATATGTC AAGAACAGGA | 1686
| CATAGCACGA | ATCTGTTACC | AGTAGGAGGA | GGATGAGCCA | CAGAAATTGC ATAATTTTCT | 1746
| AATTTCAAGT | CTTCCTGATA | CATGACTGAA | TAGTGTGGTT | CAGTGAGCTG CACTGACCTC | 1806
| TACATTTTGT | ATGATATGTA | AAACAGATTT | TTTGTAGAGC | TTACTTTTAT TATTAAATGT | 1866
| ATTGAGGTAT | TATATTTAAA | AAAAAAAAG | GAATTC | | 1902

(2) INFORMATION FOR SEQ ID NO:44:

(i) SEQUENCE CHARACTERISTICS:
        (A) LENGTH: 386 amino acids
        (B) TYPE: amino acid
        (D) TOPOLOGY: linear (ii) MOLECULE TYPE: protein (xi) SEQUENCE DESCRIPTION: SEQ ID NO:44:

```
Met His Thr Ile Phe Gln Glu Arg Asp Leu Leu Lys Thr Phe Lys Ile
 1               5                  10                  15

Pro Val Asp Thr Leu Ile Thr Tyr Leu Met Thr Leu Glu Asp His Tyr
            20                  25                  30

His Ala Asp Val Ala Tyr His Asn Asn Ile His Ala Ala Asp Val Val
        35                  40                  45

Gln Ser Thr His Val Leu Leu Ser Thr Pro Ala Leu Glu Ala Val Phe
    50                  55                  60

Thr Asp Leu Glu Ile Leu Ala Ala Ile Phe Ala Ser Ala Ile His Asp
65                  70                  75                  80

Val Asp His Pro Gly Val Ser Asn Gln Phe Leu Ile Asn Thr Asn Ser
                85                  90                  95

Glu Leu Ala Leu Met Tyr Asn Asp Ser Ser Val Leu Glu Asn His His
            100                 105                 110

Leu Ala Val Gly Phe Lys Leu Leu Gln Glu Glu Asn Cys Asp Ile Phe
        115                 120                 125

Gln Asn Leu Thr Lys Lys Gln Arg Gln Ser Leu Arg Lys Met Val Ile
    130                 135                 140

Asp Ile Val Leu Ala Thr Asp Met Ser Lys His Met Asn Leu Leu Ala
145                 150                 155                 160

Asp Leu Lys Thr Met Val Glu Thr Lys Lys Val Thr Ser Ser Gly Val
                165                 170                 175

Leu Leu Leu Asp Asn Tyr Ser Asp Arg Ile Gln Val Leu Gln Asn Met
```

|     |     |     |     |     | 180 |     |     |     |     | 185 |     |     |     |     | 190 |     |     |
|-----|-----|-----|-----|-----|-----|-----|-----|-----|-----|-----|-----|-----|-----|-----|-----|-----|-----|
| Val | His | Cys | Ala | Asp | Leu | Ser | Asn | Pro | Thr | Lys | Pro | Leu | Gln | Leu | Tyr |     |     |
|     |     | 195 |     |     |     |     | 200 |     |     |     |     | 205 |     |     |     |     |     |
| Arg | Gln | Trp | Thr | Asp | Arg | Ile | Met | Glu | Glu | Phe | Phe | Arg | Gln | Gly | Asp |     |     |
|     | 210 |     |     |     |     | 215 |     |     |     |     | 220 |     |     |     |     |     |     |
| Arg | Glu | Arg | Glu | Arg | Gly | Met | Glu | Ile | Ser | Pro | Met | Cys | Asp | Lys | His |     |     |
| 225 |     |     |     |     | 230 |     |     |     |     | 235 |     |     |     |     | 240 |     |     |
| Asn | Ala | Ser | Val | Glu | Lys | Ser | Gln | Val | Gly | Phe | Ile | Asp | Tyr | Ile | Val |     |     |
|     |     |     |     | 245 |     |     |     |     | 250 |     |     |     |     | 255 |     |     |     |
| His | Pro | Leu | Trp | Glu | Thr | Trp | Ala | Asp | Leu | Val | His | Pro | Asp | Ala | Gln |     |     |
|     |     |     | 260 |     |     |     |     | 265 |     |     |     |     | 270 |     |     |     |     |
| Asp | Ile | Leu | Asp | Thr | Leu | Glu | Asp | Asn | Arg | Glu | Trp | Tyr | Gln | Ser | Thr |     |     |
|     |     | 275 |     |     |     |     | 280 |     |     |     |     | 285 |     |     |     |     |     |
| Ile | Pro | Gln | Ser | Pro | Ser | Pro | Ala | Pro | Asp | Asp | Pro | Glu | Glu | Gly | Arg |     |     |
|     | 290 |     |     |     |     | 295 |     |     |     |     | 300 |     |     |     |     |     |     |
| Gln | Gly | Gln | Thr | Glu | Lys | Phe | Gln | Phe | Glu | Leu | Thr | Leu | Glu | Glu | Asp |     |     |
| 305 |     |     |     |     | 310 |     |     |     |     | 315 |     |     |     |     | 320 |     |     |
| Gly | Glu | Ser | Asp | Thr | Glu | Lys | Asp | Ser | Gly | Ser | Gln | Val | Glu | Glu | Asp |     |     |
|     |     |     |     | 325 |     |     |     |     | 330 |     |     |     |     | 335 |     |     |     |
| Thr | Ser | Cys | Ser | Asp | Ser | Lys | Thr | Leu | Cys | Thr | Gln | Asp | Ser | Glu | Ser |     |     |
|     |     |     | 340 |     |     |     |     | 345 |     |     |     |     | 350 |     |     |     |     |
| Thr | Glu | Ile | Pro | Leu | Asp | Glu | Gln | Val | Glu | Glu | Glu | Ala | Val | Gly | Glu |     |     |
|     |     | 355 |     |     |     |     | 360 |     |     |     |     | 365 |     |     |     |     |     |
| Glu | Glu | Glu | Ser | Gln | Pro | Glu | Ala | Cys | Val | Ile | Asp | Asp | Arg | Ser | Pro |     |     |
|     | 370 |     |     |     |     | 375 |     |     |     |     | 380 |     |     |     |     |     |     |
| Asp | Thr |     |     |     |     |     |     |     |     |     |     |     |     |     |     |     |     |
| 385 |     |     |     |     |     |     |     |     |     |     |     |     |     |     |     |     |     |

( 2 ) INFORMATION FOR SEQ ID NO:45:

( i ) SEQUENCE CHARACTERISTICS:
          ( A ) LENGTH: 1155 base pairs
          ( B ) TYPE: nucleic acid
          ( C ) STRANDEDNESS: single
          ( D ) TOPOLOGY: linear ( i i ) MOLECULE TYPE: cDNA ( i x ) FEATURE:
          ( A ) NAME/KEY: CDS
          ( B ) LOCATION: 95..762

( x i ) SEQUENCE DESCRIPTION: SEQ ID NO:45:

```
GAATTCCCTG  GCTGTGGGCT  TCAAGCTGCT  GCAGGCAGAG  AACTGCGATA  TCTTCCAGAA         60

CCTCAGCGCC  AAGCAGCGAC  TGAGTCTGCG  CAGG ATG GTC ATT GAC ATG GTG              112
                                         Met Val Ile Asp Met Val
                                          1               5

CTG GCC ACA GAC ATG TCC AAA CAC ATG AAC CTC CTG GCC GAC CTC AAG              160
Leu Ala Thr Asp Met Ser Lys His Met Asn Leu Leu Ala Asp Leu Lys
              10                  15                  20

ACC ATG GTG GAG ACC AAG AAG GTG ACA AGC CTC GGT GTC CTC CTC CTG              208
Thr Met Val Glu Thr Lys Lys Val Thr Ser Leu Gly Val Leu Leu Leu
 25                  30                  35

GAC AAC TAT TCC GAC CGA ATC CAG GTC TTG CAG AAC CTG GTG CAC TGT              256
Asp Asn Tyr Ser Asp Arg Ile Gln Val Leu Gln Asn Leu Val His Cys
         40                  45                  50

GCT GAT CTG AGC AAC CCC ACC AAG CCG CTG CCC CTG TAC CGC CAG TGG              304
Ala Asp Leu Ser Asn Pro Thr Lys Pro Leu Pro Leu Tyr Arg Gln Trp
 55                  60                  65                  70
```

```
ACG  GAC  CGC  ATC  ATG  GCC  GAG  TTC  TTC  CAG  CAG  GGA  GAC  CGC  GAG  CGT    352
Thr  Asp  Arg  Ile  Met  Ala  Glu  Phe  Phe  Gln  Gln  Gly  Asp  Arg  Glu  Arg
               75                      80                          85

GAG  TCG  GGC  CTG  GAC  ATC  AGT  CCC  ATG  TGT  GAC  AAG  CAT  ACG  GCC  TCA    400
Glu  Ser  Gly  Leu  Asp  Ile  Ser  Pro  Met  Cys  Asp  Lys  His  Thr  Ala  Ser
                    90                       95                      100

GTG  GAG  AAG  TCC  CAG  GTG  GGT  TTC  ATT  GAC  TAC  ATT  GCT  CAC  CCA  CTG    448
Val  Glu  Lys  Ser  Gln  Val  Gly  Phe  Ile  Asp  Tyr  Ile  Ala  His  Pro  Leu
               105                      110                     115

TGG  GAG  ACT  TGG  GCT  GAC  CTG  GTC  CAC  CCA  GAT  GCA  CAG  GAC  CTG  CTG    496
Trp  Glu  Thr  Trp  Ala  Asp  Leu  Val  His  Pro  Asp  Ala  Gln  Asp  Leu  Leu
          120                      125                     130

GAC  ACG  CTG  GAG  GAC  AAT  CGA  GAG  TGG  TAC  CAG  AGC  AAG  ATC  CCC  CGA    544
Asp  Thr  Leu  Glu  Asp  Asn  Arg  Glu  Trp  Tyr  Gln  Ser  Lys  Ile  Pro  Arg
135                      140                     145                     150

AGT  CCC  TCA  GAC  CTC  ACC  AAC  CCC  GAG  CGG  GAC  GGG  CCT  GAC  AGA  TTC    592
Ser  Pro  Ser  Asp  Leu  Thr  Asn  Pro  Glu  Arg  Asp  Gly  Pro  Asp  Arg  Phe
                    155                     160                     165

CAG  TTT  GAA  CTG  ACT  CTG  GAG  GAG  GCA  GAG  GAA  GAG  GAT  GAG  GAG  GAA    640
Gln  Phe  Glu  Leu  Thr  Leu  Glu  Glu  Ala  Glu  Glu  Glu  Asp  Glu  Glu  Glu
               170                      175                     180

GAA  GAG  GAG  GGG  GAA  GAG  ACA  GCT  TTA  GCC  AAA  GAG  GCC  TTG  GAG  TTG    688
Glu  Glu  Glu  Gly  Glu  Glu  Thr  Ala  Leu  Ala  Lys  Glu  Ala  Leu  Glu  Leu
               185                      190                     195

CCT  GAC  ACT  GAA  CTC  CTG  TCC  CCT  GAA  GCC  GGC  CCA  GAC  CCT  GGG  GAC    736
Pro  Asp  Thr  Glu  Leu  Leu  Ser  Pro  Glu  Ala  Gly  Pro  Asp  Pro  Gly  Asp
          200                      205                     210

TTA  CCC  CTC  GAC  AAC  CAG  AGG  ACT  TA GGGCCAGCCC TGCGTGAACT                  782
Leu  Pro  Leu  Asp  Asn  Gln  Arg  Thr
215                      220

GCAGGGGCAA  TGGATGGTAA  AGCCCTTTGG  CTCTTGGCAG  GCAGACTTTC  CAGGAAGAGG            842

CTCCATGTGG  CTCCTGCTTC  ACTTTCCCAC  CCATTTAGGG  AGACAATCAA  GCTCTTAGTT            902

ATAGGTGGCT  CCCAGGGTCT  AATTGGAGGC  ACCTGGCTGG  GGTCCACTCT  GACCCTAGAC            962

TTGCCTAAAA  GAGCTCTCTA  AGGGGCAGCC  TCTTACGATG  CCCTGGTGTC  TTTCTCCTGG           1022

GCTTCTATCC  CTGTGAGGAG  AGGTGCTGTC  TGCTGGAGCC  TCTAGTCCAC  CCTCTCCAGT           1082

GGTCACTCTT  GAGTCACATC  TGTCACTTAA  TTATTTCCTT  CTTTATCAAA  TATTTATTGC           1142

TCATCTGGAA  TTC                                                                  1155
```

( 2 ) INFORMATION FOR SEQ ID NO:46:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Met  Val  Ile  Asp  Met  Val  Leu  Ala  Thr  Asp  Met  Ser  Lys  His  Met  Asn
1                   5                        10                      15

Leu  Leu  Ala  Asp  Leu  Lys  Thr  Met  Val  Glu  Thr  Lys  Lys  Val  Thr  Ser
               20                       25                      30

Leu  Gly  Val  Leu  Leu  Leu  Asp  Asn  Tyr  Ser  Asp  Arg  Ile  Gln  Val  Leu
          35                       40                      45

Gln  Asn  Leu  Val  His  Cys  Ala  Asp  Leu  Ser  Asn  Pro  Thr  Lys  Pro  Leu
     50                       55                      60

Pro  Leu  Tyr  Arg  Gln  Trp  Thr  Asp  Arg  Ile  Met  Ala  Glu  Phe  Phe  Gln
65                       70                      75                      80
```

| | | | | | | | | | | | | |
|---|---|---|---|---|---|---|---|---|---|---|---|---|
|Gln|Gly|Asp|Arg|Glu|Arg|Glu|Ser|Gly|Leu|Asp|Ile|Ser|Pro|Met|Cys|
| | | | |85| | | |90| | | |95| | | |
|Asp|Lys|His|Thr|Ala|Ser|Val|Glu|Lys|Ser|Gln|Val|Gly|Phe|Ile|Asp|
| | | | |100| | | |105| | | |110| | | |
|Tyr|Ile|Ala|His|Pro|Leu|Trp|Glu|Thr|Trp|Ala|Asp|Leu|Val|His|Pro|
| | | | |115| | | |120| | | |125| | | |
|Asp|Ala|Gln|Asp|Leu|Leu|Asp|Thr|Leu|Glu|Asp|Asn|Arg|Glu|Trp|Tyr|
| | | | |130| | | |135| | | |140| | | |
|Gln|Ser|Lys|Ile|Pro|Arg|Ser|Pro|Ser|Asp|Leu|Thr|Asn|Pro|Glu|Arg|
|145| | | | |150| | | |155| | | |160| | |
|Asp|Gly|Pro|Asp|Arg|Phe|Gln|Phe|Glu|Leu|Thr|Leu|Glu|Glu|Ala|Glu|
| | | | |165| | | |170| | | |175| | | |
|Glu|Glu|Asp|Glu|Glu|Glu|Glu|Glu|Gly|Glu|Glu|Thr|Ala|Leu|Ala|
| | | | |180| | | |185| | | |190| | |
|Lys|Glu|Ala|Leu|Glu|Leu|Pro|Asp|Thr|Glu|Leu|Leu|Ser|Pro|Glu|Ala|
| | | | |195| | | |200| | | |205| | | |
|Gly|Pro|Asp|Pro|Gly|Asp|Leu|Pro|Leu|Asp|Asn|Gln|Arg|Thr|
| | | | |210| | | |215| | | |220| | |

( 2 ) INFORMATION FOR SEQ ID NO:47:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

TACGAAGCTT TGATGGGGTC TACTGCTAC        29

( 2 ) INFORMATION FOR SEQ ID NO:48:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

TACGAAGCTT TGATGGTTGG CTTGGCATAT C        31

( 2 ) INFORMATION FOR SEQ ID NO:49:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i v ) ANTI-SENSE: YES ( x i ) SEQUENCE DESCRIPTION: SEQ ID NO:49:

ATTAACCCTC ATAAAG        16

( 2 ) INFORMATION FOR SEQ ID NO:50:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

```
TACGAAGCTT TGATGCGCCG ACAGCCTGC                                              29
```

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

```
GGTCTCCTGT TGCAGATATT G                                                      21
```

( 2 ) INFORMATION FOR SEQ ID NO:52:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

```
TTYAARTCTN YTNCARGRNG A                                                      21
```

( 2 ) INFORMATION FOR SEQ ID NO:53:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

```
ACNATRTCTR ATNACCATYT T                                                      21
```

( 2 ) INFORMATION FOR SEQ ID NO:54:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:54:

```
Phe  Lys  Leu  Leu  Gln  Glu  Glu  Asn
 1                         5
```

( 2 ) INFORMATION FOR SEQ ID NO:55:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:55:

```
Phe  Lys  Leu  Leu  Gln  Gly  Glu  Asn
 1                         5
```

( 2 ) INFORMATION FOR SEQ ID NO:56:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:56:

Asp Met Val Ile Asp Met Val
1               5

( 2 ) INFORMATION FOR SEQ ID NO:57:

( i ) SEQUENCE CHARACTERISTICS:
       ( A ) LENGTH: 7 amino acids
       ( B ) TYPE: amino acid
       ( D ) TOPOLOGY: linear ( i i ) MOLECULE TYPE: peptide ( x i ) SEQUENCE DESCRIPTION: SEQ ID NO:57:

Asp Met Val Ile Asp Ile Val
1               5